US012350342B2

(12) United States Patent
Harding

(10) Patent No.: US 12,350,342 B2
(45) Date of Patent: Jul. 8, 2025

(54) O-LINKED GLYCOSYLATION RECOGNITION MOTIFS

(71) Applicant: VAXNEWMO LLC, St. Louis, MO (US)

(72) Inventor: Christian Harding, St. Louis, MO (US)

(73) Assignee: VAXNEWMO LLC, St. Louis, MO (US)

( * ) Notice: Subject to any disclaimer, the term of this patent is extended or adjusted under 35 U.S.C. 154(b) by 878 days.

(21) Appl. No.: 17/416,106

(22) PCT Filed: Nov. 5, 2019

(86) PCT No.: PCT/US2019/059893
§ 371 (c)(1),
(2) Date: Jun. 18, 2021

(87) PCT Pub. No.: WO2020/131236
PCT Pub. Date: Jun. 25, 2020

(65) Prior Publication Data
US 2022/0088211 A1 Mar. 24, 2022

Related U.S. Application Data

(60) Provisional application No. 62/783,971, filed on Dec. 21, 2018.

(51) Int. Cl.
*A61K 47/64* (2017.01)
*A61K 39/00* (2006.01)
*A61K 39/385* (2006.01)
*A61K 47/65* (2017.01)
*C07K 14/21* (2006.01)

(52) U.S. Cl.
CPC ........ *A61K 47/6415* (2017.08); *A61K 39/385* (2013.01); *A61K 47/646* (2017.08); *A61K 47/65* (2017.08); *C07K 14/212* (2013.01); *A61K 2039/6037* (2013.01); *A61K 2039/627* (2013.01)

(58) Field of Classification Search
None
See application file for complete search history.

(56) References Cited

U.S. PATENT DOCUMENTS

| | | | |
|---|---|---|---|
| 9,499,614 | B2 | 11/2016 | Hossler et al. |
| 10,435,704 | B2 | 10/2019 | Jarczowski et al. |
| 2011/0243980 | A1 | 10/2011 | Feldman et al. |
| 2018/0050101 | A1 | 2/2018 | Feldman et al. |
| 2018/0194812 | A1 | 7/2018 | Simon et al. |
| 2022/0054632 | A1 | 2/2022 | Follador et al. |

FOREIGN PATENT DOCUMENTS

| | | |
|---|---|---|
| JP | 2010515430 A | 5/2010 |
| WO | 2008093165 A2 | 8/2008 |
| WO | 2011109600 A1 | 9/2011 |
| WO | 2013023296 A1 | 2/2013 |
| WO | 2013067523 A1 | 5/2013 |
| WO | 2014057109 A1 | 4/2014 |
| WO | 2014072405 A1 | 5/2014 |
| WO | 2016107819 A1 | 7/2016 |
| WO | 2016134485 A1 | 9/2016 |
| WO | 2018135860 A1 | 7/2018 |
| WO | 2019106200 A1 | 6/2019 |
| WO | 2019241672 A2 | 12/2019 |
| WO | 2020131236 A1 | 6/2020 |

OTHER PUBLICATIONS

Ding et al., "Effects of N-Glycosylation Site Removal in Archaellins on the Assembly and Function of Archaella in Methanococcus Maripaludis", PLoS One, Feb. 2015, pp. 1-23, vol. 10 No. 2.
Power et al., "Genetic Characterization of Pilin Glycosylation and Phase Variation in Neisseria meningitidis", Molecular Microbiology, 2003, pp. 833-847, vol. 49, No. 3.
Price et al., "Glycoengineered Outer Membrane Vesicles: A Novel Platform for Bacterial Vaccines", Sci Rep, Apr. 22, 2016, vol. 6, No. 24931.
Rappuoli et al., "On the Mechanisms of Conjugate Vaccines", Proceedings of the National Academy of Sciences USA, Jan. 2019, pp. 14-16, vol. 116, No. 1.
Ravenscroft et al., "Purification and Characterization of a Shigella Conjugate Vaccine, Produced by Glycoengineering *Escherichia coli*", Glycobiology, 2016, pp. 51-62, vol. 26, No. 1.
Riddle et al., "Safety and Immunogenicity of a Candidate Bioconjugate Vaccine against Shigella flexneri 2a Administered to Healthy Adults: a Single-Blind, Randomized Phase I Study", Clin Vaccine Immunol, Dec. 5, 2016, pp. 908-917, vol. 23, No. 12.
Schaffer et al., "Emerging Facets of Prokaryotic Glycosylation", FEMS Microbiology Review, 2017, pp. 49-91, vol. 41, No. 1.
Schulz et al., "Identification of Bacterial Protein O-Oligosaccharyltransferases and Their Glycoprotein Substrates", PLOS One, May 2013, pp. 1-11, vol. 8, Issue 5.
Schulz et al., "Identification of Bacterial Protein O-Oligosaccharyltransferases and Their Glycoprotein Substrates", PLoS One, May 3, 2013, p. e62768, vol. 8, No. 5.
Schwarz et al., "A Combined Method of Producing Homogeneous Glycoproteins with Eukaryotic N-glycosylation", Nature Chemical Biology, Apr. 2010, pp. 264-266, vol. 6, No. 4.
Scott et al., "Diversity Within the O-Linked Protein Glycosylation Systems of Acinetobacter Species", Molecular & Cellular Proteomics, 2014, pp. 2354-2370, vol. 13, No. 9.
Search Report and Written Opinion for PCT/CA2016/050208 dated Sep. 1, 2016.
Soininen et al., "IgG Subclass Distribution of Antibodies after Vaccination of Adults with Pneumococcal Conjugate Vaccines", Vaccine, Apr. 9, 1999, pp. 1889-1897, vol. 17, No. 15-16.
Stimson et al., "Meningococcal Pilin: A Glycoprotein Substituted with Digalactosyl 2,4-diacetamido-2,4,6-trideoxyhexose", Mol Microbiol, Sep. 1995, pp. 1201-1214, vol. 17, No. 6.

(Continued)

*Primary Examiner* — Brian Gangle
(74) *Attorney, Agent, or Firm* — Thompson Coburn LLP; William A. Ph. D. J. Holtz D.

(57) ABSTRACT

Provided herein are glycoproteins containing O-linked glycosylation recognition motifs, and methods of making, for example, for use in the production of conjugate vaccines.

35 Claims, 56 Drawing Sheets

Specification includes a Sequence Listing.

(56) References Cited

OTHER PUBLICATIONS

Supplementary Partial European Search Report for EP16754717 dated Jul. 6, 2018.
Terra et al., "Recent Developments in Bacterial Protein Glycan Coupling Technology and Glycoconjugate Vaccine Design", Journal of Medical Microbiology, Jul. 2012, pp. 919-926, vol. 61, No. 7.
Vaneechoutte et al., "Naturally Transformable *Acinetobacter* sp. Strain ADP1 Belongs to the Newly Described Species *Acinetobacter baylyi*", Applied and Environmental Microbiology, Jan. 2006, pp. 932-936, vol. 72, No. 1.
Vella et al., "Glycoconjugate Vaccines: An Update", Expert Opin Biol Ther, Apr. 2015, pp. 529-546, vol. 15, No. 4.
Vik et al., "Broad Spectrum O-Linked Protein Glycosylation in the Human Pathogen *Neisseria gonorrhoeae*", Proceedings of the National Academy of Sciences USA, Mar. 2009, pp. 4447-4452, vol. 106, No. 11.
Wacker et al., "N-linked Glycosylation in Campylobacter Jejuni and its Functional Transfer into *E. coli*", Science, Nov. 29, 2002, pp. 1790-1793, vol. 298, No. 5599.
Wacker et al., "Substrate Specificity of Bacterial Oligosaccharyltransferase Suggests a Common Transfer Mechanism for the Bacterial and Eukaryotic Systems", Proceedings of the National Academy of Sciences USA, 2006, pp. 7088-7093, vol. 103, No. 18.
Wu et al., "Genome Sequencing and Comparative Analysis of Klebsiella pneumoniae NTUH-K2044, a Strain Causing Liver Abscess and Meningitis", Journal of Bacteriology, Jul. 2009, pp. 4452-4501, vol. 191, No. 14.
Wuorimaa et al., "Avidity and Subclasses of IgG after Immunization of Infants with an 11-Valent Pneumococcal Conjugate Vaccine with or without Aluminum Adjuvant", The Journal of Infectious Diseases, 2001, pp. 1211-1215, vol. 184, No. 9.
Porstendorfer et al., "ComP, A Pilin-Like Protein Essential for Natural Competence in *Acinetobacter* sp. Strain BD413: Regulation, Modification, and Cellular Localization", Journal of Bacteriology, Jul. 2000, pp. 3673-3680, vol. 182, No. 13.
"Pneumococcal Vaccination", Centers for Disease Control and Prevention—Vaccines and Preventable Diseases, <https://www.cdc.gov/vaccines/vpd/pneumo/index.html>.
Apweiler et al., "On the Frequency of Protein Glycosylation, as Deduced from Analysis of the SWISS-PROT Database", Biochim Biophys Acta, Dec. 6, 1999, pp. 4-8, vol. 1473, No. 1.
Arakawa et al., "Biosynthesis of Klebsiella K2 Capsular Polysaccharide in *Escherichia coli* HB101 Requires the Functions of rmpA and the Chromosomal cps Gene Cluster of the Virulent Strain Klebsiella pneumoniae Chedid (O1:K2), "Infection and Immunity, Jun. 1991, pp. 2043-2050, vol. 59, No. 6.
Avci et al., "A Novel Mechanism for Glycoconjugate Vaccine Activation of the Adaptive Immune System", Nature Medicine, 2011, pp. 1602-1609, vol. 17, No. 12.
Bentley et al., "Genetic Analysis of the Capsular Biosynthetic Locus from All 90 Pneumococcal Serotypes", PLoS Genetics, Mar. 2006, pp. 0262-0269, vol. 2, No. 3.
Bernatchez et al., "A Single Biofunctional UDP-GlcNAc/Glc 4-epimerase Supports the Synthesis of Three Cell Surface Glycoconjugates in Campylobacter Jejuni", Journal of Biological Chemistry, American Society for Biochemistry and Molecular Biology , Feb. 11, 2005, pp. 4792-4802, vol. 280, No. 6.
Berti et al., "Antimicrobial Glycoconjugate Vaccines: An Overview of Classic and Modern Approaches for Protein Modification", Chemical Society Reviews, 2018, pp. 9015-9025, vol. 47, No. 24.
Carboni et al., "Structure of a Protective Epitope of Group B *Streptococcus* Type III Capsular Polysaccharide", Proceedings of the National Academy of Sciences USA, May 2017, pp. 5017-5022, vol. 114, No. 19.
Castric, "pilO, a Gene Required for Glycosylation of Pseudomonas aeruginosa 1244 pilin", Microbiology, 1995, pp. 1247-1254, vol. 141, Part 5.

Cerqueira et al., "Hypothetical Protein F951_00736 [Acinetobacter soli CIP 110264]", GenBank: ENV58402.1, Nov. 25, 2019, 2 pages.
Ciocchini et al., "A Bacterial Engineered Glycoprotein as a Novel Antigen for Diagnosis of Bovine Brucellosis", Vet Microbiol, Aug. 27, 2014, pp. 455-465, vol. 172, No. 3-4.
Comer et al., "Identification of the Pseudomonas aeruginosa 1244 Pilin Glycosylation Site", Infection and Immunity, Jun. 2002, pp. 2837-2845, vol. 70, No. 6.
Comstock et al., "Bacterial Glycans: Key Mediators of Diverse Host Immune Responses", Cell, Sep. 2006, pp. 847-850, vol. 126, No. 5.
De Gregrio et al., "From Empiricism to Rational Design: A Personal Perspective of the Evolution of Vaccine Development", Nature Reviews, Jul. 2014, pp. 505-514, vol. 14, No. 7.
Dykxhoorn et al., "A Set of Compatible Tac Promoter Expression Vectors", Gene, Oct. 24, 1996, pp. 133-136, vol. 177, No. 1-2.
Faridmoayer et al., "Functional Characterization of Bacterial Oligosaccharyltransferases Involved in O-Linked Protein Glycosylation", Journal of Bacteriology, Nov. 2007, pp. 8088-8098, vol. 189, No. 22.
Feldman et al., "A Promising Bioconjugate Vaccine Against Hypervirulent Klebsiella pneumoniae", Proceedings of the National Academy of Sciences USA, Sep. 2019, pp. 18655-18663, vol. 116, No. 37.
Feldman et al., "Engineering N-linked Protein Glycosylation with Diverse O Antigen Lipopolysaccharide Structures in *Escherichia coli*", Proceedings of the National Academy of Sciences USA, Feb. 2005, pp. 3016-3021, vol. 102, No. 8.
Frasch, "Preparation of Bacterial Polysaccharide-Protein Conjugates: Analytical and Manufacturing Challenges", Vaccine, Oct. 30, 2009, pp. 6468-6470, vol. 27, No. 46.
Garcia-Quintanilla et al., "Production of a Recombinant Vaccine Candidate Against Burkholderia Pseudomallei Exploiting the Bacterial N-glycosylation Machinery", Front Microbiol, Jul. 29, 2014, vol. 5, No. 381.
Geno et al., "Pneumococcal Capsules and Their Types: Past, Present, and Future", Clinical Microbiology Reviews, Jul. 2015, pp. 871-899, vol. 28, No. 3.
Giltner et al., "Type IV Pilin Proteins: Versatile Molecular Modules", Microbiology and Molecular Biology Review, Dec. 2012, pp. 740-772, vol. 76, No. 4.
Harding et al, "Acinetobacter Strains Carry Two Functional Oligosaccharyltransferases, One Devoted Exclusively to Type IV Pilin, and the Other One Dedicated to O-glycosylation of Multiple Proteins", Molecular Microbiology, Jun. 2015, pp. 1023-1041, vol. 96, No. 5.
Harding et al., "A Platform for Glycoengineering a Polyvalent Pneumococcal Bioconjugate Vaccine Using *E. coli* as a Host", Nature Communications, 2019, pp. 1-11, vol. 10, No. 891.
Harding et al., "Acinetobacter Strains Carry Two Functional Oligosaccharyltransferases, One Devoted Exclusively to Type IV Pilin, and the Other One Dedicated to O-glycosylation of Multiple Proteins", Molecular Microbiology, 2015, pp. 1023-1041, vol. 96, No. 5.
Huttner et al., "Safety, Immunogenicity, and Preliminary Clinical Efficacy of a Vaccine Against Extraintestinal Pathogenic *Escherichia coli* in Women with a History of Recurrent Urinary Tract Infection: A Randomised, Single-Blind, Placebo-Controlled Phase 1b Trial", Lancet Infect Dis, May 2017, pp. 528-537, vol. 17, No. 5.
Huttner et al., "The Development and Early Clinical Testing of the ExPEC4V Conjugate Vaccine Against Uropathogenic *Escherichia coli*", Clin Microbiol Infect, Oct. 2018, pp. 1046-1050, vol. 10.
Ihssen et al., "Increased Efficiency of Campylobacter jejuni N-oligosaccharyltransferase PglB by Structure-Guided Engineering", Open Biology, 2015, pp. 1-10, vol. 5.
Iwashkiw et al., "Exploiting the Campylobacter Jejuni Protein Glycosylation System for Glycoengineering Vaccines and Diagnostic Tools Directed Against Brucellosis", Microb Cell Fact, Jan. 25, 2012, vol. 11, No. 13.
Iwashkiw et al., "Identification of a General O-Linked Protein Glycosylation System in Acinetobacter baumannii and Its Role in Virulence and Biofilm Formation", PLoS Pathogens, Jun. 2012, pp. 1-14, vol. 8, No. 6.

(56) References Cited

OTHER PUBLICATIONS

Iwashkiw et al., "Identification of General O-Linked Protein Glycosylation System in Acinetobacter Baumannii and Its Role in Virulence and Biofilm Formation", PLOS Pathogens, Jun. 2012, vol. 8, No. 6.

Iwashkiw et al., "Pour Some Sugar on it: The Expanding World of Bacterial Protein O-Linked Glycosylation", Molecular Microbiology, 2013, pp. 14-28, vol. 89, No. 1.

Kay et al., "Recombinant Epression of *Streptococcus pneumoniae* Capsular Polysaccharides in *Escherichia coli*", Open Biol, Apr. 13, 2016, vol. 6, No. 4.

Kovach et al., "Four New Derivatives of the Broad-Host-Range Cloning Vector pBBR1MCS, Carrying Different Antibiotic-Resistance Cassettes", Gene, Dec. 1, 1995, pp. 175-176, vol. 166, No. 1.

Kowarik et al., "Definition of the Bacterial N-Glycosylation Site Consensus Sequence", The EMBO Journal, 2006, pp. 1957-1966, vol. 25, No. 9.

Lery et al., "Comparative Analysis of Klebsiella pneumoniae Genomes Identifies a Phospholipase D Family Protein as a Novel Virulence Factor", BMC Biology, 2014, pp. 1-15, vol. 12, No. 41.

Malik, "Protein Fusion Tags for Efficient Expression and Purification of Recombinant Proteins in the Periplasmic Space of *E. coli*", 3 Biotech, 2016, pp. 1-7, vol. 6, No. 44.

Nothaft et al., "Protein Glycosylation in Bacteria: Sweeter than Ever", Nature Reviews, Nov. 2010, pp. 765-778, vol. 8, No. 11.

O'Brien et al., "Burden of Disease Caused by *Streptococcus pneumoniae* in Children Younger than 5 Years: Global Estimates", Lancet, Sep. 12, 2009, pp. 893-902, vol. 374, No. 9693.

Pace, "Glycoconjugate Vaccines", Expert Opin Biol Ther, Jan. 2013, pp. 11-33, vol. 13, No. 1.

Pan et al., "Biosynthesis of Conjugate Vaccines Using an O-Linked Glycosylation System", mBio, Mar./Apr. 2016, pp. 1-11, vol. 7, No. 2.

Pan et al., "Genetic Analysis of Capsular Polysaccharide Synthesis Gene Clusters in 79 Capsular Types of *Klebsiella* spp", Scientific Reports, 2015, pp. 1-10, vol. 5, No. 15573.

Pelicic, "Type IV Pili: e pluribus unum?", Molecular Microbiology, 2008, pp. 827-837, vol. 68, No. 4.

Pfizer, "Prevnar 13 Prescribing Information—Package Insert", FDA, Aug. 2017, 43 pages, retrieved from <https://www.fda.gov/downloads/BiologicsBloodVaccines/Vaccines/ApprovedProducts/UCM201669.pdf>.

Pilishvili et al., "Sustained Reductions in Invasive Pneumococcal Disease in the Era of Conjugate Vaccine", The Journal of Infectious Diseases, 2010, pp. 32-41, vol. 201, No. 1.

Pollard et al., "Maintaining Protection Against Invasive Bacteria with Protein-Polysaccharide Conjugate Vaccines", Nat Rev Immunol, Mar. 2009, pp. 213-220, vol. 9, No. 3.

Porstendoerfer et al., "A Novel Competence Gene, comP, Is Essential for Natural Transformation of *Acinetobacter* sp. Strain BD413", Applied and Environmental Microbiology, Nov. 1997, pp. 4150-4157, vol. 63, No. 11.

Porstendoerfer et al., "Comp [Acinetobacter baylyi]", Oct. 14, 2019, 1 page.

Yeh et al., "Capsular Serotype K1 or K2, Rather than magA and rmpA, Is a Major Virulence Determinant for Klebsiella pneumoniae Liver Abscess in Singapore and Taiwan", Journal of Clinical Microbiology, Feb. 2007, pp. 466-471, vol. 45, No. 2.

Anonymous, "pg1L2—ComP-specific O-oligosaccharyltransferase—Acinetobacter baylyi (strain ATCC 33305 / BD413 / ADP1) / UniProtKB / UniProt", Uniprot.org, Oct. 9, 2024, 5 p. Retrieved from the Internet https://www.uniprot.org/uniprotkb/Q6F7F9/entry.

Berti et al., "Structure of the Type IX Group B *Streptococcus* Capsular Polysaccharide and Its Evolutionary Relationship with Types V and VII", the Journal of Biological Chemistry, Aug. 2014, pp. 23437-23448, vol. 289, No. 34.

Cassini et al. "Attributable deaths and disability-adjusted life-years caused by infections with antibiotic-resistant bacteria in the EU and the European Economic Area in 2015: a population-levelmodelling analysis", Lancet Infectious Diseases, 2019, pp. 56-66, vol. 19.

Choi et al., "The Diversity of Lipopolysaccharide (O) and Capsular Polysaccharide (K) Antigens of Invasive Klebsiella pneumoniae in a Multi-Country Collection", Frontiers in Microbiology, Jun. 2020, 12 pages, vol. 11, No. 1249.

Clarke et al., "Molecular basis for the structural diversity in serogroup 02-antigen polysaccharides in Klebsiella pneumoniae", Journal of Biological Chemistry, 2018, pp. 4666-4679, vol. 293, No. 13.

Clarke et al., "Role of Rfe and RfbF in the Initiation of Biosynthesis of D-Galactan I, the Lipopolysaccharide O Antigen from Klebsiella pneumoniae Serotype O1", Journal of Bacteriology, Oct. 1995, pp. 5411-5418, vol. 177, No. 19.

Clarke et al., "Molecular Cloning of the rfb Region of Klebsiella pneumoniae Serotype O1:K20: the rfb Gene Cluster Is Responsible for Synthesis of the D-Galactan I O Polysaccharide", Journal of Bacteriology, Jul. 1992, pp. 4614-4621, vol. 174, No. 14.

Cohen et al., "Impact of pneumococcal conjugate vaccines for children in high- and non-high-income countries", Expert Review of Vaccines, 2017, 43 pages.

Daniels et al., "A Review of Pneumococcal Vaccines: Current Polysaccharide Vaccine Recommendations and Future Protein Antigens", Journal of Pediatric Pharmacology and Therapeutics, 2016, pp. 27-35, vol. 21, No. 1.

Dobbelsteen et al., "Immunogenicity and safety of a tetravalent *E. coli* O-antigen bioconjugate vaccine in animal models", Vaccine, 2016, pp. 4152-4160, vol. 34.

Doyle, "Pilin [Moraxella osloensis]", Genbank entry (online), National Center For Biotechnology Information, Jul. 2018, 1 page, https://www.ncbi.nlm.nih.gov/protein/STY96991.11.

Faridmoayer et al., "Extreme Substrate Promiscuity of the Neisseria Oligosaccharyl Transferase Involved in ProteinO-Glycosylation", The Journal of Biological Chemistry, Dec. 2008,p p. 34596-34604, vol. 283, No. 50.

Follador et al., "The diversity of Klebsiella pneumoniae surface polysaccharides", Microbial genomics, 2016, 15 pages.

Gerber et al., "Mechanism of Bacterial Oligosaccharyltransferase In Vitro Quantification of Sequon Binding and Catalysis", the Journal of Biological Chemistry, Mar. 2013, pp. 8849-8861, vol. 288, No. 13.

Goffin et al., "High-yield production of recombinant CRM197, a non-toxic mutant of diphtheria toxin, in the periplasm of *Escherichia coi*", Biotechnology Journal, 2017, 29 pages.

Greenfield et al., "Biosynthesis of the Polymannose Lipopolysaccharide O-antigens from *Escherichia coli* Serotypes O8 and O9a Requires a Unique Combination of Single- and Multiple-active Site Mannosyltransferases", The Journal of Biological Chemistry, Oct. 2012, pp. 35078-35091, vol. 287, No. 42.

Guachalla et al., "Discovery of monoclonal antibodies cross-reactive to novel subserotypes of K. pneumoniae O3", Scientific Report, 2017, 13 pages, vol. 7, No. 6635.

Guan et al., "Functional Analysis of the Galactosyltransferases Required for Biosynthesis of D-Galactan I, a Component of the Lipopolysaccharide O1 Antigen of Klebsiella pneumoniae", Journal of Bacteriology, Jun. 2001, pp. 3318-3327, vol. 183, No. 11.

Hampton et al., "Prevention of Antibiotic-Nonsusceptible *Streptococcus pneumoniae* With Conjugate Vaccines", Journal of Infectious Diseases, 2012, pp. 401-411, vol. 205.

Harding et al., "Glycoengineering bioconjugate vaccines, therapeutics, and diagnostics in *E. coli*", Glycobiology, 2019, pp. 519-529, vol. 29, No. 7.

Hatz et al., "Safety and immunogenicity of a candidate bioconjugate vaccine against Shigella dysenteriae type 1 administered to healthy adults: A single blind, partially randomized Phase I study", Vaccine, 2015, pp. 4594-4601, vol. 33, No. 36.

Hsieh et al., "D-galactan II is an immunodominant antigen in O1 lipopolysaccharide and affects virulence in Klebsiella pneumoniae: implication in vaccine design", Frontiers in Microbiology, Nov. 2014, 14 pages, vol. 5, No. 608.

Hug et al., "Analogies and homologies in lipopolysaccharide and glycoprotein biosynthesis in bacteria", Glycobiology, 2011, pp. 138-151, vol. 21, No. 2.

(56) References Cited

OTHER PUBLICATIONS

Hultgren et al., "Chaperone-Assisted Assembly and Molecular Architecture of Adhesive Pili", Annual Review of Microbiology, 1991, pp. 383-415, vol. 45.
Ihssen et al., "Production of glycoprotein vaccines in *Escherichia coli*", Microbial Cell Factories, 2010, vol. 9, No. 61.
Kelly et al., "Klebsiella pneumoniae O1 and O2ac antigens provide prototypes for an unusual strategy for polysaccharide antigen diversification", Journal of Biological Chemistry, 2019, pp. 10863-10876, vol. 294, No. 28.
Kelly et al., "Biosynthesis of the N-Linked Glycan in Campylobacterjejuni and Addition onto Protein through Block Transfer", Journal of Bacteriology, Apr. 2006, pp. 2427-2434, vol. 188, No. 7.
Kubler-Kielb et al., "Identification of the methyl phosphate substituent at the non-reducing terminal mannose residue of the O-specific polysaccharides of Klebsiella pneumoniae O3, Hafnia alvei PCM 1223 and *Escherichia coli* O9/O9a LPS", Carbohydrate Research, 2012, pp. 186-188, vol. 347.
Langstraat et al., "Type 3 Fimbrial Shaft (MrkA) of Klebsiella pneumoniae, but Not the Fimbrial Adhesin (MrkD), Facilitates Biofilm Formation", Infection and Immunity, Sep. 2001, p. 5805-5812, vol. 69, No. 9.
Mabry et al., "Therapeutic bispecific antibodies: The selection of stable single-chain fragments to overcome engineering obstacles", IDrugs, 2010, pp. 543-549, vol. 13, No. 8.
McCallum et al., "A High-Molecular-Weight Fraction of Smooth Lipopolysaccharide in Klebsiella Serotype O1:K20 Contains a Unique O-Antigen Epitope and Determines Resistance to Nonspecific Serum Killing", Infection and Immunity, Dec. 1989, pp. 3816-3822, vol. 57, No. 12.
Raetz et al., "Lipopolysaccharide Endotoxins", Annual Review of Biochemistry, 2002, pp. 635-700, vol. 71.
Saeki et al., "Isolation of rfb Gene Clusters Directing the Synthesis of O Polysaccharides Consisting of Mannose Homopolymers and Serological Analysis of Lipopolysaccharides", Microbiology and Immunology, 1993, pp. 601-606, vol. 37, No. 8.
Stojkovic et al., "Identification of D-Galactan-III As Part of the Lipopolysaccharide of Klebsiella pneumoniae Serotype O1", Frontiers in Microbiology, Apr. 2017, 8 pages, vol. 8, No. 684.
Ströhlein et al., "The Trifunctional Antibody Catumaxomab in Treatment of Malignant Ascites and Peritoneal Carcinomatosis", Future Oncology, 2010, pp. 1387-1394, vol. 6, No. 9.
Sun et al., "Design and production of conjugate vaccines against S. Paratyphi A using an O-linked glycosylation system in vivo", npj Vaccines, 2018, 9 pages.
Szijártó et al., "Both clades of the epidemic KPC-producing Klebsiella pneumoniae clone ST258 share a modified galactan O-antigen type", International Journal of Medical Microbiology, 2015, 10 pages.
Szymanski et al., "Evidence for a system of general protein glycosylation in Campylobacter jejuni", Molecular Microbiology, 1999, pp. 1022-1030, vol. 32, No. 5.
Tomczyk et al., "Prevention of Antibiotic-Nonsusceptible Invasive Pneumococcal Disease With the 13-Valent Pneumococcal Conjugate Vaccine", Clinical Infectious Diseases, 2016, pp. 1119-1125, vol. 62.
Valvano, "Export of O-Specific Lipopolysaccharide", Frontiers in Bioscience, 2003, pp. 452-471, vol. 8.
Mnogradov et al., "Structures of Lipopolysaccharides from Klebsiella pneumoniae", The Journal of Biological Chemistry, 2002, pp. 25070-25081, vol. 277, No. 28.
Wacker et al., "Prevention of *Staphylococcus aureus* Infections by Glycoprotein Vaccines Synthesized in *Escherichia coli*", The Journal of Infectious Diseases, 2014, pp. 1551-1561, vol. 209.
Walczak et al., "Intramolecular Donor Strand Complementation in the *E. coli* Type 1 Pilus Subunit FimA Explains the Existence of FimA Monomers As Off-Pathway Products of Pilus Assembly That Inhibit Host Cell Apoptosis", Journal of Molecular Biology, 2014, pp. 542-549, vol. 426.
Wang et al., "Target-Agnostic Identification of Functional Monoclonal Antibodies Against Klebsiella pneumoniae Multimeric MrkA Fimbrial Subunit", The Journal of Infectious Diseases, 2016, pp. 1800-1808, vol. 213.
Wedekind et al., "Refined Crystallographic Structure of Pseudomonas aeruginosa Exotoxin A and its Implications for the Molecular Mechanism of Toxicity", Journal of Molecular Biology, 2001, pp. 823-837, vol. 314.
Whitfield et al., "Biosynthesis and Export of Bacterial Lipopolysaccharides", Annual Review of Biochemistry, 2014, pp. 99-128; vol. 83.
Wick et al., "Kaptive Web: User-Friendly Capsule and Lipopolysaccharide Serotype Prediction for Klebsiella Genomes", Journal of Clinical Microbiology, Jun. 2018, 10 pages, vol. 56, No. 6.
Wyres et al., "Genomic surveillance for hypervirulence and multidrug resistance in invasive Klebsiella pneumoniae from South and Southeast Asia", Genome Medicine, 2020, 16 pages, vol. 12, No. 11.

Figure 1A,B

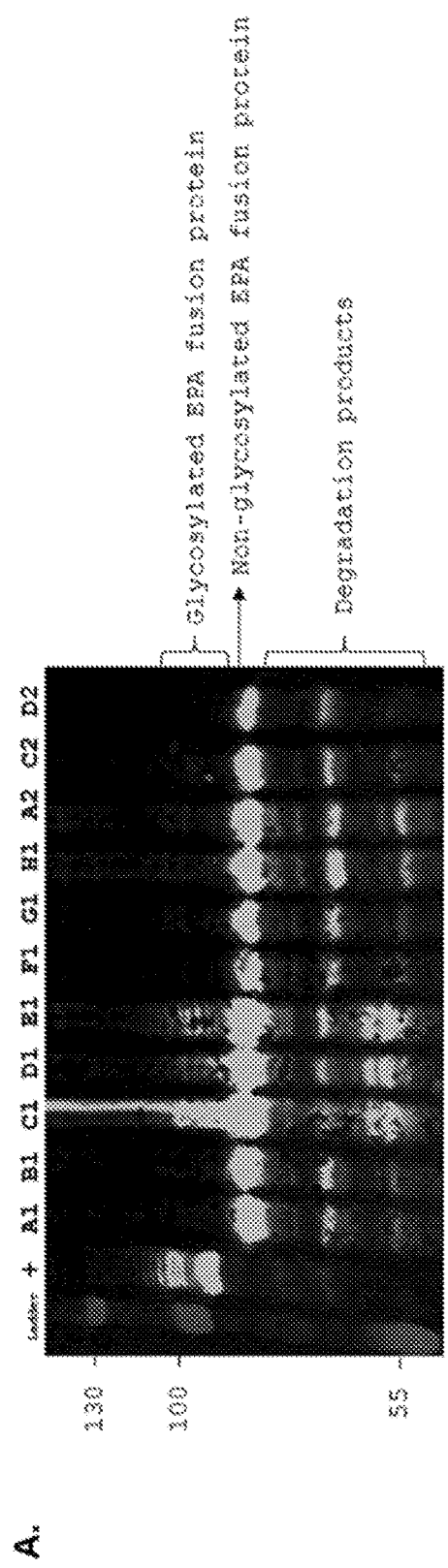

| Lane ID | ComP$_{110364}$ fragment fused to C-terminus of EPA | Glycosylation Observed |
|---|---|---|
| + | $_{28}$AVTDYTVRSRVTEGLTTASAMKATVSENIMRAGGTSMPSSGMCTGVTQIASGASAATTNVASAQCS DSDGVITVTMTDKAKGVSIKLTPSFSSTGSVGWKCTTSSDKTVPSECRG1$_{145}$ | Yes |
| A1 | $_{65}$SSGNCTGVTQIASGASAATTNVASA$_{91}$ | No |
| B1 | $_{68}$SGNCTGVTQIASGASAATTNVASAQC$_{92}$ | No |
| C1 | $_{69}$GNCTGVTQIASGASAATTNVASAQCS$_{93}$ | Yes |
| D1 | $_{70}$NCTGVTQIASGASAATTNVASAQCS$_{94}$ | Yes |
| E1 | $_{71}$CTGVTQIASGASAATTNVASAQCSD$_{95}$ | Yes |
| F1 | $_{72}$TGVTQIASGASAATTNVASAQCSDS$_{96}$ | No |
| G1 | $_{73}$GVTQIASGASAATTNVASAQCSDSD$_{97}$ | No |
| H1 | $_{74}$VTQIASGASAATTNVASAQCSDSDG$_{98}$ | No |
| A2 | $_{75}$TQIASGASAATTNVASAQCSDSDGV$_{99}$ | No |
| C2 | $_{62}$GTSMPSSGMCTGVTQIASGASAATTNVASA$_{91}$ | No |
| D2 | $_{62}$GTSMPSSGMCTGVTQIASGASAATTNVASAQ$_{92}$ | No |

Figure 3A,B

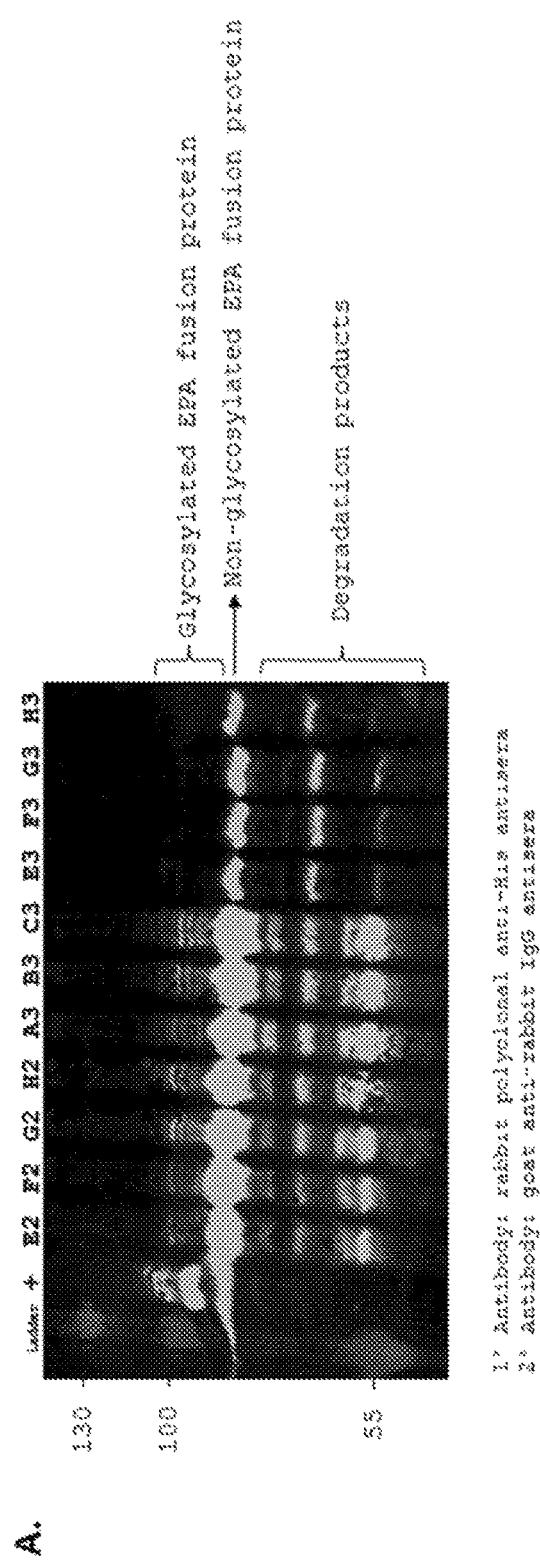
Figure 4A,B

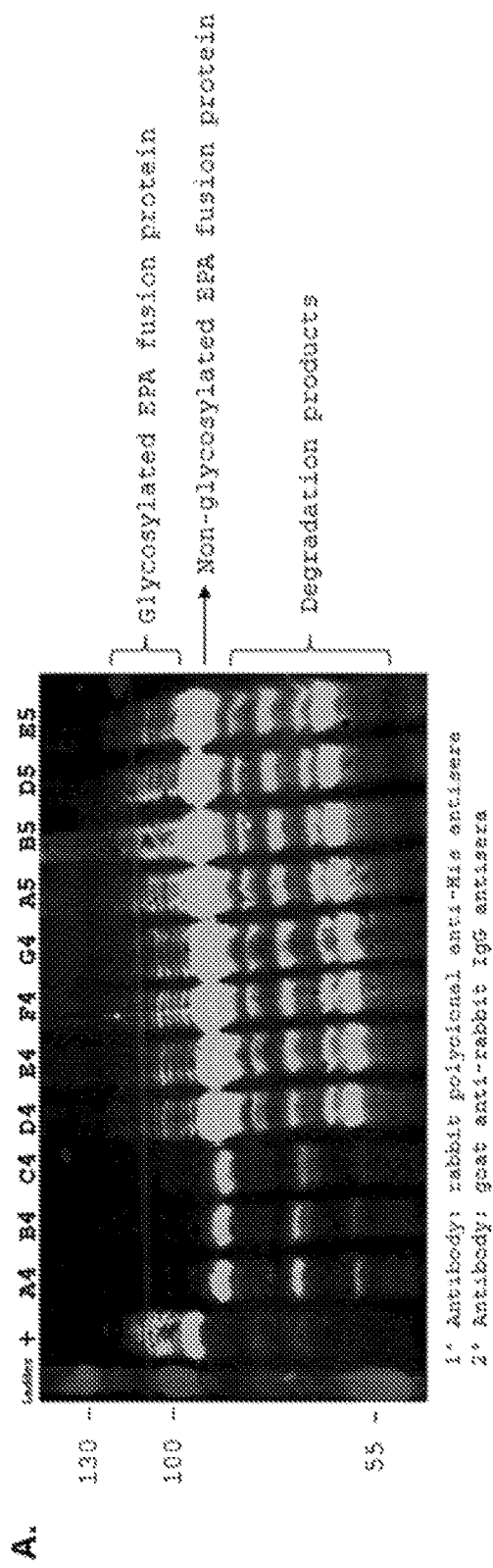
Figure 5A,B

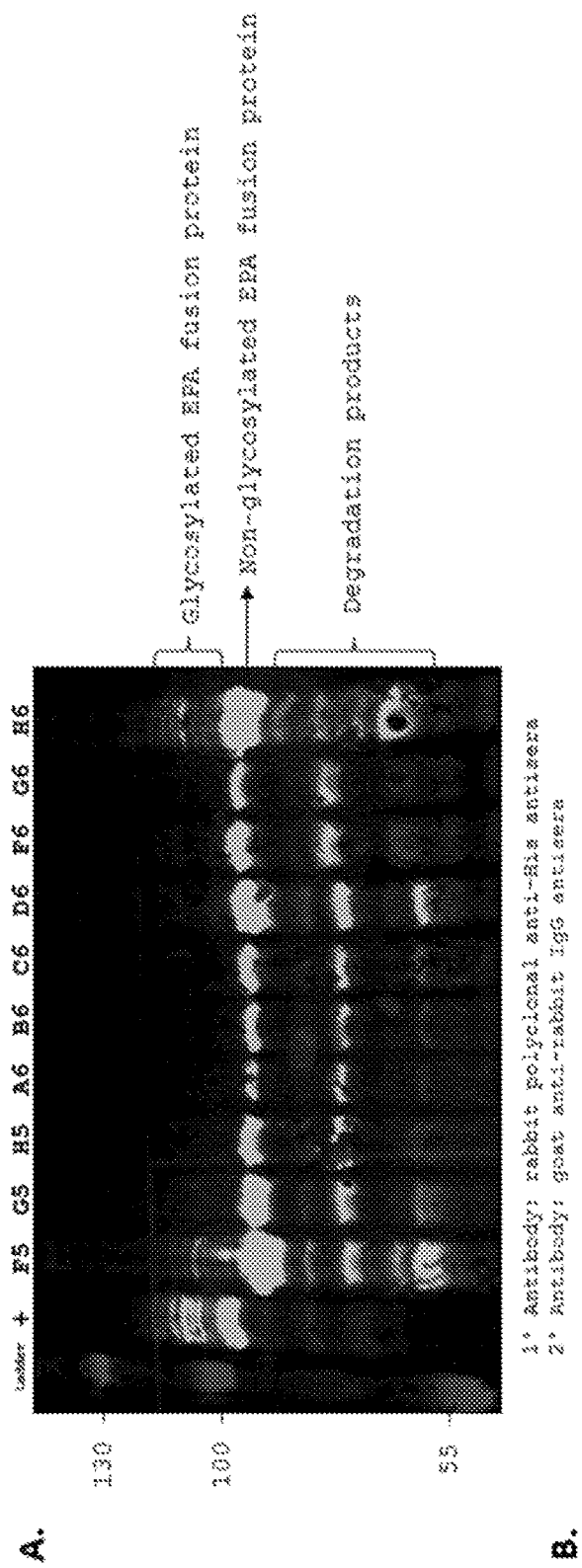
Figure 6A,B

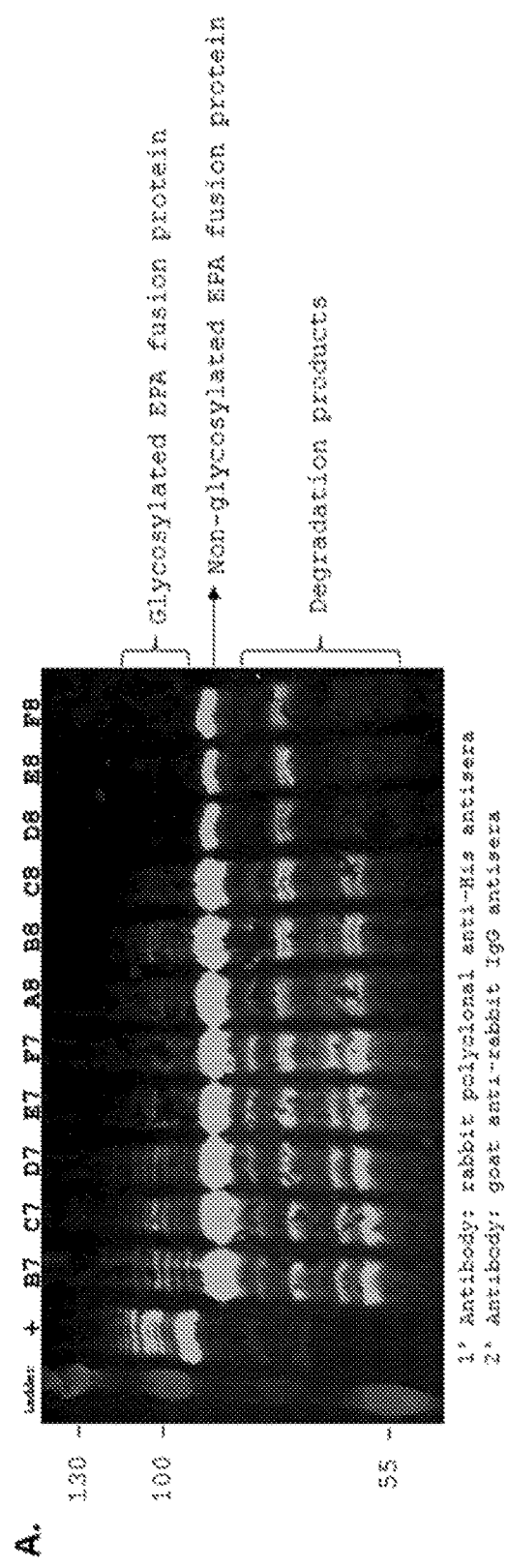
Figure 7A,B

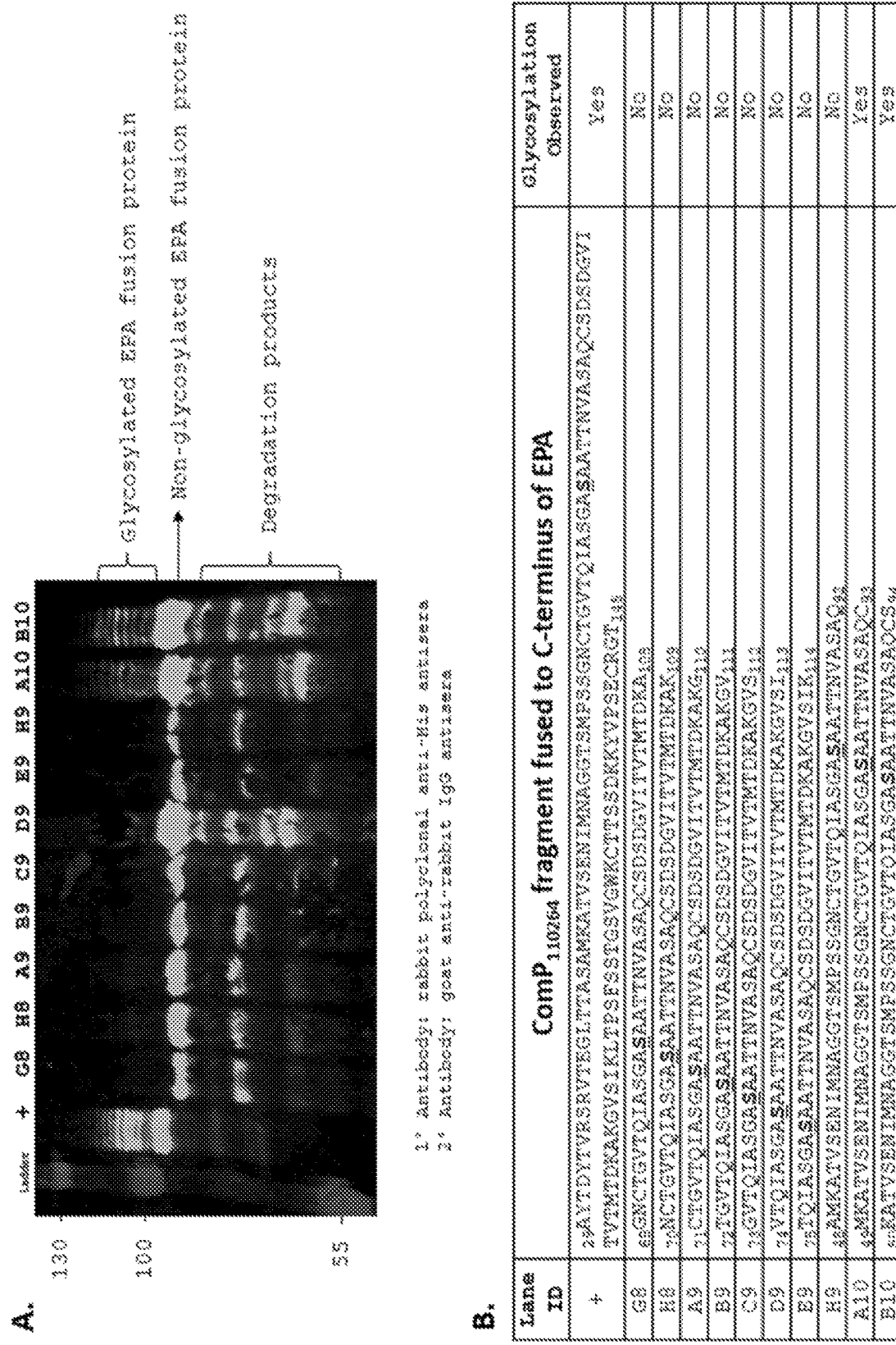
Figure 8A,B

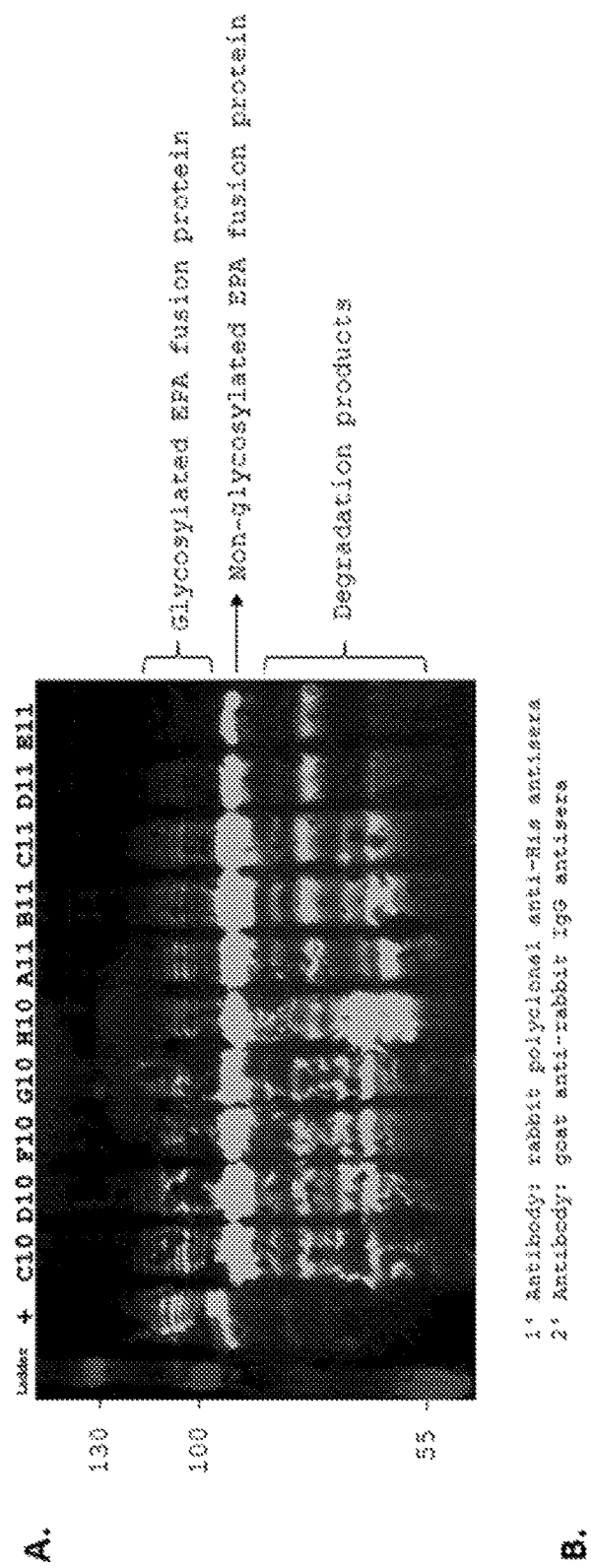
Figure 9A,B

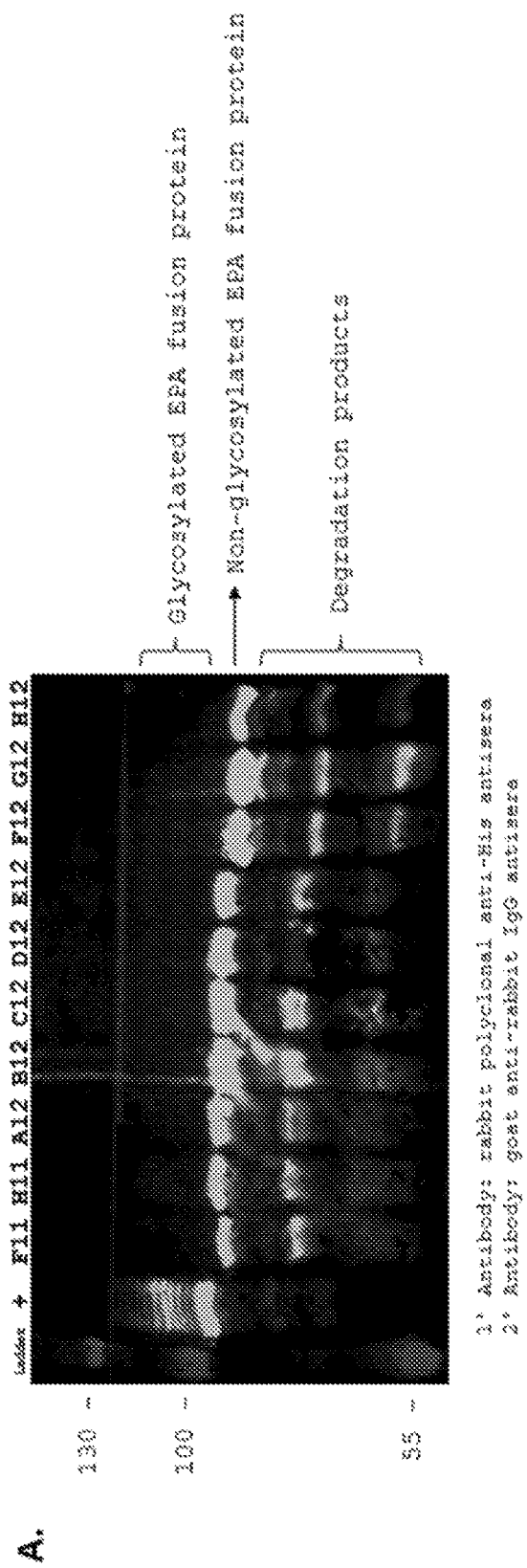
Figure 10A,B

A.
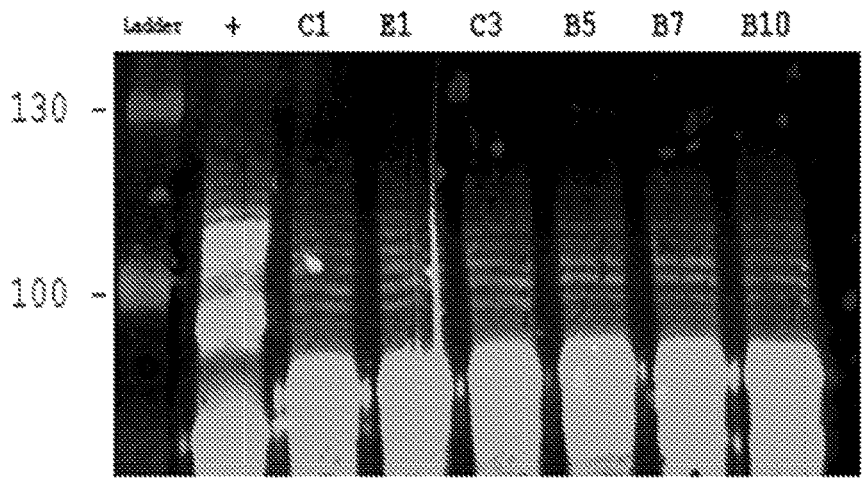
1° Antibody: rabbit polyclonal anti-exotoxin A antisera
2° Antibody: goat anti-rabbit IgG antisera
B.
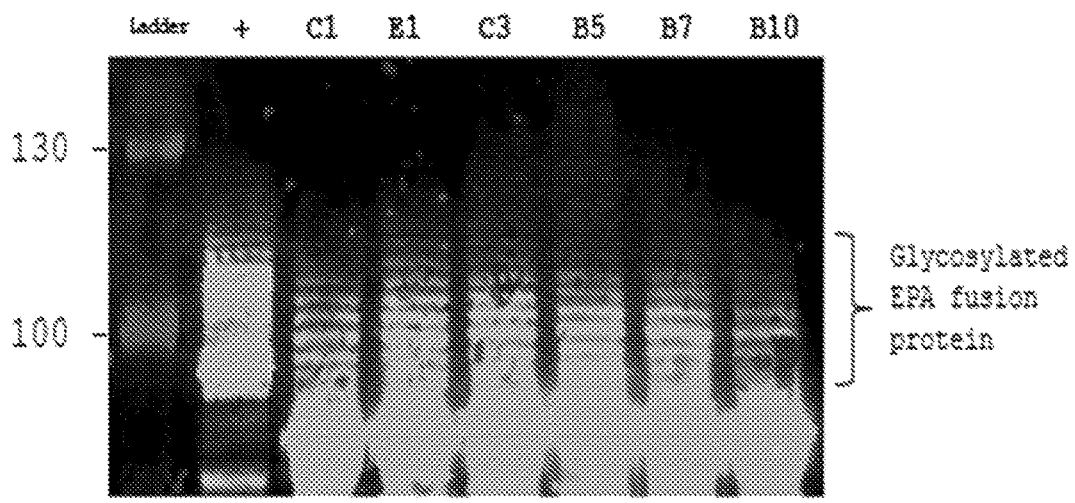
1° Antibody: rabbit polyclonal anti-His antisera
2° Antibody: goat anti-rabbit IgG antisera
Figure 11A,B

| Lane ID | ComP$_{1102d4}$ fragment fused to C-terminus of EPA | Glycosylation Observed |
|---|---|---|
| + | $_{24}$AYTDYTYRSRVTEGLTTASANKATVSENTMNAGGTSMPSSGNCTGVTQTASGASAATTNVASAQCSDSDGVT$_{145}$ | Yes |
|  | TVTMTDKAKGVSTKLTPSFSSTGSVGWKCTTSSDKTYPSECRGT$_{145}$ |  |
| C1 | $_{90}$GNCTGVTQTASGASAATTNVASAQC$_{113}$ | Yes |
| E1 | $_{92}$CTGVTQTASGASAATTNVASAQCSDSDGV$_{120}$ | Yes |
| C3 | $_{91}$NCTGVTQTASGASAATTNVASAQCSDSDGV$_{120}$ | Yes |
| B5 | $_{93}$TGVTQTASGASAATTNVASAQCSDSDGV$_{120}$ | Yes |
| B7 | $_{82}$MNAGGTSMPSSGNCTGVTQTASGASAATTNVASAQCSD$_{119}$ | Yes |
| B10 | $_{66}$KATVSENTMNAGGTSMPSSGNCTGVTQTASGASAATTNVASAQCS$_{114}$ | Yes |

Figure 11C

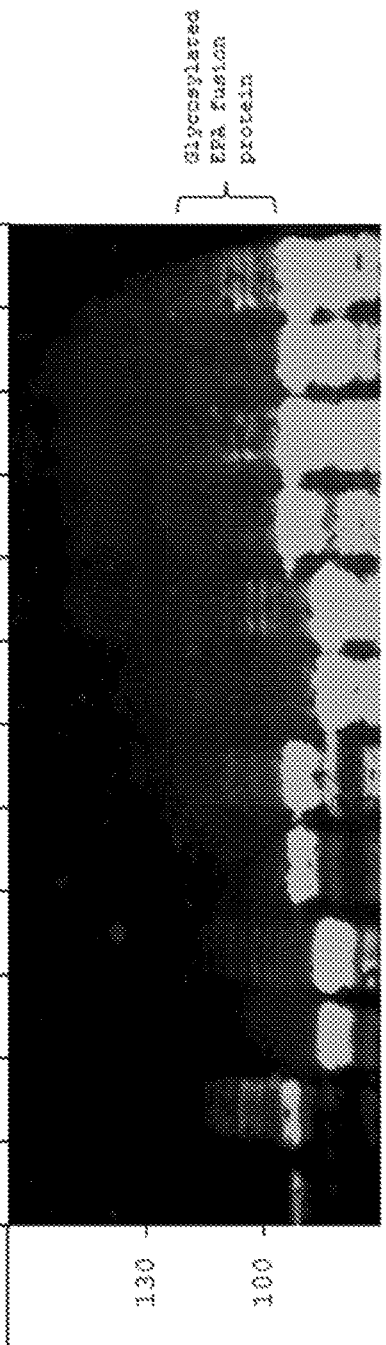
Figure 12A,B,C

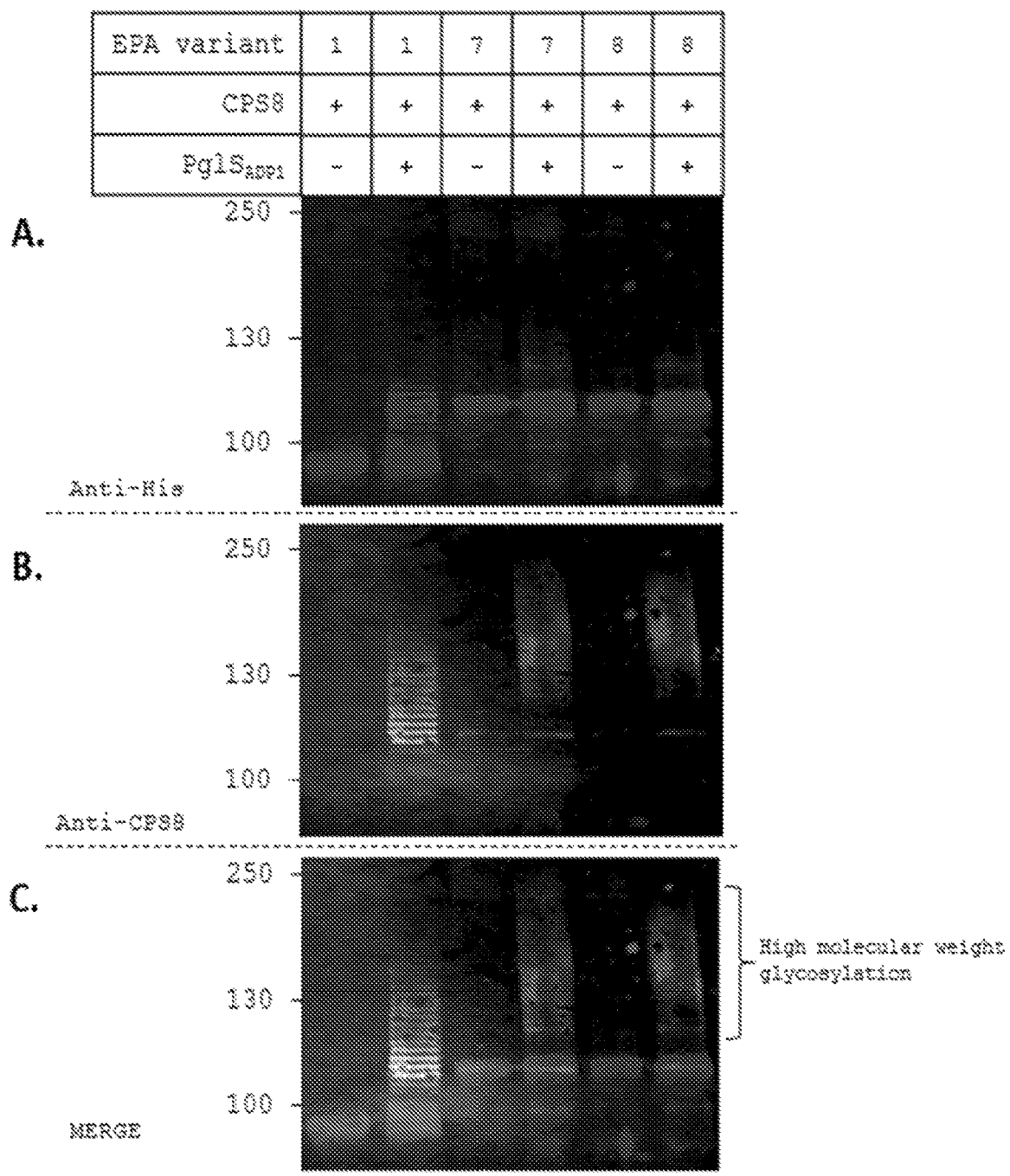
EPA Variant Legend
1 = EPA-GGGS-ComPΔ28$_{110264}$-His6X
7 = EPA-GGGS-ComPΔ28$_{110264}$-GGGGS-ComPΔ28$_{110264}$-His6X
8 = EPA-GGGS-ComPΔ28$_{110264}$-PAPAP-ComPΔ28$_{110264}$-His6X
Figure 13A,B,C

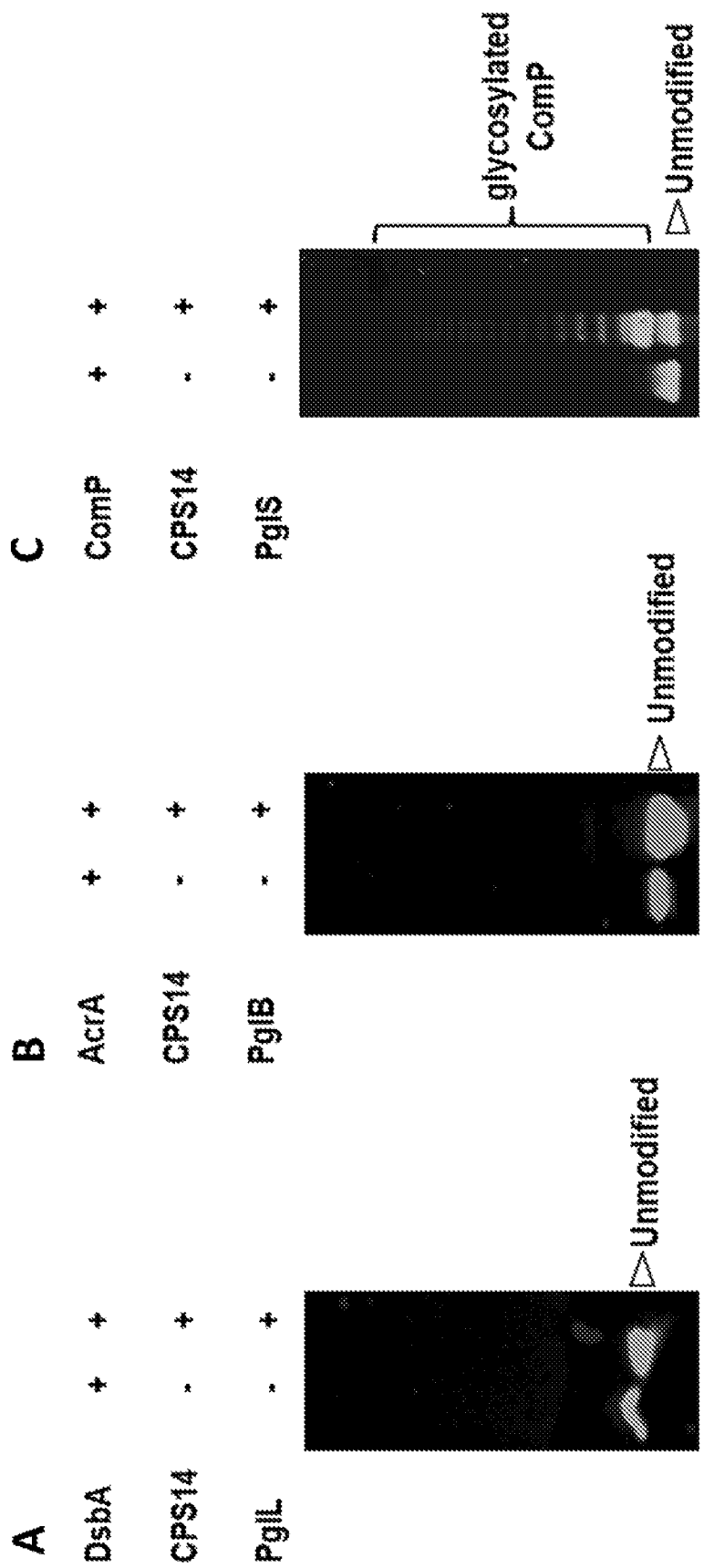
Figure 14A,B,C

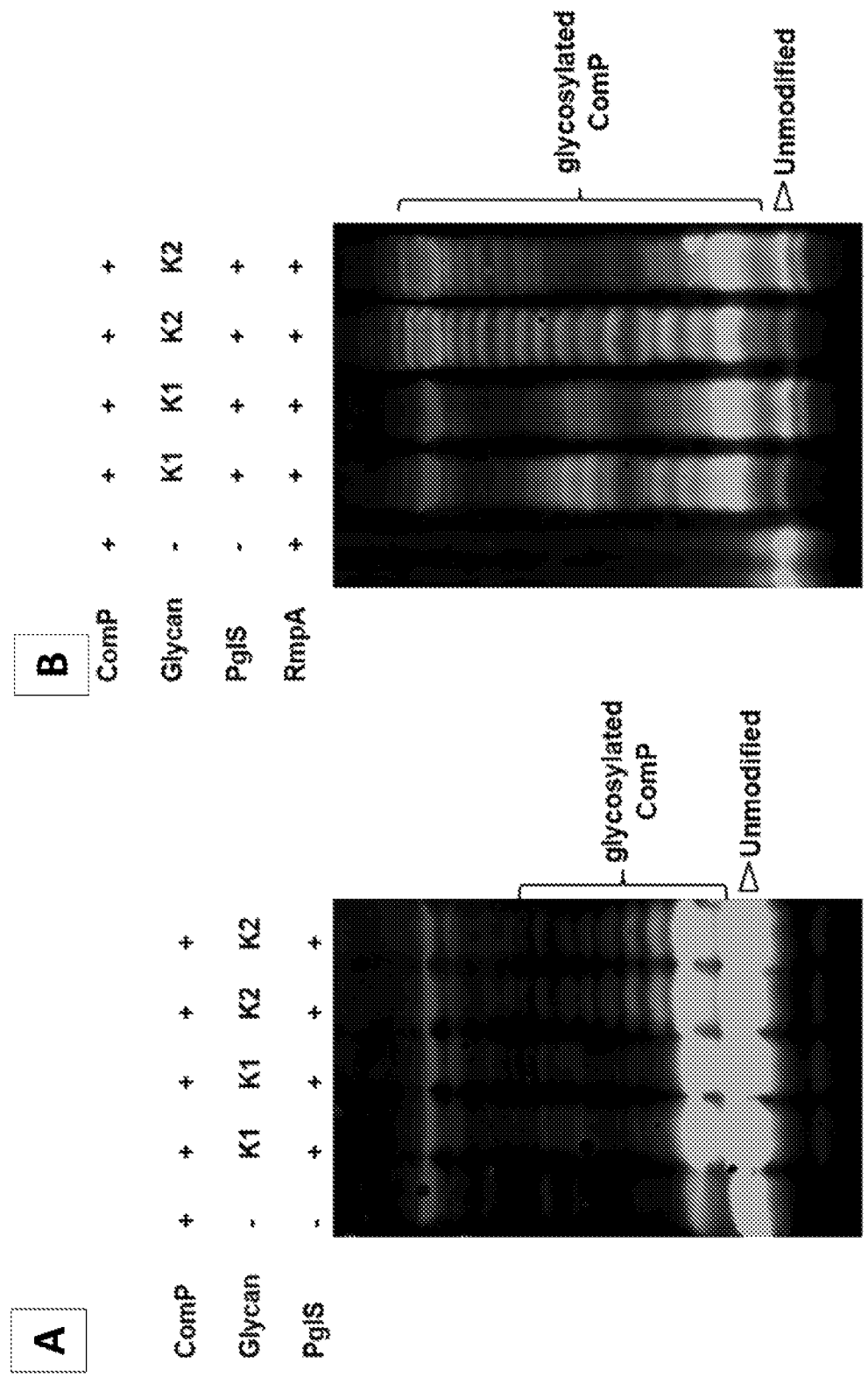
Figure 16A,B

>AAC45886.1 ComP [*Acinetobacter* sp. ADP1]
MNAQKGFTLIELMIVIAIIGILAAIAIPAYTDYTVRAR
VSEGLTAASSMKTTVSENILNAGALVAGTPSTAG
SS<u>CVGVQEISASNATTNVATATC</u>GASSAGQIIVTM
DTTKAKGANITLTPTYASGAVTWKCTTTSDKKYV
PSECRG (SEQ ID NO: 1)

>ENV58402.1 hypothetical protein F951_00736
[*Acinetobacter soli* CIP 110264]
MNAQKGFTLIELMIVIAIIGILAAIAIPAYTDYTVRSR
VTEGLTTASAMKATVSENIMNAGGTSMPSSGN<u>C
TGVTQIASGASAATTNVASAQCSDSDGVITVTMT</u>
DKAKGVSIKLTPSFSSTGSVGWKCTTSSDKKYV
PSECRGT (SEQ ID NO: 2)

>APV36638.1 competence protein [*Acinetobacter soli* GFJ-2]
MNAQKGFTLIELMIVIAIIGILAAIAIPAYTDYTVRAR
VSEGLTTASAMKATVSENILSAGQIVTGTPSTANS
<u>SCVGVQEINASSSTSNVATATC</u>SGLGVITVTMDS
TKAKGVNLTLTPTYTTSNAVTWKCTTTSDKKYVP
SECRN (SEQ ID NO: 3)

Figure 19

>PKD82822.1 competence protein [*Acinetobacter radioresistens* 50v1]
MNTQKGFTLIELMIVIAIIGILAAIAIPAYTDYTVRAR
VTEAVSTASSMKATVSENIMNAGGTQIPTSGN<u>CV
GVQTIAAS NATKNVATAT C</u>TDSTGVIVVTTTPAAK
SVPLTLTPTYTGGNVKWACSTTANFKNYVPSEC
RS (SEQ ID NO: 4)

>SNX44537.1 type IV pilus assembly protein PilA [*Acinetobacter puyangensis* ANC 4466]
MNAQKGFTLIELMIVIAIIGILAAIAIPAYTDYTVRAR
VTEALTTASAMKATVSENIMSAGGTTIASSA<u>CNG
VISAS ATTNVASSA C</u>SGSGVISVTTTAAAKGIVLTL
TPKYTGGNVAWQCTTTSGDAQKYVPSECRTTS
(SEQ ID NO: 5)

>OAL75955.1 competence protein [*Acinetobacter sp.* SFC]
MNTQKGFTLIELMIVIAIIGILAAIAIPAYTDYTVRAK
VTEAISTASAMKATVSENLMSAGGTSIVSTNAN<u>C
AGVETIGAS NKTKNVESAA C</u>TAATGVILVTTTAEA
KSVPLTLKPTYGSNVQWKCGTTAAAFKYVPSE
CRNDSSGTGF (SEQ ID NO: 6)

Figure 19 Cont.

>DsbA-GGGS-ComPΔ28$_{110264}$-His
MKKIWLALAGLVLAFSASAAQYEDGKQYTTLEKPVA
GAPQVLEFFSFFCPHCYQFEEVLHISDNVKKKLPEGV
KMTKYHVNFMGGDLGKDLTQAWAVAMALGVEDKVT
VPLFEGVQKTQTIRSASDIRDVFINAGIKGEEYDAAW
NSFVVKSLVAQQEKAAADVQLRGVPAMFVNGKYQL
NPQGMDTSNMDVFVQQYADTVKYLSEKK<u>GGGS</u>AYT
DYTVRSRVTEGLTTASAMKATVSENIMNAGGTSMPS
SGNCTGVTQIASGASAATTNVASAQCSDSDGVITVTM
TDKAKGVSIKLTPSFSSTGSVGWKCTTSSDKKYVPS
ECRGT<u>HHHHHH</u> (SEQ ID NO: 18)

Legend
DsbA – thiol disulfide oxidoreductase protein (*dsbA* gene)
MBP – maltose binding protein (*malE* gene)
DsbA$_{SP}$ – signal seuqnce of DsbA (first 19 amino acids)
EPA – exotoxin A from *Pseudomonas aeruginosa*
AAA – triple alanine linker
GGGS – glycine-glycine-glycine-serine linker
ComPΔ28$_{110264}$ – ComP from *A. soli* CIP 110264 without the first 28 amino acids
His – hexa-histidine tag

Figure 24

\>MBP-AAA-ComPΔ28₁₁₀₂₆₄-His
MKIKTGARILALSALTTMMFSASALAKIEEGKLVIWIN
GDKGYNGLAEVGKKFEKDTGIKVTVEHPDKLEEKFP
QVAATGDGPDIIFWAHDRFGGYAQSGLLAEITPDKAF
QDKLYPFTWDAVRYNGKLIAYPIAVEALSLIYNKDLLP
NPPKTWEEIPALDKELKAKGKSALMFNLQEPYFTWP
LIAADGGYAFKYENGKYDIKDVGVDNAGAKAGLTFLV
DLIKNKHMNADTDYSIAEAAFNKGETAMTINGPWAW
SNIDTSKVNYGVTVLPTFKGQPSKPFVGVLSAGINAA
SPNKELAKEFLENYLLTDEGLEAVNKDKPLGAVALKS
YEEELAKDPRIAATMENAQKGEIMPNIPQMSAFWYAV
RTAVINAASGRQTVDEALKDAQTN<u>AAA</u>AYTDYTVRS
RVTEGLTTASAMKATVSENIMNAGGTSMPSSGNCTG
VTQIASGASAATTNVASAQCSDSDGVITVTMTDKAKG
VSIKLTPSFSSTGSVGWKCTTSSDKKYVPSECRGT<u>HH</u>
<u>HHHH</u> (SEQ ID NO: 19)

Figure 24 Cont.

\>DsbA_SP-EPA-GGGS-ComPΔ28_110264-His
MKKIWLALAGLVLAFSASAAEEAFDLWNECAKACVL
DLKDGVRSSRMSVDPAIADTNGQGVLHYSMVLEGGN
DALKLAIDNALSITSDGLTIRLEGGVEPNKPVRYSYTR
QARGSWSLNWLVPIGHEKPSNIKVFIHELNAGNQLSH
MSPIYTIEMGDELLAKLARDATFFVRAHESNEMQPTL
AISHAGVSVVMAQAQPRREKRWSEWASGKVLCLLD
PLDGVYNYLAQQRCNLDDTWEGKIYRVLAGNPAKHD
LDIKPTVISHRLHFPEGGSLAALTAHQACHLPLETFTR
HRQPRGWEQLEQCGYPVQRLVALYLAARLSWNQVD
QVIRNALASPGSGGDLGEAIREQPEQARLALTLAAAE
SERFVRQGTGNDEAGAASADVVSLTCPVAAGECAG
PADSGDALLERNYPTGAEFLGDGGDISFSTRGTQNW
TVERLLQAHRQLEERGYVFVGYHGTFLEAAQSIVFG
GVRARSQDLDAIWRGFYIAGDPALAYGYAQDQEPDA
RGRIRNGALLRVYVPRSSLPGFYRTGLTLAAPEAAGE
VERLIGHPLPLRLDAITGPEEEGGRLTILGWPLAERTV
VIPSAIPTDPRNVGGDLDPSSIPDKEQAISALPDYASQ
PGKPPREDLK<u>GGGS</u>AYTDYTVRSRVTEGLTTASAMK
ATVSENIMNAGGTSMPSSGNCTGVTQIASGASAATTN
VASAQCSDSDGVITVTMTDKAKGVSIKLTPSFSSTGS
VGWKCTTSSDKKYVPSECRGT<u>HHHHHH</u> (SEQ ID
NO: 20)

Figure 24 Cont.

>AAC45886.1 ComPΔ28 [*Acinetobacter* sp. ADP1]
AYTDYTVRARVSEGLTAASSMKTTVSENILNAGA
LVAGTPSTAGSS<u>CVGVQEISASNATTNVATATCG</u>
ASSAGQIIVTMDTTKAKGANITLTPTYASGAVTWK
CTTTSDKKYVPSECRG (SEQ ID NO: 7)

>ENV58402.1 hypothetical protein F951_00736 Δ28 [*Acinetobacter soli* CIP 110264]
AYTDYTVRSRVTEGLTTASAMKATVSENIMNAGG
TSMPSSGN<u>CTGVTQIASGASAATTNVASAQCSD</u>
SDGVITVTMTDKAKGVSIKLTPSFSSTGSVGWKC
TTSSDKKYVPSECRGT (SEQ ID NO: 8)

>APV36638.1 competence protein Δ28 [*Acinetobacter soli* GFJ-2]
AYTDYTVRARVSEGLTTASAMKATVSENILSAGQI
VTGTPSTANSS<u>CVGVQEINASSSTSNVATATCSG</u>
LGVITVTMDSTKAKGVNLTLTPTYTTSNAVTWKC
TTTSDKKYVPSECRN (SEQ ID NO: 9)

Figure 27

>PKD82822.1 competence protein Δ28
[*Acinetobacter radioresistens* 50v1]
AYTDYTVRARVTEAVSTASSMKATVSENIMNAG
GTQIPTSGN<u>CVGVQTIAASNATKNVATATC</u>TDST
GVIVVTTTPAAKSVPLTLTPTYTGGNVKWACSTT
ANFKNYVPSECRS (SEQ ID NO: 10)

>SNX44537.1 type IV pilus assembly protein PilA
Δ28 [*Acinetobacter puyangensis* ANC 4466]
AYTDYTVRARVTEALTTASAMKATVSENIMSAGG
TTIASSA<u>CNGVISASATTNVASSAC</u>SGSGVISVTT
TAAAKGIVLTLTPKYTGGNVAWQCTTTSGDAQKY
VPSECRTTS (SEQ ID NO: 11)

>OAL75955.1 competence protein Δ28
[*Acinetobacter* sp. SFC]
AYTDYTVRAKVTEAISTASAMKATVSENLMSAGG
TSIVSTNAN<u>CAGVETIGASNKTKNVESAAC</u>TAAT
GVILVTTTAEAKSVPLTLKPTYTGSNVQWKCGTT
AAAFKYVPSECRNDSSGTGF (SEQ ID NO: 12)

Figure 27 Cont.

| | | |
|---|---|---|
| ADP1 | CVGVQEIS--ASNATTNVATATC | (SEQ ID NO: 13) |
| 110264 | CTGVTQIASGAGAATTNVASAQC | (SEQ IS NO: 14) |
| GFJ_2 | CVGVQEIN--ASSSTSNVATATC | (SEQ ID NO: 15) |
| SFC | CAGVETIG--ASNKTKNVESAAC | (SEQ ID NO: 16) |
| P50v1 | CVGVQTIA--ASNATKNVATATC | (SEQ ID NO: 17) |

Figure 28

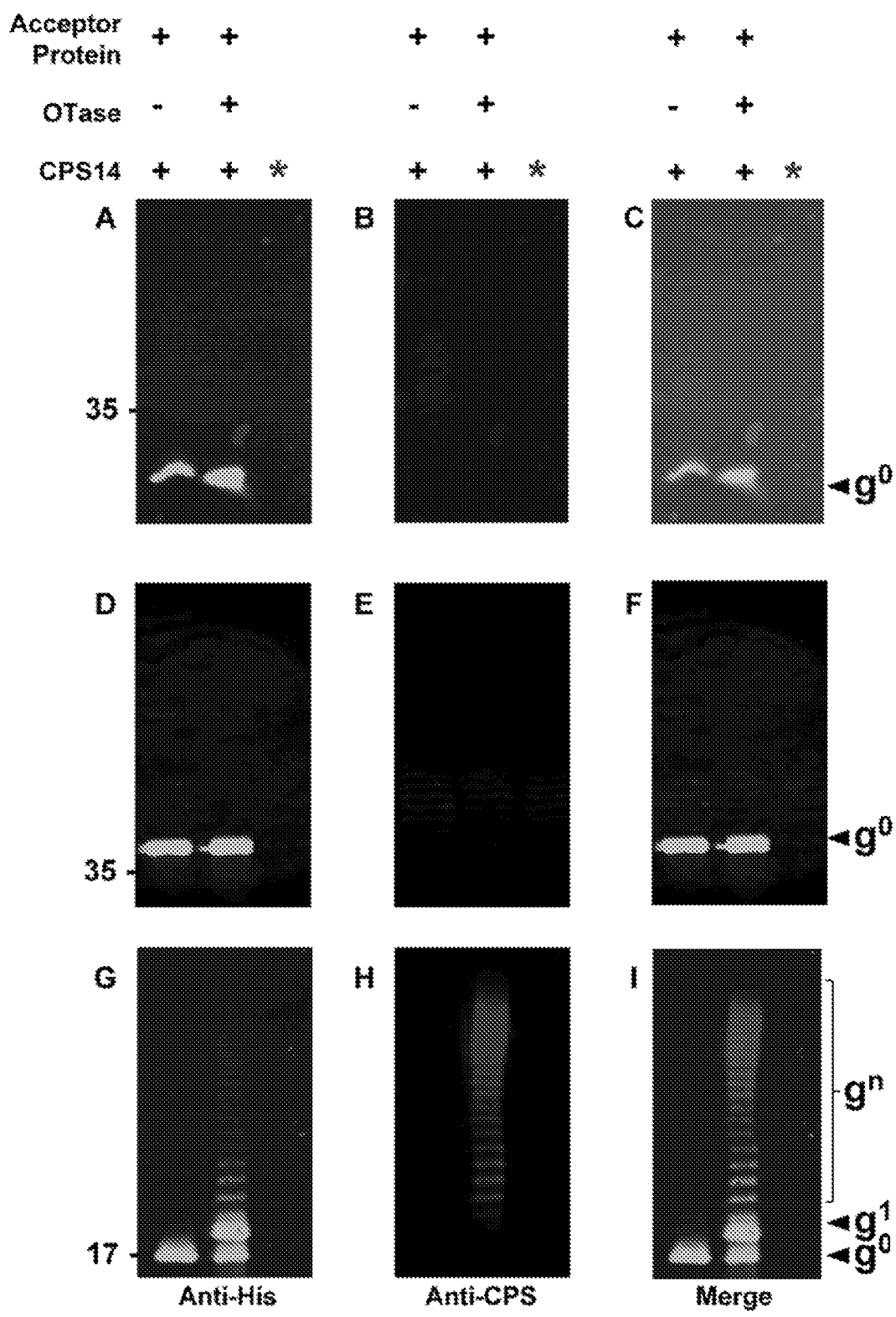
Figure 32A-I

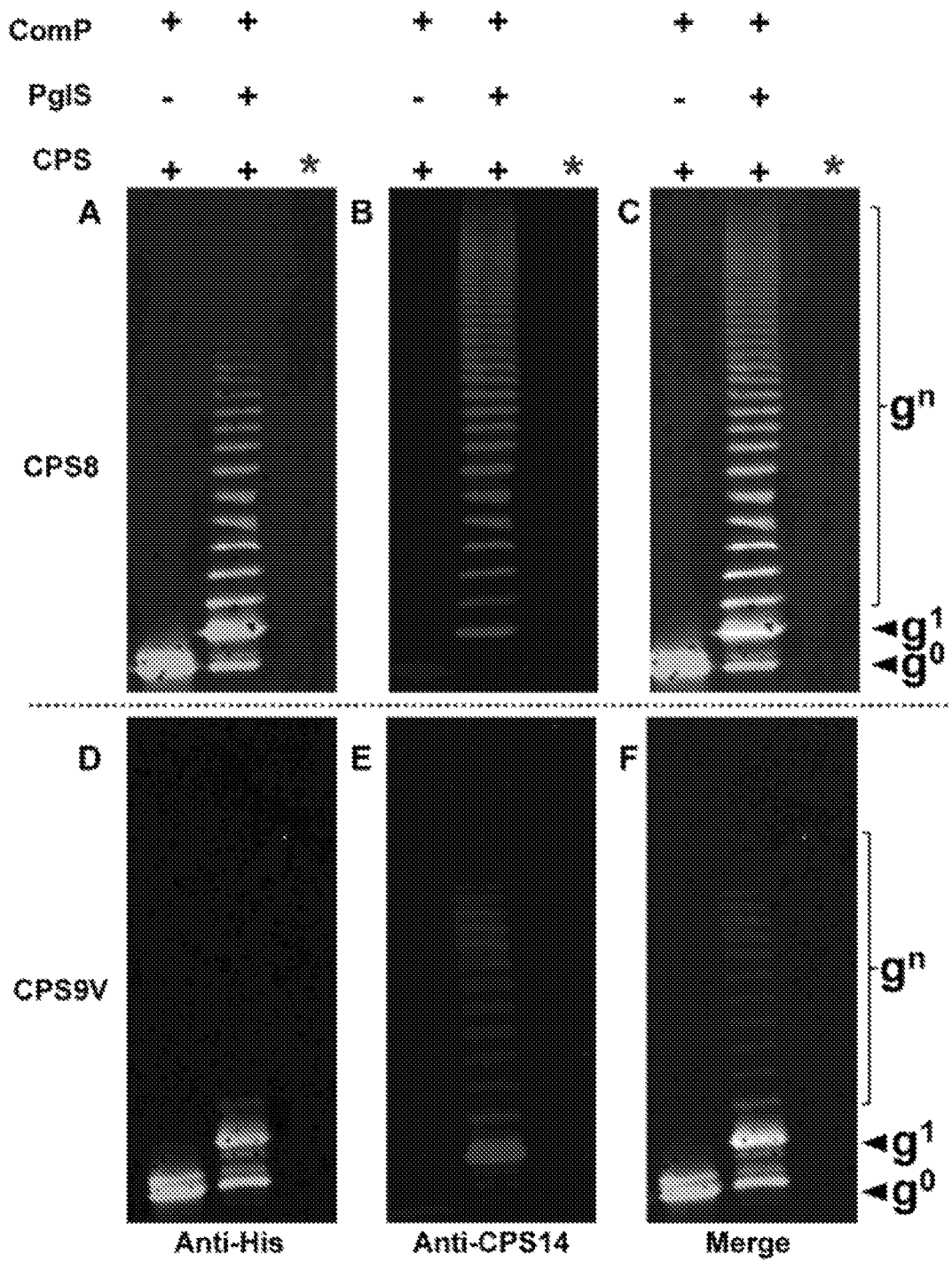
Figure 34A-F

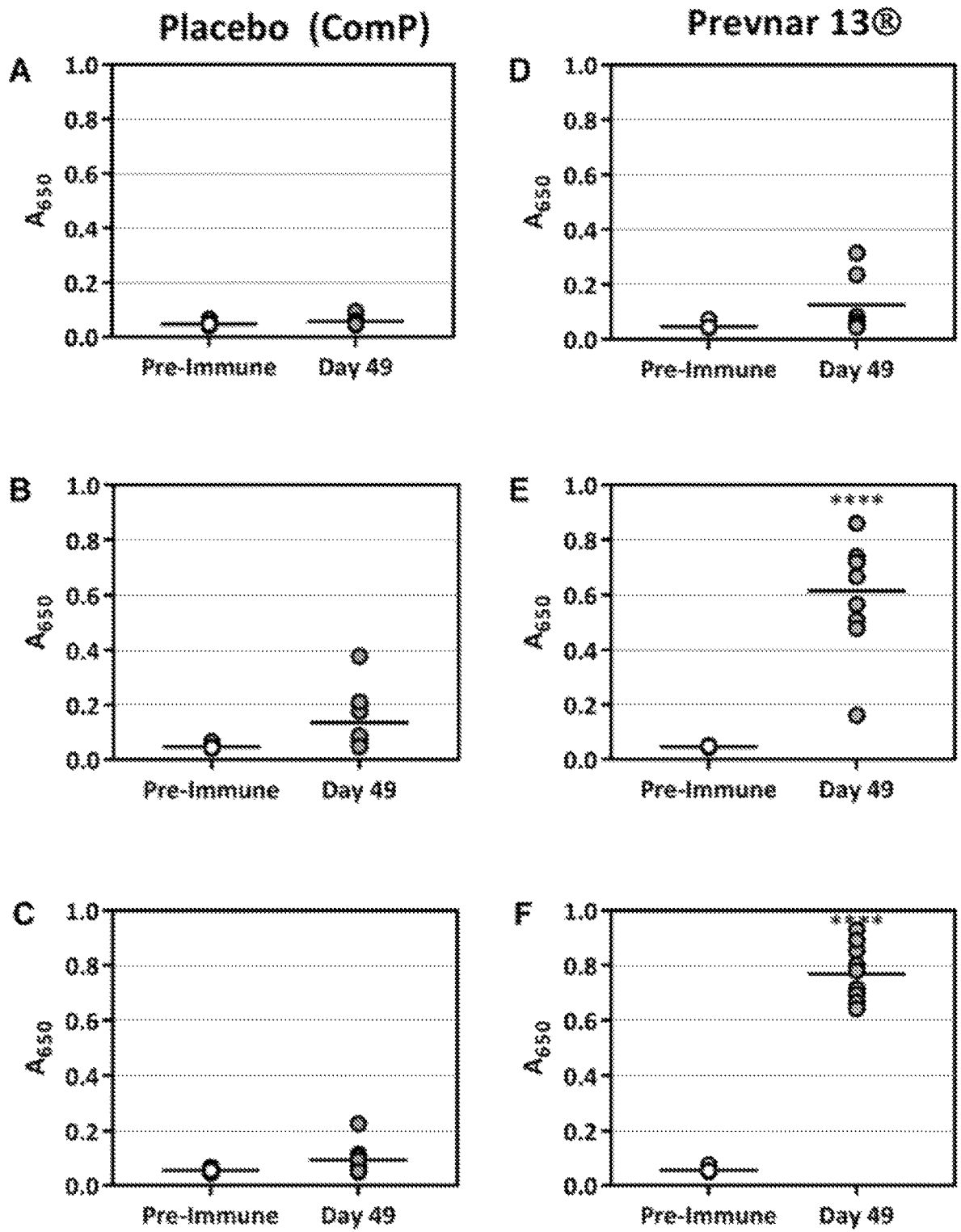
Figure 35A-F

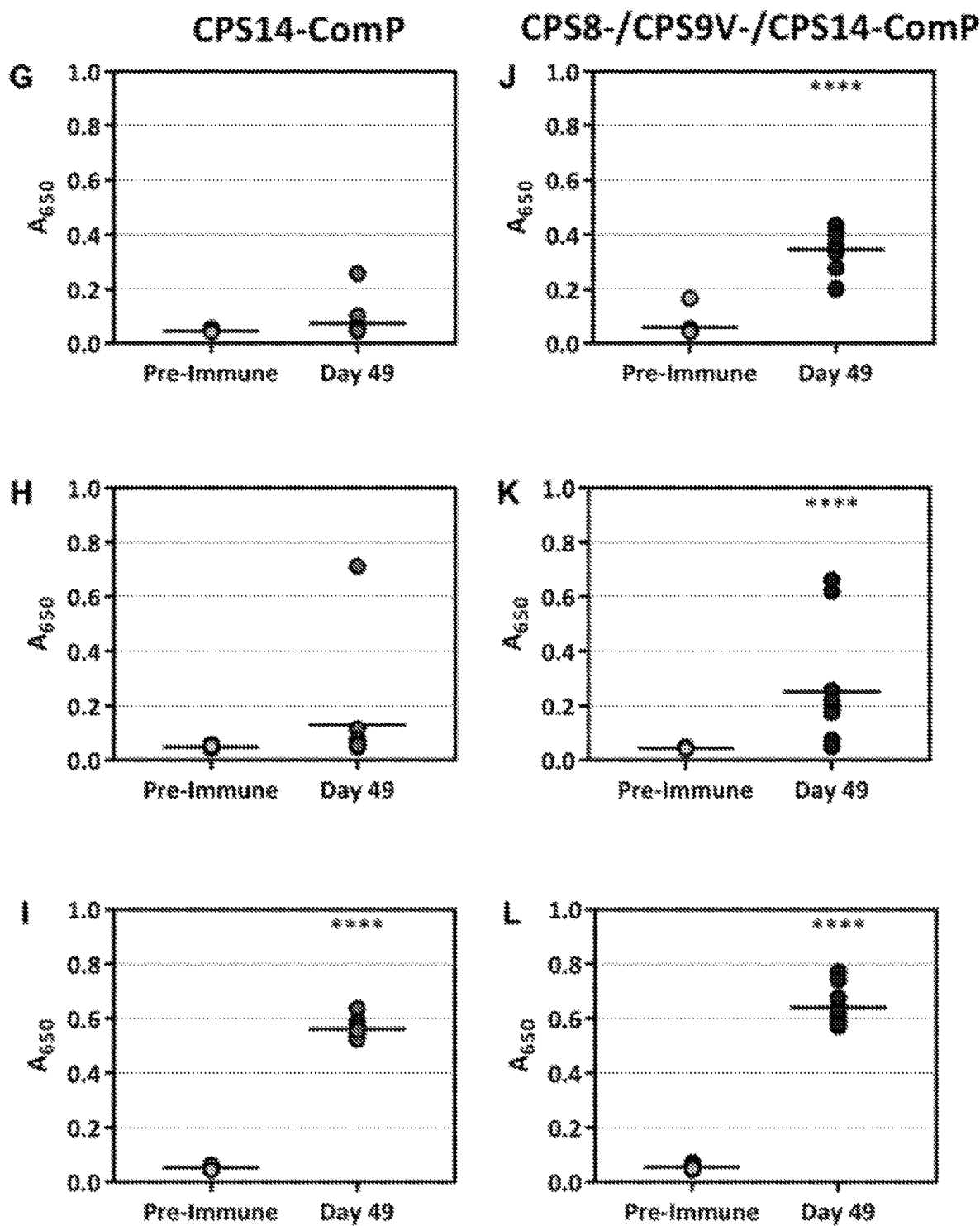
Figure 35G-L

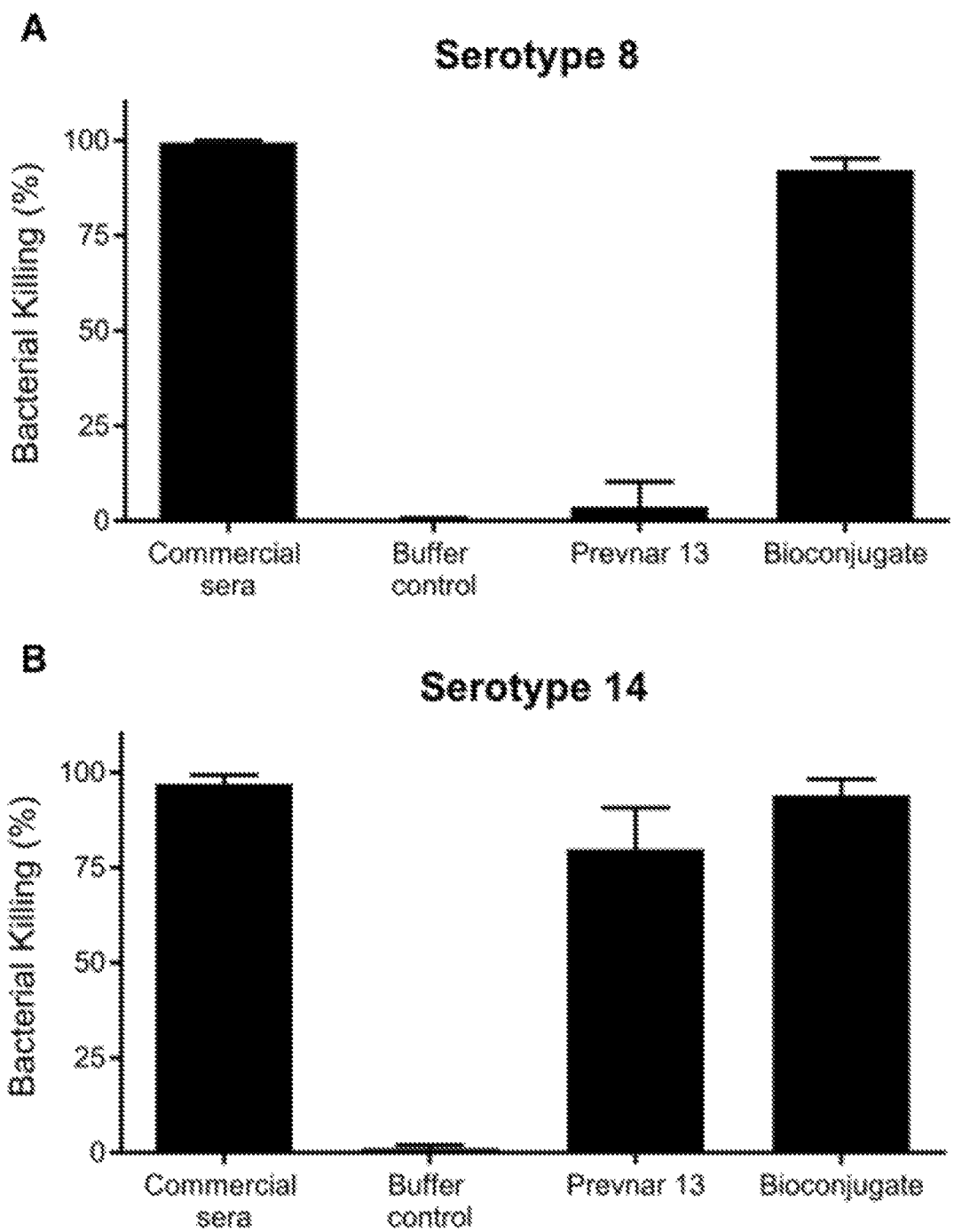
Figure 36A,B

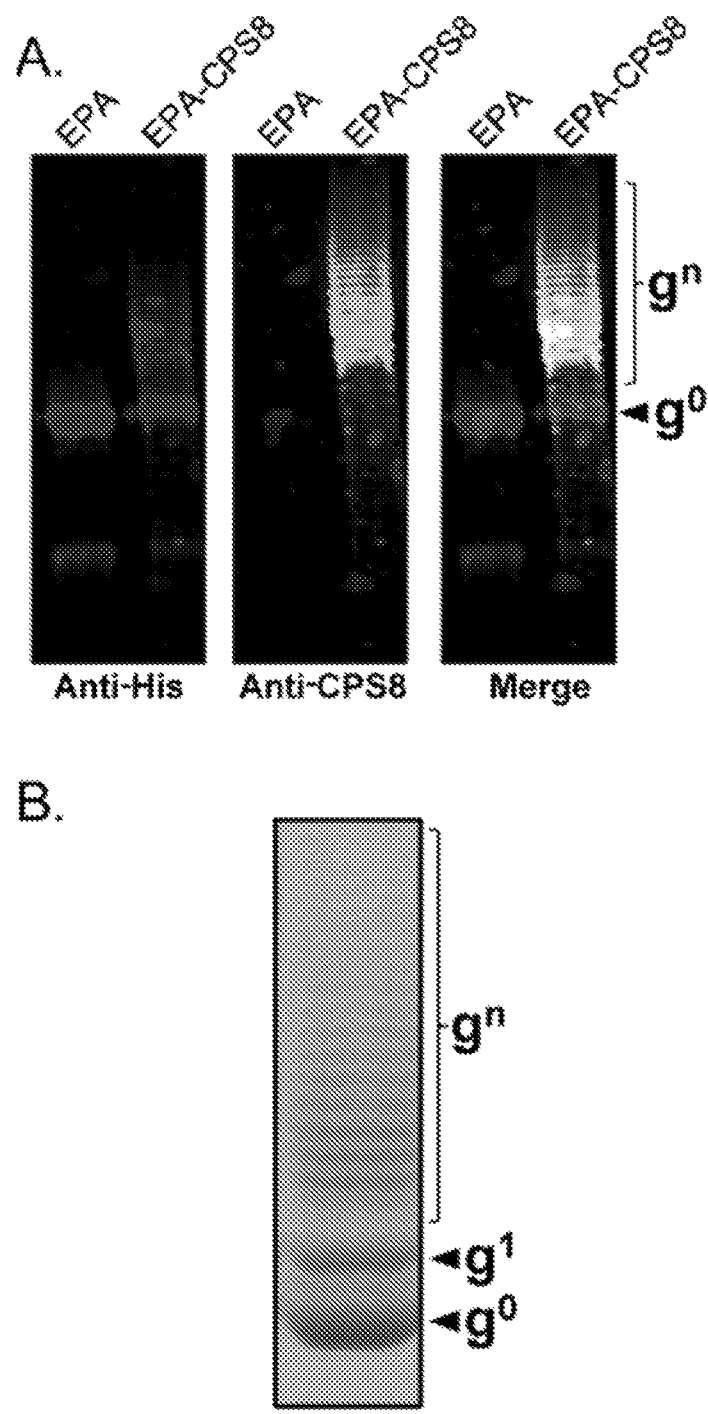
Figure 37A,B

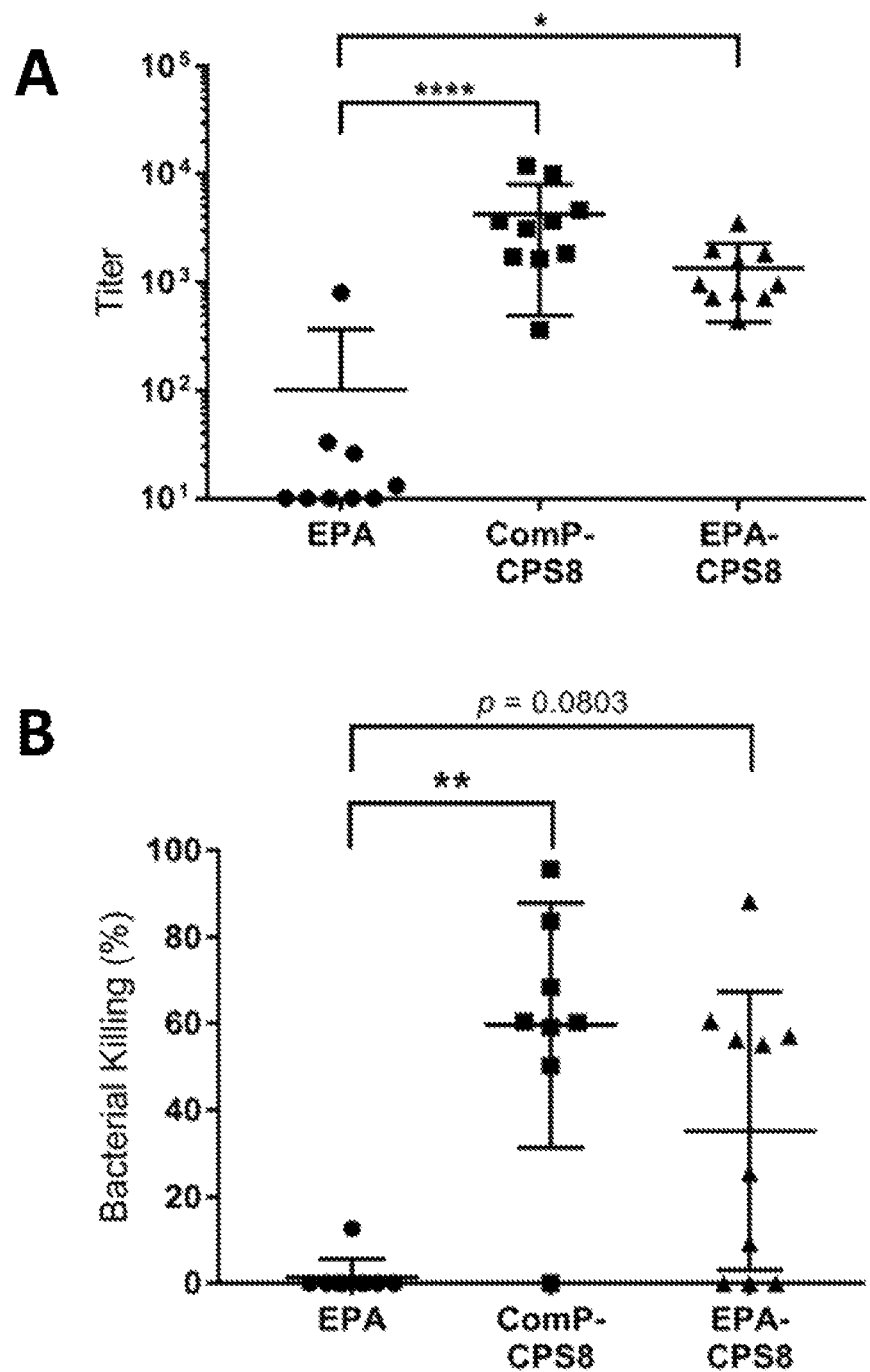
Figure 38A,B

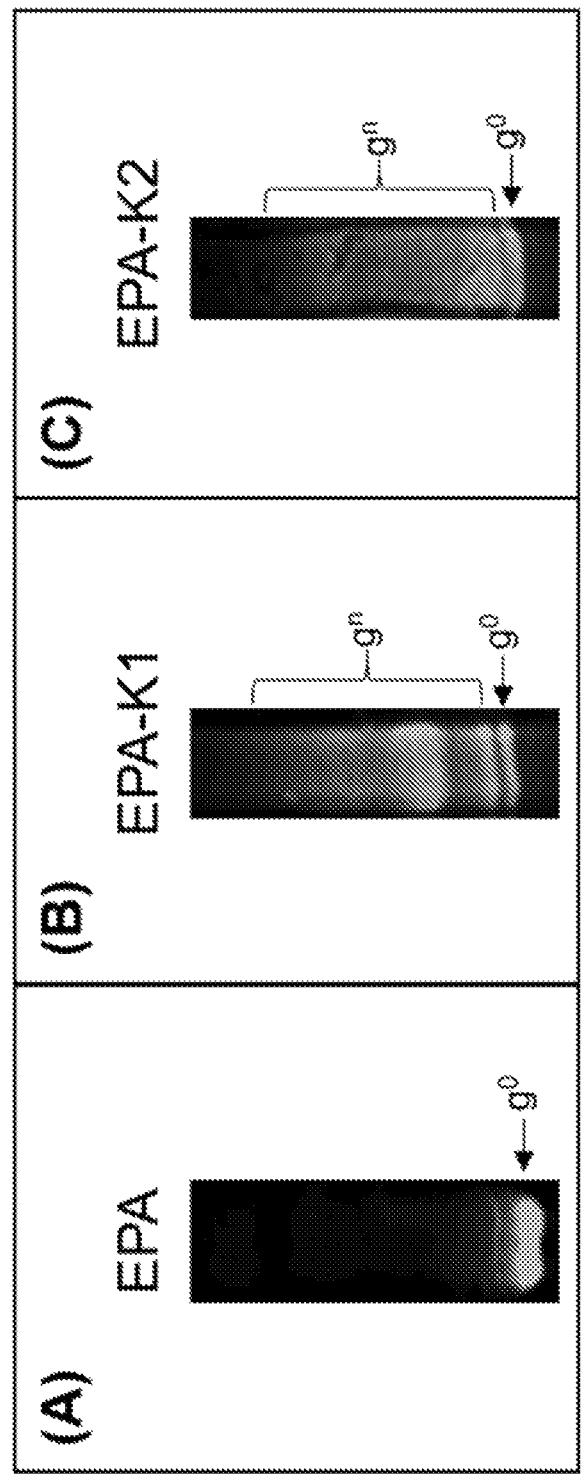
Figure 40A,B,C

```
                         SEQUENCE LISTING

<160> NUMBER OF SEQ ID NOS: 116

<210> SEQ ID NO 1
<211> LENGTH: 147
<212> TYPE: PRT
<213> ORGANISM: Acinetobacter sp.

<400> SEQUENCE: 1

Met Asn Ala Gln Lys Gly Phe Thr Leu Ile Glu Leu Met Ile Val Ile
1               5                   10                  15

Ala Ile Ile Gly Ile Leu Ala Ala Ile Ala Ile Pro Ala Tyr Thr Asp
            20                  25                  30

Tyr Thr Val Arg Ala Arg Val Ser Glu Gly Leu Thr Ala Ala Ser Ser
        35                  40                  45

Met Lys Thr Thr Val Ser Glu Asn Ile Leu Asn Ala Gly Ala Leu Val
    50                  55                  60

Ala Gly Thr Pro Ser Thr Ala Gly Ser Ser Cys Val Gly Val Gln Glu
65                  70                  75                  80

Ile Ser Ala Ser Asn Ala Thr Thr Asn Val Ala Thr Ala Thr Cys Gly
                85                  90                  95

Ala Ser Ser Ala Gly Gln Ile Ile Val Thr Met Asp Thr Thr Lys Ala
            100                 105                 110

Lys Gly Ala Asn Ile Thr Leu Thr Pro Thr Tyr Ala Ser Gly Ala Val
        115                 120                 125

Thr Trp Lys Cys Thr Thr Thr Ser Asp Lys Lys Tyr Val Pro Ser Glu
    130                 135                 140

Cys Arg Gly
145

<210> SEQ ID NO 2
<211> LENGTH: 145
<212> TYPE: PRT
<213> ORGANISM: Acinetobacter soli

<400> SEQUENCE: 2

Met Asn Ala Gln Lys Gly Phe Thr Leu Ile Glu Leu Met Ile Val Ile
1               5                   10                  15

Ala Ile Ile Gly Ile Leu Ala Ala Ile Ala Ile Pro Ala Tyr Thr Asp
            20                  25                  30

Tyr Thr Val Arg Ser Arg Val Thr Glu Gly Leu Thr Thr Ala Ser Ala
        35                  40                  45

Met Lys Ala Thr Val Ser Glu Asn Ile Met Asn Ala Gly Gly Thr Ser
    50                  55                  60

Met Pro Ser Ser Gly Asn Cys Thr Gly Val Thr Gln Ile Ala Ser Gly
65                  70                  75                  80

Ala Ser Ala Ala Thr Thr Asn Val Ala Ser Ala Gln Cys Ser Asp Ser
                85                  90                  95

Asp Gly Val Ile Thr Val Thr Met Thr Asp Lys Ala Lys Gly Val Ser
            100                 105                 110

Ile Lys Leu Thr Pro Ser Phe Ser Ser Thr Gly Ser Val Gly Trp Lys
        115                 120                 125

Cys Thr Thr Ser Ser Asp Lys Lys Tyr Val Pro Ser Glu Cys Arg Gly
    130                 135                 140
```

Thr
145

<210> SEQ ID NO 3
<211> LENGTH: 146
<212> TYPE: PRT
<213> ORGANISM: Acinetobacter soli

<400> SEQUENCE: 3

Met Asn Ala Gln Lys Gly Phe Thr Leu Ile Glu Leu Met Ile Val Ile
1               5                   10                  15

Ala Ile Ile Gly Ile Leu Ala Ala Ile Ala Ile Pro Ala Tyr Thr Asp
            20                  25                  30

Tyr Thr Val Arg Ala Arg Val Ser Glu Gly Leu Thr Thr Ala Ser Ala
        35                  40                  45

Met Lys Ala Thr Val Ser Glu Asn Ile Leu Ser Ala Gly Gln Ile Val
    50                  55                  60

Thr Gly Thr Pro Ser Thr Ala Asn Ser Ser Cys Val Gly Val Gln Glu
65                  70                  75                  80

Ile Asn Ala Ser Ser Ser Thr Ser Asn Val Ala Thr Ala Thr Cys Ser
                85                  90                  95

Gly Leu Gly Val Ile Thr Val Thr Met Asp Ser Thr Lys Ala Lys Gly
            100                 105                 110

Val Asn Leu Thr Leu Thr Pro Thr Tyr Thr Thr Ser Asn Ala Val Thr
        115                 120                 125

Trp Lys Cys Thr Thr Thr Ser Asp Lys Lys Tyr Val Pro Ser Glu Cys
    130                 135                 140

Arg Asn
145

<210> SEQ ID NO 4
<211> LENGTH: 142
<212> TYPE: PRT
<213> ORGANISM: Acinetobacter radioresistens

<400> SEQUENCE: 4

Met Asn Thr Gln Lys Gly Phe Thr Leu Ile Glu Leu Met Ile Val Ile
1               5                   10                  15

Ala Ile Ile Gly Ile Leu Ala Ala Ile Ala Ile Pro Ala Tyr Thr Asp
            20                  25                  30

Tyr Thr Val Arg Ala Arg Val Thr Glu Ala Val Ser Thr Ala Ser Ser
        35                  40                  45

Met Lys Ala Thr Val Ser Glu Asn Ile Met Asn Ala Gly Gly Thr Gln
    50                  55                  60

Ile Pro Thr Ser Gly Asn Cys Val Gly Val Gln Thr Ile Ala Ala Ser
65                  70                  75                  80

Asn Ala Thr Lys Asn Val Ala Thr Ala Thr Cys Thr Asp Ser Thr Gly
                85                  90                  95

Val Ile Val Val Thr Thr Thr Pro Ala Ala Lys Ser Val Pro Leu Thr
            100                 105                 110

Leu Thr Pro Thr Tyr Thr Gly Gly Asn Val Lys Trp Ala Cys Ser Thr
        115                 120                 125

Thr Ala Asn Phe Lys Asn Tyr Val Pro Ser Glu Cys Arg Ser
    130                 135                 140

<210> SEQ ID NO 5

```
<211> LENGTH: 140
<212> TYPE: PRT
<213> ORGANISM: Acinetobacter puyangensis

<400> SEQUENCE: 5
```

Met Asn Ala Gln Lys Gly Phe Thr Leu Ile Glu Leu Met Ile Val Ile
1               5                   10                  15

Ala Ile Ile Gly Ile Leu Ala Ala Ile Ala Ile Pro Ala Tyr Thr Asp
            20                  25                  30

Tyr Thr Val Arg Ala Arg Val Thr Glu Ala Leu Thr Thr Ala Ser Ala
        35                  40                  45

Met Lys Ala Thr Val Ser Glu Asn Ile Met Ser Ala Gly Gly Thr Thr
    50                  55                  60

Ile Ala Ser Ser Ala Cys Asn Gly Val Ile Ser Ala Ser Ala Thr Thr
65                  70                  75                  80

Asn Val Ala Ser Ser Ala Cys Ser Gly Ser Gly Val Ile Ser Val Thr
                85                  90                  95

Thr Thr Ala Ala Ala Lys Gly Ile Val Leu Thr Leu Thr Pro Lys Tyr
            100                 105                 110

Thr Gly Gly Asn Val Ala Trp Gln Cys Thr Thr Thr Ser Gly Asp Ala
        115                 120                 125

Gln Lys Tyr Val Pro Ser Glu Cys Arg Thr Thr Ser
    130                 135                 140

```
<210> SEQ ID NO 6
<211> LENGTH: 150
<212> TYPE: PRT
<213> ORGANISM: Acinetobacter sp.

<400> SEQUENCE: 6
```

Met Asn Thr Gln Lys Gly Phe Thr Leu Ile Glu Leu Met Ile Val Ile
1               5                   10                  15

Ala Ile Ile Gly Ile Leu Ala Ala Ile Ala Ile Pro Ala Tyr Thr Asp
            20                  25                  30

Tyr Thr Val Arg Ala Lys Val Thr Glu Ala Ile Ser Thr Ala Ser Ala
        35                  40                  45

Met Lys Ala Thr Val Ser Glu Asn Leu Met Ser Ala Gly Gly Thr Ser
    50                  55                  60

Ile Val Ser Thr Asn Ala Asn Cys Ala Gly Val Glu Thr Ile Gly Ala
65                  70                  75                  80

Ser Asn Lys Thr Lys Asn Val Glu Ser Ala Ala Cys Thr Ala Ala Thr
                85                  90                  95

Gly Val Ile Leu Val Thr Thr Ala Glu Ala Lys Ser Val Pro Leu
            100                 105                 110

Thr Leu Lys Pro Thr Tyr Thr Gly Ser Asn Val Gln Trp Lys Cys Gly
        115                 120                 125

Thr Thr Ala Ala Ala Phe Lys Tyr Val Pro Ser Glu Cys Arg Asn Asp
    130                 135                 140

Ser Ser Gly Thr Gly Phe
145                 150

```
<210> SEQ ID NO 7
<211> LENGTH: 119
<212> TYPE: PRT
<213> ORGANISM: Acinetobacter sp.
```

<400> SEQUENCE: 7

```
Ala Tyr Thr Asp Tyr Thr Val Arg Ala Arg Val Ser Glu Gly Leu Thr
1               5                   10                  15

Ala Ala Ser Ser Met Lys Thr Thr Val Ser Glu Asn Ile Leu Asn Ala
            20                  25                  30

Gly Ala Leu Val Ala Gly Thr Pro Ser Thr Ala Gly Ser Ser Cys Val
        35                  40                  45

Gly Val Gln Glu Ile Ser Ala Ser Asn Ala Thr Thr Asn Val Ala Thr
    50                  55                  60

Ala Thr Cys Gly Ala Ser Ser Ala Gly Gln Ile Ile Val Thr Met Asp
65                  70                  75                  80

Thr Thr Lys Ala Lys Gly Ala Asn Ile Thr Leu Thr Pro Thr Tyr Ala
                85                  90                  95

Ser Gly Ala Val Thr Trp Lys Cys Thr Thr Ser Asp Lys Lys Tyr
            100                 105                 110

Val Pro Ser Glu Cys Arg Gly
        115
```

<210> SEQ ID NO 8
<211> LENGTH: 117
<212> TYPE: PRT
<213> ORGANISM: Acinetobacter soli

<400> SEQUENCE: 8

```
Ala Tyr Thr Asp Tyr Thr Val Arg Ser Arg Val Thr Glu Gly Leu Thr
1               5                   10                  15

Thr Ala Ser Ala Met Lys Ala Thr Val Ser Glu Asn Ile Met Asn Ala
            20                  25                  30

Gly Gly Thr Ser Met Pro Ser Ser Gly Asn Cys Thr Gly Val Thr Gln
        35                  40                  45

Ile Ala Ser Gly Ala Ser Ala Ala Thr Thr Asn Val Ala Ser Ala Gln
    50                  55                  60

Cys Ser Asp Ser Asp Gly Val Ile Thr Val Thr Met Thr Asp Lys Ala
65                  70                  75                  80

Lys Gly Val Ser Ile Lys Leu Thr Pro Ser Phe Ser Ser Thr Gly Ser
                85                  90                  95

Val Gly Trp Lys Cys Thr Thr Ser Ser Asp Lys Lys Tyr Val Pro Ser
            100                 105                 110

Glu Cys Arg Gly Thr
        115
```

<210> SEQ ID NO 9
<211> LENGTH: 118
<212> TYPE: PRT
<213> ORGANISM: Acinetobacter soli

<400> SEQUENCE: 9

```
Ala Tyr Thr Asp Tyr Thr Val Arg Ala Arg Val Ser Glu Gly Leu Thr
1               5                   10                  15

Thr Ala Ser Ala Met Lys Ala Thr Val Ser Glu Asn Ile Leu Ser Ala
            20                  25                  30

Gly Gln Ile Val Thr Gly Thr Pro Ser Thr Ala Asn Ser Ser Cys Val
        35                  40                  45

Gly Val Gln Glu Ile Asn Ala Ser Ser Thr Ser Asn Val Ala Thr
    50                  55                  60
```

-continued

Ala Thr Cys Ser Gly Leu Gly Val Ile Thr Val Met Asp Ser Thr
 65                  70                  75                  80

Lys Ala Lys Gly Val Asn Leu Thr Leu Thr Pro Thr Tyr Thr Thr Ser
                 85                  90                  95

Asn Ala Val Thr Trp Lys Cys Thr Thr Thr Ser Asp Lys Lys Tyr Val
            100                 105                 110

Pro Ser Glu Cys Arg Asn
        115

<210> SEQ ID NO 10
<211> LENGTH: 114
<212> TYPE: PRT
<213> ORGANISM: Acinetobacter radioresistens

<400> SEQUENCE: 10

Ala Tyr Thr Asp Tyr Thr Val Arg Ala Arg Val Thr Glu Ala Val Ser
1               5                   10                  15

Thr Ala Ser Ser Met Lys Ala Thr Val Ser Glu Asn Ile Met Asn Ala
                20                  25                  30

Gly Gly Thr Gln Ile Pro Thr Ser Gly Asn Cys Val Gly Val Gln Thr
            35                  40                  45

Ile Ala Ala Ser Asn Ala Thr Lys Asn Val Ala Thr Ala Cys Thr
 50                  55                  60

Asp Ser Thr Gly Val Ile Val Val Thr Thr Pro Ala Ala Lys Ser
 65                  70                  75                  80

Val Pro Leu Thr Leu Thr Pro Thr Tyr Thr Gly Gly Asn Val Lys Trp
                85                  90                  95

Ala Cys Ser Thr Thr Ala Asn Phe Lys Asn Tyr Val Pro Ser Glu Cys
            100                 105                 110

Arg Ser

<210> SEQ ID NO 11
<211> LENGTH: 112
<212> TYPE: PRT
<213> ORGANISM: Acinetobacter puyangensis

<400> SEQUENCE: 11

Ala Tyr Thr Asp Tyr Thr Val Arg Ala Arg Val Thr Glu Ala Leu Thr
1               5                   10                  15

Thr Ala Ser Ala Met Lys Ala Thr Val Ser Glu Asn Ile Met Ser Ala
                20                  25                  30

Gly Gly Thr Thr Ile Ala Ser Ser Ala Cys Asn Gly Val Ile Ser Ala
            35                  40                  45

Ser Ala Thr Thr Asn Val Ala Ser Ser Ala Cys Ser Gly Ser Gly Val
 50                  55                  60

Ile Ser Val Thr Thr Ala Ala Ala Lys Gly Ile Val Leu Thr Leu
 65                  70                  75                  80

Thr Pro Lys Tyr Thr Gly Gly Asn Val Ala Trp Gln Cys Thr Thr Thr
                85                  90                  95

Ser Gly Asp Ala Gln Lys Tyr Val Pro Ser Glu Cys Arg Thr Thr Ser
            100                 105                 110

<210> SEQ ID NO 12
<211> LENGTH: 122
<212> TYPE: PRT
<213> ORGANISM: Acinetobacter sp.

<400> SEQUENCE: 12

Ala Tyr Thr Asp Tyr Thr Val Arg Ala Lys Val Thr Glu Ala Ile Ser
1               5                   10                  15

Thr Ala Ser Ala Met Lys Ala Thr Val Ser Glu Asn Leu Met Ser Ala
            20                  25                  30

Gly Gly Thr Ser Ile Val Ser Thr Asn Ala Asn Cys Ala Gly Val Glu
        35                  40                  45

Thr Ile Gly Ala Ser Asn Lys Thr Lys Asn Val Glu Ser Ala Ala Cys
    50                  55                  60

Thr Ala Ala Thr Gly Val Ile Leu Val Thr Thr Thr Ala Glu Ala Lys
65                  70                  75                  80

Ser Val Pro Leu Thr Leu Lys Pro Thr Tyr Thr Gly Ser Asn Val Gln
                85                  90                  95

Trp Lys Cys Gly Thr Thr Ala Ala Phe Lys Tyr Val Pro Ser Glu
                100                 105                 110

Cys Arg Asn Asp Ser Ser Gly Thr Gly Phe
            115                 120

<210> SEQ ID NO 13
<211> LENGTH: 21
<212> TYPE: PRT
<213> ORGANISM: Unknown
<220> FEATURE:
<223> OTHER INFORMATION: Description of Unknown:
      ComP sequence

<400> SEQUENCE: 13

Cys Val Gly Val Gln Glu Ile Ser Ala Ser Asn Ala Thr Thr Asn Val
1               5                   10                  15

Ala Thr Ala Thr Cys
            20

<210> SEQ ID NO 14
<211> LENGTH: 23
<212> TYPE: PRT
<213> ORGANISM: Unknown
<220> FEATURE:
<223> OTHER INFORMATION: Description of Unknown:
      ComP sequence

<400> SEQUENCE: 14

Cys Thr Gly Val Thr Gln Ile Ala Ser Gly Ala Ser Ala Ala Thr Thr
1               5                   10                  15

Asn Val Ala Ser Ala Gln Cys
            20

<210> SEQ ID NO 15
<211> LENGTH: 21
<212> TYPE: PRT
<213> ORGANISM: Unknown
<220> FEATURE:
<223> OTHER INFORMATION: Description of Unknown:
      ComP sequence

<400> SEQUENCE: 15

Cys Val Gly Val Gln Glu Ile Asn Ala Ser Ser Ser Thr Ser Asn Val
1               5                   10                  15

Ala Thr Ala Thr Cys
            20

```
<210> SEQ ID NO 16
<211> LENGTH: 21
<212> TYPE: PRT
<213> ORGANISM: Unknown
<220> FEATURE:
<223> OTHER INFORMATION: Description of Unknown:
      ComP sequence

<400> SEQUENCE: 16

Cys Ala Gly Val Glu Thr Ile Gly Ala Ser Asn Lys Thr Lys Asn Val
1               5                   10                  15

Glu Ser Ala Ala Cys
            20

<210> SEQ ID NO 17
<211> LENGTH: 21
<212> TYPE: PRT
<213> ORGANISM: Unknown
<220> FEATURE:
<223> OTHER INFORMATION: Description of Unknown:
      ComP sequence

<400> SEQUENCE: 17

Cys Val Gly Val Gln Thr Ile Ala Ala Ser Asn Ala Thr Lys Asn Val
1               5                   10                  15

Ala Thr Ala Thr Cys
            20

<210> SEQ ID NO 18
<211> LENGTH: 335
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Met Lys Lys Ile Trp Leu Ala Leu Ala Gly Leu Val Leu Ala Phe Ser
1               5                   10                  15

Ala Ser Ala Ala Gln Tyr Glu Asp Gly Lys Gln Tyr Thr Thr Leu Glu
            20                  25                  30

Lys Pro Val Ala Gly Ala Pro Gln Val Leu Glu Phe Phe Ser Phe Phe
        35                  40                  45

Cys Pro His Cys Tyr Gln Phe Glu Glu Val Leu His Ile Ser Asp Asn
    50                  55                  60

Val Lys Lys Lys Leu Pro Glu Gly Val Lys Met Thr Lys Tyr His Val
65                  70                  75                  80

Asn Phe Met Gly Gly Asp Leu Gly Lys Asp Leu Thr Gln Ala Trp Ala
                85                  90                  95

Val Ala Met Ala Leu Gly Val Glu Asp Lys Val Thr Val Pro Leu Phe
            100                 105                 110

Glu Gly Val Gln Lys Thr Gln Thr Ile Arg Ser Ala Ser Asp Ile Arg
        115                 120                 125

Asp Val Phe Ile Asn Ala Gly Ile Lys Gly Glu Glu Tyr Asp Ala Ala
    130                 135                 140

Trp Asn Ser Phe Val Val Lys Ser Leu Val Ala Gln Gln Glu Lys Ala
145                 150                 155                 160

Ala Ala Asp Val Gln Leu Arg Gly Val Pro Ala Met Phe Val Asn Gly
                165                 170                 175

Lys Tyr Gln Leu Asn Pro Gln Gly Met Asp Thr Ser Asn Met Asp Val
            180                 185                 190
```

```
Phe Val Gln Gln Tyr Ala Asp Thr Val Lys Tyr Leu Ser Glu Lys Lys
            195                 200                 205

Gly Gly Gly Ser Ala Tyr Thr Asp Tyr Thr Val Arg Ser Arg Val Thr
    210                 215                 220

Glu Gly Leu Thr Thr Ala Ser Ala Met Lys Ala Thr Val Ser Glu Asn
225                 230                 235                 240

Ile Met Asn Ala Gly Gly Thr Ser Met Pro Ser Ser Gly Asn Cys Thr
                245                 250                 255

Gly Val Thr Gln Ile Ala Ser Gly Ala Ser Ala Ala Thr Thr Asn Val
            260                 265                 270

Ala Ser Ala Gln Cys Ser Asp Ser Asp Gly Val Ile Thr Val Thr Met
        275                 280                 285

Thr Asp Lys Ala Lys Gly Val Ser Ile Lys Leu Thr Pro Ser Phe Ser
    290                 295                 300

Ser Thr Gly Ser Val Gly Trp Lys Cys Thr Thr Ser Ser Asp Lys Lys
305                 310                 315                 320

Tyr Val Pro Ser Glu Cys Arg Gly Thr His His His His His
                325                 330                 335

<210> SEQ ID NO 19
<211> LENGTH: 519
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Glu Glu Gly Lys
            20                  25                  30

Leu Val Ile Trp Ile Asn Gly Asp Lys Gly Tyr Asn Gly Leu Ala Glu
        35                  40                  45

Val Gly Lys Lys Phe Glu Lys Asp Thr Gly Ile Lys Val Thr Val Glu
    50                  55                  60

His Pro Asp Lys Leu Glu Glu Lys Phe Pro Gln Val Ala Ala Thr Gly
65                  70                  75                  80

Asp Gly Pro Asp Ile Ile Phe Trp Ala His Asp Arg Phe Gly Gly Tyr
                85                  90                  95

Ala Gln Ser Gly Leu Leu Ala Glu Ile Thr Pro Asp Lys Ala Phe Gln
            100                 105                 110

Asp Lys Leu Tyr Pro Phe Thr Trp Asp Ala Val Arg Tyr Asn Gly Lys
        115                 120                 125

Leu Ile Ala Tyr Pro Ile Ala Val Glu Ala Leu Ser Leu Ile Tyr Asn
    130                 135                 140

Lys Asp Leu Leu Pro Asn Pro Pro Lys Thr Trp Glu Glu Ile Pro Ala
145                 150                 155                 160

Leu Asp Lys Glu Leu Lys Ala Lys Gly Lys Ser Ala Leu Met Phe Asn
                165                 170                 175

Leu Gln Glu Pro Tyr Phe Thr Trp Pro Leu Ile Ala Ala Asp Gly Gly
            180                 185                 190

Tyr Ala Phe Lys Tyr Glu Asn Gly Lys Tyr Asp Ile Lys Asp Val Gly
        195                 200                 205
```

Val Asp Asn Ala Gly Ala Lys Ala Gly Leu Thr Phe Leu Val Asp Leu
    210                 215                 220

Ile Lys Asn Lys His Met Asn Ala Asp Thr Asp Tyr Ser Ile Ala Glu
225                 230                 235                 240

Ala Ala Phe Asn Lys Gly Glu Thr Ala Met Thr Ile Asn Gly Pro Trp
                245                 250                 255

Ala Trp Ser Asn Ile Asp Thr Ser Lys Val Asn Tyr Gly Val Thr Val
            260                 265                 270

Leu Pro Thr Phe Lys Gly Gln Pro Ser Lys Pro Phe Val Gly Val Leu
        275                 280                 285

Ser Ala Gly Ile Asn Ala Ala Ser Pro Asn Lys Glu Leu Ala Lys Glu
    290                 295                 300

Phe Leu Glu Asn Tyr Leu Leu Thr Asp Glu Gly Leu Glu Ala Val Asn
305                 310                 315                 320

Lys Asp Lys Pro Leu Gly Ala Val Ala Leu Lys Ser Tyr Glu Glu Glu
                325                 330                 335

Leu Ala Lys Asp Pro Arg Ile Ala Ala Thr Met Glu Asn Ala Gln Lys
            340                 345                 350

Gly Glu Ile Met Pro Asn Ile Pro Gln Met Ser Ala Phe Trp Tyr Ala
        355                 360                 365

Val Arg Thr Ala Val Ile Asn Ala Ala Ser Gly Arg Gln Thr Val Asp
    370                 375                 380

Glu Ala Leu Lys Asp Ala Gln Thr Asn Ala Ala Ala Tyr Thr Asp
385                 390                 395                 400

Tyr Thr Val Arg Ser Arg Val Thr Glu Gly Leu Thr Thr Ala Ser Ala
                405                 410                 415

Met Lys Ala Thr Val Ser Glu Asn Ile Met Asn Ala Gly Gly Thr Ser
            420                 425                 430

Met Pro Ser Ser Gly Asn Cys Thr Gly Val Thr Gln Ile Ala Ser Gly
        435                 440                 445

Ala Ser Ala Ala Thr Thr Asn Val Ala Ser Ala Gln Cys Ser Asp Ser
    450                 455                 460

Asp Gly Val Ile Thr Val Thr Met Thr Asp Lys Ala Lys Gly Val Ser
465                 470                 475                 480

Ile Lys Leu Thr Pro Ser Phe Ser Ser Thr Gly Ser Val Gly Trp Lys
                485                 490                 495

Cys Thr Thr Ser Ser Asp Lys Lys Tyr Val Pro Ser Glu Cys Arg Gly
            500                 505                 510

Thr His His His His His His
        515

<210> SEQ ID NO 20
<211> LENGTH: 758
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Met Lys Lys Ile Trp Leu Ala Leu Ala Gly Leu Val Leu Ala Phe Ser
1               5                   10                  15

Ala Ser Ala Ala Glu Glu Ala Phe Asp Leu Trp Asn Glu Cys Ala Lys
            20                  25                  30

```
Ala Cys Val Leu Asp Leu Lys Asp Gly Val Arg Ser Ser Arg Met Ser
        35                  40                  45

Val Asp Pro Ala Ile Ala Asp Thr Asn Gly Gln Gly Val Leu His Tyr
 50                  55                  60

Ser Met Val Leu Glu Gly Gly Asn Asp Ala Leu Lys Leu Ala Ile Asp
 65                  70                  75                  80

Asn Ala Leu Ser Ile Thr Ser Asp Gly Leu Thr Ile Arg Leu Glu Gly
                 85                  90                  95

Gly Val Glu Pro Asn Lys Pro Val Arg Tyr Ser Tyr Thr Arg Gln Ala
                100                 105                 110

Arg Gly Ser Trp Ser Leu Asn Trp Leu Val Pro Ile Gly His Glu Lys
                115                 120                 125

Pro Ser Asn Ile Lys Val Phe Ile His Glu Leu Asn Ala Gly Asn Gln
            130                 135                 140

Leu Ser His Met Ser Pro Ile Tyr Thr Ile Glu Met Gly Asp Glu Leu
145                 150                 155                 160

Leu Ala Lys Leu Ala Arg Asp Ala Thr Phe Phe Val Arg Ala His Glu
                    165                 170                 175

Ser Asn Glu Met Gln Pro Thr Leu Ala Ile Ser His Ala Gly Val Ser
                180                 185                 190

Val Val Met Ala Gln Ala Gln Pro Arg Arg Glu Lys Arg Trp Ser Glu
            195                 200                 205

Trp Ala Ser Gly Lys Val Leu Cys Leu Leu Asp Pro Leu Asp Gly Val
210                 215                 220

Tyr Asn Tyr Leu Ala Gln Gln Arg Cys Asn Leu Asp Asp Thr Trp Glu
225                 230                 235                 240

Gly Lys Ile Tyr Arg Val Leu Ala Gly Asn Pro Ala Lys His Asp Leu
                245                 250                 255

Asp Ile Lys Pro Thr Val Ile Ser His Arg Leu His Phe Pro Glu Gly
            260                 265                 270

Gly Ser Leu Ala Ala Leu Thr Ala His Gln Ala Cys His Leu Pro Leu
        275                 280                 285

Glu Thr Phe Thr Arg His Arg Gln Pro Arg Gly Trp Glu Gln Leu Glu
        290                 295                 300

Gln Cys Gly Tyr Pro Val Gln Arg Leu Val Ala Leu Tyr Leu Ala Ala
305                 310                 315                 320

Arg Leu Ser Trp Asn Gln Val Asp Gln Val Ile Arg Asn Ala Leu Ala
                325                 330                 335

Ser Pro Gly Ser Gly Gly Asp Leu Gly Glu Ala Ile Arg Glu Gln Pro
            340                 345                 350

Glu Gln Ala Arg Leu Ala Leu Thr Leu Ala Ala Glu Ser Glu Arg
        355                 360                 365

Phe Val Arg Gln Gly Thr Gly Asn Asp Glu Ala Gly Ala Ala Ser Ala
370                 375                 380

Asp Val Val Ser Leu Thr Cys Pro Val Ala Ala Gly Glu Cys Ala Gly
385                 390                 395                 400

Pro Ala Asp Ser Gly Asp Ala Leu Leu Glu Arg Asn Tyr Pro Thr Gly
                405                 410                 415

Ala Glu Phe Leu Gly Asp Gly Asp Ile Ser Phe Ser Thr Arg Gly
            420                 425                 430

Thr Gln Asn Trp Thr Val Glu Arg Leu Leu Gln Ala His Arg Gln Leu
        435                 440                 445
```

```
Glu Glu Arg Gly Tyr Val Phe Val Gly Tyr His Gly Thr Phe Leu Glu
450                 455                 460

Ala Ala Gln Ser Ile Val Phe Gly Gly Val Arg Ala Arg Ser Gln Asp
465                 470                 475                 480

Leu Asp Ala Ile Trp Arg Gly Phe Tyr Ile Ala Gly Asp Pro Ala Leu
            485                 490                 495

Ala Tyr Gly Tyr Ala Gln Asp Gln Glu Pro Asp Ala Arg Gly Arg Ile
        500                 505                 510

Arg Asn Gly Ala Leu Leu Arg Val Tyr Val Pro Arg Ser Ser Leu Pro
        515                 520                 525

Gly Phe Tyr Arg Thr Gly Leu Thr Leu Ala Ala Pro Glu Ala Ala Gly
530                 535                 540

Glu Val Glu Arg Leu Ile Gly His Pro Leu Pro Leu Arg Leu Asp Ala
545                 550                 555                 560

Ile Thr Gly Pro Glu Glu Gly Gly Arg Leu Thr Ile Leu Gly Trp
                565                 570                 575

Pro Leu Ala Glu Arg Thr Val Val Ile Pro Ser Ala Ile Pro Thr Asp
            580                 585                 590

Pro Arg Asn Val Gly Gly Asp Leu Asp Pro Ser Ser Ile Pro Asp Lys
        595                 600                 605

Glu Gln Ala Ile Ser Ala Leu Pro Asp Tyr Ala Ser Gln Pro Gly Lys
610                 615                 620

Pro Pro Arg Glu Asp Leu Lys Gly Gly Ser Ala Tyr Thr Asp Tyr
625                 630                 635                 640

Thr Val Arg Ser Arg Val Thr Glu Gly Leu Thr Thr Ala Ser Ala Met
                645                 650                 655

Lys Ala Thr Val Ser Glu Asn Ile Met Asn Ala Gly Gly Thr Ser Met
            660                 665                 670

Pro Ser Ser Gly Asn Cys Thr Gly Val Thr Gln Ile Ala Ser Gly Ala
        675                 680                 685

Ser Ala Ala Thr Thr Asn Val Ala Ser Ala Gln Cys Ser Asp Ser Asp
690                 695                 700

Gly Val Ile Thr Val Thr Met Thr Asp Lys Ala Lys Gly Val Ser Ile
705                 710                 715                 720

Lys Leu Thr Pro Ser Phe Ser Ser Thr Gly Ser Val Gly Trp Lys Cys
                725                 730                 735

Thr Thr Ser Ser Asp Lys Lys Tyr Val Pro Ser Glu Cys Arg Gly Thr
            740                 745                 750

His His His His His His
        755

<210> SEQ ID NO 21
<211> LENGTH: 5
<212> TYPE: PRT
<213> ORGANISM: Unknown
<220> FEATURE:
<223> OTHER INFORMATION: Description of Unknown:
      N-glycosylation bacterial sequence
<220> FEATURE:
<221> NAME/KEY: MOD_RES
<222> LOCATION: (2)..(2)
<223> OTHER INFORMATION: Any amino acid except Pro

<400> SEQUENCE: 21

Asp Xaa Asn Ser Thr
1               5
```

```
<210> SEQ ID NO 22
<211> LENGTH: 14
<212> TYPE: PRT
<213> ORGANISM: Unknown
<220> FEATURE:
<223> OTHER INFORMATION: Description of Unknown:
      Glycopeptide sequence

<400> SEQUENCE: 22

Ile Ser Ala Ser Asn Ala Thr Thr Asn Val Ala Thr Ala Thr
1               5                   10

<210> SEQ ID NO 23
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Gly Gly Gly Ser
1

<210> SEQ ID NO 24
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Ala Ala Ala
1

<210> SEQ ID NO 25
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Pro Ala Pro Ala Pro
1               5

<210> SEQ ID NO 26
<211> LENGTH: 21
<212> TYPE: PRT
<213> ORGANISM: Acinetobacter baylyi

<400> SEQUENCE: 26

Cys Val Gly Val Gln Glu Ile Ser Ala Ser Asn Ala Thr Thr Asn Val
1               5                   10                  15

Ala Thr Ala Thr Cys
            20

<210> SEQ ID NO 27
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
```

-continued

```
<222> LOCATION: (1)..(1)
<223> OTHER INFORMATION: V, A, or not present
<220> FEATURE:
<221> NAME/KEY: MOD_RES
<222> LOCATION: (2)..(2)
<223> OTHER INFORMATION: A, G, T, or not present
<220> FEATURE:
<221> NAME/KEY: MOD_RES
<222> LOCATION: (5)..(5)
<223> OTHER INFORMATION: P, S, or Q
<220> FEATURE:
<221> NAME/KEY: MOD_RES
<222> LOCATION: (6)..(6)
<223> OTHER INFORMATION: S, M, or I
<220> FEATURE:
<221> NAME/KEY: MOD_RES
<222> LOCATION: (7)..(7)
<223> OTHER INFORMATION: T, P, or V
<220> FEATURE:
<221> NAME/KEY: MOD_RES
<222> LOCATION: (8)..(8)
<223> OTHER INFORMATION: A, S, or T
<220> FEATURE:
<221> NAME/KEY: MOD_RES
<222> LOCATION: (9)..(9)
<223> OTHER INFORMATION: G, N, S, or T
<220> FEATURE:
<221> NAME/KEY: MOD_RES
<222> LOCATION: (10)..(10)
<223> OTHER INFORMATION: May or may not be present
<220> FEATURE:
<221> NAME/KEY: MOD_RES
<222> LOCATION: (11)..(11)
<223> OTHER INFORMATION: S, G, or A
<220> FEATURE:
<221> NAME/KEY: MOD_RES
<222> LOCATION: (12)..(12)
<223> OTHER INFORMATION: S or N
<220> FEATURE:
<221> NAME/KEY: MOD_RES
<222> LOCATION: (14)..(14)
<223> OTHER INFORMATION: V, T, or A
<220> FEATURE:
<221> NAME/KEY: MOD_RES
<222> LOCATION: (17)..(17)
<223> OTHER INFORMATION: Q, T, or E
<220> FEATURE:
<221> NAME/KEY: MOD_RES
<222> LOCATION: (18)..(18)
<223> OTHER INFORMATION: E, Q, or T
<220> FEATURE:
<221> NAME/KEY: MOD_RES
<222> LOCATION: (20)..(20)
<223> OTHER INFORMATION: S, N, A, or G
<220> FEATURE:
<221> NAME/KEY: MOD_RES
<222> LOCATION: (21)..(21)
<223> OTHER INFORMATION: May or may not be present
<220> FEATURE:
<221> NAME/KEY: MOD_RES
<222> LOCATION: (22)..(22)
<223> OTHER INFORMATION: May or may not be present
<220> FEATURE:
<221> NAME/KEY: MOD_RES
<222> LOCATION: (25)..(25)
<223> OTHER INFORMATION: N, S, or A
<220> FEATURE:
<221> NAME/KEY: MOD_RES
<222> LOCATION: (26)..(26)
<223> OTHER INFORMATION: A, S, or K
<220> FEATURE:
<221> NAME/KEY: MOD_RES
<222> LOCATION: (28)..(28)
<223> OTHER INFORMATION: T, S, or K
<220> FEATURE:
<221> NAME/KEY: MOD_RES
<222> LOCATION: (31)..(31)
<223> OTHER INFORMATION: A or E
<220> FEATURE:
```

```
<221> NAME/KEY: MOD_RES
<222> LOCATION: (32)..(32)
<223> OTHER INFORMATION: T or S
<220> FEATURE:
<221> NAME/KEY: MOD_RES
<222> LOCATION: (34)..(34)
<223> OTHER INFORMATION: T, Q, or A
<220> FEATURE:
<221> NAME/KEY: MOD_RES
<222> LOCATION: (36)..(36)
<223> OTHER INFORMATION: G, S, or T
<220> FEATURE:
<221> NAME/KEY: MOD_RES
<222> LOCATION: (37)..(37)
<223> OTHER INFORMATION: A, G, or D
<220> FEATURE:
<221> NAME/KEY: MOD_RES
<222> LOCATION: (38)..(38)
<223> OTHER INFORMATION: S, L, or A
<220> FEATURE:
<221> NAME/KEY: MOD_RES
<222> LOCATION: (39)..(39)
<223> OTHER INFORMATION: S, G, D, or T
<220> FEATURE:
<221> NAME/KEY: MOD_RES
<222> LOCATION: (40)..(40)
<223> OTHER INFORMATION: A, V, or G
<220> FEATURE:
<221> NAME/KEY: MOD_RES
<222> LOCATION: (41)..(41)
<223> OTHER INFORMATION: G, I, or V
<220> FEATURE:
<221> NAME/KEY: MOD_RES
<222> LOCATION: (42)..(42)
<223> OTHER INFORMATION: Q, T, or I
<220> FEATURE:
<221> NAME/KEY: MOD_RES
<222> LOCATION: (43)..(43)
<223> OTHER INFORMATION: I, V, T, or L
<220> FEATURE:
<221> NAME/KEY: MOD_RES
<222> LOCATION: (44)..(44)
<223> OTHER INFORMATION: I, T, or V

<400> SEQUENCE: 27

Xaa Xaa Gly Thr Xaa Xaa Xaa Xaa Xaa Asn Xaa Xaa Cys Xaa Gly Val
1               5                   10                  15

Xaa Xaa Ile Xaa Ser Gly Ala Ser Xaa Xaa Thr Xaa Asn Val Xaa Xaa
            20                  25                  30

Ala Xaa Cys Xaa Xaa Xaa Xaa Xaa Xaa Xaa Xaa Xaa
        35                  40

<210> SEQ ID NO 28
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: V, T, or A
<220> FEATURE:
<221> NAME/KEY: MOD_RES
<222> LOCATION: (5)..(5)
<223> OTHER INFORMATION: Q, T, or E
<220> FEATURE:
<221> NAME/KEY: MOD_RES
<222> LOCATION: (6)..(6)
<223> OTHER INFORMATION: E, Q, or T
<220> FEATURE:
<221> NAME/KEY: MOD_RES
<222> LOCATION: (8)..(8)
<223> OTHER INFORMATION: S, N, A, or G
```

```
<220> FEATURE:
<221> NAME/KEY: MOD_RES
<222> LOCATION: (9)..(9)
<223> OTHER INFORMATION: May or may not be present
<220> FEATURE:
<221> NAME/KEY: MOD_RES
<222> LOCATION: (10)..(10)
<223> OTHER INFORMATION: May or may not be present
<220> FEATURE:
<221> NAME/KEY: MOD_RES
<222> LOCATION: (13)..(13)
<223> OTHER INFORMATION: N, S, or A
<220> FEATURE:
<221> NAME/KEY: MOD_RES
<222> LOCATION: (14)..(14)
<223> OTHER INFORMATION: A, S, or K
<220> FEATURE:
<221> NAME/KEY: MOD_RES
<222> LOCATION: (16)..(16)
<223> OTHER INFORMATION: T, S, or K
<220> FEATURE:
<221> NAME/KEY: MOD_RES
<222> LOCATION: (19)..(19)
<223> OTHER INFORMATION: A or E
<220> FEATURE:
<221> NAME/KEY: MOD_RES
<222> LOCATION: (20)..(20)
<223> OTHER INFORMATION: T or S
<220> FEATURE:
<221> NAME/KEY: MOD_RES
<222> LOCATION: (22)..(22)
<223> OTHER INFORMATION: T, Q, or A
<220> FEATURE:
<223> OTHER INFORMATION: See specification as filed for detailed
      description of substitutions and preferred embodiments

<400> SEQUENCE: 28

Cys Xaa Gly Val Xaa Xaa Ile Xaa Ser Gly Ala Ser Xaa Xaa Thr Xaa
1               5                   10                  15

Asn Val Xaa Xaa Ala Xaa Cys
            20

<210> SEQ ID NO 29
<211> LENGTH: 117
<212> TYPE: PRT
<213> ORGANISM: Acinetobacter soli

<400> SEQUENCE: 29

Ala Tyr Thr Asp Tyr Thr Val Arg Ser Arg Val Thr Glu Gly Leu Thr
1               5                   10                  15

Thr Ala Ser Ala Met Lys Ala Thr Val Ser Glu Asn Ile Met Asn Ala
            20                  25                  30

Gly Gly Thr Ser Met Pro Ser Ser Gly Asn Cys Thr Gly Val Thr Gln
        35                  40                  45

Ile Ala Ser Gly Ala Ser Ala Ala Thr Thr Asn Val Ala Ser Ala Gln
    50                  55                  60

Cys Ser Asp Ser Asp Gly Val Ile Thr Val Thr Met Thr Asp Lys Ala
65                  70                  75                  80

Lys Gly Val Ser Ile Lys Leu Thr Pro Ser Phe Ser Ser Thr Gly Ser
                85                  90                  95

Val Gly Trp Lys Cys Thr Thr Ser Ser Asp Lys Lys Tyr Val Pro Ser
            100                 105                 110

Glu Cys Arg Gly Thr
        115

<210> SEQ ID NO 30
<211> LENGTH: 25
```

```
<212> TYPE: PRT
<213> ORGANISM: Acinetobacter soli

<400> SEQUENCE: 30

Ser Ser Gly Asn Cys Thr Gly Val Thr Gln Ile Ala Ser Gly Ala Ser
1               5                   10                  15

Ala Ala Thr Thr Asn Val Ala Ser Ala
            20                  25

<210> SEQ ID NO 31
<211> LENGTH: 25
<212> TYPE: PRT
<213> ORGANISM: Acinetobacter soli

<400> SEQUENCE: 31

Ser Gly Asn Cys Thr Gly Val Thr Gln Ile Ala Ser Gly Ala Ser Ala
1               5                   10                  15

Ala Thr Thr Asn Val Ala Ser Ala Gln
            20                  25

<210> SEQ ID NO 32
<211> LENGTH: 25
<212> TYPE: PRT
<213> ORGANISM: Acinetobacter soli

<400> SEQUENCE: 32

Gly Asn Cys Thr Gly Val Thr Gln Ile Ala Ser Gly Ala Ser Ala Ala
1               5                   10                  15

Thr Thr Asn Val Ala Ser Ala Gln Cys
            20                  25

<210> SEQ ID NO 33
<211> LENGTH: 25
<212> TYPE: PRT
<213> ORGANISM: Acinetobacter soli

<400> SEQUENCE: 33

Asn Cys Thr Gly Val Thr Gln Ile Ala Ser Gly Ala Ser Ala Ala Thr
1               5                   10                  15

Thr Asn Val Ala Ser Ala Gln Cys Ser
            20                  25

<210> SEQ ID NO 34
<211> LENGTH: 25
<212> TYPE: PRT
<213> ORGANISM: Acinetobacter soli

<400> SEQUENCE: 34

Cys Thr Gly Val Thr Gln Ile Ala Ser Gly Ala Ser Ala Ala Thr Thr
1               5                   10                  15

Asn Val Ala Ser Ala Gln Cys Ser Asp
            20                  25

<210> SEQ ID NO 35
<211> LENGTH: 25
<212> TYPE: PRT
<213> ORGANISM: Acinetobacter soli

<400> SEQUENCE: 35

Thr Gly Val Thr Gln Ile Ala Ser Gly Ala Ser Ala Ala Thr Thr Asn
1               5                   10                  15
```

```
Val Ala Ser Ala Gln Cys Ser Asp Ser
            20                  25

<210> SEQ ID NO 36
<211> LENGTH: 25
<212> TYPE: PRT
<213> ORGANISM: Acinetobacter soli

<400> SEQUENCE: 36

Gly Val Thr Gln Ile Ala Ser Gly Ala Ser Ala Ala Thr Thr Asn Val
1               5                   10                  15

Ala Ser Ala Gln Cys Ser Asp Ser Asp
            20                  25

<210> SEQ ID NO 37
<211> LENGTH: 25
<212> TYPE: PRT
<213> ORGANISM: Acinetobacter soli

<400> SEQUENCE: 37

Val Thr Gln Ile Ala Ser Gly Ala Ser Ala Ala Thr Thr Asn Val Ala
1               5                   10                  15

Ser Ala Gln Cys Ser Asp Ser Asp Gly
            20                  25

<210> SEQ ID NO 38
<211> LENGTH: 25
<212> TYPE: PRT
<213> ORGANISM: Acinetobacter soli

<400> SEQUENCE: 38

Thr Gln Ile Ala Ser Gly Ala Ser Ala Ala Thr Thr Asn Val Ala Ser
1               5                   10                  15

Ala Gln Cys Ser Asp Ser Asp Gly Val
            20                  25

<210> SEQ ID NO 39
<211> LENGTH: 30
<212> TYPE: PRT
<213> ORGANISM: Acinetobacter soli

<400> SEQUENCE: 39

Gly Thr Ser Met Pro Ser Ser Gly Asn Cys Thr Gly Val Thr Gln Ile
1               5                   10                  15

Ala Ser Gly Ala Ser Ala Ala Thr Thr Asn Val Ala Ser Ala
            20                  25                  30

<210> SEQ ID NO 40
<211> LENGTH: 30
<212> TYPE: PRT
<213> ORGANISM: Acinetobacter soli

<400> SEQUENCE: 40

Thr Ser Met Pro Ser Ser Gly Asn Cys Thr Gly Val Thr Gln Ile Ala
1               5                   10                  15

Ser Gly Ala Ser Ala Ala Thr Thr Asn Val Ala Ser Ala Gln
            20                  25                  30

<210> SEQ ID NO 41
<211> LENGTH: 30
<212> TYPE: PRT
<213> ORGANISM: Acinetobacter soli
```

```
<400> SEQUENCE: 41

Ser Met Pro Ser Ser Gly Asn Cys Thr Gly Val Thr Gln Ile Ala Ser
1               5                   10                  15

Gly Ala Ser Ala Ala Thr Thr Asn Val Ala Ser Ala Gln Cys
            20                  25                  30

<210> SEQ ID NO 42
<211> LENGTH: 30
<212> TYPE: PRT
<213> ORGANISM: Acinetobacter soli

<400> SEQUENCE: 42

Met Pro Ser Ser Gly Asn Cys Thr Gly Val Thr Gln Ile Ala Ser Gly
1               5                   10                  15

Ala Ser Ala Ala Thr Thr Asn Val Ala Ser Ala Gln Cys Ser
            20                  25                  30

<210> SEQ ID NO 43
<211> LENGTH: 30
<212> TYPE: PRT
<213> ORGANISM: Acinetobacter soli

<400> SEQUENCE: 43

Pro Ser Ser Gly Asn Cys Thr Gly Val Thr Gln Ile Ala Ser Gly Ala
1               5                   10                  15

Ser Ala Ala Thr Thr Asn Val Ala Ser Ala Gln Cys Ser Asp
            20                  25                  30

<210> SEQ ID NO 44
<211> LENGTH: 30
<212> TYPE: PRT
<213> ORGANISM: Acinetobacter soli

<400> SEQUENCE: 44

Ser Ser Gly Asn Cys Thr Gly Val Thr Gln Ile Ala Ser Gly Ala Ser
1               5                   10                  15

Ala Ala Thr Thr Asn Val Ala Ser Ala Gln Cys Ser Asp Ser
            20                  25                  30

<210> SEQ ID NO 45
<211> LENGTH: 30
<212> TYPE: PRT
<213> ORGANISM: Acinetobacter soli

<400> SEQUENCE: 45

Ser Gly Asn Cys Thr Gly Val Thr Gln Ile Ala Ser Gly Ala Ser Ala
1               5                   10                  15

Ala Thr Thr Asn Val Ala Ser Ala Gln Cys Ser Asp Ser Asp
            20                  25                  30

<210> SEQ ID NO 46
<211> LENGTH: 30
<212> TYPE: PRT
<213> ORGANISM: Acinetobacter soli

<400> SEQUENCE: 46

Gly Asn Cys Thr Gly Val Thr Gln Ile Ala Ser Gly Ala Ser Ala Ala
1               5                   10                  15

Thr Thr Asn Val Ala Ser Ala Gln Cys Ser Asp Ser Asp Gly
            20                  25                  30
```

<210> SEQ ID NO 47
<211> LENGTH: 30
<212> TYPE: PRT
<213> ORGANISM: Acinetobacter soli

<400> SEQUENCE: 47

Asn Cys Thr Gly Val Thr Gln Ile Ala Ser Gly Ala Ser Ala Ala Thr
1               5                   10                  15

Thr Asn Val Ala Ser Ala Gln Cys Ser Asp Ser Asp Gly Val
            20                  25                  30

<210> SEQ ID NO 48
<211> LENGTH: 30
<212> TYPE: PRT
<213> ORGANISM: Acinetobacter soli

<400> SEQUENCE: 48

Thr Gly Val Thr Gln Ile Ala Ser Gly Ala Ser Ala Ala Thr Thr Asn
1               5                   10                  15

Val Ala Ser Ala Gln Cys Ser Asp Ser Asp Gly Val Ile Thr
            20                  25                  30

<210> SEQ ID NO 49
<211> LENGTH: 30
<212> TYPE: PRT
<213> ORGANISM: Acinetobacter soli

<400> SEQUENCE: 49

Gly Val Thr Gln Ile Ala Ser Gly Ala Ser Ala Ala Thr Thr Asn Val
1               5                   10                  15

Ala Ser Ala Gln Cys Ser Asp Ser Asp Gly Val Ile Thr Val
            20                  25                  30

<210> SEQ ID NO 50
<211> LENGTH: 30
<212> TYPE: PRT
<213> ORGANISM: Acinetobacter soli

<400> SEQUENCE: 50

Val Thr Gln Ile Ala Ser Gly Ala Ser Ala Ala Thr Thr Asn Val Ala
1               5                   10                  15

Ser Ala Gln Cys Ser Asp Ser Asp Gly Val Ile Thr Val Thr
            20                  25                  30

<210> SEQ ID NO 51
<211> LENGTH: 30
<212> TYPE: PRT
<213> ORGANISM: Acinetobacter soli

<400> SEQUENCE: 51

Thr Gln Ile Ala Ser Gly Ala Ser Ala Ala Thr Thr Asn Val Ala Ser
1               5                   10                  15

Ala Gln Cys Ser Asp Ser Asp Gly Val Ile Thr Val Thr Met
            20                  25                  30

<210> SEQ ID NO 52
<211> LENGTH: 30
<212> TYPE: PRT
<213> ORGANISM: Acinetobacter soli

```
<400> SEQUENCE: 52

Gln Ile Ala Ser Gly Ala Ser Ala Ala Thr Thr Asn Val Ala Ser Ala
1               5                   10                  15

Gln Cys Ser Asp Ser Asp Gly Val Ile Thr Val Thr Met Thr
            20                  25                  30

<210> SEQ ID NO 53
<211> LENGTH: 35
<212> TYPE: PRT
<213> ORGANISM: Acinetobacter soli

<400> SEQUENCE: 53

Ile Met Asn Ala Gly Gly Thr Ser Met Pro Ser Ser Gly Asn Cys Thr
1               5                   10                  15

Gly Val Thr Gln Ile Ala Ser Gly Ala Ser Ala Ala Thr Thr Asn Val
            20                  25                  30

Ala Ser Ala
        35

<210> SEQ ID NO 54
<211> LENGTH: 35
<212> TYPE: PRT
<213> ORGANISM: Acinetobacter soli

<400> SEQUENCE: 54

Met Asn Ala Gly Gly Thr Ser Met Pro Ser Ser Gly Asn Cys Thr Gly
1               5                   10                  15

Val Thr Gln Ile Ala Ser Gly Ala Ser Ala Ala Thr Thr Asn Val Ala
            20                  25                  30

Ser Ala Gln
        35

<210> SEQ ID NO 55
<211> LENGTH: 35
<212> TYPE: PRT
<213> ORGANISM: Acinetobacter soli

<400> SEQUENCE: 55

Asn Ala Gly Gly Thr Ser Met Pro Ser Ser Gly Asn Cys Thr Gly Val
1               5                   10                  15

Thr Gln Ile Ala Ser Gly Ala Ser Ala Ala Thr Thr Asn Val Ala Ser
            20                  25                  30

Ala Gln Cys
        35

<210> SEQ ID NO 56
<211> LENGTH: 35
<212> TYPE: PRT
<213> ORGANISM: Acinetobacter soli

<400> SEQUENCE: 56

Ala Gly Gly Thr Ser Met Pro Ser Ser Gly Asn Cys Thr Gly Val Thr
1               5                   10                  15

Gln Ile Ala Ser Gly Ala Ser Ala Ala Thr Thr Asn Val Ala Ser Ala
            20                  25                  30

Gln Cys Ser
        35

<210> SEQ ID NO 57
```

```
<211> LENGTH: 35
<212> TYPE: PRT
<213> ORGANISM: Acinetobacter soli

<400> SEQUENCE: 57

Gly Gly Thr Ser Met Pro Ser Ser Gly Asn Cys Thr Gly Val Thr Gln
1               5                   10                  15

Ile Ala Ser Gly Ala Ser Ala Ala Thr Thr Asn Val Ala Ser Ala Gln
            20                  25                  30

Cys Ser Asp
        35

<210> SEQ ID NO 58
<211> LENGTH: 35
<212> TYPE: PRT
<213> ORGANISM: Acinetobacter soli

<400> SEQUENCE: 58

Gly Thr Ser Met Pro Ser Ser Gly Asn Cys Thr Gly Val Thr Gln Ile
1               5                   10                  15

Ala Ser Gly Ala Ser Ala Ala Thr Thr Asn Val Ala Ser Ala Gln Cys
            20                  25                  30

Ser Asp Ser
        35

<210> SEQ ID NO 59
<211> LENGTH: 35
<212> TYPE: PRT
<213> ORGANISM: Acinetobacter soli

<400> SEQUENCE: 59

Ser Met Pro Ser Ser Gly Asn Cys Thr Gly Val Thr Gln Ile Ala Ser
1               5                   10                  15

Gly Ala Ser Ala Ala Thr Thr Asn Val Ala Ser Ala Gln Cys Ser Asp
            20                  25                  30

Ser Asp Gly
        35

<210> SEQ ID NO 60
<211> LENGTH: 35
<212> TYPE: PRT
<213> ORGANISM: Acinetobacter soli

<400> SEQUENCE: 60

Met Pro Ser Ser Gly Asn Cys Thr Gly Val Thr Gln Ile Ala Ser Gly
1               5                   10                  15

Ala Ser Ala Ala Thr Thr Asn Val Ala Ser Ala Gln Cys Ser Asp Ser
            20                  25                  30

Asp Gly Val
        35

<210> SEQ ID NO 61
<211> LENGTH: 35
<212> TYPE: PRT
<213> ORGANISM: Acinetobacter soli

<400> SEQUENCE: 61

Ser Ser Gly Asn Cys Thr Gly Val Thr Gln Ile Ala Ser Gly Ala Ser
1               5                   10                  15

Ala Ala Thr Thr Asn Val Ala Ser Ala Gln Cys Ser Asp Ser Asp Gly
            20                  25                  30
```

Val Ile Thr
        35

<210> SEQ ID NO 62
<211> LENGTH: 35
<212> TYPE: PRT
<213> ORGANISM: Acinetobacter soli

<400> SEQUENCE: 62

Ser Gly Asn Cys Thr Gly Val Thr Gln Ile Ala Ser Gly Ala Ser Ala
1               5                   10                  15

Ala Thr Thr Asn Val Ala Ser Ala Gln Cys Ser Asp Ser Asp Gly Val
            20                  25                  30

Ile Thr Val
        35

<210> SEQ ID NO 63
<211> LENGTH: 35
<212> TYPE: PRT
<213> ORGANISM: Acinetobacter soli

<400> SEQUENCE: 63

Gly Asn Cys Thr Gly Val Thr Gln Ile Ala Ser Gly Ala Ser Ala Ala
1               5                   10                  15

Thr Thr Asn Val Ala Ser Ala Gln Cys Ser Asp Ser Asp Gly Val Ile
            20                  25                  30

Thr Val Thr
        35

<210> SEQ ID NO 64
<211> LENGTH: 35
<212> TYPE: PRT
<213> ORGANISM: Acinetobacter soli

<400> SEQUENCE: 64

Asn Cys Thr Gly Val Thr Gln Ile Ala Ser Gly Ala Ser Ala Ala Thr
1               5                   10                  15

Thr Asn Val Ala Ser Ala Gln Cys Ser Asp Ser Asp Gly Val Ile Thr
            20                  25                  30

Val Thr Met
        35

<210> SEQ ID NO 65
<211> LENGTH: 35
<212> TYPE: PRT
<213> ORGANISM: Acinetobacter soli

<400> SEQUENCE: 65

Cys Thr Gly Val Thr Gln Ile Ala Ser Gly Ala Ser Ala Ala Thr Thr
1               5                   10                  15

Asn Val Ala Ser Ala Gln Cys Ser Asp Ser Asp Gly Val Ile Thr Val
            20                  25                  30

Thr Met Thr
        35

<210> SEQ ID NO 66
<211> LENGTH: 35
<212> TYPE: PRT
<213> ORGANISM: Acinetobacter soli

```
<400> SEQUENCE: 66

Thr Gly Val Thr Gln Ile Ala Ser Gly Ala Ser Ala Thr Thr Asn
1               5                   10                  15

Val Ala Ser Ala Gln Cys Ser Asp Ser Asp Gly Val Ile Thr Val Thr
            20                  25                  30

Met Thr Asp
        35

<210> SEQ ID NO 67
<211> LENGTH: 35
<212> TYPE: PRT
<213> ORGANISM: Acinetobacter soli

<400> SEQUENCE: 67

Gly Val Thr Gln Ile Ala Ser Gly Ala Ser Ala Thr Thr Asn Val
1               5                   10                  15

Ala Ser Ala Gln Cys Ser Asp Ser Asp Gly Val Ile Thr Val Thr Met
            20                  25                  30

Thr Asp Lys
        35

<210> SEQ ID NO 68
<211> LENGTH: 35
<212> TYPE: PRT
<213> ORGANISM: Acinetobacter soli

<400> SEQUENCE: 68

Val Thr Gln Ile Ala Ser Gly Ala Ser Ala Thr Thr Asn Val Ala
1               5                   10                  15

Ser Ala Gln Cys Ser Asp Ser Asp Gly Val Ile Thr Val Thr Met Thr
            20                  25                  30

Asp Lys Ala
        35

<210> SEQ ID NO 69
<211> LENGTH: 35
<212> TYPE: PRT
<213> ORGANISM: Acinetobacter soli

<400> SEQUENCE: 69

Thr Gln Ile Ala Ser Gly Ala Ser Ala Thr Thr Asn Val Ala Ser
1               5                   10                  15

Ala Gln Cys Ser Asp Ser Asp Gly Val Ile Thr Val Thr Met Thr Asp
            20                  25                  30

Lys Ala Lys
        35

<210> SEQ ID NO 70
<211> LENGTH: 40
<212> TYPE: PRT
<213> ORGANISM: Acinetobacter soli

<400> SEQUENCE: 70

Thr Val Ser Glu Asn Ile Met Asn Ala Gly Gly Thr Ser Met Pro Ser
1               5                   10                  15

Ser Gly Asn Cys Thr Gly Val Thr Gln Ile Ala Ser Gly Ala Ser Ala
            20                  25                  30

Ala Thr Thr Asn Val Ala Ser Ala
        35                  40
```

<210> SEQ ID NO 71
<211> LENGTH: 40
<212> TYPE: PRT
<213> ORGANISM: Acinetobacter soli

<400> SEQUENCE: 71

Val Ser Glu Asn Ile Met Asn Ala Gly Gly Thr Ser Met Pro Ser Ser
1               5                   10                  15

Gly Asn Cys Thr Gly Val Thr Gln Ile Ala Ser Gly Ala Ser Ala Ala
            20                  25                  30

Thr Thr Asn Val Ala Ser Ala Gln
        35                  40

<210> SEQ ID NO 72
<211> LENGTH: 40
<212> TYPE: PRT
<213> ORGANISM: Acinetobacter soli

<400> SEQUENCE: 72

Ser Glu Asn Ile Met Asn Ala Gly Gly Thr Ser Met Pro Ser Ser Gly
1               5                   10                  15

Asn Cys Thr Gly Val Thr Gln Ile Ala Ser Gly Ala Ser Ala Ala Thr
            20                  25                  30

Thr Asn Val Ala Ser Ala Gln Cys
        35                  40

<210> SEQ ID NO 73
<211> LENGTH: 40
<212> TYPE: PRT
<213> ORGANISM: Acinetobacter soli

<400> SEQUENCE: 73

Asn Ile Met Asn Ala Gly Gly Thr Ser Met Pro Ser Ser Gly Asn Cys
1               5                   10                  15

Thr Gly Val Thr Gln Ile Ala Ser Gly Ala Ser Ala Ala Thr Thr Asn
            20                  25                  30

Val Ala Ser Ala Gln Cys Ser Asp
        35                  40

<210> SEQ ID NO 74
<211> LENGTH: 40
<212> TYPE: PRT
<213> ORGANISM: Acinetobacter soli

<400> SEQUENCE: 74

Ile Met Asn Ala Gly Gly Thr Ser Met Pro Ser Ser Gly Asn Cys Thr
1               5                   10                  15

Gly Val Thr Gln Ile Ala Ser Gly Ala Ser Ala Ala Thr Thr Asn Val
            20                  25                  30

Ala Ser Ala Gln Cys Ser Asp Ser
        35                  40

<210> SEQ ID NO 75
<211> LENGTH: 40
<212> TYPE: PRT
<213> ORGANISM: Acinetobacter soli

<400> SEQUENCE: 75

Met Asn Ala Gly Gly Thr Ser Met Pro Ser Ser Gly Asn Cys Thr Gly
1               5                   10                  15

Val Thr Gln Ile Ala Ser Gly Ala Ser Ala Ala Thr Thr Asn Val Ala
            20                  25                  30

Ser Ala Gln Cys Ser Asp Ser Asp
            35                  40

<210> SEQ ID NO 76
<211> LENGTH: 40
<212> TYPE: PRT
<213> ORGANISM: Acinetobacter soli

<400> SEQUENCE: 76

Asn Ala Gly Gly Thr Ser Met Pro Ser Ser Gly Asn Cys Thr Gly Val
1               5                   10                  15

Thr Gln Ile Ala Ser Gly Ala Ser Ala Ala Thr Thr Asn Val Ala Ser
            20                  25                  30

Ala Gln Cys Ser Asp Ser Asp Gly
            35                  40

<210> SEQ ID NO 77
<211> LENGTH: 40
<212> TYPE: PRT
<213> ORGANISM: Acinetobacter soli

<400> SEQUENCE: 77

Ala Gly Gly Thr Ser Met Pro Ser Ser Gly Asn Cys Thr Gly Val Thr
1               5                   10                  15

Gln Ile Ala Ser Gly Ala Ser Ala Ala Thr Thr Asn Val Ala Ser Ala
            20                  25                  30

Gln Cys Ser Asp Ser Asp Gly Val
            35                  40

<210> SEQ ID NO 78
<211> LENGTH: 40
<212> TYPE: PRT
<213> ORGANISM: Acinetobacter soli

<400> SEQUENCE: 78

Thr Ser Met Pro Ser Ser Gly Asn Cys Thr Gly Val Thr Gln Ile Ala
1               5                   10                  15

Ser Gly Ala Ser Ala Ala Thr Thr Asn Val Ala Ser Ala Gln Cys Ser
            20                  25                  30

Asp Ser Asp Gly Val Ile Thr Val
            35                  40

<210> SEQ ID NO 79
<211> LENGTH: 40
<212> TYPE: PRT
<213> ORGANISM: Acinetobacter soli

<400> SEQUENCE: 79

Ser Met Pro Ser Ser Gly Asn Cys Thr Gly Val Thr Gln Ile Ala Ser
1               5                   10                  15

Gly Ala Ser Ala Ala Thr Thr Asn Val Ala Ser Ala Gln Cys Ser Asp
            20                  25                  30

Ser Asp Gly Val Ile Thr Val Thr
            35                  40

<210> SEQ ID NO 80
<211> LENGTH: 40
<212> TYPE: PRT

-continued

<213> ORGANISM: Acinetobacter soli

<400> SEQUENCE: 80

Met Pro Ser Ser Gly Asn Cys Thr Gly Val Thr Gln Ile Ala Ser Gly
1               5                   10                  15

Ala Ser Ala Ala Thr Thr Asn Val Ala Ser Ala Gln Cys Ser Asp Ser
            20                  25                  30

Asp Gly Val Ile Thr Val Thr Met
        35                  40

<210> SEQ ID NO 81
<211> LENGTH: 40
<212> TYPE: PRT
<213> ORGANISM: Acinetobacter soli

<400> SEQUENCE: 81

Pro Ser Ser Gly Asn Cys Thr Gly Val Thr Gln Ile Ala Ser Gly Ala
1               5                   10                  15

Ser Ala Ala Thr Thr Asn Val Ala Ser Ala Gln Cys Ser Asp Ser Asp
            20                  25                  30

Gly Val Ile Thr Val Thr Met Thr
        35                  40

<210> SEQ ID NO 82
<211> LENGTH: 40
<212> TYPE: PRT
<213> ORGANISM: Acinetobacter soli

<400> SEQUENCE: 82

Ser Ser Gly Asn Cys Thr Gly Val Thr Gln Ile Ala Ser Gly Ala Ser
1               5                   10                  15

Ala Ala Thr Thr Asn Val Ala Ser Ala Gln Cys Ser Asp Ser Asp Gly
            20                  25                  30

Val Ile Thr Val Thr Met Thr Asp
        35                  40

<210> SEQ ID NO 83
<211> LENGTH: 40
<212> TYPE: PRT
<213> ORGANISM: Acinetobacter soli

<400> SEQUENCE: 83

Ser Gly Asn Cys Thr Gly Val Thr Gln Ile Ala Ser Gly Ala Ser Ala
1               5                   10                  15

Ala Thr Thr Asn Val Ala Ser Ala Gln Cys Ser Asp Ser Asp Gly Val
            20                  25                  30

Ile Thr Val Thr Met Thr Asp Lys
        35                  40

<210> SEQ ID NO 84
<211> LENGTH: 40
<212> TYPE: PRT
<213> ORGANISM: Acinetobacter soli

<400> SEQUENCE: 84

Gly Asn Cys Thr Gly Val Thr Gln Ile Ala Ser Gly Ala Ser Ala Ala
1               5                   10                  15

Thr Thr Asn Val Ala Ser Ala Gln Cys Ser Asp Ser Asp Gly Val Ile
            20                  25                  30

```
Thr Val Thr Met Thr Asp Lys Ala
        35                  40

<210> SEQ ID NO 85
<211> LENGTH: 40
<212> TYPE: PRT
<213> ORGANISM: Acinetobacter soli

<400> SEQUENCE: 85

Asn Cys Thr Gly Val Thr Gln Ile Ala Ser Gly Ala Ser Ala Ala Thr
1               5                   10                  15

Thr Asn Val Ala Ser Ala Gln Cys Ser Asp Ser Asp Gly Val Ile Thr
            20                  25                  30

Val Thr Met Thr Asp Lys Ala Lys
        35                  40

<210> SEQ ID NO 86
<211> LENGTH: 40
<212> TYPE: PRT
<213> ORGANISM: Acinetobacter soli

<400> SEQUENCE: 86

Cys Thr Gly Val Thr Gln Ile Ala Ser Gly Ala Ser Ala Ala Thr Thr
1               5                   10                  15

Asn Val Ala Ser Ala Gln Cys Ser Asp Ser Asp Gly Val Ile Thr Val
            20                  25                  30

Thr Met Thr Asp Lys Ala Lys Gly
        35                  40

<210> SEQ ID NO 87
<211> LENGTH: 40
<212> TYPE: PRT
<213> ORGANISM: Acinetobacter soli

<400> SEQUENCE: 87

Thr Gly Val Thr Gln Ile Ala Ser Gly Ala Ser Ala Ala Thr Thr Asn
1               5                   10                  15

Val Ala Ser Ala Gln Cys Ser Asp Ser Asp Gly Val Ile Thr Val Thr
            20                  25                  30

Met Thr Asp Lys Ala Lys Gly Val
        35                  40

<210> SEQ ID NO 88
<211> LENGTH: 40
<212> TYPE: PRT
<213> ORGANISM: Acinetobacter soli

<400> SEQUENCE: 88

Gly Val Thr Gln Ile Ala Ser Gly Ala Ser Ala Ala Thr Thr Asn Val
1               5                   10                  15

Ala Ser Ala Gln Cys Ser Asp Ser Asp Gly Val Ile Thr Val Thr Met
            20                  25                  30

Thr Asp Lys Ala Lys Gly Val Ser
        35                  40

<210> SEQ ID NO 89
<211> LENGTH: 40
<212> TYPE: PRT
<213> ORGANISM: Acinetobacter soli
```

<400> SEQUENCE: 89

Val Thr Gln Ile Ala Ser Gly Ala Ser Ala Thr Thr Asn Val Ala
1               5                   10                  15

Ser Ala Gln Cys Ser Asp Ser Asp Gly Val Ile Thr Val Thr Met Thr
            20                  25                  30

Asp Lys Ala Lys Gly Val Ser Ile
        35                  40

<210> SEQ ID NO 90
<211> LENGTH: 40
<212> TYPE: PRT
<213> ORGANISM: Acinetobacter soli

<400> SEQUENCE: 90

Thr Gln Ile Ala Ser Gly Ala Ser Ala Thr Thr Asn Val Ala Ser
1               5                   10                  15

Ala Gln Cys Ser Asp Ser Asp Gly Val Ile Thr Val Thr Met Thr Asp
            20                  25                  30

Lys Ala Lys Gly Val Ser Ile Lys
        35                  40

<210> SEQ ID NO 91
<211> LENGTH: 45
<212> TYPE: PRT
<213> ORGANISM: Acinetobacter soli

<400> SEQUENCE: 91

Ala Met Lys Ala Thr Val Ser Glu Asn Ile Met Asn Ala Gly Gly Thr
1               5                   10                  15

Ser Met Pro Ser Ser Gly Asn Cys Thr Gly Val Thr Gln Ile Ala Ser
            20                  25                  30

Gly Ala Ser Ala Ala Thr Thr Asn Val Ala Ser Ala Gln
        35                  40                  45

<210> SEQ ID NO 92
<211> LENGTH: 45
<212> TYPE: PRT
<213> ORGANISM: Acinetobacter soli

<400> SEQUENCE: 92

Met Lys Ala Thr Val Ser Glu Asn Ile Met Asn Ala Gly Gly Thr Ser
1               5                   10                  15

Met Pro Ser Ser Gly Asn Cys Thr Gly Val Thr Gln Ile Ala Ser Gly
            20                  25                  30

Ala Ser Ala Ala Thr Thr Asn Val Ala Ser Ala Gln Cys
        35                  40                  45

<210> SEQ ID NO 93
<211> LENGTH: 45
<212> TYPE: PRT
<213> ORGANISM: Acinetobacter soli

<400> SEQUENCE: 93

Lys Ala Thr Val Ser Glu Asn Ile Met Asn Ala Gly Gly Thr Ser Met
1               5                   10                  15

Pro Ser Ser Gly Asn Cys Thr Gly Val Thr Gln Ile Ala Ser Gly Ala
            20                  25                  30

Ser Ala Ala Thr Thr Asn Val Ala Ser Ala Gln Cys Ser
        35                  40                  45

<210> SEQ ID NO 94
<211> LENGTH: 45
<212> TYPE: PRT
<213> ORGANISM: Acinetobacter soli

<400> SEQUENCE: 94

Ala Thr Val Ser Glu Asn Ile Met Asn Ala Gly Gly Thr Ser Met Pro
1               5                   10                  15

Ser Ser Gly Asn Cys Thr Gly Val Thr Gln Ile Ala Ser Gly Ala Ser
            20                  25                  30

Ala Ala Thr Thr Asn Val Ala Ser Ala Gln Cys Ser Asp
        35                  40                  45

<210> SEQ ID NO 95
<211> LENGTH: 45
<212> TYPE: PRT
<213> ORGANISM: Acinetobacter soli

<400> SEQUENCE: 95

Thr Val Ser Glu Asn Ile Met Asn Ala Gly Gly Thr Ser Met Pro Ser
1               5                   10                  15

Ser Gly Asn Cys Thr Gly Val Thr Gln Ile Ala Ser Gly Ala Ser Ala
            20                  25                  30

Ala Thr Thr Asn Val Ala Ser Ala Gln Cys Ser Asp Ser
        35                  40                  45

<210> SEQ ID NO 96
<211> LENGTH: 45
<212> TYPE: PRT
<213> ORGANISM: Acinetobacter soli

<400> SEQUENCE: 96

Ser Glu Asn Ile Met Asn Ala Gly Gly Thr Ser Met Pro Ser Ser Gly
1               5                   10                  15

Asn Cys Thr Gly Val Thr Gln Ile Ala Ser Gly Ala Ser Ala Ala Thr
            20                  25                  30

Thr Asn Val Ala Ser Ala Gln Cys Ser Asp Ser Asp Gly
        35                  40                  45

<210> SEQ ID NO 97
<211> LENGTH: 45
<212> TYPE: PRT
<213> ORGANISM: Acinetobacter soli

<400> SEQUENCE: 97

Glu Asn Ile Met Asn Ala Gly Gly Thr Ser Met Pro Ser Ser Gly Asn
1               5                   10                  15

Cys Thr Gly Val Thr Gln Ile Ala Ser Gly Ala Ser Ala Ala Thr Thr
            20                  25                  30

Asn Val Ala Ser Ala Gln Cys Ser Asp Ser Asp Gly Val
        35                  40                  45

<210> SEQ ID NO 98
<211> LENGTH: 45
<212> TYPE: PRT
<213> ORGANISM: Acinetobacter soli

<400> SEQUENCE: 98

Asn Ile Met Asn Ala Gly Gly Thr Ser Met Pro Ser Ser Gly Asn Cys
1               5                   10                  15

Thr Gly Val Thr Gln Ile Ala Ser Gly Ala Ser Ala Ala Thr Thr Asn
            20                  25                  30

Val Ala Ser Ala Gln Cys Ser Asp Ser Asp Gly Val Ile
        35                  40                  45

<210> SEQ ID NO 99
<211> LENGTH: 45
<212> TYPE: PRT
<213> ORGANISM: Acinetobacter soli

<400> SEQUENCE: 99

Ile Met Asn Ala Gly Gly Thr Ser Met Pro Ser Ser Gly Asn Cys Thr
1               5                   10                  15

Gly Val Thr Gln Ile Ala Ser Gly Ala Ser Ala Ala Thr Thr Asn Val
            20                  25                  30

Ala Ser Ala Gln Cys Ser Asp Ser Asp Gly Val Ile Thr
        35                  40                  45

<210> SEQ ID NO 100
<211> LENGTH: 45
<212> TYPE: PRT
<213> ORGANISM: Acinetobacter soli

<400> SEQUENCE: 100

Met Asn Ala Gly Gly Thr Ser Met Pro Ser Ser Gly Asn Cys Thr Gly
1               5                   10                  15

Val Thr Gln Ile Ala Ser Gly Ala Ser Ala Ala Thr Thr Asn Val Ala
            20                  25                  30

Ser Ala Gln Cys Ser Asp Ser Asp Gly Val Ile Thr Val
        35                  40                  45

<210> SEQ ID NO 101
<211> LENGTH: 45
<212> TYPE: PRT
<213> ORGANISM: Acinetobacter soli

<400> SEQUENCE: 101

Asn Ala Gly Gly Thr Ser Met Pro Ser Ser Gly Asn Cys Thr Gly Val
1               5                   10                  15

Thr Gln Ile Ala Ser Gly Ala Ser Ala Ala Thr Thr Asn Val Ala Ser
            20                  25                  30

Ala Gln Cys Ser Asp Ser Asp Gly Val Ile Thr Val Thr
        35                  40                  45

<210> SEQ ID NO 102
<211> LENGTH: 45
<212> TYPE: PRT
<213> ORGANISM: Acinetobacter soli

<400> SEQUENCE: 102

Ala Gly Gly Thr Ser Met Pro Ser Ser Gly Asn Cys Thr Gly Val Thr
1               5                   10                  15

Gln Ile Ala Ser Gly Ala Ser Ala Ala Thr Thr Asn Val Ala Ser Ala
            20                  25                  30

Gln Cys Ser Asp Ser Asp Gly Val Ile Thr Val Thr Met
        35                  40                  45

<210> SEQ ID NO 103
<211> LENGTH: 45
<212> TYPE: PRT

<213> ORGANISM: Acinetobacter soli

<400> SEQUENCE: 103

Gly Gly Thr Ser Met Pro Ser Ser Gly Asn Cys Thr Gly Val Thr Gln
1               5                   10                  15
Ile Ala Ser Gly Ala Ser Ala Ala Thr Thr Asn Val Ala Ser Ala Gln
            20                  25                  30
Cys Ser Asp Ser Asp Gly Val Ile Thr Val Thr Met Thr
        35                  40                  45

<210> SEQ ID NO 104
<211> LENGTH: 45
<212> TYPE: PRT
<213> ORGANISM: Acinetobacter soli

<400> SEQUENCE: 104

Gly Thr Ser Met Pro Ser Ser Gly Asn Cys Thr Gly Val Thr Gln Ile
1               5                   10                  15
Ala Ser Gly Ala Ser Ala Ala Thr Thr Asn Val Ala Ser Ala Gln Cys
            20                  25                  30
Ser Asp Ser Asp Gly Val Ile Thr Val Thr Met Thr Asp
        35                  40                  45

<210> SEQ ID NO 105
<211> LENGTH: 45
<212> TYPE: PRT
<213> ORGANISM: Acinetobacter soli

<400> SEQUENCE: 105

Ser Met Pro Ser Ser Gly Asn Cys Thr Gly Val Thr Gln Ile Ala Ser
1               5                   10                  15
Gly Ala Ser Ala Ala Thr Thr Asn Val Ala Ser Ala Gln Cys Ser Asp
            20                  25                  30
Ser Asp Gly Val Ile Thr Val Thr Met Thr Asp Lys Ala
        35                  40                  45

<210> SEQ ID NO 106
<211> LENGTH: 45
<212> TYPE: PRT
<213> ORGANISM: Acinetobacter soli

<400> SEQUENCE: 106

Met Pro Ser Ser Gly Asn Cys Thr Gly Val Thr Gln Ile Ala Ser Gly
1               5                   10                  15
Ala Ser Ala Ala Thr Thr Asn Val Ala Ser Ala Gln Cys Ser Asp Ser
            20                  25                  30
Asp Gly Val Ile Thr Val Thr Met Thr Asp Lys Ala Lys
        35                  40                  45

<210> SEQ ID NO 107
<211> LENGTH: 45
<212> TYPE: PRT
<213> ORGANISM: Acinetobacter soli

<400> SEQUENCE: 107

Pro Ser Ser Gly Asn Cys Thr Gly Val Thr Gln Ile Ala Ser Gly Ala
1               5                   10                  15
Ser Ala Ala Thr Thr Asn Val Ala Ser Ala Gln Cys Ser Asp Ser Asp
            20                  25                  30

Gly Val Ile Thr Val Thr Met Thr Asp Lys Ala Lys Gly
          35                  40                  45

<210> SEQ ID NO 108
<211> LENGTH: 45
<212> TYPE: PRT
<213> ORGANISM: Acinetobacter soli

<400> SEQUENCE: 108

Ser Ser Gly Asn Cys Thr Gly Val Thr Gln Ile Ala Ser Gly Ala Ser
1               5                   10                  15

Ala Ala Thr Thr Asn Val Ala Ser Ala Gln Cys Ser Asp Ser Asp Gly
            20                  25                  30

Val Ile Thr Val Thr Met Thr Asp Lys Ala Lys Gly Val
        35                  40                  45

<210> SEQ ID NO 109
<211> LENGTH: 45
<212> TYPE: PRT
<213> ORGANISM: Acinetobacter soli

<400> SEQUENCE: 109

Ser Gly Asn Cys Thr Gly Val Thr Gln Ile Ala Ser Gly Ala Ser Ala
1               5                   10                  15

Ala Thr Thr Asn Val Ala Ser Ala Gln Cys Ser Asp Ser Asp Gly Val
            20                  25                  30

Ile Thr Val Thr Met Thr Asp Lys Ala Lys Gly Val Ser
        35                  40                  45

<210> SEQ ID NO 110
<211> LENGTH: 45
<212> TYPE: PRT
<213> ORGANISM: Acinetobacter soli

<400> SEQUENCE: 110

Gly Asn Cys Thr Gly Val Thr Gln Ile Ala Ser Gly Ala Ser Ala Ala
1               5                   10                  15

Thr Thr Asn Val Ala Ser Ala Gln Cys Ser Asp Ser Asp Gly Val Ile
            20                  25                  30

Thr Val Thr Met Thr Asp Lys Ala Lys Gly Val Ser Ile
        35                  40                  45

<210> SEQ ID NO 111
<211> LENGTH: 45
<212> TYPE: PRT
<213> ORGANISM: Acinetobacter soli

<400> SEQUENCE: 111

Asn Cys Thr Gly Val Thr Gln Ile Ala Ser Gly Ala Ser Ala Ala Thr
1               5                   10                  15

Thr Asn Val Ala Ser Ala Gln Cys Ser Asp Ser Asp Gly Val Ile Thr
            20                  25                  30

Val Thr Met Thr Asp Lys Ala Lys Gly Val Ser Ile Lys
        35                  40                  45

<210> SEQ ID NO 112
<211> LENGTH: 45
<212> TYPE: PRT
<213> ORGANISM: Acinetobacter soli

```
<400> SEQUENCE: 112

Cys Thr Gly Val Thr Gln Ile Ala Ser Gly Ala Ser Ala Ala Thr Thr
1               5                   10                  15

Asn Val Ala Ser Ala Gln Cys Ser Asp Ser Asp Gly Val Ile Thr Val
            20                  25                  30

Thr Met Thr Asp Lys Ala Lys Gly Val Ser Ile Lys Leu
        35                  40                  45

<210> SEQ ID NO 113
<211> LENGTH: 45
<212> TYPE: PRT
<213> ORGANISM: Acinetobacter soli

<400> SEQUENCE: 113

Thr Gly Val Thr Gln Ile Ala Ser Gly Ala Ser Ala Ala Thr Thr Asn
1               5                   10                  15

Val Ala Ser Ala Gln Cys Ser Asp Ser Asp Gly Val Ile Thr Val Thr
            20                  25                  30

Met Thr Asp Lys Ala Lys Gly Val Ser Ile Lys Leu Thr
        35                  40                  45

<210> SEQ ID NO 114
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 114

His His His His His His
1               5

<210> SEQ ID NO 115
<211> LENGTH: 32
<212> TYPE: PRT
<213> ORGANISM: Acinetobacter soli

<400> SEQUENCE: 115

Ser Ser Gly Asn Cys Thr Gly Val Thr Gln Ile Ala Ser Gly Ala Ser
1               5                   10                  15

Ala Ala Thr Thr Asn Val Ala Ser Ala Gln Cys Ser Asp Ser Asp Gly
            20                  25                  30

<210> SEQ ID NO 116
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Gly Gly Gly Gly Ser
1               5
```

O-LINKED GLYCOSYLATION RECOGNITION MOTIFS

CROSS-REFERENCE TO RELATED APPLICATIONS

This application is a U.S. National Phase application of PCT/US2019/059893, filed on Nov. 5, 2019, which claims the benefit of U.S. Provisional Appl. No. 62/783,971, filed on Dec. 21, 2018, both of which are incorporated herein by reference in their entireties.

This application is related to U.S. application Ser. No. 15/553,733, filed Aug. 25, 2017, which is a U.S. national stage application of PCT/CA2016/050208, filed Feb. 26, 2016, which claims the benefit of U.S. Provisional Appl. No. 62/121,439, filed on Feb. 26, 2015.

This application is also related to PCT/US2019/037251, filed Jun. 14, 2019, which claims the benefit of U.S. Provisional Appl. No. 62/685,970, filed on Jun. 16, 2018 and U.S. Provisional Appl. No. 62/783,971, filed on Dec. 21, 2018.

GOVERNMENT FUNDING STATEMENT

This invention was made with government support under R41 AI131742, and R41 AI142928 awarded by the National Institute of Health. The Government has certain rights in the invention.

REFERENCE TO SEQUENCE LISTING SUBMITTED ELECTRONICALLY

The content of the electronically submitted sequence listing in ASCII text file (Name 64100-211136_SL.txt; Size: 69615 bytes; and Date of Creation: Jun. 17, 2021) filed with the application is incorporated herein by reference in its entirety.

BACKGROUND

The first, general protein glycosylation pathway in bacteria, the N-linked glycosylation system of *Campylobacter jejuni*, was discovered two decades ago (Szymanski C M, et al. (1999) Evidence for a system of general protein glycosylation in *Campylobacter jejuni*. *Mol Microbiol* 32(5): 1022-1030). Since then, many diverse prokaryotic glycosylation systems have been characterized, including O-linked glycosylation systems that have no homologous counterparts in eukaryotic organisms (Iwashkiw J A, et al. (2013) Pour some sugar on it: the expanding world of bacterial protein O-linked glycosylation. *Mol Microbiol* 89(1):14-28). Shortly after these discoveries, glycosylation pathways were recombinantly introduced into *E. coli* creating the field of bacterial glycoengineering (Wacker M, et al. (2002) N-linked glycosylation in *Campylobacter jejuni* and its functional transfer into *E. coli*. *Science* 298(5599):1790-1793). Bacterial glycoengineering is an emerging biotechnological tool that harnesses prokaryotic glycosylation systems for the generation of recombinantly glycosylated proteins using *E. coli* or other Gram-negative organisms as a host. Currently, glycoengineering utilizes two broad approaches to recombinantly glycosylate proteins, both of which can generate N- or O-linkages: oligosaccharyltransferase (OTase)-dependent and OTase-independent.

Protein glycosylation, or the covalent attachment of carbohydrates to proteins, is a ubiquitous posttranslational modification. For the most part, protein glycosylation is characterized as either N-linked with glycans attached to asparagine residues, or as O-linked with glycans attached to serine or threonine residues. While the importance of eukaryotic glycosylation has been and continues to be a source of intensive research, prokaryotic glycosylation has only recently grabbed the attention of the scientific community with the discovery of a general N-linked protein glycosylation system in the ε-proteobacterium *Campylobacter jejuni* (Szymanski C M, et al. (1999) Evidence for a system of general protein glycosylation in *Campylobacter jejuni*. *Mol Microbiol* 32(5):1022-1030). Since the initial *C. jejuni* discovery, prokaryotic glycosylation systems have been described across a plethora of Gram-negative and Gram-positive bacteria and been shown to contribute towards normal bacterial physiology as well as pathogenesis (Iwashkiw J A, et al. (2013) Pour some sugar on it: the expanding world of bacterial protein O-linked glycosylation. *Mol Microbiol* 89(1):14-28; Nothaft H & Szymanski C M (2010) Protein glycosylation in bacteria: sweeter than ever. *Nat Rev Microbiol* 8(11):765-778); Schaffer C & Messner P (2017) Emerging facets of prokaryotic glycosylation. *FEMS Microbiol Rev* 41(1):49-91). Given the straightforward nature of prokaryotic genetics, it was only a matter of time before protein glycosylation systems were engineered and exploited for the production of designer glycoproteins in a process termed "bacterial glycoengineering".

Much like eukaryotic glycosylation, bacteria have evolved an N-linked OTase pathway, but also employ O-linked OTase systems that are unique to prokaryotic organisms. OTase-independent glycosylation occurs in the cytoplasm and relies on glycosyltransferases to transfer monosaccharides from nucleotide activated precursors for the sequential assembly of glycoproteins. Both OTase-dependent and -independent pathways are exploited for bioconjugating carbohydrates to proteins.

Bacterial surface polysaccharides are some of the first, and most abundant, microbial components encountered by the immune system during infection (Comstock L E & Kasper D L (2006) Bacterial glycans: key mediators of diverse host immune responses. *Cell* 126(5):847-850). These polysaccharides, usually in the form of capsule or O antigen attached to lipid A, serve a multitude of purposes, including protecting microbial organisms from external threats and immune clearance. Given their abundance on invading organisms as well as their biochemical distinctness from eukaryotic carbohydrates, some microbial surface polysaccharides have been used as antigens for vaccine development. However, when polysaccharides are used alone in vaccine formulations, they usually act as T-cell independent antigens and therefore do not stimulate immunoglobulin class switching and long-term B cell memory. Moreover, polysaccharide vaccines alone do not elicit protection in vulnerable groups like infants and children under two years of age. This poor immune response can be overcome by covalently attaching a polysaccharide to a protein carrier in a process known as conjugation (De Gregorio E & Rappuoli R (2014) From empiricism to rational design: a personal perspective of the evolution of vaccine development. *Nat Rev Immunol* 14(7):505-514).

Traditionally, glycoconjugate vaccines are synthesized using a semi-synthetic approach where the polysaccharide is extracted from the target bacterium, purified, chemically modified and covalently linked to a carrier protein. This approach has resulted in the commercial licensure of multiple glycoconjugate vaccines to prevent colonization and infection by *Haemophilus influenzae* type B, and multiple serotypes of *Streptococcus pneumoniae* and *Neisseria meningiditis*. For detailed reviews on semi-synthetic or synthetic glycoconjugate vaccine production please refer to the following excellent review article (Berti F & Adamo R (2018) Antimicrobial glycoconjugate vaccines: an overview of classic and modern approaches for protein modification. *Chem Soc Rev* 47(24):9015-9025). Although conjugate vaccines produced chemically have seen immense commercial success (the glycoconjugate vaccine Prevnar 13 has been Pfizer's best-selling product from 2015-2018 with over 24 billion USD in sales), their manufacturing processes are not without drawbacks; including, batch to batch variation, heterogenous product formation, large scale production of pathogenic organisms, and high manufacturing costs (Frasch C E (2009) Preparation of bacterial polysaccharide-protein conjugates: analytical and manufacturing challenges. *Vaccine* 27(46):6468-6470).

Over the last two decades, alternative strategies for producing glycoconjugate vaccines have emerged. These techniques are broad in their approach with some yielding vaccines closer to commercial licensure than others. Specifically, the advent of in vivo bacterial conjugations for manufacturing glycoconjugate vaccines have produced some of the most clinically advanced products to date. Commonly referred to as bioconjugation or protein glycan coupling technology (PGCT), the in vivo conjugation of polysaccharides to proteins for glycoconjugate vaccine production relies on OTases (Frasch C E (2009) Preparation of bacterial polysaccharide-protein conjugates: analytical and manufacturing challenges. *Vaccine* 27(46):6468-6470). It is generally considered that bioconjugation represents a simplification of the production and manufacturing process of glycoconjugate vaccines (Rappuoli R, De Gregorio E, & Costantino P (2019) On the mechanisms of conjugate vaccines. *Proc Natl Acad Sci USA* 116(1):14-16).

Both N-linking and O-linking OTases have been employed for biologically conjugating polysaccharides to carrier proteins for glycoconjugate vaccine production. Regardless of which OTase is employed, biological conjugations in any Gram-negative bacterium rely on three components: a genetic locus or loci that encode(s) for the polysaccharide biosynthesis proteins, a carrier protein to be glycosylated, and an OTase to transfer the desired carbohydrate to the carrier protein. While these three components are required, they do not necessarily need to be on three separate plasmids.

Recently, a third class of O-linking OTase was employed for bioconjugate vaccine production (Harding C M, et al. (2019) A platform for glycoengineering a polyvalent pneumococcal bioconjugate vaccine using *E. coli* as a host. *Nat Commun* 10(1):891). Much like the only other known O-linking OTases, PilO and PglL, this third class of OTase, termed PglS, naturally glycosylates a pilin like protein, ComP (Schulz B L, et al. (2013) Identification of bacterial protein O-oligosaccharyltransferases and their glycoprotein substrates. *PLoS One* 8(5):e62768). A follow up study demonstrated that PglS was indeed a pilin specific OTase, likely, only glycosylating ComP as no other glycoproteins were identified using a comprehensive glycoprotein screening approach (Harding C M, et al. (2015) *Acinetobacter* strains carry two functional oligosaccharyltransferases, one devoted exclusively to type IV pilin, and the other one dedicated to O-glycosylation of multiple proteins. *Mol Microbiol* 96(5):1023-1041). Originally characterized as a PglL ortholog from the environmental bacterium *Acinetobacter baylyi* strain *ADP*1, PglS is in fact phylogenetically distinct from PglL proteins. Strains of *Acinetobacter* that encode for a PglS protein also encode for a PglL protein, which has been shown to act as the general OTase glycosylating at least seven membrane-associated proteins in a manner similar to *Neisseria* species (Iwashkiw J A, et al. (2012) Identification of a general O-linked protein glycosylation system in *Acinetobacter baumannii* and its role in virulence and biofilm formation. *PLoS Pathog* 8(6): e1002758). In addition, some strains of *Acinetobacter* also encode for PilO OTases, making *Acinetobacter* the only known genera of bacteria carrying genes for all three O-OTase families (PilO, PglL, and PglS) (Harding C M, et al. (2015) *Acinetobacter* strains carry two functional oligosaccharyltransferases, one devoted exclusively to type IV pilin, and the other one dedicated to O-glycosylation of multiple proteins. *Mol Microbiol* 96(5):1023-1041; Iwashkiw J A, et al. (2012) Identification of a general O-linked protein glycosylation system in *Acinetobacter baumannii* and its role in virulence and biofilm formation. *PLoS Pathog* 8(6): e1002758).

Aside from phylogenetic differences, PglS glycosylates its cognate pilin at a unique serine site that is not conserved when compared to the site of glycosylation for PilE (the pilin target of PglL) or PilA (the pilin target for PilO), and is not contained within an LCR (Harding C M, et al. (2019) A platform for glycoengineering a polyvalent pneumococcal bioconjugate vaccine using *E. coli* as a host. *Nat Commun* 10(1):891). However, the most notable difference lies in the polysaccharide substrates PglS transfers. PglS is the only known OTase, both N- or O-linking, capable of transferring polysaccharides with glucose at the reducing end. Many pathogens, like *Streptococcus pneumoniae* (Geno K A, et al. (2015) Pneumococcal Capsules and Their Types: Past, Present, and Future. *Clin Microbiol Rev* 28(3):871-899), Group B *Streptococcus* (Carboni F, et al. (2017) Structure of a protective epitope of group B *Streptococcus* type III capsular polysaccharide. Proc Natl Acad Sci USA 114(19):5017-5022), and *Klebsiella pneumoniae* (Pan Y J, et al. (2015) Genetic analysis of capsular polysaccharide synthesis gene clusters in 79 capsular types of *Klebsiella* spp. *Sci Rep* 5:15573), produce capsules that contain polysaccharides with glucose at the reducing and are thus potential targets for PglS dependent bioconjugate vaccine development. Indeed, PglS was used to generate a polyvalent pneumococcal bioconjugate vaccine against serotypes 8, 9V, and 14 (all contain glucose at the reducing end) using the natural acceptor, ComP, as a carrier protein. In addition, a fragment of ComP lacking its first 28 amino acids was also able to serve as a glycotag when translationally fused to the C-terminus of exotoxin A of *P. aeruginosa* paving the way for incorporation of more conventional vaccine carriers in the PglS bioconjugation system (Harding C M, et al. (2019) A platform for glycoengineering a polyvalent pneumococcal bioconjugate vaccine using *E. coli* as a host. *Nat Commun* 10(1):891).

SUMMARY

This disclosure provides for a bioconjugate comprising an oligo- or polysaccharide covalently linked to a fusion protein: wherein the fusion protein comprises a ComP protein (ComP) glycosylation tag; wherein the ComP glycosylation tag comprises both a cysteine residue corresponding to the conserved cysteine residue at position 71 of SEQ ID NO: 2 (ComP110264: ENV58402.1) and a cysteine residue corresponding to the conserved cysteine residue at position 93 of SEQ ID NO: 2 or both a cysteine residue corresponding to the conserved cysteine residue at position 75 of SEQ ID NO: 1 (ComPADP1: AAC45886.1) and a cysteine residue corresponding to the conserved cysteine residue at position 95 of SEQ ID NO: 1; and wherein the fusion protein is glycosylated with the oligo- or polysaccharide on the ComP glycosylation tag at a serine residue corresponding to the conserved serine residue at position 82 of SEQ ID NO: 2 or position 84 of SEQ ID NO: 1. In certain embodiments, the ComP glycosylation tag does not comprise a methionine residue corresponding to the conserved methionine residue at position 104 of SEQ ID NO: 2 (ComP110264: ENV58402.1). In certain embodiments, the fusion protein of the bioconjugate does not comprise, in relationship to the ComP glycosylation tag, a methionine residue at a position that would correspond to or correspond about to the conserved methionine residue at position 104 of SEQ ID NO: 2 (ComP110264: ENV58402.1). In certain embodiments, the bioconjugate is a conjugate vaccine.

In certain aspects of this disclosure, the ComP glycosylation tag comprises or consists of an amino acid sequence selected from the group consisting of: SEQ ID NO: 32 [C1]; SEQ ID NO: 33 [D1]; SEQ ID NO: 34 [E1]; SEQ ID NO: 41 [E2]; SEQ ID NO: 42 [F2]; SEQ ID NO: 43 [G2]; SEQ ID NO: 44 [H2]; SEQ ID NO: 45 [A3]; SEQ ID NO: 46 [B3]; SEQ ID NO: 47 [C3]; SEQ ID NO: 55 [D4]; SEQ ID NO: 56 [E4]; SEQ ID NO: 57 [F4]; SEQ ID NO: 58 [G4]; SEQ ID NO: 59 [A5]; SEQ ID NO: 60 [B5]; SEQ ID NO: 61 [D5]; SEQ ID NO: 62 [E5]; SEQ ID NO: 63 [F5]; SEQ ID NO: 72 [H6]; SEQ ID NO: 73 [B7]; SEQ ID NO: 74 [C7]; SEQ ID NO: 75 [D7]; SEQ ID NO: 76 [E7]; SEQ ID NO: 77 [F7]; SEQ ID NO: 78 [A8]; SEQ ID NO: 79 [B8]; SEQ ID NO: 92 [A10]; SEQ ID NO: 93 [B10]; SEQ ID NO: 94 [C10]; SEQ ID NO: 95 [D10]; SEQ ID NO: 96 [F10]; SEQ ID NO: 97 [G10]; SEQ ID NO: 98 [H10]; SEQ ID NO: 99 [A11]; SEQ ID NO: 100 [B11]; and SEQ ID NO: 101 [C11], or a variant thereof having one, two, three, four, five, six, or seven amino acid substitutions, additions, and/or deletions, wherein the variant maintains both a cysteine residue corresponding to the conserved cysteine residue at position 75 of SEQ ID NO: 1 (ComPADP1: AAC45886.1) and a cysteine residue corresponding to the conserved cysteine residue at position 95 of SEQ ID NO: 1; and wherein the variant maintains a serine residue corresponding to the conserved serine residue at position 84 of SEQ ID NO: 1.

This disclosure provides for a ComP glycosylation tag comprising an isolated fragment of a ComP protein, wherein the fragment comprises a serine residue corresponding to the conserved serine residue at position 84 in SEQ ID NO: 1 (ComPADP1: AAC45886.1) and both a cysteine residue corresponding to the conserved cysteine residue at position 71 of SEQ ID NO: 2 (ComP110264: ENV58402.1) and a cysteine residue corresponding to the conserved cysteine residue at position 93 of SEQ ID NO: 2 or both a cysteine residue corresponding to the conserved cysteine residue at position 75 of SEQ ID NO: 1 (ComPADP1: AAC45886.1) and a cysteine residue corresponding to the conserved cysteine residue at position 95 of SEQ ID NO: 1. In certain embodiments, the ComP glycosylation tag does not comprise a methionine residue corresponding to the conserved methionine residue at position 104 of SEQ ID NO: 2 (ComP110264: ENV58402.1). In certain embodiments, wherein the amino acid sequence of the ComP glycosylation tag does not extend in the C-terminus direction beyond the amino acid residue corresponding to position 103 of SEQ ID NO: 2 (ComP110264: ENV58402.1).

Provided for herein is a fusion protein comprising a ComP glycosylation tag of this disclosure.

Also provided for herein is a method of in vivo conjugation of an oligo- or polysaccharide to an acceptor polypeptide, the method comprising covalently linking the oligo- or polysaccharide to the acceptor polypeptide with a PglS oligosaccharyltransferase (OTase), wherein the acceptor polypeptide comprises the ComP glycosylation tag of this disclosure; optionally, wherein the ComP glycosylation tag is linked to a heterologous carrier protein.

Also provided for herein is a host cell comprising (a) a genetic cluster encoding for the proteins required to synthesize an oligo- or polysaccharide; (b) a PglS OTase; and (3) an acceptor polypeptide comprising the ComP glycosylation tag of this disclosure.

Also provided for herein is an isolated nucleic acid encoding the ComP glycosylation tag and/or the fusion protein of this disclosure and a host cell comprising said isolated nucleic acid.

Also provided for herein is a composition comprising the conjugate vaccine or the fusion protein of thisi disclosure, and an adjuvant.

A method of inducing a host immune response against a bacterial pathogen comprising administering to a subject in need of the immune response an effective amount of the conjugate vaccine, the fusion protein, or a composition of this disclosure.

Also provided for herein is a method of preventing or treating a bacterial disease and/or infection in a subject comprising administering to a subject in need thereof the conjugate vaccine, the fusion protein, or a composition of this disclosure.

Also provided for herein is a method of producing a pneumococcal conjugate vaccine against pneumococcal infection comprising isolating the bioconjugate or glycosylated fusion protein of this disclosure and combining the isolated conjugate vaccine or isolated glycosylated fusion protein with an adjuvant.

BRIEF DESCRIPTION OF THE DRAWINGS

FIG. 3A and FIG. 3B show PglS$_{ADP1}$ glycosylating recombinant fusion proteins composed of fragments of ComP$_{110264}$ containing the cysteine residues in position 71 and 93 that flank the previously established site of glycosylation at serine 82. (A) Western blot analysis of *E. coli* whole cell lysates co-expressing PglS$_{ADP1}$, the pneumococcal serotype 8 capsular polysaccharide, and a fusion protein that contains a fragment of $ComP_{110264}$. $PglS_{ADP1}$ was only able to glycosylate those recombinant fusion proteins that contained fragments of $ComP_{110264}$ that contained cysteine 71, serine 82, and cysteine 93. Specifically, fusion proteins C1, D1, and E1 were found to be glycosylated as indicated by the immunoreactive bands running at a higher molecular weight. The "+" sample (SEQ ID NO: 29) acts as a positive control as this fusion protein containing the $ComP_{110264}$ fragment consisting of amino acids 29 to 145 has previously been shown to be efficiently glycosylated by $PglS_{ADP1}$. (B) Table format defining the fragment of $ComP_{110264}$ used for recombinant fusion glycosylation experiment and summarizing western blot observations for the presence or absence of glycosylation. For illustrative purposes, serine 82, the site of known PglS dependent glycosylation, is in bold underlined font.

FIG. 4A and FIG. 4B show $PglS_{ADP1}$ glycosylating recombinant fusion proteins composed of fragments of $ComP_{110264}$ containing the cysteine residues in position 71 and 93 that flank the previously established site of glycosylation at serine 82. (A) Western blot analysis of E. coli whole cell lysates co-expressing $PglS_{ADP1}$, the pneumococcal serotype 8 capsular polysaccharide, and a fusion protein that contains a fragment of $ComP_{110264}$. $PglS_{ADP1}$ was only able to glycosylate those recombinant fusion proteins that contained fragments of $ComP_{110264}$ that contained cysteine 71, serine 82, and cysteine 93. Specifically, fusion proteins E2, F2, G2, H2, A3, B3, and C3 were found to be glycosylated as indicated by the immunoreactive bands running at a higher molecular weight. The "+" sample (SEQ ID NO: 29) acts as a positive control as this fusion protein containing the $ComP_{110264}$ fragment consisting of amino acids 29 to 145 has previously been shown to be efficiently glycosylated by $PglS_{ADP1}$. (B) Table format defining the fragment of $ComP_{110264}$ used for recombinant fusion glycosylation experiment and summarizing western blot observations for the presence or absence of glycosylation. For illustrative purposes, serine 82, the site of known PglS dependent glycosylation, is in bold underlined font.

FIG. 5A and FIG. 5B show $PglS_{ADP1}$ glycosylating recombinant fusion proteins composed of fragments of $ComP_{110264}$ containing the cysteine residues in position 71 and 93 that flank the previously established site of glycosylation at serine 82. (A) Western blot analysis of E. coli whole cell lysates co-expressing $PglS_{ADP1}$, the pneumococcal serotype 8 capsular polysaccharide, and a fusion protein that contains a fragment of $ComP_{110264}$. $PglS_{ADP1}$ was only able to glycosylate those recombinant fusion proteins that contained fragments of $ComP_{110264}$ that contained cysteine 71, serine 82, and cysteine 93. Specifically, fusion proteins D4, E4, F4, G4, A5, B5, D5, and E5 were found to be glycosylated as indicated by the immunoreactive bands running at a higher molecular weight. The "+" sample (SEQ ID NO: 29) acts as a positive control as this fusion protein containing the $ComP_{110264}$ fragment consisting of amino acids 29 to 145 has previously been shown to be efficiently glycosylated by $PglS_{ADP1}$. (B) Table format defining the fragment of $ComP_{110264}$ used for recombinant fusion glycosylation experiment and summarizing western blot observations for the presence or absence of glycosylation. For illustrative purposes, serine 82, the site of known PglS dependent glycosylation, is in bold underlined font.

FIG. 6A and FIG. 6B show $PglS_{ADP1}$ glycosylating recombinant fusion proteins composed of fragments of $ComP_{110264}$ containing the cysteine residues in position 71 and 93 that flank the previously established site of glycosylation at serine 82. (A) Western blot analysis of E. coli whole cell lysates co-expressing $PglS_{ADP1}$, the pneumococcal serotype 8 capsular polysaccharide, and a fusion protein that contains a fragment of $ComP_{110264}$. $PglS_{ADP1}$ was only able to glycosylate those recombinant fusion proteins that contained fragments of $ComP_{110264}$ that contained cysteine 71, serine 82, and cysteine 93. Specifically, fusion proteins F5 and H6 were found to be glycosylated as indicated by the immunoreactive bands running at a higher molecular weight. The "+" sample (SEQ ID NO: 29) acts as a positive control as this fusion protein containing the $ComP_{110264}$ fragment consisting of amino acids 29 to 145 has previously been shown to be efficiently glycosylated by $PglS_{ADP1}$. (B) Table format defining the fragment of $ComP_{110264}$ used for recombinant fusion glycosylation experiment and summarizing western blot observations for the presence or absence of glycosylation. For illustrative purposes, serine 82, the site of known PglS dependent glycosylation, is in bold underlined font.

FIG. 7A and FIG. 7B show $PglS_{ADP1}$ glycosylation being blocked by the methionine at position 104 even in the presence of the cysteine 71, serine 82, and cysteine 93. (A) Western blot analysis of E. coli whole cell lysates co-expressing $PglS_{ADP1}$, the pneumococcal serotype 8 capsular polysaccharide, and a fusion protein that contains a fragment of $ComP_{110264}$. $PglS_{ADP1}$ was only able to glycosylate those recombinant fusion proteins that contained fragments of $ComP_{110264}$ that contained cysteine 71, serine 82, cysteine 93 and lacked methionine 104. Specifically, fusion proteins B7, C7, D7, E7, F7, A8, and B8 were found to be glycosylated as indicated by the immunoreactive bands running at a higher molecular weight. The "+" sample (SEQ ID NO: 29) acts as a positive control as this fusion protein containing the $ComP_{110264}$ fragment consisting of amino acids 29 to 145 has previously been shown to be efficiently glycosylated by $PglS^{ADP1}$. (B) Table format defining the fragment of $ComP_{110264}$ used for recombinant fusion glycosylation experiment and summarizing western blot observations for the presence or absence of glycosylation. For illustrative purposes, serine 82, the site of known PglS dependent glycosylation, is in bold underlined font.

FIG. 8A and FIG. 8B show that $PglS_{ADP1}$ glycosylation of serine 82 is not blocked by the presence of multiple methionine residues 5' of cysteine 71 and cysteine 93. (A) Western blot analysis of E. coli whole cell lysates co-expressing $PglS_{ADP1}$, the pneumococcal serotype 8 capsular polysaccharide, and a fusion protein that contains a fragment of $ComP_{110264}$. $PglS_{ADP1}$ was only able to glycosylate those recombinant fusion proteins that contained fragments of $ComP_{110264}$ that contained cysteine 71, serine 82, cysteine 93 and lacked methionine 104. Specifically, fusion proteins A10 and B10 were found to be glycosylated as indicated by the immunoreactive bands running at a higher molecular weight. The "+" sample (SEQ ID NO: 29) acts as a positive control as this fusion protein containing the $ComP_{110264}$ fragment consisting of amino acids 29 to 145 has previously been shown to be efficiently glycosylated by $PglS^{ADP1}$. (B) Table format defining the fragment of $ComP_{110264}$ used for recombinant fusion glycosylation experiment and summarizing western blot observations for the presence or absence of glycosylation. For illustrative purposes, serine 82, the site of known PglS dependent glycosylation, is in bold underlined font.

FIG. 9A and FIG. 9B show that $PglS_{ADP1}$ glycosylation of serine 82 is not blocked by the presence of multiple methionine residues 5' of cysteine 71 and cysteine 93. (A) Western blot analysis of E. coli whole cell lysates co-expressing PglS$_{ADP1}$, the pneumococcal serotype 8 capsular polysaccharide, and a fusion protein that contains a fragment of ComP$_{110264}$. PglS$_{ADP1}$ was only able to glycosylate those recombinant fusion proteins that contained fragments of ComP$_{110264}$ that contained cysteine 71, serine 82, cysteine 93 and lacked methionine 104. Specifically, fusion proteins C10, D10, F10, G10, H10, A11, B11, and C11 were found to be glycosylated as indicated by the immunoreactive bands running at a higher molecular weight. The "+" sample (SEQ ID NO: 29) acts as a positive control as this fusion protein containing the ComP$_{110264}$ fragment consisting of amino acids 29 to 145 has previously been shown to be efficiently glycosylated by PglS$^{ADP1}$. (B) Table format defining the fragment of ComP$_{110264}$ used for recombinant fusion glycosylation experiment and summarizing western blot observations for the presence or absence of glycosylation. For illustrative purposes, serine 82, the site of known PglS dependent glycosylation, is in bold underlined font.

FIG. 10A and FIG. 10B shows that PglS$_{ADP1}$ glycosylation of serine 82 is blocked by the presence methionine at position 104. (A) Western blot analysis of *E. coli* whole cell lysates co-expressing PglS$_{ADP1}$, the pneumococcal serotype 8 capsular polysaccharide, and a fusion protein that contains a fragment of ComP$_{110264}$. PglS$_{ADP1}$ was only able to glycosylate those recombinant fusion proteins that contained fragments of ComP$_{110264}$ that contained cysteine 71, serine 82, cysteine 93 and lacked methionine 104. Specifically, none of the fusion proteins were found to be glycosylated by PglS$_{ADP1}$. The "+" sample (SEQ ID NO: 29) acts as a positive control as this fusion protein containing the ComP$_{110264}$ fragment consisting of amino acids 29 to 145 has previously been shown to be efficiently glycosylated by PglS$^{ADP1}$. (B) Table format defining the fragment of ComP$_{110264}$ used for recombinant fusion glycosylation experiment and summarizing western blot observations for the presence or absence of glycosylation. For illustrative purposes, serine 82, the site of known PglS dependent glycosylation, is in bold underlined font.

FIG. 11A and FIG. 11B show fragments of ComP$_{110264}$ displaying efficient glycosylation by PglS$_{ADP1}$ with the serotype 8 pneumococcal capsular polysaccharide. Western blot analysis of *E. coli* whole cell lysates co-expressing PglS$_{ADP1}$, the pneumococcal serotype 8 capsular polysaccharide, and a fusion protein that contains a fragment of ComP$_{110264}$. Western blots were run in duplicate and probed with either the anti-exotoxin A antisera (A) or anti-His antisera (B). The different ComP$_{110264}$ fragments all showed similar levels of glycosylation as indicated by the immunoreactive bands running at a higher molecular weight. All fragments contain cysteine 71, serine 82, and cysteine 93.

FIG. 11C shows in table format the fragments of ComP$_{110264}$ used for recombinant fusion glycosylation experiment and summarizing western blot observations for the presence of glycosylation. For illustrative purposes, serine 82, the site of known PglS dependent glycosylation, is in bold underlined font.

FIG. 12A, FIG. 12B, and FIG. 12C show that N-terminal or C-terminal O-linked glycosylation motifs translationally fused to the EPA carrier protein are glycosylated in the presence of PglS$_{ADP1}$. (A) Figure legend defining the features of each EPA carrier fusion protein used for this experiment. Six different fusion proteins were employed as denoted by the presence of a single O-linked glycosylation tag or a double glycosylation tag. (B) The D5 and D5' ComP$_{110264}$ amino acid fragment sequences. (C) Western blot analysis of *E. coli* whole cell lysates co-expressing the pneumococcal CPS8 and a fusion carrier protein in the presence or absence of PglS$_{ADP1}$. The D5 and D5' glycosylation motifs, whether N-terminal, C-terminal, in tandem or both N- and C-terminal were all glycosylated only in the presence of PglS$_{ADP1}$.

FIG. 13A, FIG. 13B, and FIG. 13C show that two ComP$_{110264}$ fragments translationally fused in tandem at the C-terminus of a carrier protein are glycosylated with high molecular weight polysaccharides. Fusion proteins were purified from *E. coli* cells co-expressing the pneumococcal serotype 8 capsular polysaccharide in the presence or absence of PglS$_{ADP1}$. (A) Western blot analysis of Nickel affinity purified EPA fusion proteins probed with the anti-His antibody shows both the unglycoyslated EPA carrier protein and the higher molecular weight EPA carrier protein glycosylated with the pneumococcal CPS8. (B) Western blot analysis of Nickel affinity purified EPA fusion proteins probed with the anti-CPS8 antibody shows the presence of the CPS8 polysaccharide only in samples that co-expressed PglS$_{ADP1}$. In addition, EPA carrier proteins containing two ComP$_{110264}$ fragments lacking the first 28 amino acids (ComPΔ28$_{110264}$) separated by either a glycine-glycine-glycine-serine (GGGS; SEQ ID NO: 23) or proline-alanine-proline-alanine-proline (PAPAP; SEQ ID NO: 25) linker are glycosylated with high molecular weight pneumococcal CPS8. (C) Merged western blot images of 13A and 13B showing both anti-His (red channel) and anti-CPS8 (green channel).

FIG. 14A, FIG. 14B, and FIG. 14C show that PglS (C), but not PglB (B) or PglL (A), can conjugate pneumococcal CPS14 to its cognate acceptor/carrier protein. Western blot analysis on *E. coli* whole cell lysates probing for hexa-histidine tagged acceptor protein variants.

FIG. 16A and FIG. 16B show that PglS$_{ADP1}$ can transfer the K1 and K2 capsular polysaccharides of *K. pneumoniae* to ComP$_{ADP1}$. Western blot analysis on *E. coli* whole cell lysates probing for hexa-histidine tagged ComP$_{ADP1}$ variants and RNA polymerase. RNA polymerase was used as a loading control.

FIG. 19 lists ComP ortholog amino acid sequences. The site of predicted glycosylation is bolded, flanked by a predicted disulfide bond (underlined) linking the predicted alpha beta loop to the beta strand region.

FIG. 24 shows amino acid sequences of representative ComPΔ28$_{110264}$ fusion proteins.

FIG. 27 lists ComP Δ28 ortholog amino acid sequences in which the amino acids corresponding to the 28 N-terminal amino acids of SEQ ID NO: 1 (ComPADp1: AAC45886.1) have been removed. The site of predicted glycosylation is bolded, flanked by a predicted disulfide bond (underlined) linking the predicted alpha beta loop to the beta strand region.

FIG. 28 shows an alignment of a region ComP sequences including the serine (S) residue (boxed) corresponding to the serine residue at position 84 of SEQ ID NO: 1 (ComP$_{ADP1}$: AAC45886.1).

FIG. 32A-I shows that the oligosaccharyltransferase PglS can glycosylate the acceptor protein ComP with the pneumococcal CPS14 polysaccharide. *E. coli* SDB1 cells co-expressing an acceptor protein (DsbA, AcrA, or ComP), an OTase (PglL, PglB, or PglS), and the CPS14 polysaccharide were analyzed for protein glycosylation via western blot analysis of the affinity purified acceptor proteins. (A-C): DsbA purified from SDB1 cells in the presence or absence of PglL. (A): Anti-His channel probing for hexa-histidine tagged DsbA. (B): Anti-glycan channel probing for CPS14. (C): Merged images for panels A and B. (D-F): AcrA purified from SDB1 cells in the presence or absence of PglB. (D): Anti-His channel probing for hexa-histidine tagged AcrA. (E): Anti-glycan channel probing for CPS14. (F): Merged images for panels D and E. (G-I): ComP purified from SDB1 cells in the presence or absence of PglS. (G): Anti-His channel probing for hexa-histidine tagged ComP. (H): Anti-glycan channel probing for CPS14. (I): Merged images for panels G and H. The asterisk indicates samples that were proteinase K treated for 1 h at 55° C.

FIG. 34A-F shows Western blot analysis of CPS8-ComP and CPS9V-ComP glycoproteins. *E. coli* SDB1 cells were prepared co-expressing ComP, PglS, and either the pneumococcal CPS8 or CPS9V. Affinity purified glycosylated ComP from each strain was analyzed for protein glycosylation via western blot analysis. (A-C): Western blot analysis of CPS8-ComP bioconjugates compared against ComP alone (A): Anti-His channel probing for hexa-histidine tagged ComP purified from SDB1 expressing CPS8 in the presence or absence of PglS. (B): Anti-glycan channel probing for CPS8. (C): Merged images for panels A and B. (D-F): Western blot analysis of CPS9V-ComP bioconjugates compared against ComP alone (D): Anti-His channel probing for hexa-histidine tagged ComP purified from SDB1 expressing CPS9V in the presence or absence of PglS. (E): Anti-glycan channel probing for CPS9V. (F): Merged images for panels D and E. The asterisk indicates samples that were proteinase K treated for 1 h at 55° C.

FIG. 35A-F shows IgG responses of mice vaccinated with ComP, PREVNAR 13®, a monovalent CPS14-ComP bioconjugate and a trivalent CPS8-/CPS9V-/CPS14-ComP bioconjugate. Groups of mice were vaccinated with ComP alone, PREVNAR 13®, a monovalent CPS14-ComP bioconjugate vaccine, or a CPS8-/CPS9V-/CPS14-ComP bioconjugate vaccine. Sera was collected on day 49 and analyzed for serotype specific IgG responses via ELISA compared against sera collected on day 0. (A-C): No detectable increases in IgG responses were detected in placebo vaccinated mice for serotypes 8 (A), 9V (B), or 14 (C). (D-F): PREVNAR 13® vaccinated mice did not have detectable IgG responses titer increases to serotype 8 (D), but did have IgG responses increases in IgG titers specific to serotype 9V (E) and 14 (F). Unpaired t-tests (Mann-Whitney) were performed to statistically analyze pre-immune sera from day 49 sera. P values for each case tested were **** p=0.0001. Each dot represents a single vaccinated mouse. Error bars indicate the standard deviation of the mean.

FIG. 35G-L shows IgG responses of mice vaccinated with ComP, PREVNAR 13®, a monovalent CPS14-ComP bioconjugate and a trivalent CPS8-/CPS9V-/CPS14-ComP bioconjugate. Groups of mice were vaccinated with ComP alone, PREVNAR 13®, a monovalent CPS14-ComP bioconjugate vaccine, or a CPS8-/CPS9V-/CPS14-ComP bioconjugate vaccine. Sera was collected on day 49 and analyzed for serotype specific IgG responses via ELISA compared against sera collected on day 0. (G-I): Mice vaccinated with a CPS14-ComP bioconjugate vaccine did not have IgG responses detectable increases in IgG titers specific to serotypes 8 (G) or 9V (H), but did have IgG responses statistically significant IgG titer increases to serotype 14 (I). (J-L): Trivalent CPS8-/CPS9V-/CPS14-ComP bioconjugate vaccinated mice all had statistically significant IgG responses increases in IgG titers to serotypes 8 (J), 9V (K), and 14 (L). Unpaired t-tests (Mann-Whitney) were performed to statistically analyze pre-immune sera from day 49 sera. P values for each case tested were **** p=0.0001. Each dot represents a single vaccinated mouse. Error bars indicate the standard deviation of the mean.

FIG. 36A and FIG. 36B shows bactericidal activity of sera from vaccinated mice against S. pneumoniae serotypes 8 and 14. Opsonophagocytosis assays (OPA) of sera from mice vaccinated with either buffer control, PREVNAR 13®, or bioconjugate vaccine against both S. pneumoniae serotypes 8 (A) and 14 (B). Serotype-specific commercial rabbit anti-S. pneumoniae sera were used as positive controls. A 5% (v/v) sample serum and a bacterial MOI of 0.01 were added to fresh whole blood from naive mice to perform the assay. Viable bacterial counts were performed after 4 h of incubation. To determine bacterial killing, viable bacterial counts from tubes incubated with sample sera were compared to those incubated with control naive mouse sera. Results are expressed as percent bacterial killing for individual mice, with horizontal bars representing the standard deviation of the mean.

FIG. 37A and FIG. 37B shows analysis of EPA glycosylation with the CPS8 capsular polysaccharide. Western blot analysis of EPA-CPS8 bioconjugates compared against EPA alone. (A—Left panel) Anti-His channel probing for hexahistidine tagged EPA purified from SDB1 expressing CPS8 in the presence or absence of PglS. (A—Middle panel) Anti-glycan channel probing for CPS8. (A—Right panel) Merged images for left and middle panels. (B): EPA-CPS8 separated on a SDS polyacrylamide gel stained with Coomassie.

FIG. 38A and FIG. 38B shows analysis of immune responses to ComP-CPS8 and EPA-CPS8 bioconjugates in mice. (A): Titers of CPS8 IgG antibodies in mice immunized with CPS8 bioconjugate vaccines. Mouse groups were as follows: EPA (n=9, mice vaccinated with 5 µg of total protein), ComP-CPS8 (n=10, mice vaccinated with 5 µg total polysaccharide), and EPA-CPS8 (n=10, mice vaccinated with 100 ng of total polysaccharide). All mice were immunized with 100 µL of a vaccine diluted 1:1 with Imject Alum Adjuvant on days 1, 14, and 28. Sera were collected on day 4. For the titration, ELISA plates were coated with whole cell serotype 8 pneumococci and incubated with 2-fold serial dilutions of sera. Titers for individual mice are shown, with horizontal bars representing the standard error of the mean. Statistically significant titers compared to the EPA placebo group are denoted with asterisk and were determined using Kruskal-Wallis one-way Anova. , P=0.0223 and , P<0.0001. For analysis and representation purposes, negative titer values (<100) were given an arbitrary value of 10. (B): Opsonophagocytosis killing of S. pneumoniae serotype 8 by day 42 sera from mice immunized with ComP-CPS8 and EPA-CPS8 bioconjugate vaccines. The same mouse groups described for the IgG titers were employed for the OPA.A 40% (vol/vol) sample of serum and bacterial MOI of 0.01 were added to fresh whole blood from naive mice to perform the assay. Results are expressed as percent bacterial killing for individual mice, with horizontal bars representing the standard error of the mean. Statistically significant killing compared to the EPA placebo group is denoted with asterisk and were determined using Kruskal-Wallis one-way Anova. , P=0.0015.

FIG. 40A, FIG. 40B, and FIG. 40C shows an analysis of EPA glycosylation with the Klebsiella pneumoniae K1 and K2 capsular polysaccharides. Western blot analysis of purified the (A) non-glycosylated EPA, (B) EPA glycosylated with the K. pneumoniae K1 capsular polysaccharide, or (C) EPA glycosylated with the K. pneumoniae K2 capsular polysaccharide. The "g°" denotes the non-glycosylated EPA fusion and "g'''" denotes the EPA fusion glycosylated with different sized K1 or K2 repeating subunits as depicted in panel B or C, respectively.

DETAILED DESCRIPTION

Figure 1:
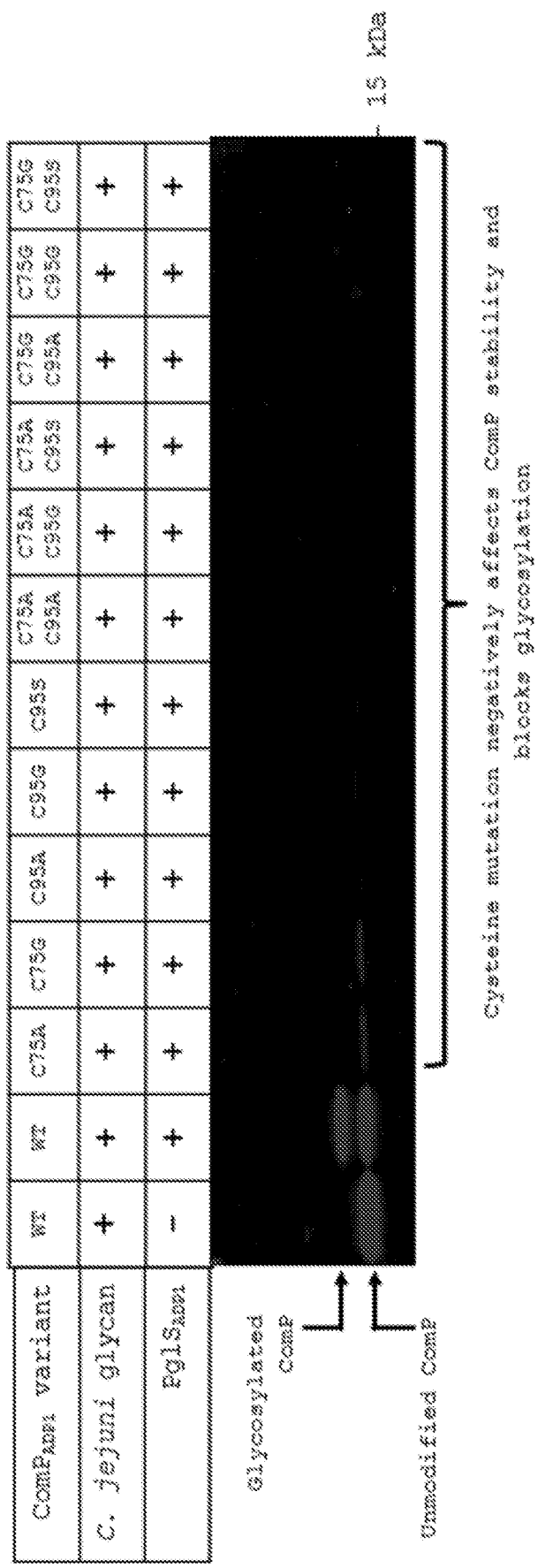
FIG. 1A and FIG. 1B show that the cysteine residues flanking immediately serine 84 in ComP from *Acinetobacter baylyi* ADP1 (ComP$_{ADP1}$) contribute to PglS dependent glycosylation and ComP stability. (A) illustrates the amino acid sequence of ComP$_{ADP1}$ from amino acid residues 75 to 95 with the two cysteine residues flanking serine 84, the site of PglS dependent glycosylation. (B) shows that point mutational exchange of either cysteine 75, cysteine 95, or both cysteine 75 and 95 to alanine, glycine, or serine negatively affects ComP stability and blocks glycosylation of serine 84 by PglS with the *Campylobacter jejuni* heptasaccharide. Western blot analysis of *E. coli* whole cell lysates co-expressing PglS, the *C. jejuni* heptasaccharide, and a variant of ComP$_{ADP1}$ *E. coli* strains expressing the single mutants C95A, C95G, and C95S as well as the double mutants C75A/C95A, C75A/C95G, C75A/C95S, C75G/C95A, C75G/C95G, and C75G/C95S all had ComP levels that were below the level of detection indicating the inherent instability of these mutant proteins and the importance of the Cysteine 75 and Cysteine 95.

To the extent necessary to provide descriptive support, the subject matter and/or text of the appended claims is incorporated herein by reference in their entirety.

It will be understood by all readers of this written description that the exemplary aspects and embodiments described and claimed herein may be suitably practiced in the absence of any recited feature, element or step that is, or is not, specifically disclosed herein.

Definitions

It is to be noted that the term "a" or "an" entity refers to one or more of that entity; for example, "a polysaccharide," is understood to represent one or more polysaccharides. As such, the terms "a" (or "an"), "one or more," and "at least one" can be used interchangeably herein.

Furthermore, "and/or" where used herein is to be taken as specific disclosure of each of the specified features or components with or without the other. Thus, the term and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

It is understood that wherever aspects are described herein with the language "comprising" or "comprises" otherwise analogous aspects described in terms of "consisting of," "consists of," "consisting essentially of," and/or "consists essentially of," and the like are also provided.

Unless defined otherwise, technical and scientific terms used herein have the same meaning as commonly understood by one of ordinary skill in the art to which this disclosure is related.

Numeric ranges are inclusive of the numbers defining the range. Even when not explicitly identified by "and any range in between," or the like, where a list of values is recited, e.g., 1, 2, 3, or 4, unless otherwise stated, the disclosure specifically includes any range in between the values, e.g., 1 to 3, 1 to 4, 2 to 4, etc.

The headings provided herein are solely for ease of reference and are not limitations of the various aspects or aspects of the disclosure, which can be had by reference to the specification as a whole.

As used herein, the term "non-naturally occurring" substance, composition, entity, and/or any combination of substances, compositions, or entities, or any grammatical variants thereof, is a conditional term that explicitly excludes, but only excludes, those forms of the substance, composition, entity, and/or any combination of substances, compositions, or entities that are well-understood by persons of ordinary skill in the art as being "naturally-occurring," or that are, or might be at any time, determined or interpreted by a judge or an administrative or judicial body to be, "naturally-occurring."

As used herein, the term "polypeptide" is intended to encompass a singular "polypeptide" as well as plural "polypeptides," and refers to a molecule composed of monomers (amino acids) linearly linked by amide bonds (also known as peptide bonds). The term "polypeptide" refers to any chain or chains of two or more amino acids, and does not refer to a specific length of the product. Thus, peptides, dipeptides, tripeptides, oligopeptides, "protein," "amino acid chain," or any other term used to refer to a chain or chains of two or more amino acids are included within the definition of "polypeptide," and the term "polypeptide" can be used instead of, or interchangeably with any of these terms. The term "polypeptide" is also intended to refer to the products of post-expression modifications of the polypeptide, including without limitation glycosylation, acetylation, phosphorylation, amidation, derivatization by known protecting/blocking groups, proteolytic cleavage, or modification by non-standard amino acids. A polypeptide can be derived from a natural biological source or produced by recombinant technology, but is not necessarily translated from a designated nucleic acid sequence. It can be generated in any manner, including by chemical synthesis.

A "protein" as used herein can refer to a single polypeptide, i.e., a single amino acid chain as defined above, but can also refer to two or more polypeptides that are associated, e.g., by disulfide bonds, hydrogen bonds, or hydrophobic interactions, to produce a multimeric protein.

By an "isolated" polypeptide or a fragment, variant, or derivative thereof is intended a polypeptide that is not in its natural milieu. No particular level of purification is required. For example, an isolated polypeptide can be removed from its native or natural environment. Recombinantly produced polypeptides and proteins expressed in host cells are considered isolated as disclosed herein, as are recombinant polypeptides that have been separated, fractionated, or partially or substantially purified by any suitable technique.

As used herein, the term "non-naturally occurring" polypeptide, or any grammatical variants thereof, is a conditional term that explicitly excludes, but only excludes, those forms of the polypeptide that are well-understood by persons of ordinary skill in the art as being "naturally-occurring," or that are, or might be at any time, determined or interpreted by a judge or an administrative or judicial body to be, "naturally-occurring."

Disclosed herein are certain binding molecules, or antigen-binding fragments, variants, or derivatives thereof. Unless specifically referring to full-sized antibodies such as naturally-occurring antibodies, the term "binding molecule" encompasses full-sized antibodies as well as antigen-binding fragments, variants, analogs, or derivatives of such antibodies, e.g., naturally-occurring antibody or immunoglobulin molecules or engineered antibody molecules or fragments that bind antigen in a manner similar to antibody molecules.

As used herein, the term "binding molecule" refers in its broadest sense to a molecule that specifically binds an antigenic determinant. As described further herein, a binding molecule can comprise one of more "binding domains." As used herein, a "binding domain" is a two- or three-dimensional polypeptide structure that cans specifically bind a given antigenic determinant, or epitope. A non-limiting example of a binding molecule is an antibody or fragment thereof that comprises a binding domain that specifically binds an antigenic determinant or epitope. Another example of a binding molecule is a bispecific antibody comprising a first binding domain binding to a first epitope, and a second binding domain binding to a second epitope.

The terms "antibody" and "immunoglobulin" can be used interchangeably herein. An antibody (or a fragment, variant, or derivative thereof as disclosed herein comprises at least the variable domain of a heavy chain and at least the variable domains of a heavy chain and a light chain. Basic immunoglobulin structures in vertebrate systems are relatively well understood. See, e.g., Harlow et al., Antibodies: A Laboratory Manual, (Cold Spring Harbor Laboratory Press, 2nd ed. 1988).

Binding molecules, e.g., antibodies or antigen-binding fragments, variants, or derivatives thereof include, but are not limited to, polyclonal, monoclonal, human, humanized, or chimeric antibodies, single chain antibodies, epitope-binding fragments, e.g., Fab, Fab' and F(ab')2, Fd, Fvs, single-chain Fvs (scFv), single-chain antibodies, disulfide-linked Fvs (sdFv), fragments comprising either a VL or VH domain, fragments produced by a Fab expression library. ScFv molecules are known in the art and are described, e.g., in U.S. Pat. No. 5,892,019. Immunoglobulin or antibody molecules encompassed by this disclosure can be of any type (e.g., IgG, IgE, IgM, IgD, IgA, and IgY), class (e.g., IgG1, IgG2, IgG3, IgG4, IgA1 and IgA2) or subclass of immunoglobulin molecule.

By "specifically binds," it is meant that a binding molecule, e.g., an antibody or fragment, variant, or derivative thereof binds to an epitope via its antigen binding domain, and that the binding entails some complementarity between the antigen binding domain and the epitope. According to this definition, a binding molecule is said to "specifically bind" to an epitope when it binds to that epitope, via its antigen-binding domain more readily than it would bind to a random, unrelated epitope. The term "specificity" is used herein to qualify the relative affinity by which a certain binding molecule binds to a certain epitope. For example, binding molecule "A" can be deemed to have a higher specificity for a given epitope than binding molecule "B," or binding molecule "A" can be said to bind to epitope "C" with a higher specificity than it has for related epitope "D."

The term "bispecific antibody" as used herein refers to an antibody that has binding sites for two different antigens within a single antibody molecule. It will be appreciated that other molecules in addition to the canonical antibody structure can be constructed with two binding specificities. It will further be appreciated that antigen binding by bispecific antibodies can be simultaneous or sequential. Triomas and hybrid hybridomas are two examples of cell lines that can secrete bispecific antibodies. Bispecific antibodies can also be constructed by recombinant means. (Strohlein and Heiss, Future Oncol. 6:1387-94 (2010); Mabry and Snavely, IDrugs. 13:543-9 (2010)). A bispecific antibody can also be a diabody.

The term "polynucleotide" is intended to encompass a singular nucleic acid as well as plural nucleic acids, and refers to an isolated nucleic acid molecule or construct, e.g., messenger RNA (mRNA) or plasmid DNA (pDNA). A polynucleotide can comprise a conventional phosphodiester bond or a non-conventional bond (e.g., an amide bond, such as found in peptide nucleic acids (PNA)). The term "nucleic acid" refers to any one or more nucleic acid segments, e.g., DNA or RNA fragments, present in a polynucleotide. By "isolated" nucleic acid or polynucleotide is intended a nucleic acid molecule, DNA or RNA, which has been removed from its native environment. For example, a recombinant polynucleotide encoding a polypeptide subunit contained in a vector is considered isolated as disclosed herein. Further examples of an isolated polynucleotide include recombinant polynucleotides maintained in heterologous host cells or purified (partially or substantially) polynucleotides in solution. Isolated RNA molecules include in vivo or in vitro RNA transcripts of polynucleotides. Isolated polynucleotides or nucleic acids further include such molecules produced synthetically. In addition, polynucleotide or a nucleic acid can be or can include a regulatory element such as a promoter, ribosome binding site, or a transcription terminator.

As used herein, a "non-naturally occurring" polynucleotide, or any grammatical variants thereof, is a conditional definition that explicitly excludes, but only excludes, those forms of the polynucleotide that are well-understood by persons of ordinary skill in the art as being "naturally-occurring," or that are, or that might be at any time, determined or interpreted by a judge or an administrative or judicial body to be, "naturally-occurring."

In certain embodiments, the polynucleotide or nucleic acid is DNA. In other embodiments, a polynucleotide can be RNA.

A "vector" is nucleic acid molecule as introduced into a host cell, thereby producing a transformed host cell. A vector can include nucleic acid sequences that permit it to replicate in a host cell, such as an origin of replication. A vector can also include one or more selectable marker gene and other genetic elements known in the art.

A "transformed" cell, or a "host" cell, is a cell into which a nucleic acid molecule has been introduced by molecular biology techniques. As used herein, the term transformation encompasses those techniques by which a nucleic acid molecule can be introduced into such a cell, including transfection with viral vectors, transformation with plasmid vectors, and introduction of naked DNA by electroporation, lipofection, and particle gun acceleration. A transformed cell or a host cell can be a bacterial cell or a eukaryotic cell.

The term "expression" as used herein refers to a process by which a gene produces a biochemical, for example, a polypeptide. The process includes any manifestation of the functional presence of the gene within the cell including, without limitation, gene knockdown as well as both transient expression and stable expression. It includes without limitation transcription of the gene into messenger RNA (mRNA), and the translation of such mRNA into polypeptide(s). If the final desired product is a biochemical, expression includes the creation of that biochemical and any precursors. Expression of a gene produces a "gene product." As used herein, a gene product can be either a nucleic acid, e.g., a messenger RNA produced by transcription of a gene, or a polypeptide that is translated from a transcript. Gene products described herein further include nucleic acids with post transcriptional modifications, e.g., polyadenylation, or polypeptides with post translational modifications, e.g., methylation, glycosylation, the addition of lipids, association with other protein subunits, proteolytic cleavage, and the like.

As used herein the terms "treat," "treatment," or "treatment of" (e.g., in the phrase "treating a subject") refers to reducing the potential for disease pathology, reducing the occurrence of disease symptoms, e.g., to an extent that the subject has a longer survival rate or reduced discomfort. For example, treating can refer to the ability of a therapy when administered to a subject, to reduce disease symptoms, signs, or causes. Treating also refers to mitigating or decreasing at least one clinical symptom and/or inhibition or delay in the progression of the condition and/or prevention or delay of the onset of a disease or illness.

By "subject" or "individual" or "animal" or "patient" or "mammal," is meant any subject, particularly a mammalian subject, for whom diagnosis, prognosis, or therapy is desired. Mammalian subjects include humans, domestic animals, farm animals, sports animals, and zoo animals, including, e.g., humans, non-human primates, dogs, cats, guinea pigs, rabbits, rats, mice, horses, cattle, bears, and so on.

The term "pharmaceutical composition" refers to a preparation that is in such form as to permit the biological activity of the active ingredient to be effective, and that contains no additional components that are unacceptably toxic to a subject to which the composition would be administered. Such composition can be sterile.

An "effective amount" of an antibody as disclosed herein is an amount sufficient to carry out a specifically stated purpose. An "effective amount" can be determined empirically and in a routine manner, in relation to the stated purpose.

Overview

Conjugate vaccines, consisting of a polysaccharide linked to a protein, are lifesaving prophylactics. Traditionally, conjugate vaccines are manufactured using chemical methodologies. However, in vivo bacterial conjugations have emerged as manufacturing alternatives. In vivo conjugation (bioconjugation) is reliant upon an oligosaccharyltransferase to attach polysaccharides to proteins. Currently, the oligosaccharyltransferases employed for bioconjugations are not suitable for the generation of conjugate vaccines when the polysaccharides contain glucose at the reducing end. This limitation has enormous implications as ~75% of *Streptococcus pneumoniae* capsules contain glucose as the reducing end sugar. Disclosed herein is the use of an O-linked oligosaccharyltransferase to generate the first ever polyvalent pneumococcal bioconjugate vaccine with polysaccharides containing glucose at their reducing end. Pneumococcal bioconjugates were immunogenic, protective, and rapidly produced with recombinant techniques. Certain aspects disclosed herein provide for the engineering, characterization, and immunological responses of a polyvalent pneumococcal bioconjugate vaccine using the natural acceptor protein ComP as a vaccine carrier as well as a monovalent pneumococcal bioconjugate vaccine using a conventional vaccine carrier; e.g., in certain aspects, containing the *Pseudomonas aeruginosa* exotoxin A protein. This establishes a platform to overcome limitations of other conjugating enzymes enabling the development of bioconjugate vaccines for many important human and animal pathogens.

Even with the introduction and implementation of pneumococcal conjugate vaccines over the last two decades, ~1.5 million deaths are still attributed to *S. pneumoniae* each year. This is due in part to the 90+ serotypes of *S. pneumoniae* and the complex manufacturing methods required to synthesize pneumococcal conjugate vaccines. Together these factors hinder global distribution and development of broader, more protective variations of the vaccines. To expedite development and lower manufacturing costs, disclosed herein is a platform for developing conjugate vaccines, for example pneumococcal conjugate vaccines, using in vivo conjugation. This streamlined process has the potential to complement existing manufacturing pipelines or completely bypass the dependency on chemical conjugation methodologies, enabling the production of a more comprehensive conjugate vaccines.

Traditional, chemical conjugate vaccine synthesis is considered complex, costly, and laborious (Frasch, C. E. *Vaccine* 27, 6468-6470 (2009)) however, in vivo conjugation has been thoroughly progressing as a viable biosynthetic alternative (Huttner, A. et al. *Lancet Infect Dis* 17, 528-537 (2017)). These strides are best highlighted by the successes of GlycoVaxyn, (now LimmaTech Biologics AG an independent company with direct ties to GlaxoSmithKline), a clinical stage biopharmaceutical company with multiple bioconjugate vaccines in various phases of clinical trials, one of which (Flexyn2a) has just completed a Phase 2b challenge study. Although GlycoVaxyn has been at the forefront of the in vivo conjugation revolution, the ability to glycosylate carrier/acceptor proteins with polysaccharides containing glucose (Glc) as the reducing end sugar has been elusive and, expectedly, has stymied the development of a pneumococcal bioconjugate vaccine.

The oligosaccharyltransferase PglS—previously referred to as PglL by Schulz et al. (PMID23658772) and PglL$_{ComP}$ by Harding et al. 2015 (PMID 26727908)—was only recently characterized as a functional OTase (Schulz, B. L. et al. *PLoS One* 8, e62768 (2013)). Subsequent mass spectrometry studies on total glycopeptides demonstrated that PglS does not act as a general PglL-like OTase, glycosylating multiple periplasmic and outer membrane proteins (Harding, C. M. et al. *Mol Microbiol* 96, 1023-1041 (2015)). In fact, the genome of *A. baylyi* ADP1 encodes for two OTase, a PglL-like ortholog (UniProtKB/Swiss-Prot: Q6FFS6.1), which acts as the general OTase and PglS (UniProtKB/Swiss-Prot: Q6F7F9.1), which glycosylates a single protein, ComP (Harding, C. M. et al. *Mol Microbiol* 96, 1023-1041 (2015)).

ComP is orthologous to type IV pilin proteins, like PilA from *Pseudomonas aeruginosa* and PilE from *Neisseria meningiditis*, both of which are glycosylated by the OTases TfpO (Castric, P. *Microbiology* 141 (Pt 5), 1247-1254 (1995)) and PglL (Power, P. M. et al. *Mol Microbiol* 49, 833-847 (2003)), respectively. Although TfpO and PglL also glycosylate their cognate pilins at serine residues, the sites of glycosylation differ between each system. TfpO glycosylates its cognate pilin at a C-terminal serine residue (Comer, J. E., Marshall, M. A., Blanch, V. J., Deal, C. D. & Castric, P. *Infect Immun* 70, 2837-2845 (2002)), which is not present in ComP. PglL glycosylates PilE at an internal serine located at position 63 (Stimson, E. et al. *Mol Microbiol* 17, 1201-1214 (1995)). ComP also contains serine residues near position 63 and the surrounding residues show moderate conservation to PilE from *N. meningiditis*. Comprehensive glycopeptide analysis, however, revealed this serine and the surrounding residues were not the site of glycosylation in ComP. PglS glycosylates ComP at a single serine residue located at position corresponding to the conserved serine at position 84 of ComP$_{ADP1}$: AAC4588631 (SEQ ID NO: 1) (also corresponding to the conserved serine at position 82 of ComP$_{110264}$: ENV58402.1 (SEQ ID NO: 2)), which is a novel glycosylation site not previously found within the type IV pilin superfamily. The ability of PglS to transfer polysaccharides containing glucose as the reducing end sugar coupled with the identification of a novel site of glycosylation within the pilin superfamilies demonstrates that PglS is a functionally distinct OTase from PglL and TfpO.

PglS, but not PglB or PglL, transferred polysaccharides containing glucose at their reducing end to the acceptor protein ComP. Two classes of OTases, PglB and PglL, have previously been employed for in vivo conjugation (Feldman, M. F. et al. *Proc Natl Acad Sci USA* 102, 3016-3021 (2005); Faridmoayer, A., Fentabil, M. A., Mills, D. C., Klassen, J. S. & Feldman, M. F. *J Bacteriol* 189, 8088-8098 (2007)). PglB, the first OTase described, preferentially transfers glycans containing an acetamido-group at the C-2 position of the reducing end (i.e. N-acetylglucosamine), as it is believed to play a role in substrate recognition (Wacker, M. et al. *Proc Natl Acad Sci USA* 103, 7088-7093 (2006)). However, polysaccharides with galactose (Gal) at the reducing end, such as the *S. enterica Typhimurium* O antigen, can be transferred by an engineered PglB variant (Ihssen, J. et al. *Open Biol* 5, 140227 (2015)). The second described OTase, PglL from *N. meningiditis*, has more relaxed substrate specificity than PglB, naturally transferring polysaccharides with an acetamido-group at the C-2 position as well as polysaccharides containing galactose (Gal) at the reducing end (Faridmoayer, A., Fentabil, M. A., Mills, D. C., Klassen, J. S. & Feldman, M. F. *J Bacteriol* 189, 8088-8098 (2007); Pan, C. et al. MBio 7 (2016)). However, there is no evidence available for PglB or PglL mediated transfer of polysaccharides containing glucose (Glc) at the reducing end, which is of particular interest given that the majority of pneumococcal CPSs contain glucose at the reducing end (Geno, K. A. et al. *Clin Microbiol Rev* 28, 871-899 (2015)). The ability of PglB and PglL to transfer the pneumococcal serotype 14 capsular polysaccharide (CPS14) to their cognate glycosylation targets, AcrA (Wacker, M. et al. Science 298, 1790-1793 (2002)) and DsbA (Vik, A. et al. *Proc Natl Acad Sci USA* 106, 4447-4452 (2009)), respectively, was tested. As seen in FIG. 14A and FIG. 14B, both acceptor proteins were expressed; however, no evidence for CPS14 glycosylation to either acceptor protein was observed.

*Acinetobacter* species have been describes as containing three O-linked OTases; a general PglL OTase responsible for glycosylating multiple proteins, and two pilin-specific OTases (Harding, C. M. *Mol Microbiol* 96, 1023-1041 (2015)). The first pilin-specific OTase is an ortholog of TfpO (also known as PilO) and is not employed for in vivo conjugation systems due to its inability to transfer polysaccharides with more than one repeating unit (Faridmoayer, A., Fentabil, M. A., Mills, D. C., Klassen J. S. & Feldman, M. F. *J Bacteriol* 189, 8088-8098 (2007)). The second pilin specific OTase, PglS glycosylates a single protein, the type IV pilin ComP[28]. A bioinformatic analysis indicated that PglS is the archetype of a distinct family of OTases. Given that PglS represents a new class of O-OTase, its ability to transfer pneumococcal CPS14 to its cognate acceptor protein, ComP (Harding, C. M. et al. *Mol Microbiol* 96, 1023-1041 (2015)) was tested. As seen in FIG. 14C, co-expression of the CPS14 biosynthetic locus in conjunction with PglS and a hexa-his tagged variant of ComP resulted in a typical ladder-like pattern of bands compatible with protein glycosylation when analyzed via western blotting (FIG. 14B). The higher molecular weight, modal distribution of signals is indicative of protein glycosylation with repeating glycan subunits of increasing molecular weight. Together, these results indicate that, unlike the previously characterized OTases, PglS is able to transfer polysaccharides with glucose at the reducing end.

Figure 15:
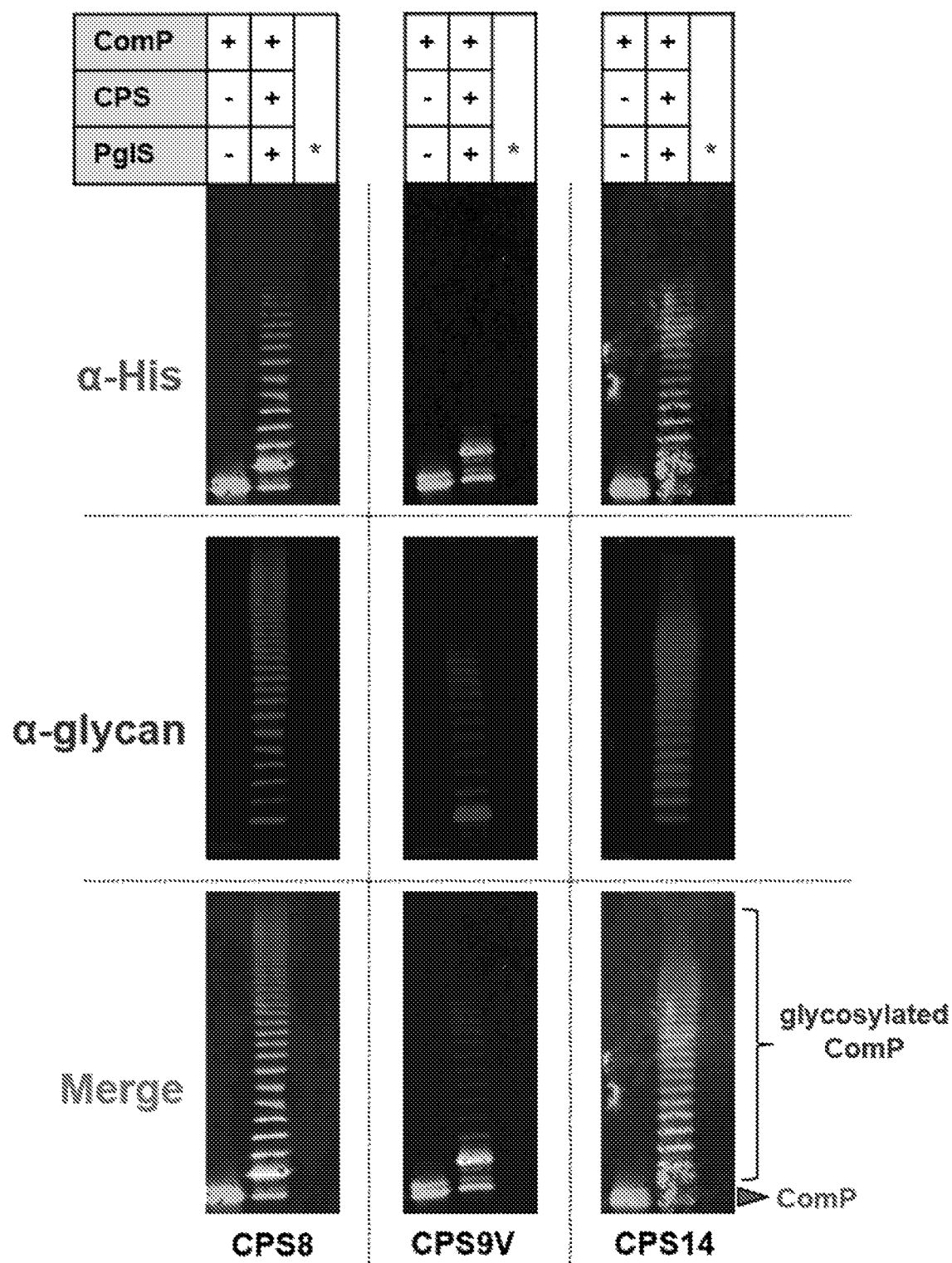
FIG. 15 shows that PglS from *A. baylyi* ADP1 (PglS$_{ADP1}$) can transfer multiple pneumococcal capsular polysaccharides to ComP from *A. baylyi* ADP1 (ComP$_{ADP1}$). Western blot analysis on purified ComP$_{ADP1}$ variants probing for hexa-histidine tagged ComP$_{ADP1}$ variants and either pneumococcal CPS8 (left), CPS9V (middle), or CPS14 (right). Co-localization of the anti-His signals with the anti-glycan signals indicates that ComP$_{ADP1}$ was glycosylated with the correct pneumococcal polysaccharide. The asterisk indicates samples that were treated with proteinase K for 2 hours.

There are more than 90 serotypes of *S. pneumoniae* (Geno, K. A. et al. *Clin Microbiol Rev* 28, 871-899 (2015)). Many increasingly prevalent serotypes, like serotypes 8, 22F, and 33F are not included in currently licensed vaccines. Therefore, the versatility was tested of PglS to generate a multivalent pneumococcal bioconjugate vaccine against two serotypes included in Prevnar 13 (serotype 9V and 14) and one serotype not included (serotype 8) (Package Insert-Prevnar 13 FDA, on the world wide web at fda.gov/downloads/BiologicsBloodVaccinesNaccines/ApprovedProducts/UCM201669.pdf)). Importantly, all of three of these capsular polysaccharides contain glucose as the reducing end sugar (Geno, K. A. et al. *Clin Microbiol Rev* 28, 871-899 (2015)). As seen in FIG. 15, western blot analysis of affinity purified proteins from whole cells co-expressing PglS, a hexa-his tagger ComP variant, and either CPS8, CPS9V, or CPS14 resulted in the generation CPS-specific bioconjugates. Moreover, antisera specific to either the CPS8, CPS9V, or CPS14 antigens also reacted to the anti-His reactive bands, indicating that ComP-His was glycosylated with the correct polysaccharides. To confirm that the material purified was not contaminated with lipid-linked polysaccharides, the samples were treated with proteinase K and observed a loss of signal when analyzed via western blotting, confirming that the bioconjugates were proteinaceous.

Therefore, it was demonstrated that PglS can transfer *S. pneumoniae* polysaccharides to ComP, wherein PglB and PglL could not. Specifically, PglS is the only OTase in the known universe capable of transferring polysaccharides with glucose at the reducing end. In certain aspects, PglS can be used to transfer any lipid-linked oligosaccharide or polysaccharide (collectively referred to herein as "oligo- or polysaccharide") containing glucose at the reducing end to ComP or a fusion protein containing a fragment of ComP.

PglS can transfer capsular polysaccharides of *Klebsiella* to ComP. *Klebsiella pneumonia* (*K. pneumoniae*), a Gram negative opportunistic human pathogen, produces a capsular polysaccharide known to be important for virulence. To date at least 79 antigenically distinct capsular polysaccharides have been described for *Klebsiella* species (Pan, Y. J. et al. *Sci Rep* 5, 15573 (2015)). Furthermore, *K. pneumoniae* is known to produce at least 59 of the 77 capsular polysaccharides, more than half of which contain glucose as the reducing end sugar (Pan, Y. J. et al. *Sci Rep* 5, 15573 (2015)). To determine if PglS could transfer *K. pneumoniae* capsular polysaccharides to ComP, the genes encoding for the proteins required for the synthesis of either the K1 or the K2 capsular polysaccharides were cloned into the IPTG inducible pBBR1MCS-2 vector (Kovach, M. E. et al. Gene 166, 175-176 (1995)). The K1 capsule gene locus was cloned from *K. pneumoniae* NTUH K-2044, a previously characterized K1 capsule producing strain (Wu, K. M. et al. J Bacteriol 191, 4492-4501 (2009)). The K2 capsule gene locus was cloned from *K. pneumoniae* 52.145, a previously characterized K2 capsule producing strain (Lery, L. M. et al. BMC Biol 12, 41 (2014)). The K1 or the K2 capsular polysaccharide expressing plasmids were then individually introduced into *E. coli* co-expressing PglS OTase and the acceptor protein ComP from a separate plasmid vector. To enhance expression of K1 and K2 specific polysaccharides, the *K. pneumoniae* transcriptional activator rmpA from *K. pneumoniae* NTUH K-2044 was subsequently cloned into pACT3 (Dykxhoorn, D. M., St Pierre, R. & Linn, T. Gene 177, 133-136 (1996)), a low copy, IPTG inducible vector as it has previously been characterized as a regulator of capsule in *K. pneumoniae* (Arakawa, Y. et al. *Infect Immun* 59, 2043-2050 (1991)); Yeh, K. M. et al. *J Clin Microbiol* 45, 466-471 (2007)). Introduction of the rmpA gene into *E. coli* strains co-expressing PglS and hexa-his tagged ComP variant and either the K1 or K2 capsular polysaccharides from *K. pneumoniae*, resulted robust expression and detection of higher molecular ComP bioconjugates as indicated by the typical ladder-like pattern of bands compatible with protein glycosylation when analyzed via western blotting (FIG. 16B). The modal distribution of signals is indicative of protein glycosylation with repeating glycan subunits of increasing molecular weight. Thus collectively, PglS was able to glycosylate ComP with the K1 and K2 capsular polysaccharides from *K. pneumonia*. Increased efficiency of conjugation was observed with co-expression of the transcriptional activator rmpA from *K. pneumoniae*.

PglS can transfer *K. pneumoniae* polysaccharides to ComP. Given that most *K. pneumoniae* capsular polysaccharides contain glucose as the reducing end sugar, the only other commercially licensed OTases (PglB and PglL) should be unable to generate conjugate vaccines using these polysaccharides. Moreover, co-expression of the transcriptional activator, RmpA, with the capsule gene cluster enhanced capsule expression to detectably levels. In certain aspects, the method for producing *Klebsiella* conjugates can be used to generate a pan *Klebsiella* conjugate vaccine encompassing all serotypes—including other species such as *K. varricola, K michiganensis*, and *K. oxytoca*.

Figure 17A:
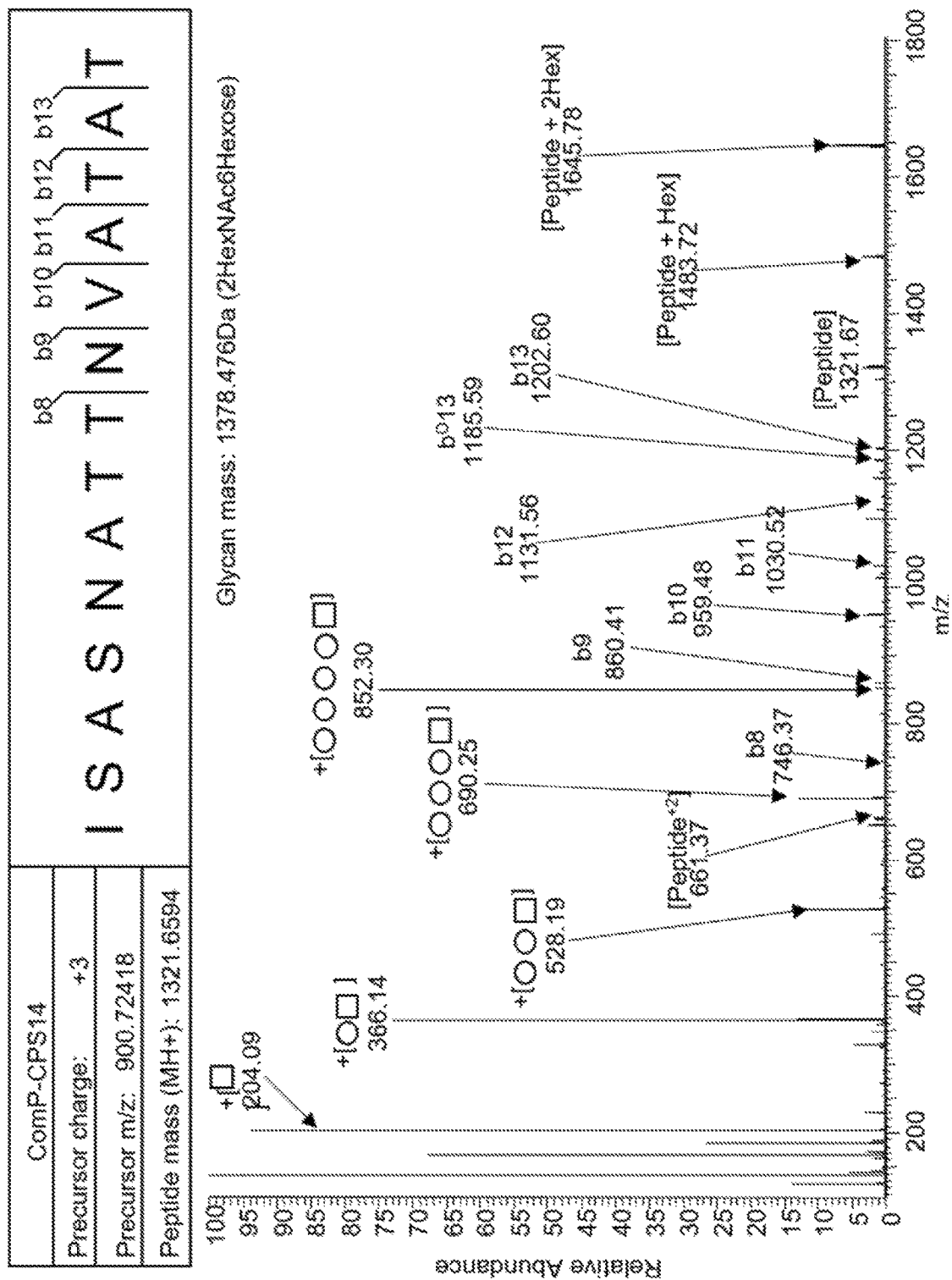
FIG. 17A shows mass spectrometry of CPS14-ComP$_{ADP1}$ identified a single glycosylated peptide. ISASNATTN-VATAT (SEQ ID NO: 22).
Figure 17B:
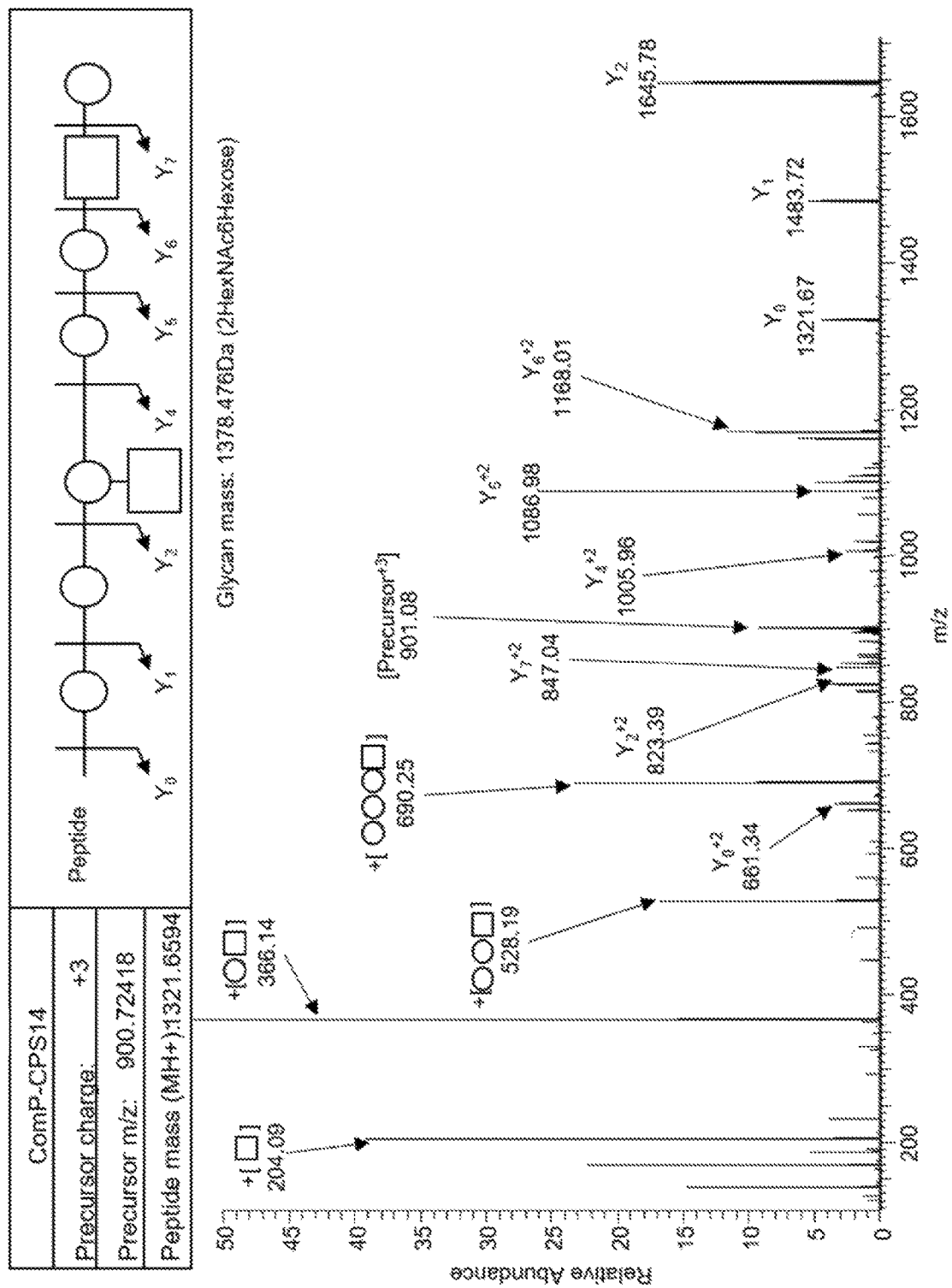
FIG. 17B shows mass spectrometry of CPS14-ComP$_{ADP1}$ identified a single glycosylated peptide.
Figure 29:
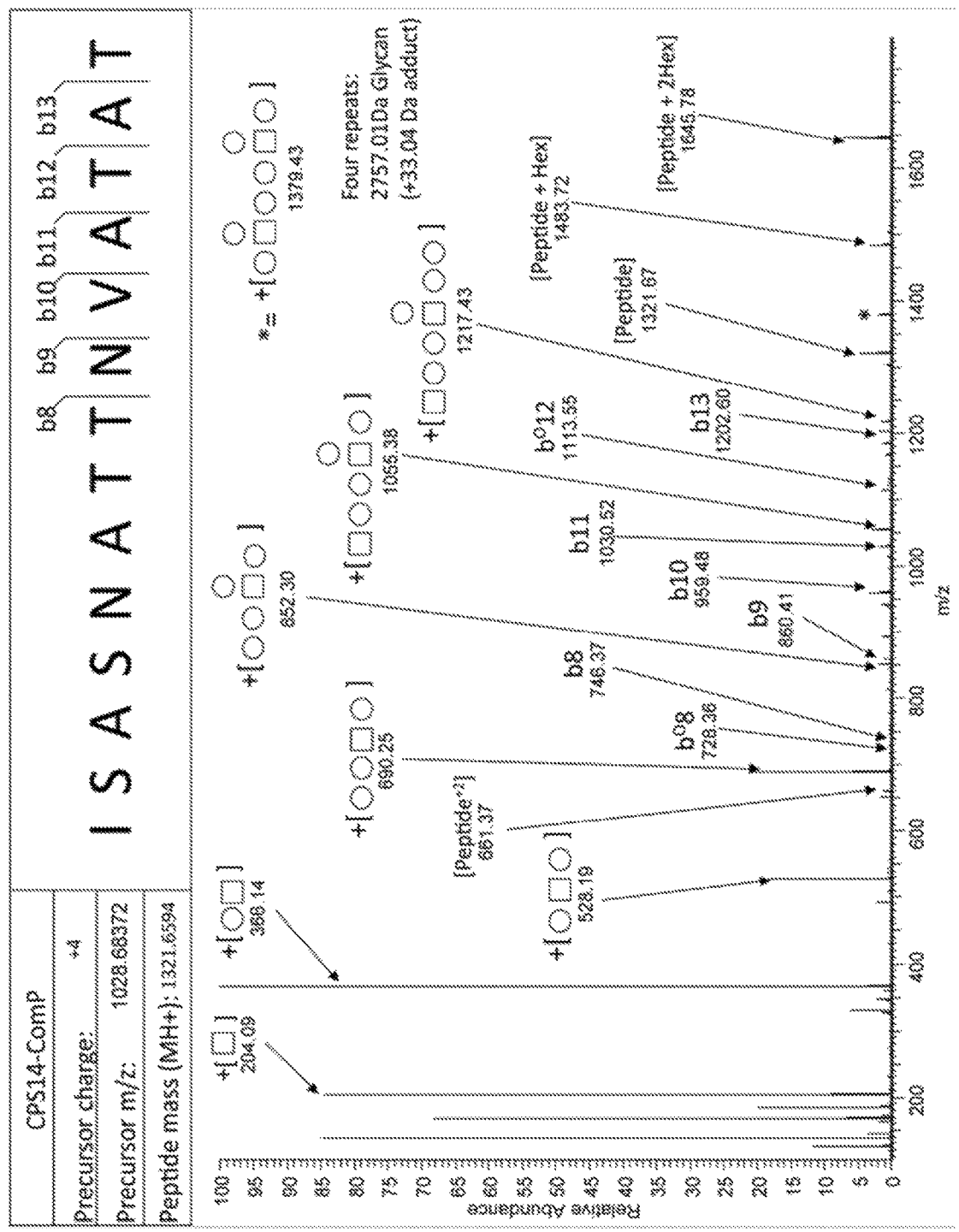
FIG. 29 shows higher energy collisional dissociation (HCD) fragmentation spectra of GluC digested CPS14-ComP bioconjugates. GluC digested CPS14-ComP was subjected to HCD fragmentation enabling the confirmation of a semi-GluC derived single peptide attached to a glycan with the CPS14 repeating subunit. Additional glycopeptides were also observed decorated with extended glycans corresponding to up to four tetrasaccharide repeat units.

Mass spectrometry and site directed mutagenesis confirm PglS is an O-linked OTase and reveal that ComP is glycosylated at a serine residue corresponding to position 84 of $COMP_{ADP1}$. N-glycosylation in bacteria generally occurs within the sequon D-X-N-S-T (SEQ ID NO: 21), where X is any amino acid but proline (Kowarik, M. et al. *EMBO J* 25, 1957-1966 (2006)). On the contrary, O-glycosylation does not seem to follow a defined sequon. Most 0-glycosylation events in bacterial proteins occur in regions of low complexity (LCR), rich in serine, alanine, and proline (Vik, A. et al. *Proc Natl Acad Sci USA* 106, 4447-4452 (2009)). Alternatively, some pilins are O-glycosylated at a C-terminal serine residue (Comer, J. E., Marshall, M. A., Blanch, V. J., Deal, C. D. & Castric, P. *Infect Immun* 70, 2837-2845 (2002)). ComP does not appear to have an obvious LCR or a C-terminal serine residue homologous to those found in other pilin like proteins and therefore mass spectrometry was employed to determine the site(s) of glycosylation. Purified CPS14-ComP bioconjugates were subjected to proteolytic digestion, ZIC-HILIC glycopeptide enrichment, and multiple MS analyses. As seen in FIG. 17A and FIG. 17B, a single glycopeptide consisting of the peptide ISASNAT-TNVATAT (SEQ ID NO: 22) was identified attached to a glycan that matched the published CPS14 composition (Geno, K. A. et al. *Clin Microbiol Rev* 28, 871-899 (2015)). To enable confirmation of both the peptide and attached glycan sequences, multiple collision energies regimes were performed to confirm the glycosylation of the semi-GluC derived peptide ISASNATTNVATAT (SEQ ID NO: 22) with a 1378.47 Da glycan corresponding to $HexNA_{C2}Hexose_6$ (FIG. 17B). Additional glycopeptides were also observed decorated with extended glycans corresponding to up to four tetrasaccharide repeat units (FIG. 29).

Figure 18:
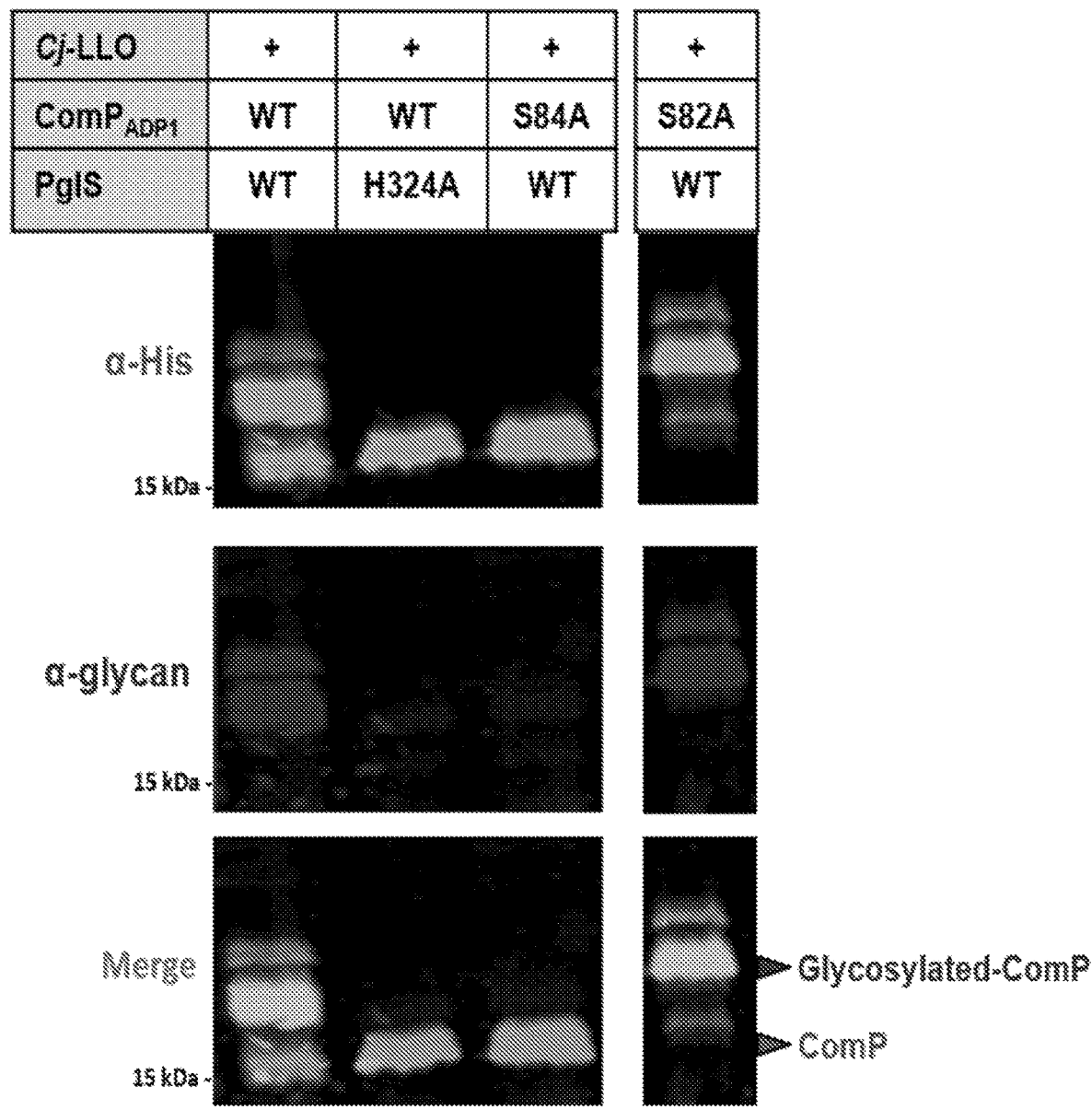
FIG. 18 shows Serine 84 of ComPADP1 is the site of PglS dependent glycosylation. Western blot analysis on *E. coli* whole cell lysates probing for hexa-histidine tagged ComP$_{ADP1}$ variants and the *Campylobacter jejuni* heptasaccharide. The ComP[S84A]$_{ADP1}$ variant was expressed; however, was not glycosylated as indicated by the absence of any reactive bands probing with the anti-hR6 heptasaccharide antisera.
Figure 30:
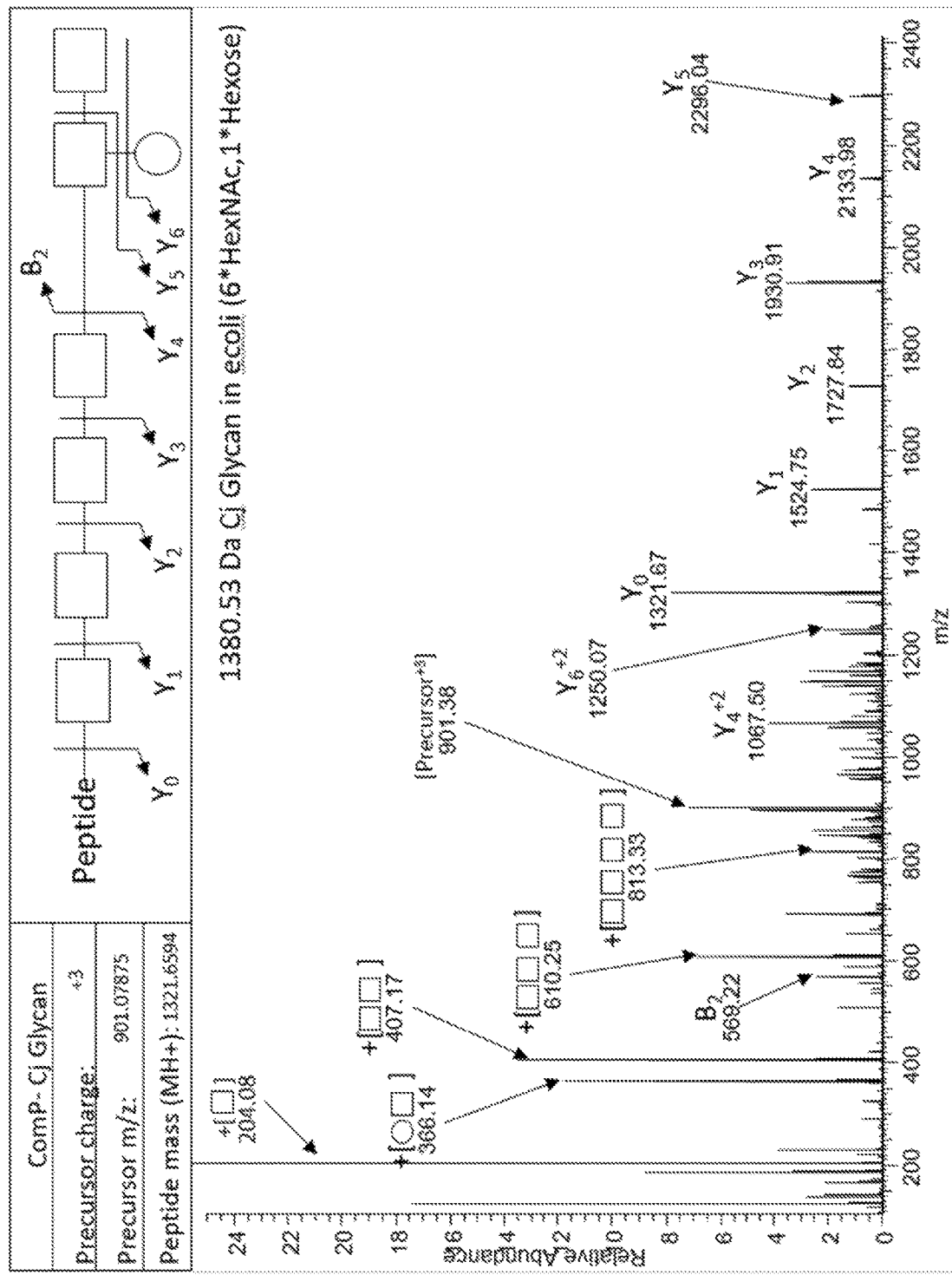
FIG. 30 shows higher energy collisional dissociation (HCD) fragmentation spectra of GluC digested ComP glycosylated with the *C. jejuni* heptasaccharide (ComP-Glycan$_{Cj}$). GluC digested ComP-Glycan$_{Cj}$ was subjected to HCD fragmentation enabling the confirmation of a single peptide attached to a glycan with the CPS14 repeating subunit. Low collision energies regimes were undertaken to confirm the glycosylation of the peptide ISASNATTN-VATAT (SEQ ID NO: 22) with a 1380.53 Da glycan corresponding to 6*HexNAc,1*Hexose.
Figure 31:
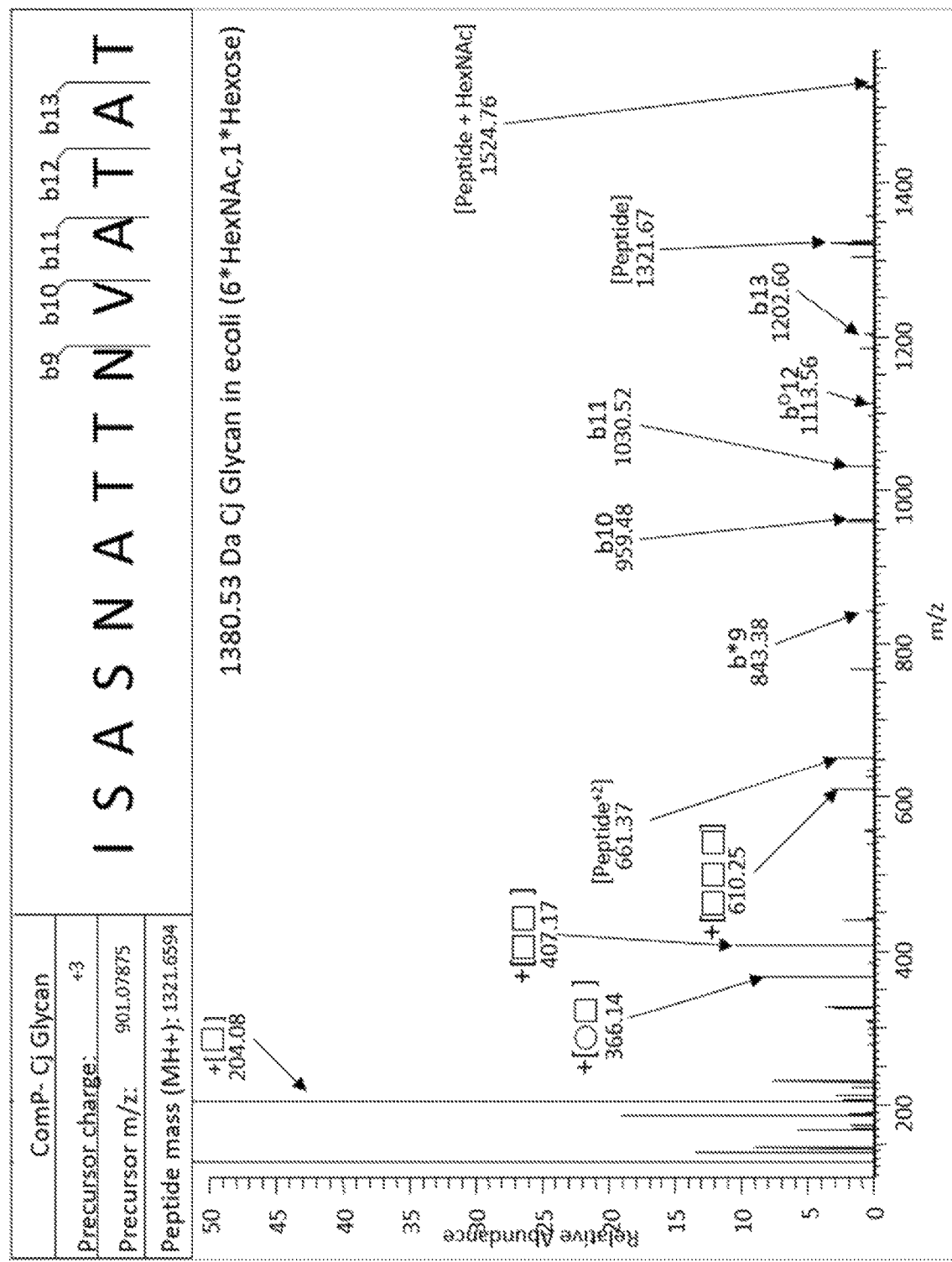
FIG. 31 shows higher energy collisional dissociation (HCD) fragmentation spectra of GluC digested ComP glycosylated with the *C. jejuni* heptasaccharide (ComP-Glycan$_{Cj}$). GluC digested ComP-Glycan$_{Cj}$ was subjected to HCD fragmentation enabling the confirmation of a single peptide attached to a glycan with the CPS14 repeating subunit. High collision energies regimes were undertaken to confirm the glycosylation of the peptide ISASNATTN-VATAT (SEQ ID NO: 22) with a 1380.53 Da glycan corresponding to 6*HexNAc,1*Hexose.
Figure 33A:
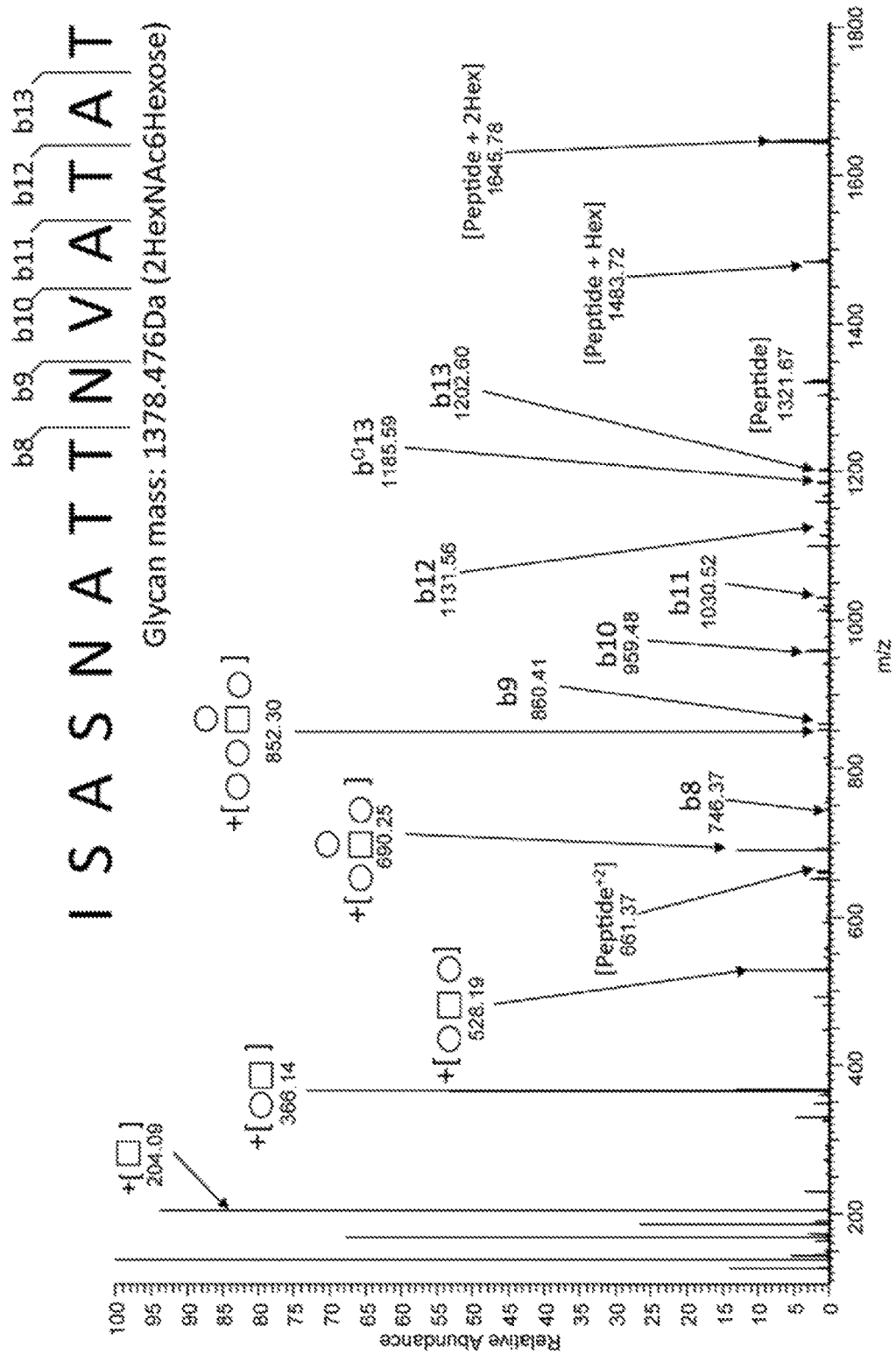
FIG. 33A and FIG. 33B show higher energy collisional dissociation (HCD) fragmentation spectra of GluC digested CPS14-ComP bioconjugates. GluC digested CPS14-ComP was subjected to HCD fragmentation enabling the confirmation of a single peptide attached to a glycan with the CPS14 repeating subunit. High collision energies (A) and low collision energies (B) regimes were undertaken to confirm the glycosylation of the peptide ISASNATTN-VATAT (SEQ ID NO: 22) with a 1378.47 Da glycan corresponding to HexNAc2Hexose6.
Figure 33B:
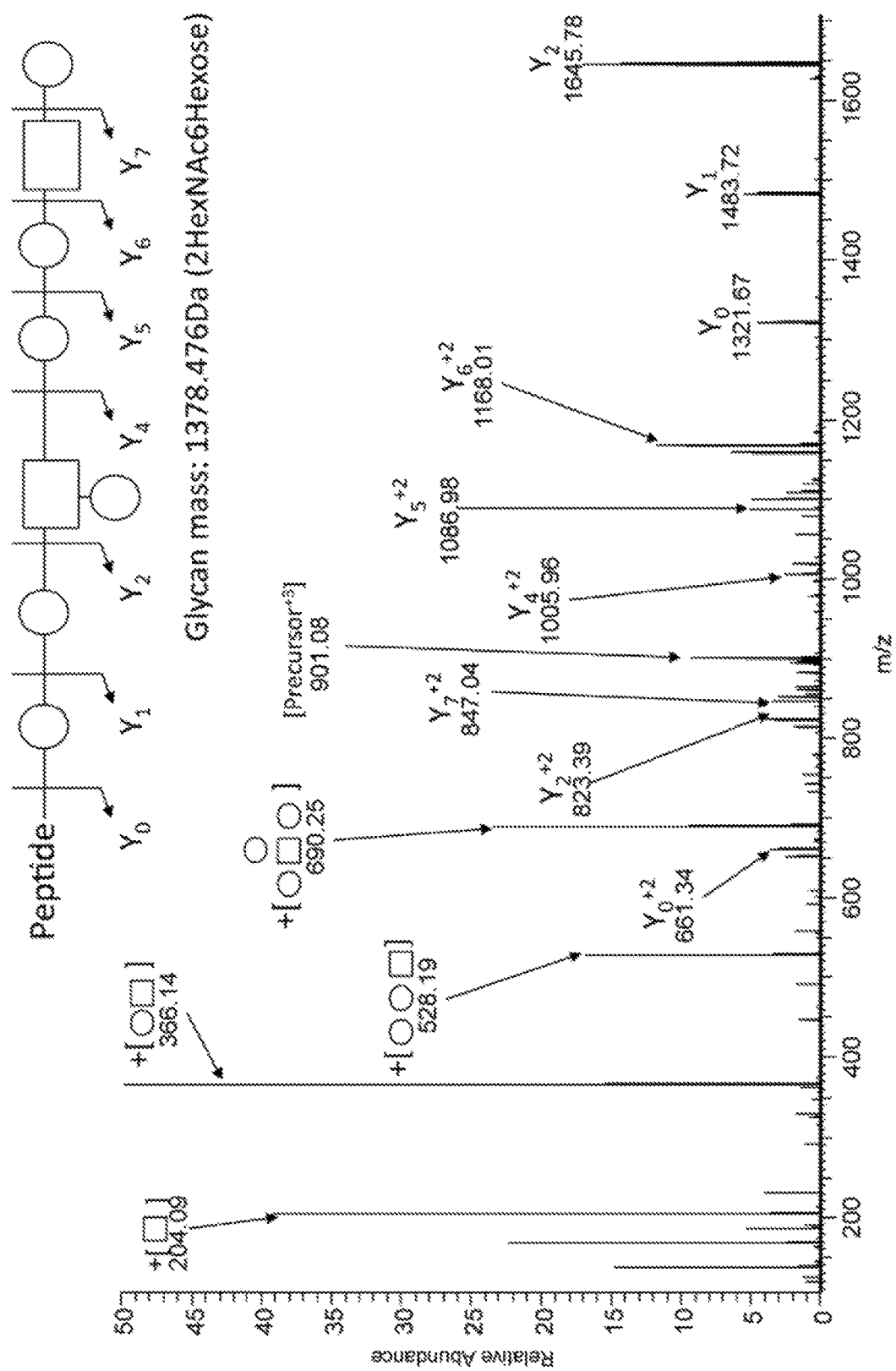
Figure 37C:
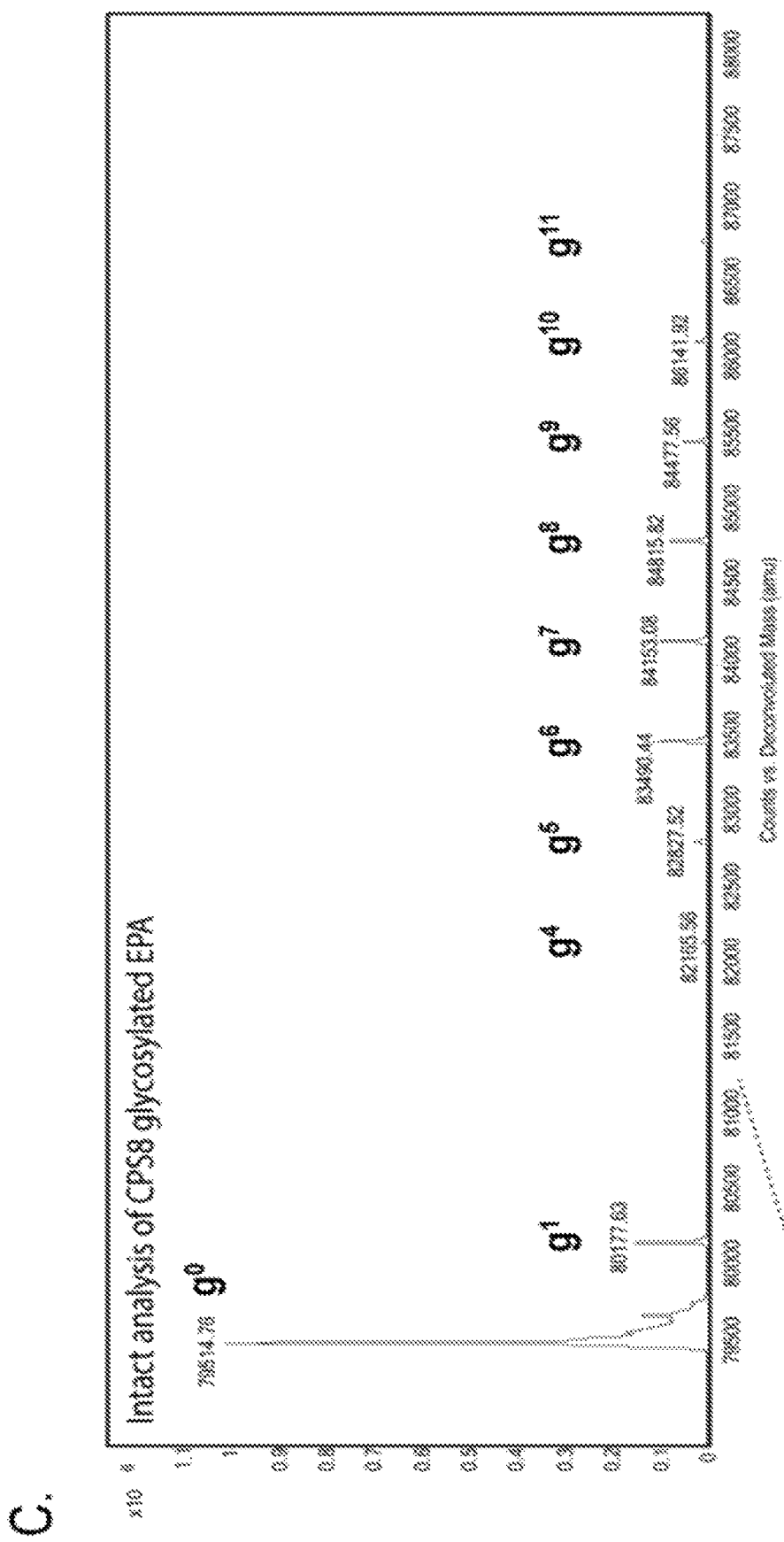
FIG. 37C shows intact protein mass spectrometry analysis showing the MS1 mass spectra for purified EPA-CPS8. The EPA fusion protein has a theoretical mass of 79,526.15 Daltons and can be observed as the peak at 79,514.76. The EPA fusion protein was also observed in multiple states of increasing mass corresponding to the CPS8 repeating subunit, which has a theoretical mass of 662 Daltons. Varying glycoforms of the EPA-CPS8 were observed and are denoted by "g$^{numeric}$", where "g" stands for glycoform and the "numeric" corresponds to the number of repeating CPS8 subunits. The EPA fusion protein was modified with up to 11 repeating subunits of the CPS8 glycan. Panel D provides a zoomed in view of the varying EPA-CPS8 glycoforms.
Figure 37D:
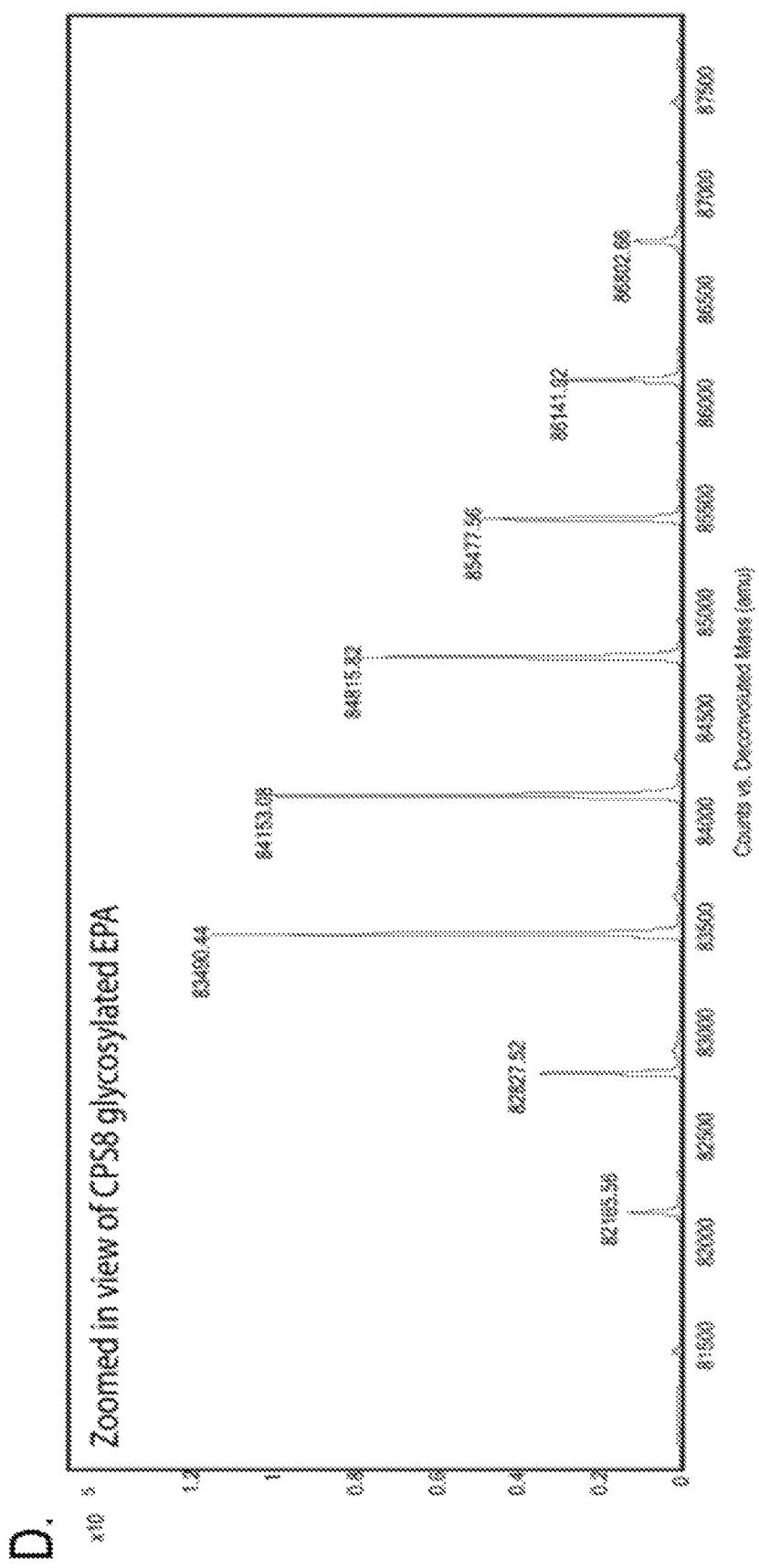
FIG. 37D provides a zoomed in view of the varying EPA-CPS8 glycoforms from FIG. 37C.

It was previously shown that *Acinetobacter* species predominantly glycosylate proteins at serine residues and thus it was hypothesized that either serine (S) 82 or 84—as numbered in SEQ ID NO: 1—was the site of glycosylation (Scott, N. E. et al. *Mol Cell Proteomics* 13, 2354-2370 (2014)). To determine which serine residue was the site of glycosylation, these serine residues were individually mutated to alanine (A) and the glycosylation status of both mutant proteins was analyzed. For this experiment, the biosynthetic locus for the *C. jejuni* heptasaccharide was employed as the donor glycan, as glycosylation is readily detectable with the hR6 anti-glycan antisera as well as by an increase in electrophoretic mobility (Schwarz, F. et al. *Nat Chem Biol* 6, 264-266 (2010)). As shown in FIG. 18, wild type hexa-his tagged ComP was glycosylated with the *C. jejuni* heptasaccharide as indicated by its increased electrophoretic mobility and co-localization with hR6 antisera signal when co-expressed with PglS. MS analysis also confirmed the presence of the *C. jejuni* heptasaccharide on the identical semi-GluC derived peptide ISASNATTN-VATAT (SEQ ID NO: 22) modified by CPS14 (FIG. 30 and FIG. 31). As a negative control, a catalytically inactive PglS mutant (H324A) was generated, that when co-expressed with the *C. jejuni* heptasacchride glycan was unable to glycosylate wild type ComP. Site directed mutagenesis was performed and it was observed that glycosylation of ComP with the *C. jejuni* heptasaccharide was abolished in the ComP[S84A] mutant, whereas ComP[S82A] was glycosylated at wild-type levels. Together, these results indicate that ComP is singly glycosylated at serine 84 (as numbered in SEQ ID NO: 1) by PglS, which is a unique site that is different than other previously characterized pilin like proteins. This corresponds to serine 82 as numbered in SEQ ID NO: 2.

Bioinformatic features of ComP pilin orthologs. ComP was first described as a factor required for natural transformation in *Acinetobacter* baylyi ADP1 (Porstendorfer, D., Drotschmann, U. & Averhoff, B. *Appl Environ Microbiol* 63, 4150-4157 (1997)). In a subsequent study, it was demonstrated that ComP from *A. baylyi* ADP1 (herein referred to as $ComP_{ADP1}$) was glycosylated by a novel OTase, PglS, located immediately downstream of ComP, and not the general OTase PglL located elsewhere on the chromosome (Harding, C. M. et al. Mol Microbiol 96, 1023-1041 (2015)). The $ComP_{ADP1}$ protein (NCBI identifier AAC45886.1) belongs to a family of proteins called type IV pilins. Specifically, ComP shares homology to type IVa major pilins (Giltner, C. L., Nguyen, Y. & Burrows, L. L. *Microbiol Mol Biol Rev* 76, 740-772 (2012)). Type IVa pilins share high sequence homology at their N-terminus, which encode for the highly conserved leader sequence and N-terminal alpha helix; however, the C-terminus display remarkable divergences across genera and even within species (Giltner, C. L., Nguyen, Y. & Burrows, L. L. *Microbiol Mol Biol Rev* 76, 740-772 (2012)). To help differentiate ComP orthologs from other type IVa pilin proteins, such as, PilA from *A. baumannii, P. aeruginosa*, and *Haemophilus influenzae* as well as PilE from *Neisseria* species (Pelicic, V. *Mol Microbiol* 68, 827-837 (2008)), a BLASTp analysis was performed comparing the primary amino acid sequence of $ComP_{ADP1}$ against all proteins from bacteria in the *Acinetobacter* genus. Expectedly, many *Acinetobacter* type IVa pilin orthologs, including $COMP_{ADP1}$, share high homology at their N-termini; however, very few proteins display high sequence conservation across the entire amino acid sequence of ComP. At least six ComP orthologs (FIG. 19) were identified based on the presence of the conserved serine at position 84 relative to $ComP_{ADP1}$ as well as a conserved disulfide bond flanking the site of predicted glycosylation connecting the predicted alpha beta loop to the beta strand region (Giltner, C. L., Nguyen, Y. & Burrows, L. L. *Microbiol Mol Biol Rev* 76, 740-772 (2012)). Furthermore, all six ComP orthologs carry both a pglS homolog immediately downstream of the comP gene as well as a pglL homolog located elsewhere in the chromosome. Together, at least the presence of the conserved serine at position 84, the disulfide loop flanking the site of glycosylation, the presence of a pglS gene immediately downstream of comP, and the presence of a pglL homolog located elsewhere on the chromosome differentiate ComP pilin variants from other type IVa pilin variants.

Therefore, features common to ComP proteins are disclosed herein that identify ComP orthologs in different *Acinetobacter* species. ComP proteins can be differentiated from other pilins by the presence of the conserved glycosylated serine located at position 84 relative to the ADP1 ComP protein and the presence of a disulfide loop flanking the site of glycosylation. In addition, the presence of a pglS homolog immediately downstream of ComP is an indicator of ComP. Further to be classified as a PglS OTase protein rather than a PglL OTase protein, the OTase downstream of ComP must display higher sequence conservation with PglS (ACIAD3337) when compared to PglL (ACIAD0103) in *A. baylyi* ADP1. It is also evident to one of ordinary skill in the art that in any embodiment disclosed herein, a ComP protein comprises and is capable of being glycosylated on a serine residue corresponding to the conserved serine residue at position 84 of SEQ ID NO: 1 ($ComP_{ADP1}$: AAC45886.1).

Figure 20:
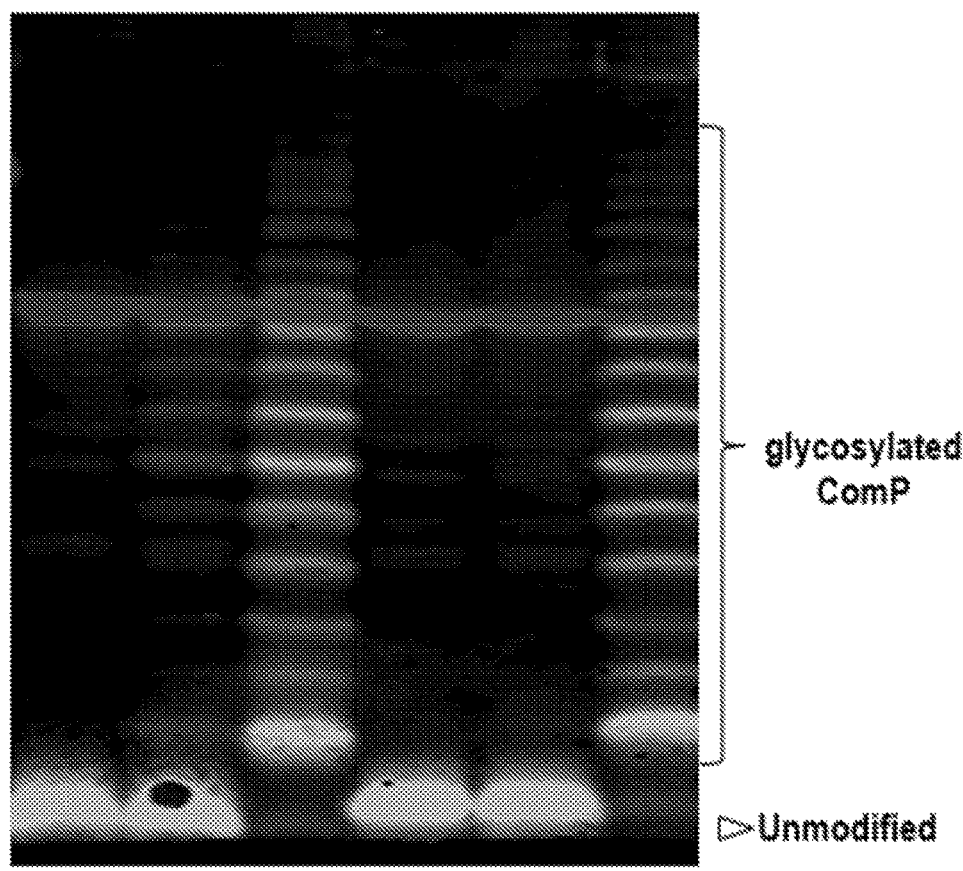
FIG. 20 shows that PglS$_{ADP1}$, but not PglS$_{110264}$, efficiently glycosylates both its cognate ComP$_{ADP1}$ as well as ComP$_{110264}$ from *A. soli* CIP 110264. Western blot analysis on *E. coli* whole cell lysates probing for hexa-histidine tagged ComP variants and RNA polymerase. RNA polymerase was used as a loading control.

ComP from *A. soli* CIP 110264 is glycosylated by PglS from *A. baylyi* ADP1. Given the presence of multiple ComP orthologs, whether PglS from *A. baylyi* ADP1 was able to glycosylate a divergent ComP protein was investigated. The ComP protein from *A. soli* CIP 110264 ($ComP_{110264}$) is 71% identical at the amino acid level when compared to $ComP_{ADP1}$. However, consistent with the features above, $ComP_{110264}$ contains the predicted disulfide bridge between the predicted alpha-beta loop and the second beta strand as well as the conserved serine located at position 84 relative to $ComP_{ADP1}$. Moreover, a PglS ortholog can be found immediately downstream of $ComP_{110264}$. To determine whether PglS from *A. baylyi* ADP1 ($PglS_{ADP1}$) could glycosylate $ComP_{110264}$, $PglS_{ADP1}$ was cloned into pACT3 and $ComP_{110264}$ into pEXT20 (Dykxhoorn, D. M., St Pierre, R. & Linn, T. Gene 177, 133-136 (1996)) and these plasmids were introduced into *E. coli* expressing the serotype 8 capsular polysaccharide (CPS8) from *S. pneumoniae*. Further, the converse experiment was performed by cloning and expressing PglS from *A. soli* CIP 110264 ($PglS_{110264}$) with $ComP_{ADP1}$. As seen in FIG. 20, $PglS_{110264}$ minimally glycosylated its cognate acceptor pilin $ComP_{110264}$ as indicated by higher molecular weight ComP pilin variants when compared to whole cell lysates lacking $PglS_{110264}$. Based on western blot analysis, $PglS_{110264}$ appeared to not glycosylate $ComP_{ADP1}$. On the other hand, $PglS_{ADP1}$ efficiently glycosylated both $ComP_{ADP1}$ and $ComP_{110264}$ as indicated by the robust increase of His-reactive signals of increasing electrophoretic mobility. Collectively, $PglS_{ADP1}$ appears to be an optimal OTase from heterologous glycosylation in *E. coli* with a unique ability to cross glycosylate multiple ComP substrates. Thus it was demonstrated that PglS proteins from different *Acinetobacter* species can glycosylate divergent, non-native ComP sequences.

Figure 21:
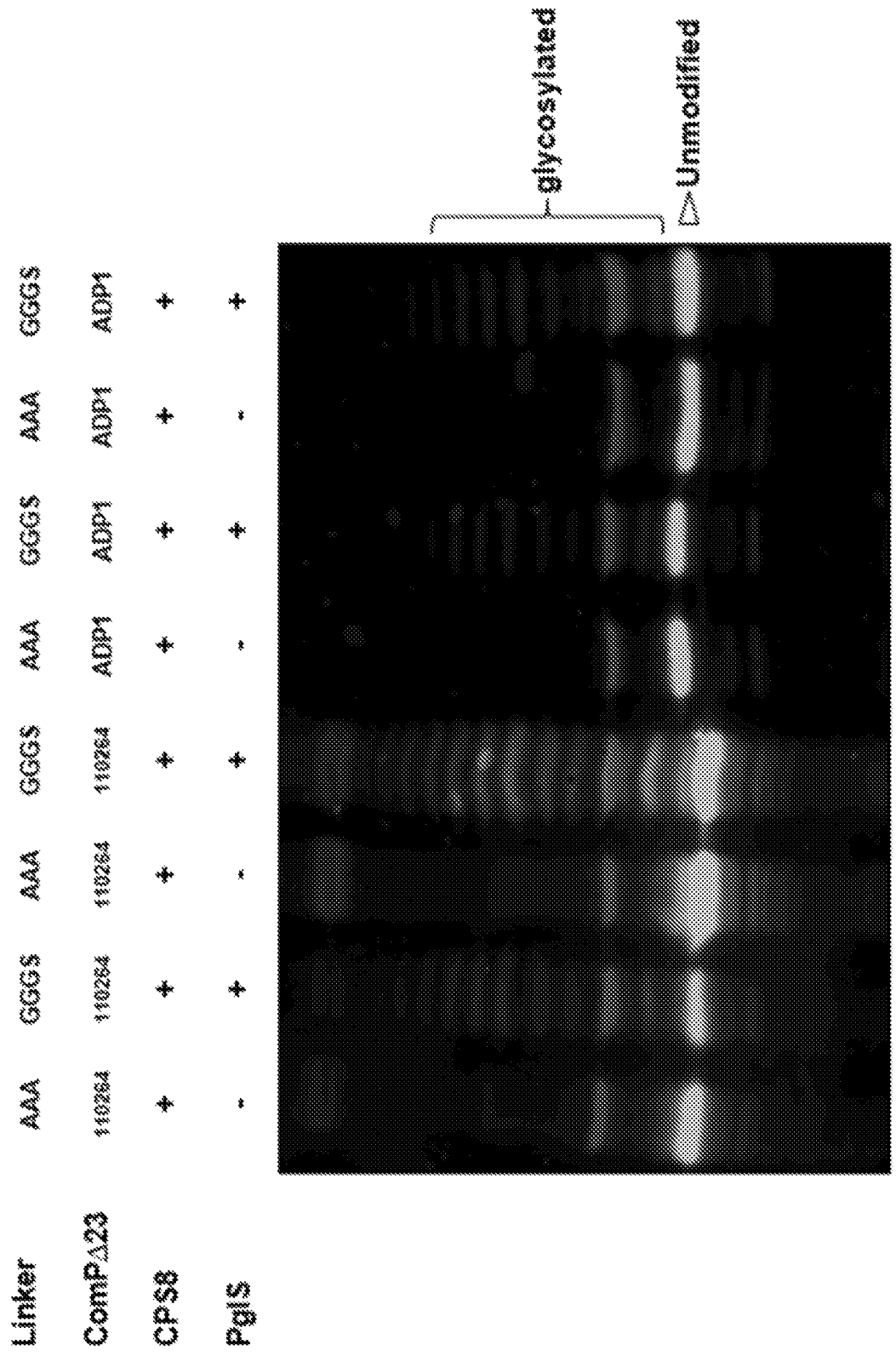
FIG. 21 shows that PglS$_{ADP1}$ efficiently glycosylates DsbA-ComPΔ28$_{110264}$ fusions but not DsbA-ComPΔ28$_{ADP1}$ fusions. All fusions either had a triple alanine peptide (AAA; SEQ ID NO: 24) or glycine-glycine-glycine-serine peptide (GGGS; SEQ ID NO: 23) linking DsbA to either a hexa-histidine tagged ComPΔ28$_{110264}$ or ComPΔ28$_{ADP1}$. Western blot analysis on *E. coli* whole cell lysates probing for hexa-histidine tagged ComP variants and RNA polymerase. RNA polymerase was used as a loading control.
Figure 22:
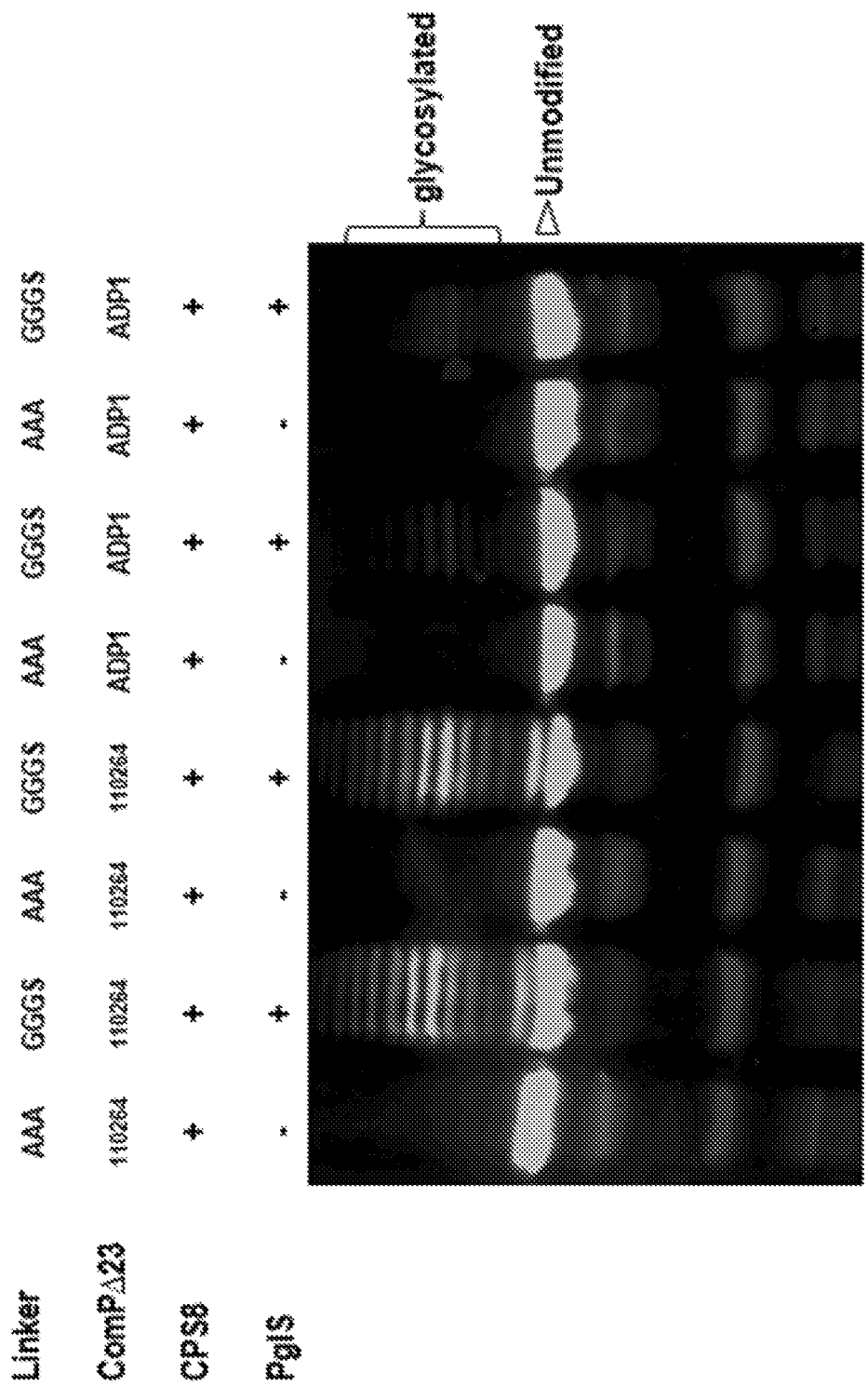
FIG. 22 shows that PglS$_{ADP1}$ efficiently glycosylates MBP-ComPΔ28$_{110264}$ fusions but not MBP-ComPΔ28$_{ADP1}$ fusions. All fusions either had a triple alanine peptide (AAA; SEQ ID NO: 24) or glycine-glycine-glycine-serine peptide (GGGS; SEQ ID NO: 23) linking maltose binding protein (MBP) to either a hexa-histidine tagged ComPΔ28$_{110264}$ or ComPΔ28$_{ADP1}$. Western blot analysis on *E. coli* whole cell lysates probing for hexa-histidine tagged ComP variants and RNA polymerase. RNA polymerase was used as a loading control.
Figure 23:
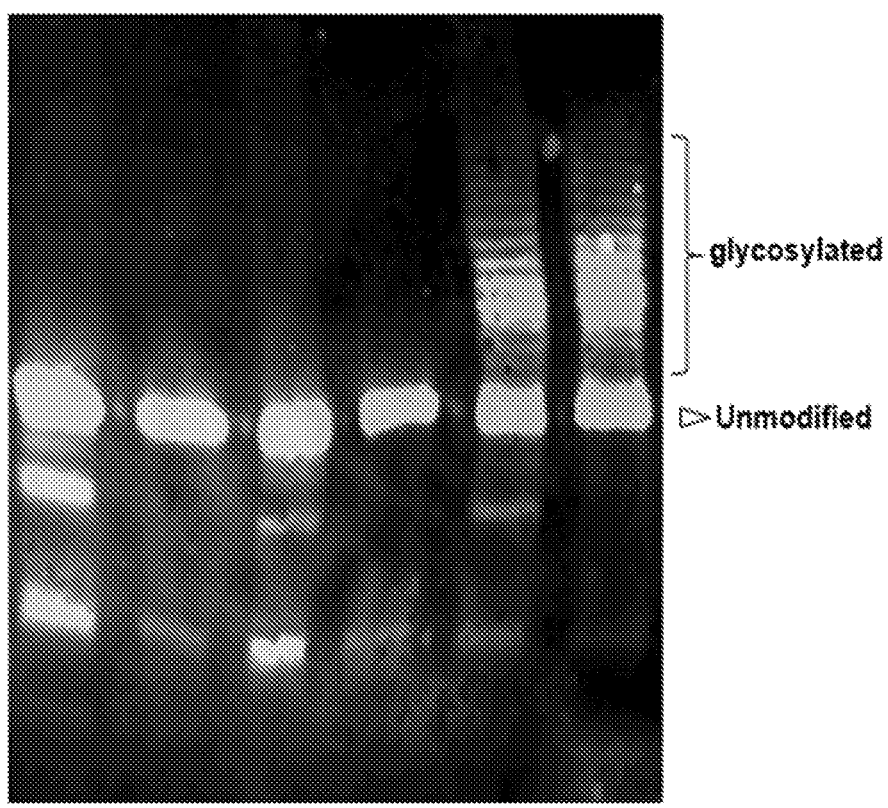
FIG. 23. PglS$_{ADP1}$, but not PglS$_{110264}$, efficiently EPA-GGGS-ComPΔ28$_{110264}$ fusions. Western blot analysis on *E. coli* whole cell lysates or periplasmic extracts probing for hexa-histidine tagged ComP variants. EPA-GGGS—exotoxin A with a glycine-glycine-glycine-serine peptide (GGGS; SEQ ID NO: 23) linking a hexa-histidine tagged ComPΔ28$_{110264}$ variant.

Generation of a soluble, periplasmic fusion protein capable of being glycosylated by PglS. All members of type IVa pilin family are considered membrane proteins as part of their N-terminal alpha helix is embedded within the inner membrane (Giltner, C. L., Nguyen, Y. & Burrows, L. L. *Microbiol Mol Biol Rev* 76, 740-772 (2012)). Therefore, in order to generate soluble variants of ComP that are able to be glycosylated by PglS, translational fusions were constructed of truncated ComP fragment proteins onto three different carrier proteins. The carrier proteins, DsbA and MalE (also known as maltose binding protein—MBP) from *E. coli*, were selected as suitable carriers as both have been previously shown to facilitate periplasmic localization and solubility of acceptor proteins fused at their C-termini (Malik, A. Biotech 6, 44 (2016)). Exotoxin A from *Pseudomonas aeruginosa* (EPA) was also selected as it has been previously shown to act as an immunogenic carrier protein in other conjugate vaccine formulations (Ravenscroft, N. et al. *Glycobiology* 26, 51-62 (2016)). Fusion proteins consisted of a leader sequence, carrier protein, a short linker peptide, a ComP variant without the first 28 amino acids, and a hexa-histidine tag. The first 28 amino acids of $ComP_{ADP1}$ and $ComP_{110264}$ were removed as these amino acids contain the leader sequence as well as the hydrophobic region of the N-terminal alpha helix predicted to be embedded into the inner membrane. Fusion constructs were then introduced into *E. coli* expressing the pneumococcal serotype 8 capsular polysaccharide (CPS8) and either pACT3 alone or pACT3 carrying $pglS_{110264}$ or $pglS_{ADP1}$. As seen in FIG. 21, *E. coli* cells expressing either DsbA-AAA-$ComP\Delta28_{110264}$ or DsbA-GGGS-$ComP\Delta28_{110264}$ in combination with $PglS_{ADP1}$ demonstrated detectable levels of glycosylation as indicated by the modal distribution of his reactive signals of increasing electrophoretic mobility. *E. coli* cells expressing fusions containing $ComP\Delta28_{ADP1}$ did not demonstrate any detectable glycosylation. The same glycosylation pattern was observed for *E. coli* cells expressing maltose binding protein (MBP) fusions. Specifically, as seen in FIG. 22, *E. coli* cells expressing either MBP-AAA-$ComP\Delta28_{110264}$ or MBP-GGGS-$ComP\Delta28_{110264}$ in combination with $PglS_{ADP1}$ demonstrated detectable levels of glycosylation as indicated by the modal distribution of anti-His reactive signals; whereas, fusions with $ComP\Delta28_{ADP1}$ were only minimally glycosylated. Lastly, to demonstrate that a previously established carrier protein used for conjugate vaccine formulations could be glycosylated by PglS with the pneumococcal CPS8, a fusion protein was engineered containing the DsbA signal peptide sequence fused to EPA. The $ComP\Delta28_{110264}$ peptide was then fused with glycine-glycine-glycine-serine (GGGS; SEQ ID NO: 23) linker to the C-terminus of EPA and tested for glycosylation in the presence and absence of $PglS_{ADP1}$ in both whole cell extracts and in periplasmic extracts. As seen in FIG. 23, EPA-GGGS-$ComP\Delta28_{110264}$ constructs were found to be glycosylated in both the whole cell extract and periplasmic extracts of cells co-expressing the CPS8 glycan and $PglS_{ADP1}$ as indicated by the modal distribution of anti-His reactive signals. No detectable glycosylation was observed in samples lacking a PglS ortholog or in the samples expressing $PglS_{110264}$. Collectively, $PglS_{ADP1}$ is an optimal OTase for transferring polysaccharides containing glucose at the reducing end to truncated ComP fusion proteins. Specific amino acid sequences for each fusion construct are shown in FIG. 24.

Figure 25A:
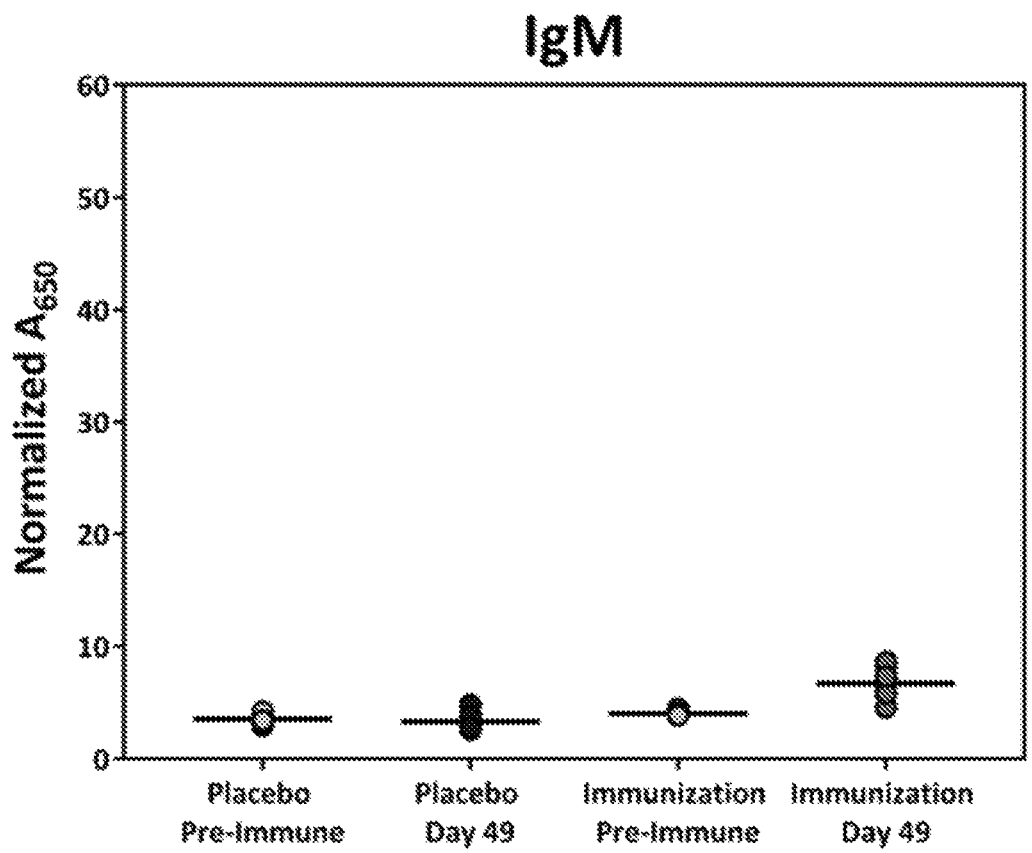
FIG. 25A, FIG. 25B, and FIG. 25C show that a monovalent CPS14-ComP$_{ADP1}$ bioconjugate vaccine induces serotype specific IgG antibodies.
Figure 25B:
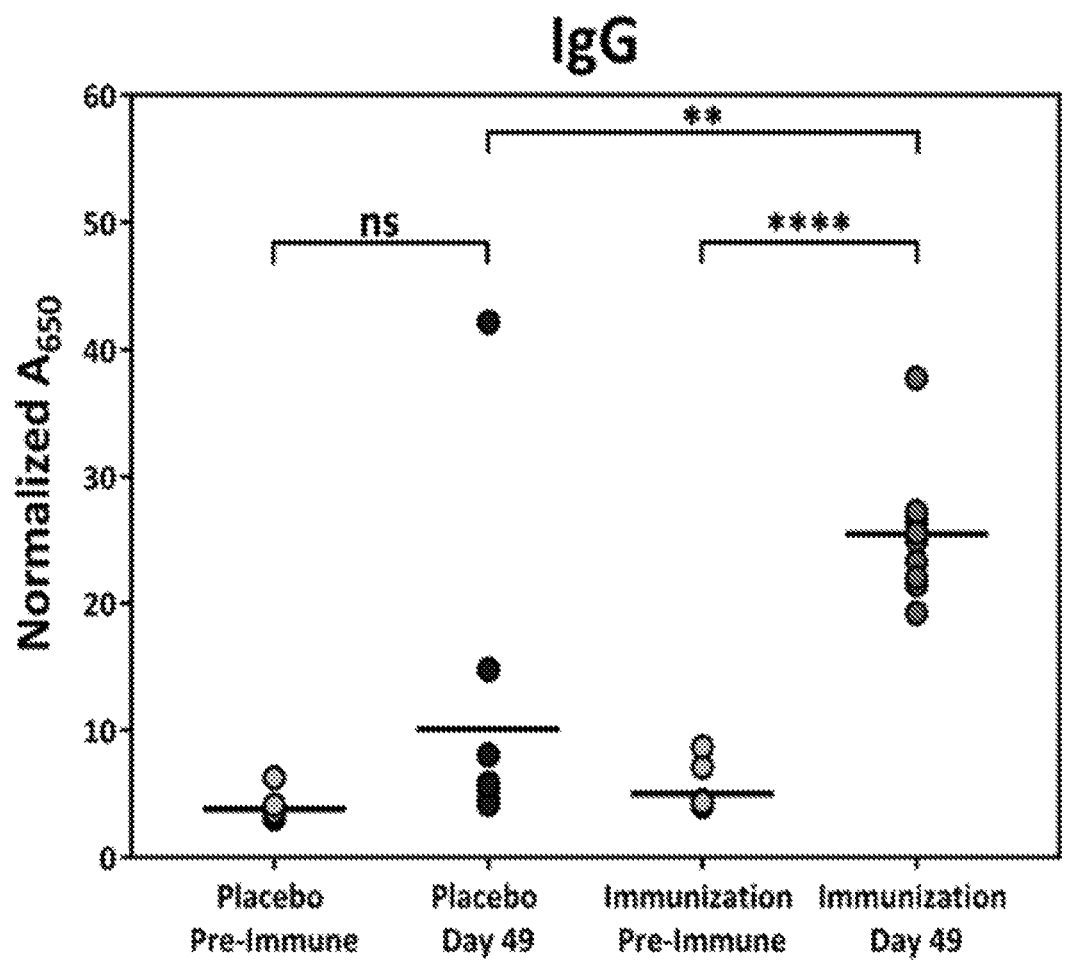

Immunization with a glycosylated ComP bioconjugate elicits an immune response. T-cell dependent immune responses to conjugate vaccines are characterized by the secretion of high affinity IgG1 antibody (Avci, F. Y., Li, X., Tsuji, M. & Kasper, D. L. *Nat Med* 17, 1602-1609 (2011)). The immunogenicity of a CPS14-ComP bioconjugate in a murine vaccination model was evaluated. As seen in FIG. 25A, sera collected from mice vaccinated with a CPS14-ComP bioconjugate had a significant increase in CPS14 specific IgG titers but not IgM titers. Further, secondary HRP-tagged anti-IgG subtype antibodies were employed to determine which of the IgG subtypes had elevated titers. As seen in FIG. 25B, IgG1 titers appeared to be higher than the other subtypes.

Figure 25C:
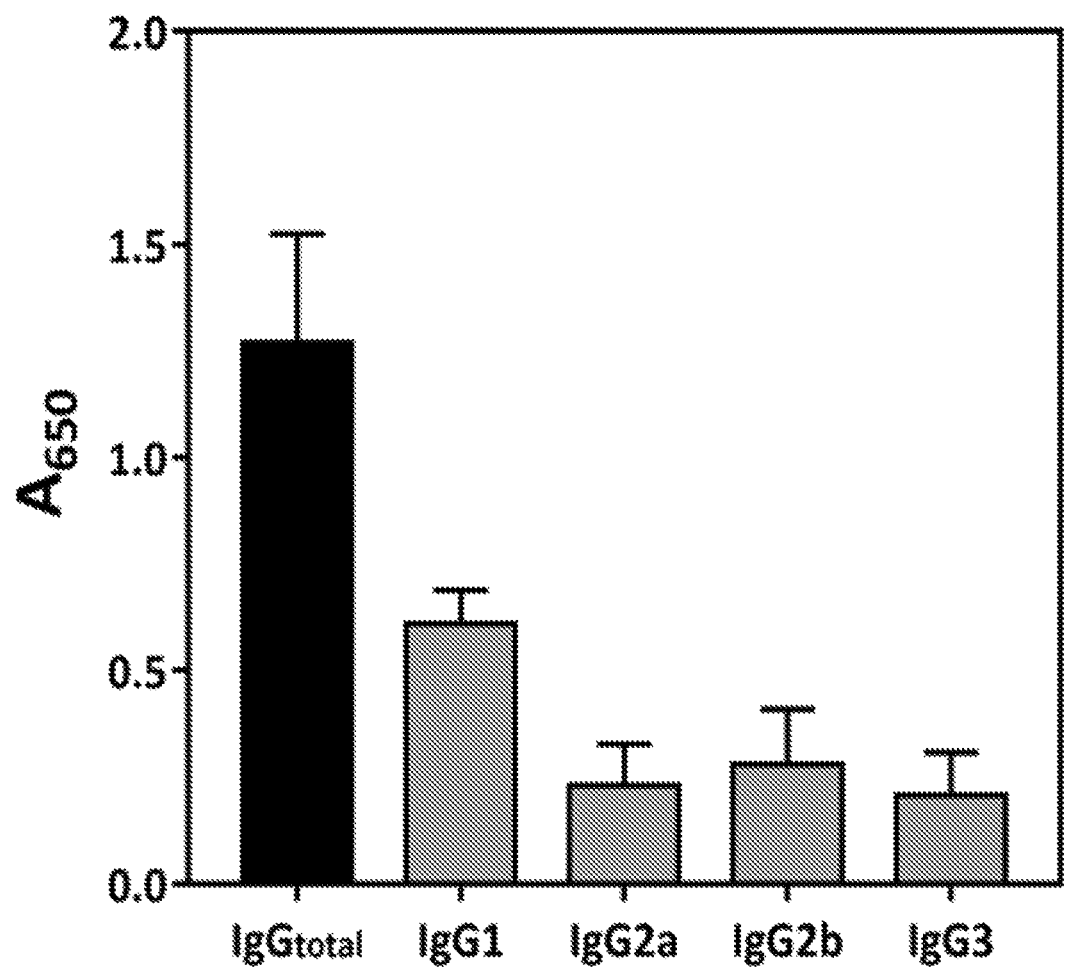
Figure 26:
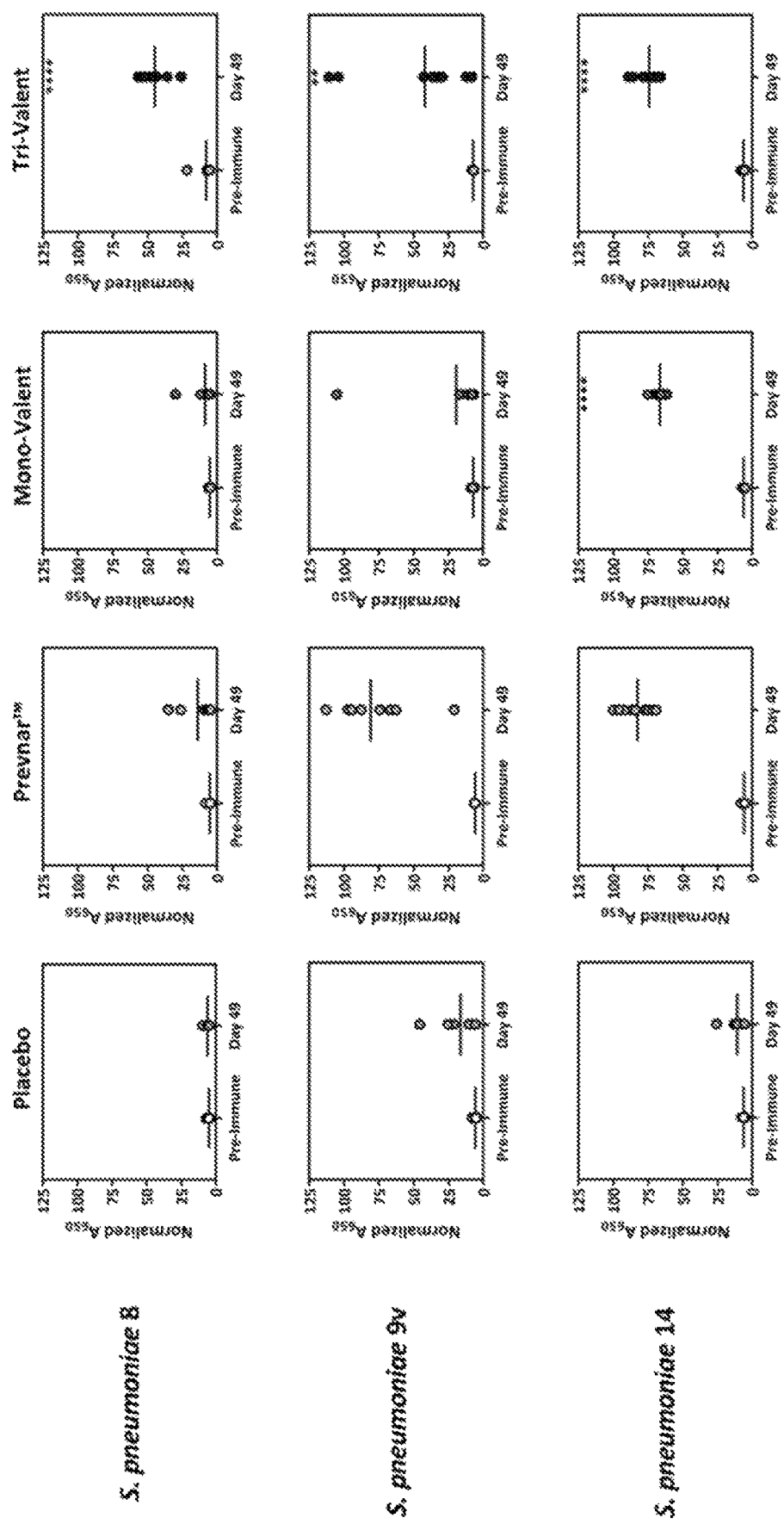
FIG. 26 shows that a trivalent bioconjugate vaccine against serotypes 8, 9V, and 14 induces serotype specific IgG titers at comparable levels to Prevnar 13.

Next, a second vaccination trial was performed comparing the immunogenicity of a trivalent CPS8-, CPS9V-, and CPS14-ComP bioconjugate to the current standard of care, PREVNAR 13®. Serotypes 9V and 14 are included in PREVNAR 13® and elevated IgG titers could be seen in PREVNAR 13® immunized mice against these two serotypes (FIG. 26). The monovalent immunization against serotype 14 also showed significant induction of serotype specific IgG titers, which were similar to the preliminary immunization (FIG. 25 and FIG. 26). Mice receiving the trivalent bioconjugate, all had elevations in serotype specific IgG titers when compared to control as expected, day 49 sera have shown much more elevated IgG tires for serotypes 8 and 14 compared to serotype 9V. Nevertheless, IgG titers against 9V were still significantly higher than the placebo (FIG. 26).

Provide herein are bioconjugates comprising an oligo- or polysaccharide linked to a fusion protein. In certain embodiments, the oligo- or polysaccharide is covalently linked to the fusion protein. In certain embodiments, the fusion protein comprises a ComP protein (ComP). In certain other embodiments, the fusion protein comprises a glycosylation tag of a ComP protein (as described in detail elsewhere herein).

Figure 39A:
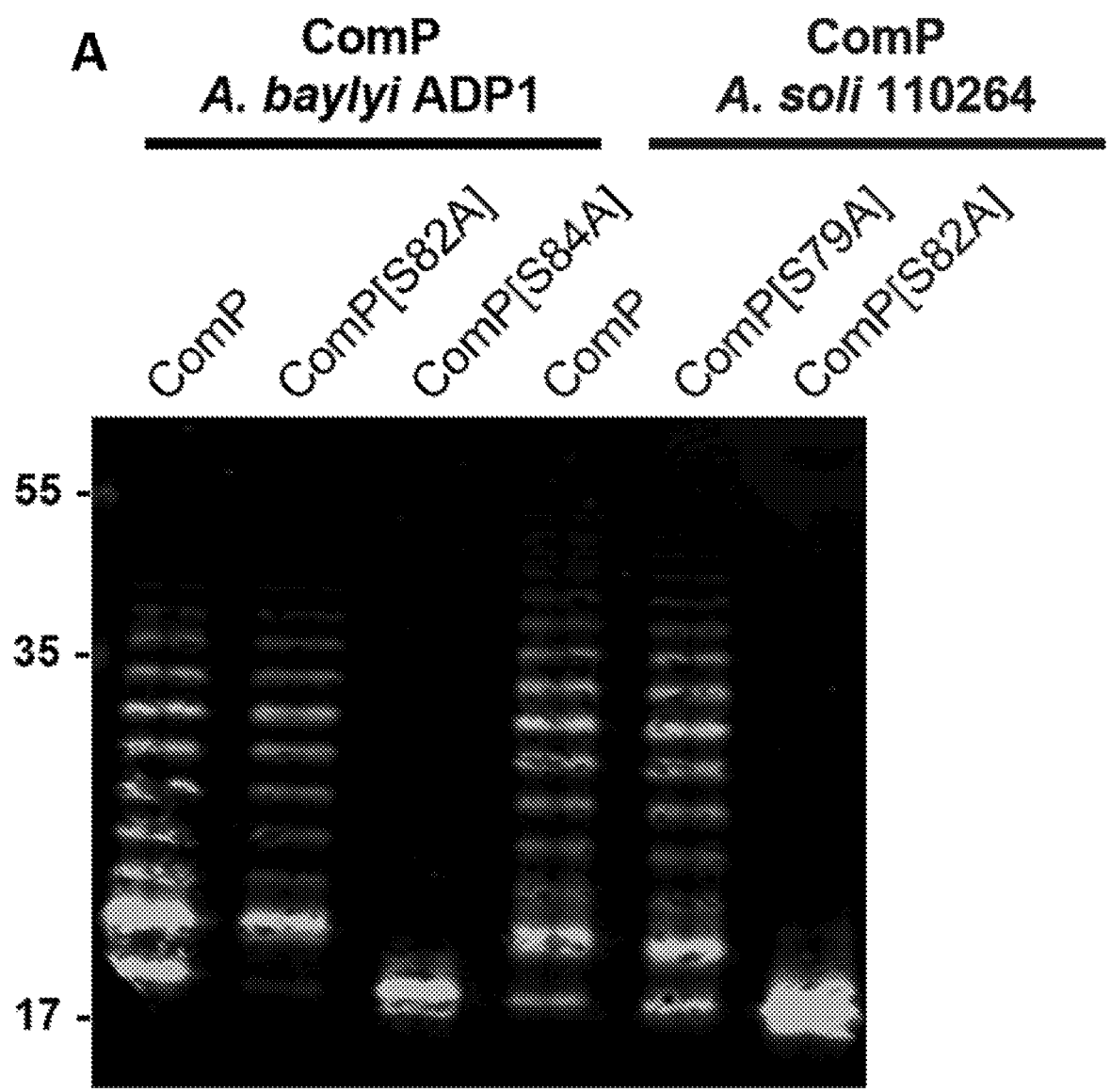
FIG. 39A, FIG. 39B, and FIG. 39C shows that a conserved and homologous serine is believed to be the site of glycosylation in ComP proteins from A. baylyi ADP1 and A. soli 110264. Serines 82 and 84 of ComPADP1 and the homologous serines 79 and 82 of ComP$_{110264}$ were mutated to an alanine and probed for glycosylation in the presence of PglS and the serotype 8 capsular polysaccharide. (A-C) SDB1 cells expressing ComP variants in the presence of PglS and CPS8 were probed via western blotting for protein glycosylation. (A) Anti-His channel probing for ComP expression and glycosylation. (B) Anti-glycan channel probing for CPS8. (C) Merged image for panels A and B.
Figure 39B:
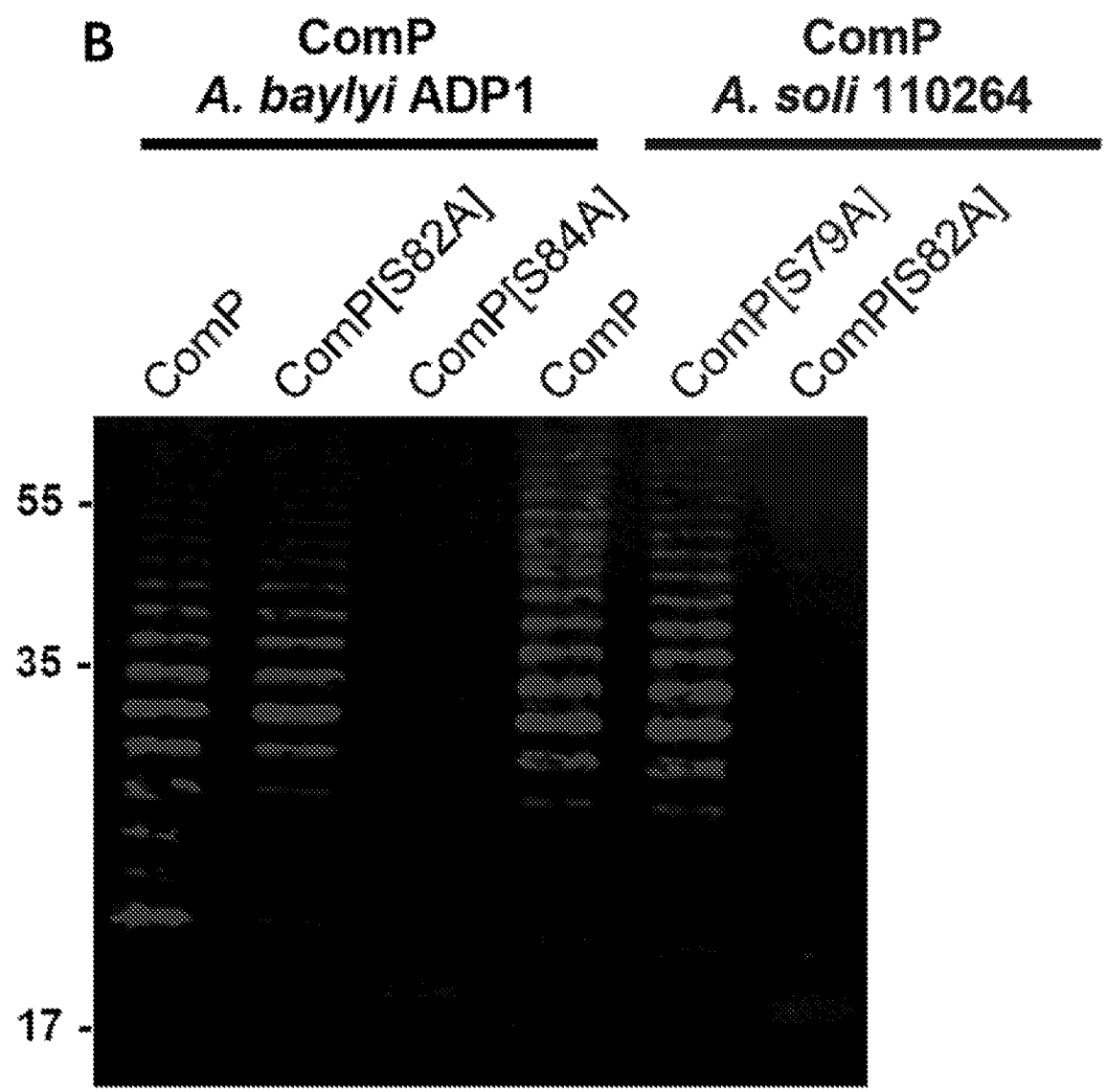
Figure 39C:
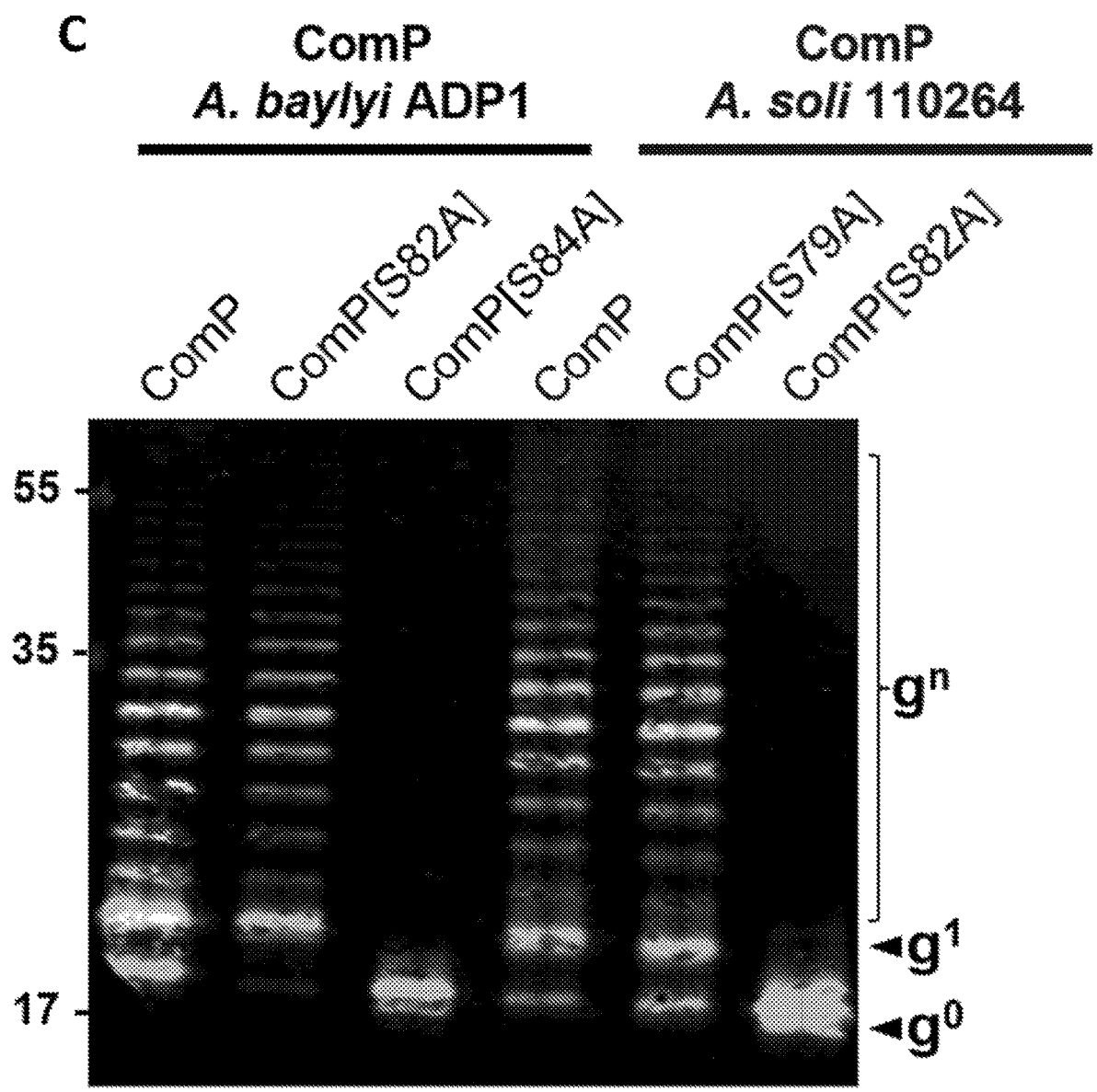
Figure 41A:
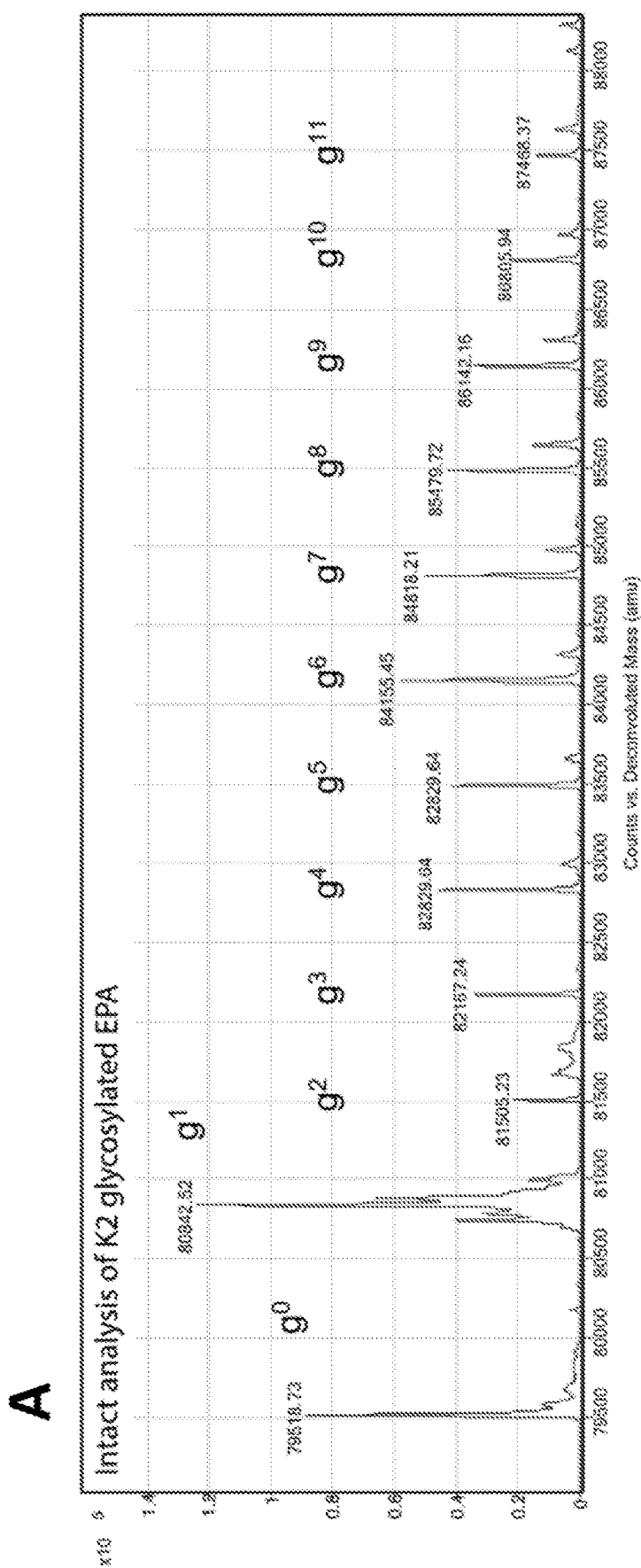
FIG. 41A and FIG. 41B shows intact protein mass spectrometry analysis showing the MS1 mass spectra for purified EPA-K2. The EPA fusion protein has a theoretical mass of 79,526.15 Daltons and can be observed as the peak at 79,518.73. The EPA fusion protein was also observed in multiple states of increasing mass corresponding to the K. pneumoniae K2 capsular polysaccharide repeating subunit, which has a theoretical mass of 662 Daltons. (A) Varying glycoforms of the EPA-K2 were observed and are denoted by "g$^{numeric}$", where "g" stands for glycoform and "numeric" corresponds to the number of repeating K2 subunits. The EPA fusion protein was modified with up to 11 repeating subunits of the K2 capsule. (B) A zoomed in view of A is also provided.
Figure 41B:
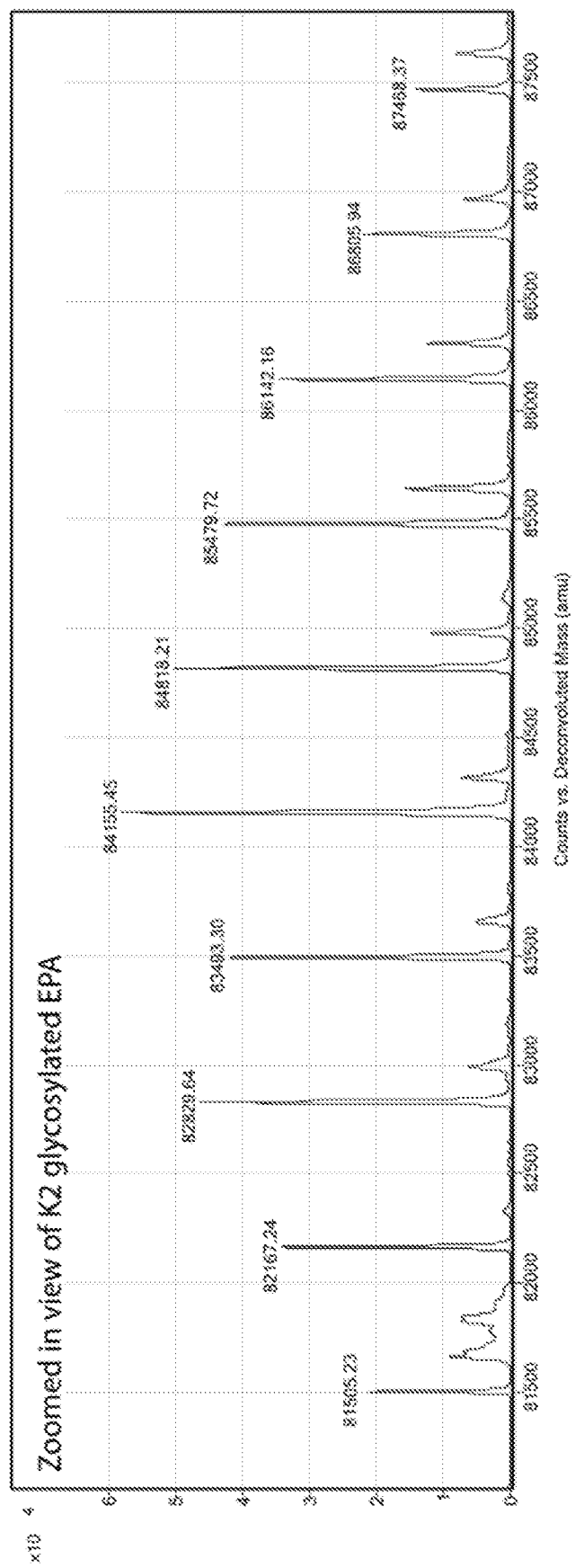

As disclosed herein, it has been discovered that ComP is glycosylated on a serine (S) residue. This serine residue is conserved in ComP proteins and corresponds to position 84 of SEQ ID NO: 1 (ComP$_{ADP1}$: AAC45886.1). This serine residue also corresponds to position 82 of SEQ ID NO: 2 (ComP$_{110264}$: ENV58402.1) (FIGS. 39A, B, and C). Thus, in certain aspects, a fusion protein (and thus the bioconjugate) is glycosylated with an oligo- or polysaccharide on a ComP glycosylation tag thereof at a serine residue corresponding to the serine residue at position 84 of SEQ ID NO: 1 (ComP$_{ADP1}$: AAC45886.1) or corresponding to the serine residue at position 82 of SEQ ID NO: 2. FIG. 28 shows an alignment of a region of ComP sequences including the serine (S) residue (boxed) corresponding to the serine residue at position 84 of SEQ ID NO: 1 (ComP$_{ADP1}$: AAC45886.1), which is conserved across the ComP sequences. In certain embodiments, in order to be able to be glycosylated, the ComP glycosylation tag comprises both a cysteine residue corresponding to the conserved cysteine residue at position 75 of SEQ ID NO: 1 (ComP$_{ADP1}$: AAC45886.1) and a cysteine residue corresponding to the conserved cysteine residue at position 95 of SEQ ID NO: 1. Or, similarly described, in certain embodiments, in order to be able to be glycosylated, the ComP glycosylation tag comprises both a cysteine residue corresponding to the conserved cysteine residue at position 71 of SEQ ID NO: 2 (ComP$_{ADP1}$: AAC45886.1) and a cysteine residue corresponding to the conserved cysteine residue at position 93 of SEQ ID NO: 2.

In certain embodiments of a bioconjugate of this disclosure, the oligo- or polysaccharide comprises a glucose at its reducing end.

One of ordinary skill in the art would recognize that by aligning ComP sequences with SEQ ID NO: 1, (e.g., either full sequences or partial sequences) the conserved serine residue of a non-SEQ ID NO: 1 ComP protein disclosed herein, corresponding to the serine residue at position 84 of SEQ ID NO: 1, can be identified. Further, one of ordinary skill in the art would recognize that by aligning ComP sequences with SEQ ID NO: 1, other residues, regions, and/or features corresponding to residues, regions, and/or features of SEQ ID NO: 1 as referred to herein can be identified in the non-SEQ ID NO: 1 ComP sequence and referenced in relation to SEQ ID NO:1. And, while reference is generally made herein to SEQ ID NO: 1, by analogy, reference can similarly be made to any residue, region, feature and the like of any ComP sequence disclosed herein, for example, in reference to SEQ ID NO: 2.

A ComP protein is a protein that has been identified as ComP protein consistent with the description provided herein. For example, representative examples of ComP proteins include, but are not limited to: AAC45886.1 ComP [*Acinetobacter* sp. ADP1]; ENV58402.1 hypothetical protein F951_00736 [*Acinetobacter soli* CIP 110264]; APV36638.1 competence protein [*Acinetobacter soli* GFJ-2]; PKD82822.1 competence protein [*Acinetobacter radioresistens* 50v1]; SNX44537.1 type IV pilus assembly protein PilA [*Acinetobacter puyangensis* ANC 4466]; and OAL75955.1 competence protein [*Acinetobacter* sp. SFC]. In certain aspects, a ComP protein comprises an amino acid sequence that is at least 50%, 60%, 70%, 75%, 80%, 85%, 90%, 95%, 96%, 97%, 98%, 99%, or 100% identical to SEQ ID NO: 1 (ComP$_{ADP1}$: AAC45886.1) and contains a serine residue corresponding to the conserved serine residue at position 84 of SEQ ID NO: 1 (ComP$_{ADP1}$: AAC45886.1). SEQ ID NO: 1 comprises a leader sequence of 28 amino acids. In certain aspects, a ComP protein comprises an amino acid sequence that is at least 50%, 60%, 70%, 75%, 80%, 85%, 90%, 95%, 97%, 98%, 99%, or 100% identical to SEQ ID NO: 7 (ComPΔ28$_{ADP1}$), SEQ ID NO: 8 (ComPΔ28$_{110264}$), SEQ ID NO: 9 (ComPΔ28$_{GFJ-3}$), SEQ ID NO: 10 (ComPΔ28$_{P50v1}$), SEQ ID NO: 11 (ComPΔ28$_{4466}$), or SEQ ID NO: 12 (ComPΔ28$_{SFC}$) that do not include the 28 amino acid leader sequence but do contain a serine residue corresponding to the conserved serine residue at position 84 of SEQ ID NO: 1 (ComP$_{ADP1}$: AAC45886.1). In certain aspects, a ComP protein comprises an amino acid sequence that is at least 50%, 60%, 70%, 75%, 80%, 85%, 90%, 95%, 97%, 98%, 99%, or 100% identical to SEQ ID NO: 7 (ComPΔ28$_{ADP1}$) that does not include the 28 amino acid leader sequence but does contain a serine residue corresponding to the conserved serine residue at position 84 of SEQ ID NO: 1 (ComP$_{ADP1}$: AAC45886.1). In certain aspects, the ComP protein comprises SEQ ID NO: 7 (ComPΔ28$_{ADP1}$), SEQ ID NO: 8 (ComPΔ28$_{110264}$), SEQ ID NO: 9 (ComPΔ28$_{GFJ-2}$), SEQ ID NO: 10 (ComPΔ28$_{P50v1}$), SEQ ID NO: 11 (ComPΔ28$_{4466}$), or SEQ ID NO: 12 (ComPΔ28$_{SFC}$). In certain aspects, the ComP protein is SEQ ID NO: 1 (ComP$_{ADP1}$: AAC45886.1), SEQ ID NO: 2 (ComP$_{110264}$: ENV58402.1), SEQ ID NO: 3 (ComP$_{GFJ-2}$: APV36638.1), SEQ ID NO: 4 (ComP$_{50v1}$: PKD82822.1), SEQ ID NO: 5 (ComP$_{4466}$: SNX44537.1), or SEQ ID NO: 6 (ComP$_{SFC}$: OAL75955.1).

In certain aspects, the bioconjugate is produced in vivo in a host cell such as by any of the methods of production disclosed herein. In certain aspects, the bioconjugate is produced in a bacterial cell, a fungal cell, a yeast cell, an avian cell, an algal cell, an insect cell, or a mammalian cell. In certain aspects, the bioconjugate is produced in a cell free system. Examples of the use of a cell free system utilizing OTases other than PglS can be found in WO2013/067523A1, which in incorporated herein by reference.

It has been discovered that a methionine residue corresponding to the conserved methionine residue at position 104 of SEQ ID NO: 2 (ComP$_{110264}$: ENV58402.1) can have an inhibitory effect on glycosylation when present in a ComP glycosylation tag even though the full length ComP protein comprising this methionine residue is glycosylated. Thus, in certain embodiments, the ComP glycosylation tag of this disclosure does not comprise a methionine residue corresponding to the conserved methionine residue at position 104 of SEQ ID NO: 2 (ComP$_{110264}$: ENV58402.1). For example, in certain embodiments, such methionine residue in a ComP amino acid sequence is substituted with another amino acid that does not exhibit an inhibitory effect or is deleted from the ComP glycosylation tag amino acid sequence. In certain embodiments, the amino acid sequence of the ComP glycosylation tag does not extend in the C-terminus direction beyond the amino acid residue corresponding to position 103 of SEQ ID NO: 2 (ComP$_{110264}$: ENV58402.1). For example, in certain embodiments, the amino acid sequence of the ComP glycosylation tag ends with the residue corresponding to position 93, 94, 95, 96, 97, 98, 99, 100, 101, 102, or 103 of SEQ ID NO: 2 (ComP$_{110264}$:

ENV58402.1). One of ordinary skill in the art would recognize that a fusion protein comprising a ComP glycosylation tag likewise would not comprise a methionine residue at a position corresponding to or corresponding about to the conserved methionine residue at position 104 of SEQ ID NO: 2 (ComP$_{110264}$: ENV58402.1) in relation to the ComP glycosylation tag, even if the methionine residue is attributed to a sequence of the fusion protein not as belonging to the ComP glycosylation tag sequence. For example, in certain embodiments, the fusion protein of the bioconjugate does not comprise, in relationship to the ComP glycosylation tag, a methionine residue at a position that would correspond to or correspond about to the conserved methionine residue at position 104 of SEQ ID NO: 2 (ComP$_{110264}$: ENV58402.1). In certain embodiments, the fusion protein of the bioconjugate does not comprise, in relationship to the ComP glycosylation tag, a methionine residue at a position that would correspond to the conserved methionine residue at position 104 of SEQ ID NO: 2 (ComP$_{110264}$: ENV58402.1).

A ComP glycosylation tag of the current disclosure is generally not a full length ComP protein. In certain embodiments of any ComP glycosylation tag described herein, the ComP glycosylation tag has a length of between 18 and 50 amino acids in length, for example, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 amino acids in length. In certain embodiments, the glycosylation tag has length of between 21 and 45 amino acids in length. In certain embodiments, the glycosylation tag has a length of between 23 and 45 amino acids in length.

The ComP glycosylation tag of the current disclosure can be a fragment, a variant, or a variant fragment of a ComP protein as described anywhere herein. In certain embodiments, the ComP protein comprises an amino acid sequence that is at least 50%, 60%, 70%, 75%, 80%, 85%, 90%, 95%, 96%, 97%, 98%, 99%, or 100% identical to SEQ ID NO: 7 (ComPΔ28$_{ADP1}$), SEQ ID NO: 8 (ComPΔ28$_{116264}$), SEQ ID NO: 9 (ComPΔ28$_{GFJ-2}$), SEQ ID NO: 10 (ComPΔ28$_{P50v1}$), SEQ ID NO: 11 (ComPΔ28$_{4466}$), or SEQ ID NO: 12 (ComPΔ28$_{SFC}$). For example, in certain embodiments, the ComP protein comprises an amino acid sequence that is at least 50%, 60%, 70%, 75%, 80%, 85%, 90%, 95%, 96%, 97%, 98%, 99%, or 100% identical to SEQ ID NO: 7 (ComPΔ28$_{ADP1}$) or SEQ ID NO: 8 (ComPΔ28$_{1106264}$). In certain embodiments, the ComP protein comprises SEQ ID NO: 7 (ComPΔ28$_{ADP1}$), SEQ ID NO: 8 (ComPΔ28$_{110264}$), SEQ ID NO: 9 (ComPΔ28$_{GFJ-2}$), SEQ ID NO: 10 (ComPΔ28$_{P50v1}$), SEQ ID NO: 11 (ComPΔ28$_{4466}$), or SEQ ID NO: 12 (ComPΔ28$_{SFC}$). Further, in certain embodiments, the ComP protein comprises an amino acid sequence that is at least 50%, 60%, 70%, 75%, 80%, 85%, 90%, 95%, 96%, 97%, 98%, 99%, or 100% identical to SEQ ID NO: 1 (ComP$_{ADP1}$: AAC45886.1), SEQ ID NO: 2 (ComP$_{110264}$: ENV58402.1), SEQ ID NO: 3 (ComP$_{G}$FJ-2: APV36638.1), SEQ ID NO: 4 (Comp$_{50v1}$: PKD82822.1), SEQ ID NO: 5 (ComP$_{4466}$: SNX44537.1), or SEQ ID NO: 6 (ComP$_{SFC}$: OAL75955.1). For example, in certain embodiments, the ComP protein comprises an amino acid sequence that is at least 50%, 60%, 70%, 75%, 80%, 85%, 90%, 95%, 96%, 97%, 98%, 99%, or 100% identical to SEQ ID NO: 1 (ComP$_{ADP1}$: AAC45886.1) or SEQ ID NO: 2 (ComP$_{110264}$: ENV58402.1). Further, in certain embodiments, the ComP protein comprises SEQ ID NO: 1 (ComP$_{ADP1}$: AAC45886.1), SEQ ID NO: 2 (ComP$_{110264}$: ENV58402.1), SEQ ID NO: 3 (ComP$_{GFJ-2}$: APV36638.1), SEQ ID NO: 4 (Comp$_{50v1}$: PKD82822.1), SEQ ID NO: 5 (ComP$_{4466}$: SNX44537.1), or SEQ ID NO: 6 (ComP$_{SFC}$: OAL75955.1).

In certain embodiments, a ComP glycosylation tag of the current disclosure can be defined as comprising or consisting of the amino acid consensus sequence of SEQ ID NO: 27:

(SEQ ID NO: 27)
$X_1X_2GTX_5X_6X_7X_8X_9X_{10}X_{11}X_{12}\underline{C}X_{14}GVX_{17}X_{18}IX_{20}X_{21}X_{22}\mathbf{AS}X_{25}X_{26}TX_{28}N$
$VX_{31}X_{32}AX_{34}\underline{C}X_{36}X_{37}X_{38}X_{39}X_{40}X_{41}X_{42}X_{43}X_{44}$ wherein: $X_1$ is V, A, or no amino acid;
$X_2$ is A, G, T, or no amino acid;
$X_5$ is P, S, or Q;
$X_6$ is S, M, or I;
$X_7$ is T, P, or V;
$X_8$ is A, S, or T;
$X_9$ is G, N, S, or T;
$X_{10}$ is N or no amino acid;
$X_{11}$ is S, G, or A;
$X_{12}$ is S or N;
$X_{14}$ is V, T, or A;
$X_{17}$ is Q, T, or E;
$X_{18}$ is E, Q, or T;
$X_{20}$ is S, N, A, or G;
$X_{21}$ is S or no amino acid;
$X_{22}$ is G or no amino acid;
$X_{25}$ is N, S, or A;
$X_{26}$ is A, S, or K;
$X_{28}$ is T, S, or K;
$X_{31}$ is A or E;
$X_{32}$ is T or S;
$X_{34}$ is T, Q, or A;
$X_{36}$ is G, S, or T;
$X_{37}$ is A, G, or D;
$X_{38}$ is S, L, or A;
$X_{39}$ is S, G, D, or T;
$X_{40}$ is A, V, or G;
$X_{41}$ is G, I, or V;
$X_{42}$ is Q, T, or I;
$X_{43}$ is I, V, T, or L; and
$X_{44}$ is I, T, or V.

In certain embodiments, a ComP glycosylation tag comprises or consists of a fragment of the amino acid consensus sequence of SEQ ID NO: 27, wherein the fragment retains the cysteine residue at position 13 of SEQ ID NO: 27, the cysteine residue at position 35 of SEQ ID NO: 27, and the serine residue at position 24 of SEQ ID NO: 27. In certain embodiments, a ComP glycosylation tag comprises or consists of a variant of the amino acid consensus sequence of SEQ ID NO: 27 or a fragment thereof, having one, two, three, four, five, six, or seven amino acid substitutions, additions, and/or deletions, however, wherein the variant maintains the cysteine residue at position 13 of SEQ ID NO: 27, the cysteine residue at position 35 of SEQ ID NO: 27, and the serine residue at position 24 of SEQ ID NO: 27. In certain embodiments, the amino acid substitution is a conservative amino acid substitution. As disclosed herein, in certain embodiments, a ComP glycosylation tag comprising SEQ ID NO: 27 does not comprise a methionine residue in a position corresponding to the conserved methionine residue at position 104 of SEQ ID NO: 2 (ComP$_{110264}$: ENV58402.1). Further, in certain embodiments, the amino acid sequence of a ComP glycosylation tag comprising SEQ ID NO: 27 does not extend in the C-terminus direction beyond the amino acid residue corresponding to position 44 of SEQ ID NO: 27. In certain embodiments, a ComP glycosylation tag comprising or consisting of the amino acid consensus sequence of SEQ ID NO: 27 or fragment and/or variant thereof is not more than 25, 30, 40, 45, or 50 amino acids in length.

In certain embodiments, a ComP glycosylation tag of the current disclosure can be defined as comprising or consisting of the amino acid consensus sequence of SEQ ID NO: 28:

(SEQ ID NO: 28)
$CX_2GVX_5X_6IX_8X_9X_{10}ASX_{13}X_{14}TX_{16}NVX_{19}X_{20}AX_{22}C$ wherein:

$X_2$ is V, T, or A, optionally V;
$X_5$ is Q, T, or E, optionally Q;
$X_6$ is E, Q, or T;
$X_8$ is S, N, A, or G;
$X_9$ is S or no amino acid;
$X_{10}$ is G or no amino acid;
$X_{13}$ is N, S, or A, optionally N;
$X_{14}$ is A, S, or K, optionally A;
$X_{16}$ is T, S, or K;
$X_{19}$ is A or E, optionally A;
$X_{20}$ is T or S, optionally T; or
$X_{22}$ is T, Q, or A, optionally T.

In certain embodiments, a ComP glycosylation tag comprises or consists of a variant of the amino acid consensus sequence of SEQ ID NO: 28 having one, two, three, four, five, six, or seven amino acid substitutions, additions, and/or deletions, however, wherein the variant maintains the cysteine residue at position 1 of SEQ ID NO: 28, the cysteine residue at position 23 of SEQ ID NO: 28, and the serine residue at position 12 of SEQ ID NO: 28. In certain embodiments, the amino acid substitution is a conservative amino acid substitution.

In certain embodiments, a ComP glycosylation tag comprising SEQ ID NO: 28 does not comprise a methionine residue in a position corresponding to the conserved methionine residue at position 104 of SEQ ID NO: 2 ($ComP_{110264}$: ENV58402.1). Further, in certain embodiments, the amino acid sequence of a ComP glycosylation tag comprising SEQ ID NO: 28 does not extend in the C-terminus direction beyond the amino acid residue corresponding to position 103 of SEQ ID NO: 2 ($ComP_{110264}$: ENV58402.1). In certain embodiments, a ComP glycosylation tag comprising the amino acid consensus sequence of SEQ ID NO: 28 or variant thereof is not more than 25, 30, 40, 45, or 50 amino acids in length.

In certain embodiments, the ComP glycosylation tag comprises or consists of a variant thereof having one, two, three, four, five, six, or seven amino acid substitutions, additions, and/or deletions of an amino acid sequence selected from the group consisting of: SEQ ID NO: 32 [C1]; SEQ ID NO: 33 [D1]; SEQ ID NO: 34 [E1]; SEQ ID NO: 41 [E2]; SEQ ID NO: 42 [F2]; SEQ ID NO: 43 [G2]; SEQ ID NO: 44 [H2]; SEQ ID NO: 45 [A3]; SEQ ID NO: 46 [B3]; SEQ ID NO: 47 [C3]; SEQ ID NO: 55 [D4]; SEQ ID NO: 56 [E4]; SEQ ID NO: 57 [F4]; SEQ ID NO: 58 [G4]; SEQ ID NO: 59 [A5]; SEQ ID NO: 60 [B5]; SEQ ID NO: 61 [D5]; SEQ ID NO: 62 [E5]; SEQ ID NO: 63 [F5]; SEQ ID NO: 72 [H6]; SEQ ID NO: 73 [B7]; SEQ ID NO: 74 [C7]; SEQ ID NO: 75 [D7]; SEQ ID NO: 76 [E7]; SEQ ID NO: 77 [F7]; SEQ ID NO: 78 [A8]; SEQ ID NO: 79 [B8]; SEQ ID NO: 92 [A10]; SEQ ID NO: 93 [B10]; SEQ ID NO: 94 [C10]; SEQ ID NO: 95 [D10]; SEQ ID NO: 96 [F10]; SEQ ID NO: 97 [G10]; SEQ ID NO: 98 [H10]; SEQ ID NO: 99 [A11]; SEQ ID NO: 100 [B11]; and SEQ ID NO: 101 [C11], wherein the variant maintains both a cysteine residue corresponding to the conserved cysteine residue at position 75 of SEQ ID NO: 1 ($ComP_{ADP1}$: AAC45886.1) and a cysteine residue corresponding to the conserved cysteine residue at position 95 of SEQ ID NO: 1 and the variant maintains a serine residue corresponding to the conserved serine residue at position 84 of SEQ ID NO: 1. In certain embodiments, the amino acid substitution is a conservative amino acid substitution. Further, in certain embodiments, the ComP glycosylation tag comprises or consists of an amino acid sequence selected from the group consisting of: SEQ ID NO: 32 [C1]; SEQ ID NO: 33 [D1]; SEQ ID NO: 34 [E1]; SEQ ID NO: 41 [E2]; SEQ ID NO: 42 [F2]; SEQ ID NO: 43 [G2]; SEQ ID NO: 44 [H2]; SEQ ID NO: 45 [A3]; SEQ ID NO: 46 [B3]; SEQ ID NO: 47 [C3]; SEQ ID NO: 55 [D4]; SEQ ID NO: 56 [E4]; SEQ ID NO: 57 [F4]; SEQ ID NO: 58 [G4]; SEQ ID NO: 59 [A5]; SEQ ID NO: 60 [B5]; SEQ ID NO: 61 [D5]; SEQ ID NO: 62 [E5]; SEQ ID NO: 63 [F5]; SEQ ID NO: 72 [H6]; SEQ ID NO: 73 [B7]; SEQ ID NO: 74 [C7]; SEQ ID NO: 75 [D7]; SEQ ID NO: 76 [E7]; SEQ ID NO: 77 [F7]; SEQ ID NO: 78 [A8]; SEQ ID NO: 79 [B8]; SEQ ID NO: 92 [A10]; SEQ ID NO: 93 [B10]; SEQ ID NO: 94 [C10]; SEQ ID NO: 95 [D10]; SEQ ID NO: 96 [F10]; SEQ ID NO: 97 [G10]; SEQ ID NO: 98 [H10]; SEQ ID NO: 99 [A11]; SEQ ID NO: 100 [B11]; and SEQ ID NO: 101 [C11]. In certain embodiments, such a ComP glycosylation tag comprising one of the above sequences or variants thereof does not comprise a methionine residue in a position corresponding to the conserved methionine residue at position 104 of SEQ ID NO: 2 ($ComP_{110264}$: ENV58402.1). Further, in certain embodiments, the amino acid sequence of such a ComP glycosylation tag comprising one of the above sequences or variants thereof does not extend in the C-terminus direction beyond the amino acid residue corresponding to position 103 of SEQ ID NO: 2 ($ComP_{110264}$: ENV58402.1). In certain embodiments, a ComP glycosylation tag comprising an amino acid sequence and/or variant thereof listed above is not more than 25, 30, 40, 45, or 50 amino acids in length. In certain embodiments, a ComP glycosylation tag consists of an amino acid sequence selected from the group consisting of: SEQ ID NO: 32 [C1]; SEQ ID NO: 33 [D1]; SEQ ID NO: 34 [E1]; SEQ ID NO: 41 [E2]; SEQ ID NO: 42 [F2]; SEQ ID NO: 43 [G2]; SEQ ID NO: 44 [H2]; SEQ ID NO: 45 [A3]; SEQ ID NO: 46 [B3]; SEQ ID NO: 47 [C3]; SEQ ID NO: 55 [D4]; SEQ ID NO: 56 [E4]; SEQ ID NO: 57 [F4]; SEQ ID NO: 58 [G4]; SEQ ID NO: 59 [A5]; SEQ ID NO: 60 [B5]; SEQ ID NO: 61 [D5]; SEQ ID NO: 62 [E5]; SEQ ID NO: 63 [F5]; SEQ ID NO: 72 [H6]; SEQ ID NO: 73 [B7]; SEQ ID NO: 74 [C7]; SEQ ID NO: 75 [D7]; SEQ ID NO: 76 [E7]; SEQ ID NO: 77 [F7]; SEQ ID NO: 78 [A8]; SEQ ID NO: 79 [B8]; SEQ ID NO: 92 [A10]; SEQ ID NO: 93 [B10]; SEQ ID NO: 94 [C10]; SEQ ID NO: 95 [D10]; SEQ ID NO: 96 [F10]; SEQ ID NO: 97 [G10]; SEQ ID NO: 98 [H10]; SEQ ID NO: 99 [A11]; SEQ ID NO: 100 [B11]; and SEQ ID NO: 101 [C11].

In certain embodiments, the oligo- or polysaccharide for conjugation to the glycosylation tag, fusion protein, and/or bioconjugate is produced by a bacteria from the genus *Streptococcus*. For example, in certain embodiments, the polysaccharide is a *S. pneumoniae, S. agalactiae*, or *S. suis* capsular polysaccharide. Further, in certain embodiments, the capsular polysaccharide is CPS14, CPS8, CPS9V, or CPS15b. In certain other embodiments, the oligo- or polysaccharide is produced by a bacteria from the genus *Klebsiella*. For example, in certain embodiments, the polysaccharide is a *Klebsiella pneumoniae, Klebsiella varricola, Klebsiella michinganenis*, or *Klebsiella oxytoca* capsular polysaccharide. In certain embodiments, the polysaccharide is a *Klebsiella pneumoniae* capsular polysaccharide. Further, in certain embodiments, the polysaccharide is a serotype K1 or serotype K2 capsular polysaccharide of *Klebsiella pneumoniae*.

In certain embodiments, the bioconjugate is produced in vivo. For example, in certain embodiments, the bioconjugate is produced in a bacterial cell.

As the bioconjugate comprises an oligo- or polysaccharide covalently linked to a fusion protein, in certain applications, it may be advantageous to form a fusion protein with a carrier protein or fragment thereof. In certain embodiments, the carrier protein is one recognized in the art as useful in producing conjugate vaccines. In certain embodiments, when a ComP glycosylation tag fragment is fused to a carrier protein or fragment thereof, the glycosylation tag fragment and thus the fusion protein, can be glycosylated at the conserved serine residue described elsewhere herein. In certain embodiments, the fusion protein comprises a carrier protein selected from the group consisting of diphtheria toxoid CRM197, tetanus toxoid, *Pseudomonas aeruginosa* Exotoxin A (EPA), tetanus toxin C fragment, cholera toxin B subunit, *Haemophilus* influenza protein D, or a fragment thereof. In certain embodiments, the carrier protein or fragment thereof is linked to the ComP glycosylation tag via an amino acid linker, for example (GGGS)$_n$ (SEQ ID NO: 23), wherein n is at least one or AAA (SEQ ID NO: 24). In order to increase the potential immunogenicity of a ComP fusion protein, it may be advantageous to include more than one glycosylation tag. Thus, in certain embodiments, the fusion protein comprise two or more, three or more, four or more, five or more, six or more, eight or more, ten or more, fifteen or more, or twenty or more ComP glycosylation tags. In certain embodiments, the fusion protein comprises any of 2, 3, 4, 5, 6, 7, 8, 9, 10, 11, 12, 13, 14, 15, or 20 to any of 3, 4, 5, 6, 7, 8, 9, 10, 11, 12, 13, 14, 15, 20, or 25 ComP glycosylation tags. In certain embodiments, multiple glycosylation tags are arranged in tandem to one another in the fusion protein. In certain embodiments, multiple glycosylation tags are arranged apart from one another in the fusion protein, for example separated by sequences of carrier protein. In certain embodiments, the glycosylation tag(s) can be, for example, located at the N-terminal end of the carrier protein and/or fusion protein. In certain embodiments, the glycosylation tag(s) can be, for example, located at the C-terminal end of the carrier protein and/or fusion protein. In certain embodiments, the glycosylation tag(s) can be located internally within the carrier protein and/or fusions protein, for example, wherein a glycosylation tag is located between multiple carrier proteins in a fusion protein. In certain embodiments, the multiple carrier proteins can be identical in type or different in type. In certain embodiments, the glycosylation tags can be identical in type or different in type. In certain embodiments, these ComP glycosylation tags are identical. In certain embodiments, at least two of the ComP glycosylation tags differ from each other. In certain embodiments, at least three, at least four, or at least five of the ComP glycosylation tags all differ from each other. Further, in certain embodiments, none of the ComP glycosylation tags are the same.

A bioconjugate of this invention may have one of numerous uses including, but not limited to, use as a conjugate vaccine. For example, in certain embodiments, the conjugate vaccine is a vaccine against *Streptococcus pneumoniae* serotype 8, *Streptococcus pneumoniae* serotype 1, *Streptococcus pneumoniae* serotype 2, *Streptococcus pneumoniae* serotype 4, *Streptococcus pneumoniae* serotype 5, *Streptococcus pneumoniae* serotype 6A, *Streptococcus pneumoniae* serotype 6B, *Streptococcus pneumoniae* serotype 7F, *Streptococcus pneumoniae* serotype 9N, *Streptococcus pneumoniae* serotype 9V, *Streptococcus pneumoniae* serotype 10A, *Streptococcus pneumoniae* serotype 11A, *Streptococcus pneumoniae* serotype 12F, *Streptococcus pneumoniae* serotype 14, *Streptococcus pneumoniae* serotype 15B, *Streptococcus pneumoniae* serotype 17F, *Streptococcus pneumoniae* serotype 18C, *Streptococcus pneumoniae* serotype 19F, *Streptococcus pneumoniae* serotype 19A, *Streptococcus pneumoniae* serotype 20, *Streptococcus pneumoniae* serotype 22F, *Streptococcus pneumoniae* serotype 23F, *Streptococcus pneumoniae* serotype 33F, *Klebsiella pneumoniae* serotype K1, *Klebsiella pneumoniae* serotype K2, *Klebsiella pneumoniae* serotype K5, *Klebsiella pneumoniae* serotype K16, *Klebsiella pneumoniae* serotype K20, *Klebsiella pneumoniae* serotype K54, *Klebsiella pneumoniae* serotype K57, *Streptococcus agalactiae* serotype Ia, *Streptococcus agalactiae* serotype Ib, *Streptococcus agalactiae* serotype II, *Streptococcus agalactiae* serotype III, *Streptococcus agalactiae* serotype IV, *Streptococcus agalactiae* serotype V, *Streptococcus agalactiae* serotype VI, *Streptococcus agalactiae* serotype VII, *Streptococcus agalactiae* serotype VIII, *Streptococcus agalactiae* serotype IX, *Streptococcus pyogenes* Group A Carbohydrate, *Enterococcus faecalis* serotype A, *Enterococcus faecalis* serotype B, *Enterococcus faecalis* serotype C, *Enterococcus faecalis* serotype D, *Enterococcus faecium* capsular polysaccharide and lipotechoic acid, *Moraxella catarrhalis* lipooligosaccharide A, *Moraxella catarrhalis* lipooligosaccharide B, *Moraxella catarrhalis* lipooligosaccharide C, and *Staphylococcus aureus* lipotechoic acid. In certain embodiments, the conjugate vaccine is useful because it induces an immune response when administered to a subject. In certain embodiments, the immune response elicits long term memory (memory B and T cells), is an antibody response, and is optionally a serotype-specific antibody response. In certain embodiments, the antibody response is an IgG or IgM response. For example, in certain embodiments the antibody response can be an IgG response, and in certain embodiments, an IgG1 response. In certain embodiments, the conjugate vaccine generates immunological memory in a subject administered the vaccine.

Provided for herein is a fusion protein as disclosed in further detail elsewhere herein and comprising a ComP glycosylation tag as disclosed in detail elsewhere herein. In certain embodiments, the fusion protein is glycosylated at a serine residue on the glycosylation tag corresponding to the serine residue at position 84 of SEQ ID NO: 1 (ComP$_{ADP1}$: AAC45886.1). In certain embodiments, the fusion protein is glycosylated with an oligo- or polysaccharide. In certain embodiments, the oligo- or polysaccharide is produced by a bacteria from the genus *Streptococcus* such as, for example, a *S. pneumoniae, S. agalactiae*, or *S. suis* capsular polysaccharide. In certain embodiments, the capsular polysaccharide is CPS14, CPS8, CPS9V, or CPS15b. In certain embodiments, the oligo- or polysaccharide is produced by a bacteria from the genus *Klebsiella*, for example, a *Klebsiella pneumoniae, Klebsiella varricola, Klebsiella michinganenis*, or *Klebsiella oxytoca* capsular polysaccharide. In certain embodiments, the polysaccharide is a *Klebsiella pneumoniae* capsular polysaccharide. In certain embodiments, the polysaccharide is a serotype K1 or serotype K2 capsular polysaccharide of *Klebsiella pneumoniae*. In certain of any embodiments disclosed herein, the oligo- or polysaccharide comprises a glucose at its reducing end. Certain embodiments are drawn a fusion protein wherein the fusion protein is produced in vivo. For example, in certain embodiments, the fusion protein is produced in a mammalian cell, fungal cell, yeast cell, insect cell, avian cell, algal cell, or bacterial cell. In certain embodiments, the fusion protein is produced in a bacterial cell, for example, E. coli.

Disclosed herein are methods for the in vivo conjugation of an oligo- or polysaccharide to a polypeptide (in vivo glycosylation). In certain embodiments, the method comprises covalently linking the oligo- or polysaccharide to the polypeptide with a PglS oligosaccharyltransferase (OTase) (described elsewhere herein). In certain embodiments, the polypeptide comprises a ComP protein or a glycosylation tag thereof. In certain embodiments, the polypeptide comprises a ComP protein or a glycosylation tag thereof linked to a heterologous polypeptide such as a carrier protein. Representative examples of PglS OTases include, but are not limited to $PglS_{110264}$, $PglS_{ADP1}$, $PglS_{GFJ-2}$, $PglS_{50v10}$, $PglS_{4466}$, and $PglS_{SFC}$. ComP proteins are described in detail elsewhere and representative examples include, but are not limited to $ComP_{110264}$, $ComP_{ADP1}$, $ComP_{GFJ-2}$, $ComP_{50v10}$, $ComP_{4466}$, and $ComP_{SFC}$. It will be recognized that while a PglS OTase from an organism would naturally glycosylate the ComP protein from that organism (e.g., $PglS_{110264}$ glycosylates $ComP_{110264}$) in certain embodiments, a PglS from one organism glycosylates a ComP from a different organism (e.g., $PglS_{ADP1}$ glycosylates $ComP_{110264}$). For example, in certain aspects, the PglS OTase is $PglS_{ADP1}$. In certain embodiments, where the PglS OTase is $PglS_{ADP1}$, the ComP protein glycosylated is not $ComP_{ADP1}$. For example, in certain embodiments where the PglS OTase is $PglS_{ADP1}$, the ComP protein is $ComP_{110264}$. Of course, it will be recognized that a PglS OTase does not naturally glycosylate a ComP protein or a glycosylation tag fragment thereof, even from the same organism as the PglS Otase, when the ComP protein or glycosylation tag fragment thereof is linked to a heterologous carrier protein.

In certain embodiments for any combination of PglS and ComP, the ComP protein or glycosylation tag fragment thereof is glycosylated at a serine residue corresponding to the serine residue at position 84 of SEQ ID NO: 1 (Com-$P_{ADP1}$: AAC45886.1).

In certain embodiments disclosed herein, the in vivo glycosylation occurs in a host cell. In certain embodiments, for example, the host cell can be a mammalian cell, fungal cell, yeast cell, insect cell, avian cell, algal cell, or bacterial cell. In certain embodiments, the host cell is a bacterial cell, for example, E. coli.

In certain embodiments, the method comprises culturing a host cell comprising the components necessary for the conjugation of the oligo- or polysaccharide to the polypeptide. In general, these components are the oligosaccharyltransferase, the acceptor polypeptide to be glycosylated, and the oligo- or polysaccharide. In certain embodiments, the method comprises culturing a host cell that comprises: (a) a genetic cluster encoding for the proteins required to synthesize the oligo- or polysaccharide; (b) a PglS OTase; and (3) the acceptor polypeptide. Further, it has been discovered that production of the oligo- or polysaccharide can be enhanced by a transcriptional activator. In certain embodiments, the production of the oligo- or polysaccharide is enhanced by the K. pneumoniae transcriptional activator rmpA (K. pneumoniae NTUH K-2044) or a homolog of the K. pneumoniae transcriptional activator rmpA (K. pneumoniae NTUH K-2044). In certain embodiments, the method further comprises expressing and/or providing such a transcriptional activator in the host cell along with the other components.

In certain embodiments, the carrier protein linked to the ComP glycosylation tag is, for example, diphtheria toxoid CRM197, tetanus toxoid, Pseudomonas aeruginosa Exotoxin A (EPA), tetanus toxin C fragment, cholera toxin B subunit, Haemophilus influenza protein D, or a fragment thereof.

Certain embodiments, are directed to a method a conjugate vaccine comprising a bioconjugate of this disclosure or a method of producing such conjugate vaccine.

Certain embodiments also provide for a host cell comprising the components for in vivo glycosylation of an acceptor ComP protein or glycosylation tag fragment thereof. In certain embodiments, a host cell comprises: (a) a genetic cluster encoding for the proteins required to synthesize an oligo- or polysaccharide; (b) a PglS OTase; and (3) an acceptor polypeptide comprising a ComP protein or a glycosylation tag fragment thereof. In certain embodiments, the acceptor polypeptide is a fusion protein. In certain embodiments, the host cell further comprises a transcriptional activator such as described above along with the other components.

In certain embodiments, a host cell comprises an isolated nucleic acid encoding a PglS OTase. In certain embodiments a host cell comprises an isolated nucleic acid encoding the ComP acceptor polypeptide. In certain embodiments, a host cell comprises a genetic cluster encoding for the proteins required to synthesize an oligo- or polysaccharide. In certain embodiments, a host cell comprises at least two of an isolated nucleic acid encoding a PglS OTase, an isolated nucleic acid encoding the ComP acceptor polypeptide, and genetic cluster encoding for the proteins required to synthesize an oligo- or polysaccharide. In embodiments aspects, a host cell comprises a nucleic acid encoding a PglS OTase of one organism and a nucleic acid encoding the ComP acceptor polypeptide from a different organism.

Certain embodiments also provide for an isolated nucleic acid encoding the ComP protein, ComP glycosylation tag fragment, and/or ComP fusion protein described anywhere herein. In certain embodiments, an isolated nucleic acid referred to herein is a vector or is contained within a vector. In certain embodiments, an isolated nucleic acid referred to herein is inserted and/or has been incorporated into a heterologous genome or a heterologous region of a genome.

Disclosed herein is a pneumococcal bioconjugate vaccine containing a conventional vaccine carrier. Certain embodiments comprise the use of a ComP fragment as a glycosylation tag (aka "glycotag"). In certain embodiments, the glycosylation tag can be added to the C-terminus and/or N-terminus of a carrier protein. For example, in certain embodiments, the glycosylation tag is added to the C-terminus of the conventional carrier protein Pseudomonas aeruginosa Exotoxin A (EPA). It has been demonstrated that in certain embodiments, the glycosylation tag/carrier fusion protein can be paired with the CPS8 polysaccharide and use of PglS, generating a carrier protein-CPS8 bioconjugate, a first of its kind pneumococcal bioconjugate vaccine. For example, in certain embodiments, an EPA fusion can be paired with the CPS8 polysaccharide and use of PglS, generating an EPA-CPS8 bioconjugate. It was demonstrated that the EPA-CPS8 bioconjugate vaccine elicited high IgG titers specific to serotype 8 specific that were protective as determined via bactericidal killing. Importantly, vaccination with as little as 100 ng of polysaccharide in the EPA-CPS8 bioconjugate was able to provide protection. Thus, certain embodiments provide for a CPS8 pneumococcal bioconjugate vaccine.

It is contemplated that a conjugate vaccine (such as the EPA vaccine construct) can comprise additional/multiple sites of glycosylation to increase the glycan to protein ratio as well as expand upon the number of serotypes in order to develop a comprehensive pneumococcal bioconjugate vaccine.

In certain embodiments, a bioconjugate or glycosylated fusion protein disclosed herein is a conjugate vaccine that can be administered to a subject for the prevention and/or treatment of an infection and/or disease. In certain embodiments, the conjugate vaccine is a prophylaxis that can be used, e.g., to immunize a subject against an infection and/or disease. In certain embodiments, the bioconjugate is associated with (such as in a therapeutic composition) and/or administered with an adjuvant. Certain embodiments provide for a composition (such as a therapeutic composition) comprising a conjugate vaccine described herein and an adjuvant. In certain embodiments, when the conjugate vaccine is administered to a subject, it induces an immune response. In certain embodiments, the immune response elicits long term memory (memory B and T cells). In certain embodiments, the immune is an antibody response. In certain embodiments, the antibody response is a serotype-specific antibody response. In certain embodiments, the antibody response is an IgG or IgM response. In certain embodiments where the antibody response is an IgG response, the IgG response is an IgG1 response. Further, in certain embodiments, the conjugate vaccine generates immunological memory in a subject administered the vaccine.

Certain embodiments also provide for producing a vaccine against an infection and/or disease. In certain embodiments a method comprises isolating a bioconjugate or fusion protein disclosed herein (conjugate vaccine) and combining the conjugate vaccine with an adjuvant. In certain embodiments, the infection is a localized or systemic infection of skin, soft tissue, blood, or an organ, or is auto-immune in nature. In certain embodiments, the vaccine is a conjugate vaccine against pneumococcal infection. In certain embodiments, the disease is pneumonia. In certain embodiments, the infection is a systemic infection and/or an infection of the blood. In certain embodiments, the subject is a mammal. For example, in certain embodiments, a pig or a human.

Importantly, the aspects disclosed herein are not limited to pneumococcal polysaccharides, but in fact, have vast applicability for generating bioconjugate vaccines for many important human and animal pathogens that are incompatible with PglB and PglL. Notable examples include the human pathogens *Klebsiella pneumoniae* and Group B *Streptococcus* as well as the swine pathogen *S. suis*, all immensely relevant pathogens with no licensed vaccines available.

Provided herein are methods of inducing a host immune response against a pathogen. In certain embodiments, the pathogen is a bacterial pathogen. In certain embodiments, the host is immunized against the pathogen. In certain embodiments, the method comprises administering to a subject in need of the immune response an effective amount of a ComP conjugate vaccine, glycosylated fusion protein, or any other therapeutic/immunogenic composition disclosed herein. Certain embodiments provide a conjugate vaccine, glycosylated fusion protein, or other therapeutic/immunogenic composition disclosed herein for use in inducing a host immune response against a bacterial pathogen and immunization against the bacterial pathogen. Examples of immune responses include but are not limited to an innate response, an adaptive response, a humoral response, an antibody response, cell mediated response, a B cell response, a T cell response, cytokine upregulation or downregulation, immune system cross-talk, and a combination of two or more of said immune responses. In certain embodiments, the immune response is an antibody response. In certain embodiments, the immune response is an innate response, a humoral response, an antibody response, a T cell response, or a combination of two or more of said immune responses.

Also provided herein are methods of preventing or treating a bacterial disease and/or infection in a subject comprising administering to a subject in need thereof a conjugate vaccine, a fusion protein, or a composition disclosed herein. In certain embodiments, the infection is a localized or systemic infection of skin, soft tissue, blood, or an organ, or is auto-immune in nature. In certain embodiments, the disease is pneumonia. In certain embodiments, the infection is a systemic infection and/or an infection of the blood. In certain embodiments disclosed herein, the subject is a vertebrate. In certain embodiments the subject is a mammal such as a dog, cat, cow, horse, pig, mouse, rat, rabbit, sheep, goat, guinea pig, monkey, ape, etc. And, for example, in certain embodiments the mammal is a human.

In any of the embodiments of administration disclose herein, the composition is administered via intramuscular injection, intradermal injection, intraperitoneal injection, subcutaneous injection, intravenous injection, oral administration, mucosal administration, intranasal administration, or pulmonary administration.

EXAMPLES

Example 1. Determination that Cysteine Residues Flanking the Site of Glycosylation in ComP Contribute to ComP Stability and Glycosylation Previously, it was demonstrated that the ComP protein from *Acinetobacter baylyi* ADP1 ($ComP_{ADP1}$) and *A. soli* strain 110264 ($ComP_{110264}$) are glycosylated at a homologous serine residue located at position 84 or 82, respectively, by the O-linking OTase PglS (Harding C M, et al. (2019) A platform for glycoengineering a polyvalent pneumococcal bioconjugate vaccine using *E. coli* as a host. Nat Commun 10(1):891). Specifically, it was shown that the S84A point mutant of $ComP_{ADP1}$ and the S82A point mutant of $ComP_{110264}$ were not able to be glycosylated with the serotype 8 pneumococcal capsular polysaccharide by PglS. To further analyze the role of other amino acids important for PglS-dependent glycosylation, a series of point mutants were generated to alter the conserved cysteine residues flanking the site of glycosylation located at positions 75 and 95 of $ComP_{ADP1}$ (FIG. 1A).

A series of point mutants was first generated replacing cysteine 75 with either alanine or glycine as these mutants would block the formation of a disulfide bond that may be formed between cysteines 75 and 95. The point mutants were then introduced into *E. coli* SDB1 co-expressing the *C. jejuni* heptasaccharide biosynthetic gene cluster and $PglS_{ADP1}$. As seen in FIG. 1B, mutation of cysteine 75 significantly reduced the expression of the ComP protein mutants compared to wildtype (WT) ComP. In particularly, the C75A and C75G mutants displayed very low levels of protein expression and it appeared to exist only as a low molecular weight unglycosylated form. Next, a second series of point mutants was generated replacing cysteine 95 with either alanine, glycine or serine and then again introduced these mutant ComP constructs into *E. coli* SDB1 co-expressing the *C. jejuni* heptasaccharide biosynthetic gene cluster and PglS$_{ADP1}$. As seen in FIG. 1B, ComP mutants were unable to be detected with either alanine, glycine, or serine in replace of cysteine 95. Last, a series of double point mutations was generated consisting of all the permutations of cysteine 75 with alanine or glycine and cysteine 95 with alanine, glycine, or serine. As seen in FIG. 1B, ComP double mutants were unable to be detected. Based on the lack of detectable expression for the different ComP point mutant variants, it is likely that the cysteine residues located at positions 75 and 95 form a disulfide bond flanking the site of glycosylation at serine 84. Blocking the formation of this disulfide bond appears detrimental to protein stability and protein glycosylation.

Figure 2:
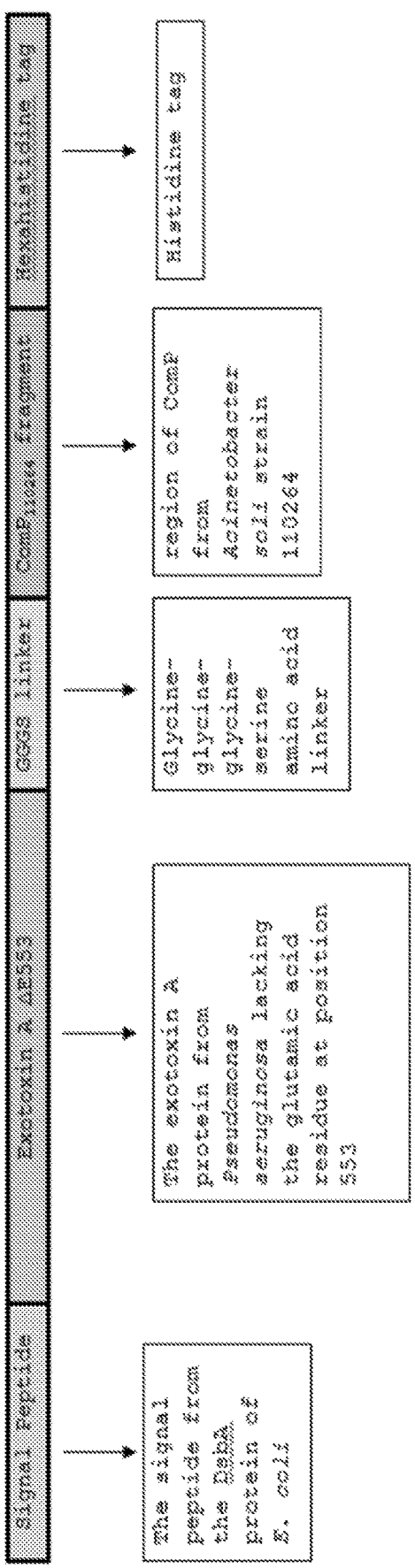
FIG. 2 shows a schematic of the recombinant fusion protein containing a C-terminal fragment of ComP from *Acinetobacter soli* strain 110264 (herein referred to as ComP$_{110264}$).

Example 2. A Short PglS-Dependent O-Linking Recognition Motif is Determined Via a Reductive Cloning Strategy It was demonstrated that a translational fusion containing ComP$_{110264}$ lacking the first 28 amino acids (herein referred to as ComPΔ28$_{110264}$) fused at the C-terminus of a genetically inactivated variant of the exotoxin A protein from *Pseudomonas aeruginosa* (EPA) was efficiently glycosylated by PglS with multiple pneumococcal and *K. pneumoniae* capsular polysaccharides (Harding C M, et al. (2019) A platform for glycoengineering a polyvalent pneumococcal bioconjugate vaccine using *E. coli* as a host. *Nat Commun* 10(1):891; Feldman M F, et al. (2019) A promising bioconjugate vaccine against hypervirulent *Klebsiella pneumoniae*. *Proc Natl Acad Sci USA*). In order to shorten and define the minimal recognition site required for PglS dependent glycosylation, a reductive cloning strategy was pursued whereby fragments of ComP$_{110264}$ were translationally fused to the C-terminus of the EPA protein in between a glycine-glycine-glycine-serine (GGGS) linker and a hexahistidine tag (FIG. 2). Specifically, multiple constructs were generated containing either a 25, 30, 35, 40, or 45 amino acid fragment of ComP$_{110264}$. Each fragment, irrespective of size, was shifted by one amino acid towards the stop codon of ComP$_{110264}$. As an example, the first construct contained a 25 amino acid fragment of ComP$_{110264}$ spanning residues 67 to 91, the second construct contained a 25 amino acid fragment of ComP$_{110264}$ spanning residues 68 to 92, the third construct contained a 25 amino acid fragment of ComP$_{110264}$ spanning residues 69 to 93 and so on. All fragments contained serine 82, the site of PglS glycosylation. EPA fusion constructs were then introduced into *E. coli* SDB1 co-expressing PglS$_{ADP1}$ and the pneumococcal CPS8.

As can be seen in FIG. 3, three constructs containing a short 25 amino acid fragment of ComP$_{110264}$ were found to be glycosylated by PglS$_{ADP1}$ with the pneumococcal CPS8 as determined by a decreased electrophoretic mobility and the presence of multiple glycoforms (observed as a modal, ladder-like distribution above the unglycosylated protein) when analyzed via western blot. As a positive control, the EPA fusion containing the ComPΔ28$_{110264}$ fragment was included as this protein has previously been established to be glycosylated by PglS$_{ADP1}$ with the CPS8. It is noteworthy that the only three 25 amino acid constructs found to be glycosylated: C1 (SEQ ID NO: 32); D1 (SEQ ID NO: 33); and E1 (SEQ ID NO: 34), all contained the conserved cysteine residues predicted to form a disulfide bond flanking the site of ComP$_{110264}$ glycosylation (serine 82).

As can be seen in FIG. 3 and FIG. 4, seven constructs containing a 30 amino acid fragment of ComP$_{110264}$ were found to be glycosylated by PglS$_{ADP1}$ with the pneumococcal CPS8: E2 (SEQ ID NO: 41); F2 (SEQ ID NO: 42); G2 (SEQ ID NO: 43); H2 (SEQ ID NO: 44); A3 (SEQ ID NO: 45); B3 (SEQ ID NO: 46); C3 (SEQ ID NO: 47). All seven constructs contained the conserved cysteine residues predicted to form a disulfide bond flanking the site of ComP$_{110264}$ glycosylation.

As can be seen in FIG. 5 and FIG. 6, nine constructs containing a 35 amino acid fragment of ComP$_{110264}$ were found to be glycosylated by PglS$_{ADP1}$ with the pneumococcal CPS8: D4 (SEQ ID NO: 55); E4 (SEQ ID NO: 56); F4 (SEQ ID NO: 57); G4 (SEQ ID NO: 58); A5 (SEQ ID NO: 59); B5 (SEQ ID NO: 60); D5 (SEQ ID NO: 61); E5 (SEQ ID NO: 62); F5 (SEQ ID NO: 63). All nine contained the conserved cysteine residues predicted to form a disulfide bond flanking the site of ComP$_{110264}$ glycosylation.

As can be seen in FIG. 6 and FIG. 7, eight constructs containing a 40 amino acid fragment of ComP$_{110264}$ were found to be glycosylated by PglS$_{ADP1}$ with the pneumococcal CPS8: H6 (SEQ ID NO: 72); B7 (SEQ ID NO: 73); C7 (SEQ ID NO: 74); D7 (SEQ ID NO: 75); E7 (SEQ ID NO: 76); F7 (SEQ ID NO: 77); A8 (SEQ ID NO: 78); B8 (SEQ ID NO: 79). All eight contained the conserved cysteine residues predicted to form a disulfide bond flanking the site of ComP$_{110264}$ glycosylation.

As seen in FIG. 8, FIG. 9, and FIG. 10, ten constructs containing a 45 amino acid fragment of ComP$_{110264}$ were found to be glycosylated by PglS$_{ADP1}$ with the pneumococcal CPS8: A10 (SEQ ID NO: 92); B10 (SEQ ID NO: 93); C10 (SEQ ID NO: 94); D10 (SEQ ID NO: 95); F10 (SEQ ID NO: 96); G10 (SEQ ID NO: 97); H10 (SEQ ID NO: 98); A11 (SEQ ID NO: 99); B11 (SEQ ID NO: 100); C11 (SEQ ID NO: 101). Again, all ten contained the conserved cysteine residues predicted to form a disulfide bond flanking the site of ComP$_{110264}$ glycosylation.

Based on the data presented in FIG. 3, FIG. 4, FIG. 5, FIG. 6, FIG. 7, FIG. 8, FIG. 9, and FIG. 10, the cysteine residues located at position 71 and 93 are necessary for glycosylation by PglS$_{ADP1}$ when translationally fused to the C-terminus of the EPA carrier protein. In addition, the methionine residue located in position 104 appears to block PglS$_{ADP1}$ glycosylation when a part of the C-terminal glycosylation tag. This is particularly evidenced by the fact that constructs G5 (SEQ ID NO: 64), C8 (SEQ ID NO: 80), and D11 (SEQ ID NO: 102) each contain the required cysteines at position 71 and 93, but did not display any signs of glycosylation. While G5 (SEQ ID NO: 64), C8 (SEQ ID NO: 80), and D11 (SEQ ID NO: 102) contain fragments of ComP$_{110264}$ of 35, 40, and 45 amino acids in length, respectively, each fragment terminates with the methionine at position 104, demonstrating that this residue is sufficient to block glycosylation when included in the C-terminal glycotag. Moreover, all constructs containing methionine 104 in addition to the cysteines in position 71 and 93 did not display any sign of glycosylation (G5 (SEQ ID NO: 64), H5 (SEQ ID NO: 65), C8 (SEQ ID NO: 80), D8 (SEQ ID NO: 81), E8 (SEQ ID NO: 82), F8 (SEQ ID NO: 83), G8 (SEQ ID NO: 84), H8 (SEQ ID NO: 85), A9 (SEQ ID NO: 86), D11 (SEQ ID NO: 102), E11 (SEQ ID NO: 103), F11 (SEQ ID NO: 104), H11 (SEQ ID NO: 105), A12 (SEQ ID NO: 106), B12 (SEQ ID NO: 107), C12 (SEQ ID NO: 108), D12 (SEQ ID NO: 109), E12 (SEQ ID NO: 110), F12 (SEQ ID NO: 111), G12 (SEQ ID NO: 112). Table 1 provides a summary of all ComP$_{110264}$ fragments tested for their ability to serve as O-linking glycosylation recognition motifs by PglS$_{ADP1}$.

TABLE 1

| ID | SEQ ID NO: | ComP$_{110264}$ fragment fused to C-terminus of EPA | Glycosylation observed |
|---|---|---|---|
| A1 | 30 | $_{67}$SSGNCTGVTQIASGASAATTNVASA$_{91}$ | − |
| B1 | 31 | $_{68}$SGNCTGVTQIASGASAATTNVASAQ$_{92}$ | − |
| C1 | 32 | $_{69}$GNCTGVTQIASGASAATTNVASAQC$_{93}$ | + |
| D1 | 33 | $_{70}$NCTGVTQIASGASAATTNVASAQCS$_{94}$ | + |
| E1 | 34 | $_{71}$CTGVTQIASGASAATTNVASAQCSD$_{95}$ | + |
| F1 | 35 | $_{72}$TGVTQIASGASAATTNVASAQCSDS$_{96}$ | − |
| G1 | 36 | $_{73}$GVTQIASGASAATTNVASAQCSDSD$_{97}$ | − |
| H1 | 37 | $_{74}$VTQIASGASAATTNVASAQCSDSDG$_{98}$ | − |
| A2 | 38 | $_{75}$TQIASGASAATTNVASAQCSDSDGV$_{99}$ | − |
| C2 | 39 | $_{62}$GTSMPSSGNCTGVTQIASGASAATTNVASA$_{91}$ | − |
| D2 | 40 | $_{63}$TSMPSSGNCTGVTQIASGASAATTNVASAQ$_{92}$ | − |
| E2 | 41 | $_{64}$SMPSSGNCTGVTQIASGASAATTNVASAQC$_{93}$ | + |
| F2 | 42 | $_{65}$MPSSGNCTGVTQIASGASAATTNVASAQCS$_{94}$ | + |
| G2 | 43 | $_{66}$PSSGNCTGVTQIASGASAATTNVASAQCSD$_{95}$ | + |
| H2 | 44 | $_{67}$SSGNCTGVTQIASGASAATTNVASAQCSDS$_{96}$ | + |
| A3 | 45 | $_{68}$SGNCTGVTQIASGASAATTNVASAQCSDSD$_{97}$ | + |
| B3 | 46 | $_{69}$GNCTGVTQIASGASAATTNVASAQCSDSDG$_{98}$ | + |
| C3 | 47 | $_{70}$NCTGVTQIASGASAATTNVASAQCSDSDGV$_{99}$ | + |
| E3 | 48 | $_{72}$TGVTQIASGASAATTNVASAQCSDSDGVIT$_{101}$ | − |
| F3 | 49 | $_{73}$GVTQIASGASAATTNVASAQCSDSDGVITV$_{102}$ | − |
| G3 | 50 | $_{74}$VTQIASGASAATTNVASAQCSDSDGVITVT$_{103}$ | − |
| H3 | 51 | $_{75}$TQIASGASAATTNVASAQCSDSDGVITVTM$_{104}$ | − |
| A4 | 52 | $_{76}$QIASGASAATTNVASAQCSDSDGVITVTMT$_{105}$ | − |
| B4 | 53 | $_{57}$IMNAGGTSMPSSGNCTGVTQIASGASAATTNVASA$_{91}$ | − |
| C4 | 54 | $_{58}$MNAGGTSMPSSGNCTGVTQIASGASAATTNVASAQ$_{92}$ | − |
| D4 | 55 | $_{59}$NAGGTSMPSSGNCTGVTQIASGASAATTNVASAQC$_{93}$ | + |
| E4 | 56 | $_{60}$AGGTSMPSSGNCTGVTQIASGASAATTNVASAQCS$_{94}$ | + |
| F4 | 57 | $_{61}$GGTSMPSSGNCTGVTQIASGASAATTNVASAQCSD$_{95}$ | + |
| G4 | 58 | $_{62}$GTSMPSSGNCTGVTQIASGASAATTNVASAQCSDS$_{96}$ | + |
| A5 | 59 | $_{64}$SMPSSGNCTGVTQIASGASAATTNVASAQCSDSDG$_{98}$ | + |
| B5 | 60 | $_{65}$MPSSGNCTGVTQIASGASAATTNVASAQCSDSDGV$_{99}$ | + |
| D5 | 61 | $_{67}$SSGNCTGVTQIASGASAATTNVASAQCSDSDGVIT$_{101}$ | + |
| E5 | 62 | $_{68}$SGNCTGVTQIASGASAATTNVASAQCSDSDGVITV$_{102}$ | + |
| F5 | 63 | $_{69}$GNCTGVTQIASGASAATTNVASAQCSDSDGVITVT$_{103}$ | + |
| G5 | 64 | $_{70}$NCTGVTQIASGASAATTNVASAQCSDSDGVITVTM$_{104}$ | − |
| H5 | 65 | $_{71}$CTGVTQIASGASAATTNVASAQCSDSDGVITVTMT$_{105}$ | − |

TABLE 1-continued

| ID | SEQ ID NO: | ComP$_{110264}$ fragment fused to C-terminus of EPA | Glycosylation observed |
|---|---|---|---|
| A6 | 66 | $_{72}$TGVTQIASGASAATTNVASAQCSDSDGVITVTMTD$_{106}$ | − |
| B6 | 67 | $_{73}$GVTQIASGASAATTNVASAQCSDSDGVITVTMTDK$_{107}$ | − |
| C6 | 68 | $_{74}$VTQIASGASAATTNVASAQCSDSDGVITVTMTDKA$_{108}$ | − |
| D6 | 69 | $_{75}$TQIASGASAATTNVASAQCSDSDGVITVTMTDKAK$_{109}$ | − |
| F6 | 70 | $_{52}$TVSENIMNAGGTSMPSSGNCTGVTQIASGASAATTNVASA$_{91}$ | − |
| G6 | 71 | $_{53}$VSENIMNAGGTSMPSSGNCTGVTQIASGASAATTNVASAQ$_{92}$ | − |
| H6 | 72 | $_{54}$SENIMNAGGTSMPSSGNCTGVTQIASGASAATTNVASAQC$_{93}$ | + |
| B7 | 73 | $_{55}$NIMNAGGTSMPSSGNCTGVTQIASGASAATTNVASAQCSD$_{95}$ | + |
| C7 | 74 | $_{57}$IMNAGGTSMPSSGNCTGVTQIASGASAATTNVASAQCSDS$_{96}$ | + |
| D7 | 75 | $_{58}$MNAGGTSMPSSGNCTGVTQIASGASAATTNVASAQCSDSD$_{97}$ | + |
| E7 | 76 | $_{59}$NAGGTSMPSSGNCTGVTQIASGASAATTNVASAQCSDSDG$_{98}$ | + |
| F7 | 77 | $_{60}$AGGTSMPSSGNCTGVTQIASGASAATTNVASAQCSDSDGV$_{99}$ | + |
| A8 | 78 | $_{63}$TSMPSSGNCTGVTQIASGASAATTNVASAQCSDSDGVITV$_{102}$ | + |
| B8 | 79 | $_{64}$SMPSSGNCTGVTQIASGASAATTNVASAQCSDSDGVITVT$_{103}$ | + |
| C8 | 80 | $_{65}$MPSSGNCTGVTQIASGASAATTNVASAQCSDSDGVITVTM$_{104}$ | − |
| D8 | 81 | $_{66}$PSSGNCTGVTQIASGASAATTNVASAQCSDSDGVITVTMT$_{105}$ | − |
| E8 | 82 | $_{67}$SSGNCTGVTQIASGASAATTNVASAQCSDSDGVITVTMTD$_{106}$ | − |
| F8 | 83 | $_{68}$SGNCTGVTQIASGASAATTNVASAQCSDSDGVITVTMTDK$_{107}$ | − |
| G8 | 84 | $_{69}$GNCTGVTQIASGASAATTNVASAQCSDSDGVITVTMTDKA$_{108}$ | − |
| H8 | 85 | $_{70}$NCTGVTQIASGASAATTNVASAQCSDSDGVITVTMTDKAK$_{109}$ | − |
| A9 | 86 | $_{71}$CTGVTQIASGASAATTNVASAQCSDSDGVITVTMTDKAKG$_{110}$ | − |
| B9 | 87 | $_{72}$TGVTQIASGASAATTNVASAQCSDSDGVITVTMTDKAKGV$_{111}$ | − |
| C9 | 88 | $_{73}$GVTQIASGASAATTNVASAQCSDSDGVITVTMTDKAKGVS$_{112}$ | − |
| D9 | 89 | $_{74}$VTQIASGASAATTNVASAQCSDSDGVITVTMTDKAKGVSI$_{113}$ | − |
| E9 | 90 | $_{75}$TQIASGASAATTNVASAQCSDSDGVITVTMTDKAKGVSIK$_{114}$ | − |
| H9 | 91 | $_{48}$AMKATVSENIMNAGGTSMPSSGNCTGVTQIASGASAATTNVASAQ$_{92}$ | − |
| A10 | 92 | $_{49}$MKATVSENIMNAGGTSMPSSGNCTGVTQIASGASAATTNVASAQC$_{93}$ | + |
| B10 | 93 | $_{50}$KATVSENIMNAGGTSMPSSGNCTGVTQIASGASAATTNVASAQCS$_{94}$ | + |
| C10 | 94 | $_{51}$ATVSENIMNAGGTSMPSSGNCTGVTQIASGASAATTNVASAQCSD$_{95}$ | + |
| D10 | 95 | $_{52}$TVSENIMNAGGTSMPSSGNCTGVTQIASGASAATTNVASAQCSDS$_{96}$ | + |
| F10 | 96 | $_{54}$SENIMNAGGTSMPSSGNCTGVTQIASGASAATTNVASAQCSDSDG$_{98}$ | + |
| G10 | 97 | $_{55}$ENIMNAGGTSMPSSGNCTGVTQIASGASAATTNVASAQCSDSDGV$_{99}$ | + |
| H10 | 98 | $_{56}$NIMNAGGTSMPSSGNCTGVTQIASGASAATTNVASAQCSDSDGVI$_{100}$ | + |
| A11 | 99 | $_{57}$IMNAGGTSMPSSGNCTGVTQIASGASAATTNVASAQCSDSDGVIT$_{101}$ | + |
| B11 | 100 | $_{58}$MNAGGTSMPSSGNCTGVTQIASGASAATTNVASAQCSDSDGVITV$_{102}$ | + |

TABLE 1-continued

| ID | SEQ ID NO: | ComP$_{110264}$ fragment fused to C-terminus of EPA | Glycosylation observed |
|---|---|---|---|
| C11 | 101 | $_{59}$NAGGTSMPSSGNCTGVTQIASGASAATTNVASAQCSDSDGVITVT$_{103}$ | + |
| D11 | 102 | $_{60}$AGGTSMPSSGNCTGVTQIASGASAATTNVASAQCSDSDGVITVTM$_{104}$ | – |
| E11 | 103 | $_{61}$GGTSMPSSGNCTGVTQIASGASAATTNVASAQCSDSDGVITVTMT$_{105}$ | – |
| F11 | 104 | $_{62}$GTSMPSSGNCTGVTQIASGASAATTNVASAQCSDSDGVITVTMTD$_{106}$ | – |
| H11 | 105 | $_{64}$SMPSSGNCTGVTQIASGASAATTNVASAQCSDSDGVITVTMTDKA$_{108}$ | – |
| A12 | 106 | $_{65}$MPSSGNCTGVTQIASGASAATTNVASAQCSDSDGVITVTMTDKAK$_{109}$ | – |
| B12 | 107 | $_{66}$PSSGNCTGVTQIASGASAATTNVASAQCSDSDGVITVTMTDKAKG$_{110}$ | – |
| C12 | 108 | $_{67}$SSGNCTGVTQIASGASAATTNVASAQCSDSDGVITVTMTDKAKGV$_{111}$ | – |
| D12 | 109 | $_{68}$SGNCTGVTQIASGASAATTNVASAQCSDSDGVITVTMTDKAKGVS$_{112}$ | – |
| E12 | 110 | $_{69}$GNCTGVTQIASGASAATTNVASAQCSDSDGVITVTMTDKAKGVSI$_{113}$ | – |
| F12 | 111 | $_{70}$NCTGVTQIASGASAATTNVASAQCSDSDGVITVTMTDKAKGVSIK$_{114}$ | – |
| G12 | 112 | $_{71}$CTGVTQIASGASAATTNVASAQCSDSDGVITVTMTDKAKGVSIKL$_{115}$ | – |
| H12 | 113 | $_{72}$TGVTQIASGASAATTNVASAQCSDSDGVITVTMTDKAKGVSIKLT$_{116}$ | – |

O-linking glycosylation recognition motifs can be glycosylated by PglSA$_{ADP1}$ when translationally fused N-terminally, in tandem at the N- or C-terminus, or simultaneously at the N- and C-terminus. Based on the data presented above, the D5 (SEQ ID NO: 61) fragment of ComP$_{110264}$ was selected for follow up experiments whereby the D5 (SEQ ID NO: 61) fragment or a derivative thereof (D5') was translationally fused to N-terminus and C-terminus in different combinations as outlined in FIG. 12A and FIG. 12B. As a positive control, the EPA fusion containing the ComPΔ28$_{110264}$ fragment was included as this protein has previously been established to be glycosylated by PglS$_{ADP1}$ with the CPS8. EPA fusion constructs were then introduced into E. coli SDB1 co-expressing the pneumococcal CPS8 in the presence of absence of PglS$_{ADP1}$. As seen in FIG. 12C, all EPA-ComP$_{110264}$ fusion constructs were glycosylated with the pneumococcal CPS8 indicating that ComP$_{110264}$ O-linking glycosylation recognition motifs can be translationally fused in multiple combinations at the N-terminus or C-terminus and still be glycosylated by PglS$_{ADP1}$.

Example 3. A Tandem, C-Terminally Fused Double ComPΔ28$_{110264}$ Glycosylation Tag is Glycosylated by PglS$_{ADP1}$ EPA fusion constructs were built containing a tandem, C-terminally fused double ComPΔ28$_{110264}$ glycosylation tag. The ComPΔ28$_{110264}$ glycosylation tags were separated by either a glycine-glycine-glycine-glycine-serine (GGGS) linker (SEQ ID NO: 23) or by a proline-alanine-proline-alanine-proline (PAPAP) linker (SEQ ID NO: 25). Both constructs contained a hexahistidine tag to aid downstream purification. As a positive control, the EPA fusion containing the ComPΔ28$_{110264}$ fragment was included as this protein has previously been established to be glycosylated by PglS$_{ADP1}$ with the CPS8. The double tag EPA fusion constructs were then introduced into E. coli SDB1 co-expressing the pneumococcal CPS8 in the presence of absence of PglS$_{ADP1}$. As can be seen in FIG. 13, EPA variant 7 and EPA variant 8 were both glycosylated the pneumococcal CPS8 when PglS$_{ADP1}$ was present. Moreover, the glycosylation appeared as very high molecular weight with immunoreactivity approaching the 250 kDa marker.

The present disclosure is not to be limited in scope by the specific aspects described or preceding Examples which are intended as single illustrations of individual aspects of the disclosure, and any compositions or methods which are functionally equivalent are within the scope of this disclosure. Indeed, various modifications of the disclosure in addition to those shown and described herein will become apparent to those skilled in the art from the foregoing description and accompanying drawings. Such modifications are intended to fall within the scope of the appended claims.

All publications and patent applications mentioned in this specification are herein incorporated by reference to the same extent as if each individual publication or patent application was specifically and individually indicated to be incorporated by reference.

REFERENCES

1. O'Brien, K. L. et al. Burden of disease caused by Streptococcus pneumoniae in children younger than 5 years: global estimates. Lancet 374, 893-902, doi: 10.1016/50140-6736(09)61204-6 (2009).
2. Pneumococcal conjugate vaccine for childhood immunization—WHO position paper. Wkly Epidemiol Rec 82, 93-104 (2007).
3. Prevention, C. f. D. C. a. Pneumococcal Vaccination, <https://www.cdc.gov/vaccines/vpd/pneumo/index.html>
4. Pace, D. Glycoconjugate vaccines. Expert Opin Biol Ther 13, 11-33, doi:10.1517/14712598.2012.725718 (2013).
5. Vella, M. & Pace, D. Glycoconjugate vaccines: an update. Expert Opin Biol Ther 15, 529-546, doi:10.1517/14712598.2015.993375 (2015).
6. Pollard, A. J., Perrett, K. P. & Beverley, P. C. Maintaining protection against invasive bacteria with protein-polysaccharide conjugate vaccines. Nat Rev Immunol 9, 213-220, doi:10.1038/nri2494 (2009).

7. Avci, F. Y., Li, X., Tsuji, M. & Kasper, D. L. A mechanism for glycoconjugate vaccine activation of the adaptive immune system and its implications for vaccine design. Nat Med 17, 1602-1609, doi:10.1038/nm.2535 (2011).
8. Package Insert—Prevnar 13—FDA, <https://www.fda.gov/downloads/BiologicsBloodVaccines/Vaccines/ApprovedProducts/UCM201669.pdf>
9. Prevention, C. f D. C. a. Vaccines for Children Program (VFC), <https://www.cdc.gov/vaccines/programs/vfc/awardees/vaccine-management/price-list/index.html> (2018).
10. Pfizer Inc. 2017 Financial Report, <https://www.sec.gov/Archives/edgar/data/78003/000007800318000027/pfe-exhibit13x12312017x10k.htm> (2018).
11. Frasch, C. E. Preparation of bacterial polysaccharide-protein conjugates: analytical and manufacturing challenges. Vaccine 27, 6468-6470, doi:10.1016/j.vaccine.2009.06.013 (2009).
12. Huttner, A. & Gambillara, V. The development and early clinical testing of the ExPEC4V conjugate vaccine against uropathogenic *Escherichia coli*. Clin Microbiol Infect, doi:10.1016/j.cmi.2018.05.009 (2018).
13. Huttner, A. et al. Safety, immunogenicity, and preliminary clinical efficacy of a vaccine against extraintestinal pathogenic *Escherichia coli* in women with a history of recurrent urinary tract infection: a randomised, single-blind, placebo-controlled phase 1b trial. Lancet Infect Dis 17, 528-537, doi:10.1016/S1473-3099(17)30108-1 (2017).
14. Riddle, M. S. et al. Safety and Immunogenicity of a Candidate Bioconjugate Vaccine against *Shigella flexneri* 2a Administered to Healthy Adults: a Single-Blind, Randomized Phase I Study. Clin Vaccine Immunol 23, 908-917, doi:10.1128/CVI.00224-16 (2016).
15. Apweiler, R., Hermjakob, H. & Sharon, N. On the frequency of protein glycosylation, as deduced from analysis of the SWISS-PROT database. Biochim Biophys Acta 1473, 4-8 (1999).
16. Nothaft, H. & Szymanski, C. M. Protein glycosylation in bacteria: sweeter than ever. Nat Rev Microbiol 8, 765-778, doi:10.1038/nrmicro2383 (2010).
17. Iwashkiw, J. A., Vozza, N. F., Kinsella, R. L. & Feldman, M. F. Pour some sugar on it: the expanding world of bacterial protein O-linked glycosylation. Mol Microbiol 89, 14-28, doi:10.1111/mmi.12265 (2013).
18. Ciocchini, A. E. et al. A bacterial engineered glycoprotein as a novel antigen for diagnosis of bovine brucellosis. Vet Microbiol 172, 455-465, doi:10.1016/j.vetmic.2014.04.014 (2014).
19. Garcia-Quintanilla, F., Iwashkiw, J. A., Price, N. L., Stratilo, C. & Feldman, M. F. Production of a recombinant vaccine candidate against *Burkholderia pseudomallei* exploiting the bacterial N-glycosylation machinery. Front Microbiol 5, 381, doi: 10.3389/fmicb.2014.00381 (2014).
20. Iwashkiw, J. A. et al. Exploiting the *Campylobacter jejuni* protein glycosylation system for glycoengineering vaccines and diagnostic tools directed against brucellosis. Microb Cell Fact 11, 13, doi:10.1186/1475-2859-11-13 (2012).
21. Wacker, M. et al. Substrate specificity of bacterial oligosaccharyltransferase suggests a common transfer mechanism for the bacterial and eukaryotic systems. Proc Natl Acad Sci USA 103, 7088-7093, doi:10.1073/pnas.0509207103 (2006).
22. Feldman, M. F. et al. Engineering N-linked protein glycosylation with diverse O antigen lipopolysaccharide structures in *Escherichia coli*. Proc Natl Acad Sci USA 102, 3016-3021, doi:10.1073/pnas.0500044102 (2005).
23. Faridmoayer, A., Fentabil, M. A., Mills, D. C., Klassen, J. S. & Feldman, M. F. Functional characterization of bacterial oligosaccharyltransferases involved in O-linked protein glycosylation. J Bacteriol 189, 8088-8098, doi: 10.1128/JB.01318-07 (2007).
24. Geno, K. A. et al. Pneumococcal Capsules and Their Types: Past, Present, and Future. Clin Microbiol Rev 28, 871-899, doi:10.1128/CMR.00024-15 (2015).
25. Ihssen, J. et al. Increased efficiency of *Campylobacter jejuni* N-oligosaccharyltransferase PglB by structure-guided engineering. Open Biol 5, 140227, doi:10.1098/rsob.140227 (2015).
26. Pan, C. et al. Biosynthesis of Conjugate Vaccines Using an O-Linked Glycosylation System. MBio 7, e00443-00416, doi:10.1128/mBio.00443-16 (2016).
27. Wacker, M. et al. N-linked glycosylation in *Campylobacter jejuni* and its functional transfer into *E. coli*. Science 298, 1790-1793, doi:10.1126/science.298.5599.1790 (2002).
28. Vik, A. et al. Broad spectrum O-linked protein glycosylation in the human pathogen *Neisseria gonorrhoeae*. Proc Natl Acad Sci USA 106, 4447-4452, doi:10.1073/pnas.0809504106 (2009).
29. Harding, C. M. et al. *Acinetobacter* strains carry two functional oligosaccharyltransferases, one devoted exclusively to type IV pilin, and the other one dedicated to O-glycosylation of multiple proteins. Mol Microbiol 96, 1023-1041, doi:10.1111/mmi.12986 (2015).
30. Pan, Y. J. et al. Genetic analysis of capsular polysaccharide synthesis gene clusters in 79 capsular types of *Klebsiella* spp. Sci Rep 5, 15573, doi:10.1038/srep15573 (2015).
31. Kovach, M. E. et al. Four new derivatives of the broad-host-range cloning vector pBBR1MCS, carrying different antibiotic-resistance cassettes. Gene 166, 175-176 (1995).
32. Wu, K. M. et al. Genome sequencing and comparative analysis of *Klebsiella pneumoniae* NTUH-K2044, a strain causing liver abscess and meningitis. J Bacteriol 191, 4492-4501, doi:10.1128/JB.00315-09 (2009).
33. Lery, L. M. et al. Comparative analysis of *Klebsiella pneumoniae* genomes identifies a phospholipase D family protein as a novel virulence factor. BMC Biol 12, 41, doi:10.1186/1741-7007-12-41 (2014).
34. Dykxhoorn, D. M., St Pierre, R. & Linn, T. A set of compatible tac promoter expression vectors. Gene 177, 133-136 (1996).
35. Arakawa, Y. et al. Biosynthesis of *Klebsiella* K2 capsular polysaccharide in *Escherichia coli* HB101 requires the functions of rmpA and the chromosomal cps gene cluster of the virulent strain *Klebsiella pneumoniae* Chedid (01: K2). Infect Immun 59, 2043-2050 (1991).
36. Yeh, K. M. et al. Capsular serotype K1 or K2, rather than magA and rmpA, is a major virulence determinant for *Klebsiella pneumoniae* liver abscess in Singapore and Taiwan. J Clin Microbiol 45, 466-471, doi:10.1128/JCM.01150-06 (2007).
37. Kowarik, M. et al. Definition of the bacterial N-glycosylation site consensus sequence. EMBO J 25, 1957-1966, doi:10.1038/sj.emboj.7601087 (2006).
38. Comer, J. E., Marshall, M. A., Blanch, V. J., Deal, C. D. & Castric, P. Identification of the *Pseudomonas aeruginosa* 1244 pilin glycosylation site. Infect Immun 70, 2837-2845 (2002).

39. Scott, N. E. et al. Diversity within the O-linked protein glycosylation systems of *acinetobacter* species. Mol Cell Proteomics 13, 2354-2370, doi:10.1074/mcp.M114.038315 (2014).
40. Schwarz, F. et al. A combined method for producing homogeneous glycoproteins with eukaryotic N-glycosylation. Nat Chem Biol 6, 264-266, doi:10.1038/nchembio.314 (2010).
41. Porstendorfer, D., Drotschmann, U. & Averhoff, B. A novel competence gene, comP, is essential for natural transformation of *Acinetobacter* sp. strain BD413. Appl Environ Microbiol 63, 4150-4157 (1997).
42. Giltner, C. L., Nguyen, Y. & Burrows, L. L. Type IV pilin proteins: versatile molecular modules. Microbiol Mol Biol Rev 76, 740-772, doi:10.1128/MMBR.00035-12 (2012).
43. Pelicic, V. Type IV pili: e pluribus unum? Mol Microbiol 68, 827-837, doi:10.1110.1365-2958.2008.06197.x (2008).
44. Malik, A. Protein fusion tags for efficient expression and purification of recombinant proteins in the periplasmic space of *E. coli*. 3 Biotech 6, 44, doi:10.1007/s13205-016-0397-7 (2016).
45. Ravenscroft, N. et al. Purification and characterization of a *Shigella* conjugate vaccine, produced by glycoengineering *Escherichia coli*. Glycobiology 26, 51-62, doi: 10.1093/glycob/cwv077 (2016).
46. Schulz, B. L. et al. Identification of bacterial protein O-oligosaccharyltransferases and their glycoprotein substrates. PLoS One 8, e62768, doi:10.1371/journal.pone.0062768 (2013).
47. Castric, P. pilO, a gene required for glycosylation of *Pseudomonas aeruginosa* 1244 pilin. Microbiology 141 (Pt 5), 1247-1254, doi:10.1099/13500872-141-5-1247 (1995).
48. Power, P. M. et al. Genetic characterization of pilin glycosylation and phase variation in *Neisseria meningitidis*. Mol Microbiol 49, 833-847 (2003).
49. Stimson, E. et al. Meningococcal pilin: a glycoprotein substituted with digalactosyl 2,4-diacetamido-2,4,6-trideoxyhexose. Mol Microbiol 17, 1201-1214 (1995).
50. Ishihama, Y., Rappsilber, J. & Mann, M. Modular stop and go extraction tips with stacked disks for parallel and multidimensional Peptide fractionation in proteomics. J Proteome Res 5, 988-994, doi:10.1021/pr050385q (2006).
51. Rappsilber, J., Mann, M. & Ishihama, Y. Protocol for micro-purification, enrichment, pre-fractionation and storage of peptides for proteomics using StageTips. Nature protocols 2, 1896-1906, doi:10.1038/nprot.2007.261 (2007).
52. Roepstorff, P. & Fohlman, J. Proposal for a common nomenclature for sequence ions in mass spectra of peptides. Biomed Mass Spectrom 11, 601, doi:10.1002/bms.1200111109 (1984).
53. Haurat, M. F. et al. Selective sorting of cargo proteins into bacterial membrane vesicles. J Biol Chem 286, 1269-1276, doi:10.1074/jbc.M110.185744 (2011).
54. Price, N. L. et al. Glycoengineered Outer Membrane Vesicles: A Novel Platform for Bacterial Vaccines. Sci Rep 6, 24931, doi:10.1038/srep24931 (2016).
55. Kay, E. J., Yates, L. E., Terra, V. S., Cuccui, J. & Wren, B. W. Recombinant expression of *Streptococcus pneumoniae* capsular polysaccharides in *Escherichia coli*. Open Biol 6, 150243, doi:10.1098/rsob.150243 (2016).
56. Szymanski C M, Yao R, Ewing C P, Trust T J, & Guerry P (1999) Evidence for a system of general protein glycosylation in *Campylobacter jejuni*. Mol Microbiol 32(5): 1022-1030.
57. Iwashkiw J A, Vozza N F, Kinsella R L, & Feldman M F (2013) Pour some sugar on it: the expanding world of bacterial protein O-linked glycosylation. Mol Microbiol 89(1):14-28.
58. Wacker M, et al. (2002) N-linked glycosylation in *Campylobacter jejuni* and its functional transfer into *E. coli*. Science 298(5599):1790-1793.
59. Nothaft H & Szymanski C M (2010) Protein glycosylation in bacteria: sweeter than ever. Nat Rev Microbiol 8(11):765-778.
60. Schaffer C & Messner P (2017) Emerging facets of prokaryotic glycosylation. FEMS Microbiol Rev 41(1): 49-91.
61. Comstock L E & Kasper D L (2006) Bacterial glycans: key mediators of diverse host immune responses. Cell 126(5):847-850.
62. De Gregorio E & Rappuoli R (2014) From empiricism to rational design: a personal perspective of the evolution of vaccine development. Nat Rev Immunol 14(7):505-514.
63. Berti F & Adamo R (2018) Antimicrobial glycoconjugate vaccines: an overview of classic and modern approaches for protein modification. Chem Soc Rev 47(24):9015-9025.
64. Frasch C E (2009) Preparation of bacterial polysaccharide-protein conjugates: analytical and manufacturing challenges. Vaccine 27(46):6468-6470.
65. Terra V S, et al. (2012) Recent developments in bacterial protein glycan coupling technology and glycoconjugate vaccine design. J Med Microbiol 61(Pt 7):919-926.
66. Rappuoli R, De Gregorio E, & Costantino P (2019) On the mechanisms of conjugate vaccines. Proc Natl Acad Sci USA 116(1):14-16.
67. Harding C M, et al. (2019) A platform for glycoengineering a polyvalent pneumococcal bioconjugate vaccine using *E. coli* as a host. Nat Commun 10(1):891.
68. Porstendorfer D, Gohl O, Mayer F, & Averhoff B (2000) ComP, a pilin-like protein essential for natural competence in *Acinetobacter* sp. Strain BD413: regulation, modification, and cellular localization. J Bacteriol 182 (13):3673-3680.
69. Schulz B L, et al. (2013) Identification of bacterial protein O-oligosaccharyltransferases and their glycoprotein substrates. PLoS One 8(5):e62768.
70. Harding C M, et al. (2015) *Acinetobacter* strains carry two functional oligosaccharyltransferases, one devoted exclusively to type IV pilin, and the other one dedicated to O-glycosylation of multiple proteins. Mol Microbiol 96(5):1023-1041.
71. Iwashkiw J A, et al. (2012) Identification of a general O-linked protein glycosylation system in *Acinetobacter baumannii* and its role in virulence and biofilm formation. PLoS Pathog 8(6):e1002758.
72. Geno K A, et al. (2015) Pneumococcal Capsules and Their Types: Past, Present, and Future. Clin Microbiol Rev 28(3):871-899.
73. Carboni F, et al. (2017) Structure of a protective epitope of group B *Streptococcus* type III capsular polysaccharide. Proc Natl Acad Sci USA 114(19):5017-5022.
74. Pan Y J, et al. (2015) Genetic analysis of capsular polysaccharide synthesis gene clusters in 79 capsular types of *Klebsiella* spp. Sci Rep 5:15573.

75. Feldman M F, et al. (2019) A promising bioconjugate vaccine against hypervirulent *Klebsiella pneumoniae*. Proc Natl Acad Sci USA.

What is claimed is:

1. A bioconjugate comprising an oligo- or polysaccharide covalently linked to a fusion protein:
   wherein the fusion protein comprises a ComP protein (ComP) glycosylation tag comprising an isolated fragment or variant thereof of a ComP protein;
   wherein the ComP glycosylation tag has a length of between 18 and 50 amino acids;
   wherein the ComP glycosylation tag comprises both a cysteine residue corresponding to the conserved cysteine residue at position 71 of SEQ ID NO: 2 (ComP$_{110264}$: ENV58402.1) and a cysteine residue corresponding to the conserved cysteine residue at position 93 of SEQ ID NO: 2;

wherein the fusion protein is glycosylated with the oligo- or polysaccharide on the ComP glycosylation tag at a serine residue corresponding to the conserved serine residue at position 82 of SEQ ID NO: 2;

wherein the ComP glycosylation tag does not comprise a methionine residue corresponding to the conserved methionine residue at position 104 of SEQ ID NO: 2 (ComP$_{110264}$: ENV58402.1); and wherein the fusion protein of the bioconjugate does not comprise, in relationship to the ComP glycosylation tag, a methionine residue at a position that would correspond to or correspond about to the conserved methionine residue at position 104 of SEQ ID NO: 2 (ComP$_{110264}$: ENV58402.1).

2. The bioconjugate of claim 1, wherein the amino acid sequence of the ComP glycosylation tag does not extend in the C-terminus direction beyond the amino acid residue corresponding to position 103 of SEQ ID NO: 2 (ComP$_{110264}$: ENV58402.1).

3. The bioconjugate of claim 1 wherein the ComP protein comprises an amino acid sequence that is at least 70% identical to SEQ ID NO: 7 (ComPΔ28$_{ADP1}$) or SEQ ID NO: 8 (ComPΔ28$_{110264}$).

4. The bioconjugate of claim 1, wherein the ComP glycosylation tag comprises the amino acid consensus sequence of:

(SEQ ID NO: 28)
CX$_2$GVX$_5$X$_6$IX$_8$X$_9$X$_{10}$ASX$_{13}$X$_{14}$TX$_{16}$NVX$_{19}$X$_{20}$AX$_{22}$C wherein:
X$_2$ is V, T, or A;
X$_5$ is Q, T, or E;
X$_6$ is E, Q, or T;
X$_8$ is S, N, A, or G;
X$_9$ is S or no amino acid;
X$_{10}$ is G or no amino acid;
X$_{13}$ is N, S, or A;
X$_{14}$ is A, S, or K;
X$_{16}$ is T, S, or K;
X$_{19}$ is A or E;
X$_{20}$ is T or S; or
X$_{22}$ is T, Q, or A,
or a variant thereof having one, two, or three amino acid substitutions, additions, and/or deletions,
wherein the variant maintains the cysteine residue at position 1 of SEQ ID NO: 28, the cysteine residue at position 23 of SEQ ID NO: 28, and the serine residue at position 12 of SEQ ID NO: 28.

5. The bioconjugate of claim 1, wherein the oligo- or polysaccharide is produced by a bacteria from the genus *Streptococcus*.

6. The bioconjugate of claim 5, wherein the polysaccharide is a capsular polysaccharide and wherein the capsular polysaccharide is CPS14, CPS8, CPS9V, or CPS15b.

7. The bioconjugate of claim 1, wherein the oligo- or polysaccharide is produced by a bacteria from the genus *Klebsiella*.

8. The bioconjugate of claim 7, wherein the polysaccharide is a serotype K1 or serotype K2 capsular polysaccharide of *Klebsiella pneumoniae*.

9. The bioconjugate of claim 1, wherein the oligo- or polysaccharide comprises a glucose at its reducing end.

10. The bioconjugate of claim 1, wherein the bioconjugate is a conjugate vaccine.

11. The bioconjugate of claim 10, wherein the conjugate vaccine is a vaccine against *Streptococcus pneumoniae* serotype 8.

12. A fusion protein comprising a ComP glycosylation tag comprising an isolated fragment or variant thereof of a ComP protein,
wherein the fragment comprises a serine residue corresponding to the conserved serine residue at position 82 in SEQ ID NO: 2 (ComP110264: ENV58402.1) and both a cysteine residue corresponding to the conserved cysteine residue at position 71 of SEQ ID NO: 2 and a cysteine residue corresponding to the conserved cysteine residue at position 93 of SEQ ID NO: 2;
wherein the ComP glycosylation tag has a length of between 18 and 50 amino acids;
wherein the ComP glycosylation tag does not comprise a methionine residue corresponding to the conserved methionine residue at position 104 of SEQ ID NO: 2 (ComP$_{110264}$: ENV58402.1); and
wherein the fusion protein does not comprise, in relationship to the ComP glycosylation tag, a methionine residue at a position that would correspond to or correspond about to the conserved methionine residue at position 104 of SEQ ID NO: 2 (ComP$_{110264}$: ENV58402.1).

13. The fusion protein of claim 12, wherein the amino acid sequence of the ComP glycosylation tag does not extend in the C-terminus direction beyond the amino acid residue corresponding to position 103 of SEQ ID NO: 2 (ComP$_{110264}$: ENV58402.1).

14. The fusion protein of claim 12, wherein the ComP protein comprises an amino acid sequence that is at least 70% identical to SEQ ID NO: 7 (ComPΔ28$_{ADP1}$) or SEQ ID NO: 8 (ComPΔ28$_{110264}$).

15. The fusion protein of claim 12, wherein the ComP glycosylation tag comprises the amino acid consensus sequence of:

(SEQ ID NO: 28)
CX$_2$GVX$_5$X$_6$IX$_8$X$_9$X$_{10}$ASX$_{13}$X$_{14}$TX$_{16}$NVX$_{19}$X$_{20}$AX$_{22}$C wherein:
X$_2$ is V, T, or A;
X$_5$ is Q, T, or E;
X$_6$ is E, Q, or T;
X$_8$ is S, N, A, or G;
X$_9$ is S or no amino acid;
X$_{10}$ is G or no amino acid;
X$_{13}$ is N, S, or A;
X$_{14}$ is A, S, or K;
X$_{16}$ is T, S, or K;
X$_{19}$ is A or E;
X$_{20}$ is T or S; or
X$_{22}$ is T, Q, or A,
or a variant thereof having one, two, or three amino acid substitutions, additions, and/or deletions,
wherein the variant maintains the cysteine residue at position 13 of SEQ ID NO: 28, the cysteine residue at position 35 of SEQ ID NO: 28, and the serine residue at position 24 of SEQ ID NO: 28.

16. The fusion protein of claim 12, wherein the oligo- or polysaccharide comprises a glucose at its reducing end.

17. The fusion protein of claim 12, wherein the fusion protein comprises a carrier protein selected from the group consisting of diphtheria toxoid CRM197, tetanus toxoid, *Pseudomonas aeruginosa* Exotoxin A (EPA), tetanus toxin C fragment, cholera toxin B subunit, and *Haemophilus influenza* protein D, or a fragment thereof.

18. The fusion protein of claim 12, wherein the ComP glycosylation tag is located at the N-terminal end of the fusion protein, at the C-terminal end of the fusion protein, and/or internally within the fusion protein.

19. The fusion protein of claim 12, wherein the fusion protein comprises two or more ComP glycosylation tags.

20. The fusion protein of claim 12, wherein the fusion protein comprises 2 to 10 ComP glycosylation tags.

21. The fusion protein of claim 19, wherein the ComP glycosylation tags are identical.

22. The fusion protein of claim 19, wherein at least two of the ComP glycosylation tags differ from each other.

23. A composition comprising the conjugate vaccine of claim 10, and an adjuvant.

24. A method of inducing a host immune response against a bacterial pathogen, the method comprising administering to a subject in need of the immune response an effective amount of the conjugate vaccine of claim 10.

25. A method of preventing or treating a bacterial disease and/or infection in a subject comprising administering to a subject in need thereof the conjugate vaccine of claim 10.

26. A method of producing a pneumococcal conjugate vaccine against pneumococcal infection, the method comprising:
   (a) isolating the bioconjugate of claim 1; and
   (b) combining the isolated bioconjugate with an adjuvant.

27. The bioconjugate of claim 3, wherein the ComP protein comprises SEQ ID NO: 7 (ComPΔ28$_{ADP1}$), SEQ ID NO: 8 (ComPΔ28$_{110264}$), SEQ ID NO: 9 (ComPΔ28$_{GFJ-2}$), SEQ ID NO: 10 (ComPΔ28$_{P50v1}$), SEQ ID NO: 11 (ComPΔ28$_{4466}$), or SEQ ID NO: 12 (ComPΔ28$_{SFC}$).

28. The fusion protein of claim 12, wherein the fusion protein is glycosylated at the serine residue on the glycosylation tag corresponding to the serine residue at position 82 of SEQ ID NO: 2.

29. The fusion protein of claim 14, wherein the ComP protein comprises SEQ ID NO: 7 (ComPΔ28$_{ADP1}$), SEQ ID NO: 8 (ComPΔ28$_{110264}$), SEQ ID NO: 9 (ComPΔ28$_{GFJ-2}$), SEQ ID NO: 10 (ComPΔ28$_{P50v1}$), SEQ ID NO: 11 (ComPΔ28$_{4466}$), or SEQ ID NO: 12 (ComPΔ28$_{SFC}$).

30. The bioconjugate of claim 1, wherein the ComP glycosylation tag comprises an amino acid sequence selected from the group consisting of: SEQ ID NO: 32 [C1]; SEQ ID NO: 33 [D1]; SEQ ID NO: 34 [E1]; SEQ ID NO: 41 [E2]; SEQ ID NO: 42 [F2]; SEQ ID NO: 43 [G2]; SEQ ID NO: 44 [H2]; SEQ ID NO: 45 [A3]; SEQ ID NO: 46 [B3]; SEQ ID NO: 47 [C3]; SEQ ID NO: 55 [D4]; SEQ ID NO: 56 [E4]; SEQ ID NO: 57 [F4]; SEQ ID NO: 58 [G4]; SEQ ID NO: 59 [A5]; SEQ ID NO: 60 [B5]; SEQ ID NO: 61 [D5]; SEQ ID NO: 62 [E5]; SEQ ID NO: 63 [F5]; SEQ ID NO: 72 [H6]; SEQ ID NO: 73 [B7]; SEQ ID NO: 74 [C7]; SEQ ID NO: 75 [D7]; SEQ ID NO: 76 [E7]; SEQ ID NO: 77 [F7]; SEQ ID NO: 78 [A8]; SEQ ID NO: 79 [B8]; SEQ ID NO: 92 [A10]; SEQ ID NO: 93 [B10]; SEQ ID NO: 94 [C10]; SEQ ID NO: 95 [D10]; SEQ ID NO: 96 [F10]; SEQ ID NO: 97 [G10]; SEQ ID NO: 98 [H10]; SEQ ID NO: 99 [A11]; SEQ ID NO: 100 [B11]; and SEQ ID NO: 101 [C11],
   or a variant thereof having one, two, or three amino acid substitutions, additions, and/or deletions,
   wherein the variant maintains both a cysteine residue corresponding to the conserved cysteine residue at position 75 of SEQ ID NO: 1 (ComP$_{ADP1}$: AAC45886.1) and a cysteine residue corresponding to the conserved cysteine residue at position 95 of SEQ ID NO: 1; and
   wherein the variant maintains a serine residue corresponding to the conserved serine residue at position 84 of SEQ ID NO: 1.

31. The bioconjugate of claim 1, wherein the ComP glycosylation tag comprises an amino acid sequence selected from the group consisting of: SEQ ID NO: 32 [C1]; SEQ ID NO: 33 [D1]; SEQ ID NO: 34 [E1]; SEQ ID NO: 41 [E2]; SEQ ID NO: 42 [F2]; SEQ ID NO: 43 [G2]; SEQ ID NO: 44 [H2]; SEQ ID NO: 45 [A3]; SEQ ID NO: 46 [B3]; SEQ ID NO: 47 [C3]; SEQ ID NO: 55 [D4]; SEQ ID NO: 56 [E4]; SEQ ID NO: 57 [F4]; SEQ ID NO: 58 [G4]; SEQ ID NO: 59 [A5]; SEQ ID NO: 60 [B5]; SEQ ID NO: 61 [D5]; SEQ ID NO: 62 [E5]; SEQ ID NO: 63 [F5]; SEQ ID NO: 72 [H6]; SEQ ID NO: 73 [B7]; SEQ ID NO: 74 [C7]; SEQ ID NO: 75 [D7]; SEQ ID NO: 76 [E7]; SEQ ID NO: 77 [F7]; SEQ ID NO: 78 [A8]; SEQ ID NO: 79 [B8]; SEQ ID NO: 92 [A10]; SEQ ID NO: 93 [B10]; SEQ ID NO: 94 [C10]; SEQ ID NO: 95 [D10]; SEQ ID NO: 96 [F10]; SEQ ID NO: 97 [G10]; SEQ ID NO: 98 [H10]; SEQ ID NO: 99 [A11]; SEQ ID NO: 100 [B11]; and SEQ ID NO: 101 [C11].

32. The bioconjugate of claim 1, wherein the ComP glycosylation tag consists of an amino acid sequence selected from the group consisting of: SEQ ID NO: 32 [C1]; SEQ ID NO: 33 [D1]; SEQ ID NO: 34 [E1]; SEQ ID NO: 41 [E2]; SEQ ID NO: 42 [F2]; SEQ ID NO: 43 [G2]; SEQ ID NO: 44 [H2]; SEQ ID NO: 45 [A3]; SEQ ID NO: 46 [B3]; SEQ ID NO: 47 [C3]; SEQ ID NO: 55 [D4]; SEQ ID NO: 56 [E4]; SEQ ID NO: 57 [F4]; SEQ ID NO: 58 [G4]; SEQ ID NO: 59 [A5]; SEQ ID NO: 60 [B5]; SEQ ID NO: 61 [D5]; SEQ ID NO: 62 [E5]; SEQ ID NO: 63 [F5]; SEQ ID NO: 72 [H6]; SEQ ID NO: 73 [B7]; SEQ ID NO: 74 [C7]; SEQ ID NO: 75 [D7]; SEQ ID NO: 76 [E7]; SEQ ID NO: 77 [F7]; SEQ ID NO: 78 [A8]; SEQ ID NO: 79 [B8]; SEQ ID NO: 92 [A10]; SEQ ID NO: 93 [B10]; SEQ ID NO: 94 [C10]; SEQ ID NO: 95 [D10]; SEQ ID NO: 96 [F10]; SEQ ID NO: 97 [G10]; SEQ ID NO: 98 [H10]; SEQ ID NO: 99 [A11]; SEQ ID NO: 100 [B11]; and SEQ ID NO: 101 [C11].

33. The fusion protein of claim 12, wherein the ComP glycosylation tag comprises an amino acid sequence selected from the group consisting of: SEQ ID NO: 32 [C1]; SEQ ID NO: 33 [D1]; SEQ ID NO: 34 [E1]; SEQ ID NO: 41 [E2]; SEQ ID NO: 42 [F2]; SEQ ID NO: 43 [G2]; SEQ ID NO: 44 [H2]; SEQ ID NO: 45 [A3]; SEQ ID NO: 46 [B3]; SEQ ID NO: 47 [C3]; SEQ ID NO: 55 [D4]; SEQ ID NO: 56 [E4]; SEQ ID NO: 57 [F4]; SEQ ID NO: 58 [G4]; SEQ ID NO: 59 [A5]; SEQ ID NO: 60 [B5]; SEQ ID NO: 61 [D5]; SEQ ID NO: 62 [E5]; SEQ ID NO: 63 [F5]; SEQ ID NO: 72 [H6]; SEQ ID NO: 73 [B7]; SEQ ID NO: 74 [C7]; SEQ ID NO: 75 [D7]; SEQ ID NO: 76 [E7]; SEQ ID NO: 77 [F7]; SEQ ID NO: 78 [A8]; SEQ ID NO: 79 [B8]; SEQ ID NO: 92 [A10]; SEQ ID NO: 93 [B10]; SEQ ID NO: 94 [C10]; SEQ ID NO: 95 [D10]; SEQ ID NO: 96 [F10]; SEQ ID NO: 97 [G10]; SEQ ID NO: 98 [H10]; SEQ ID NO: 99 [A11]; SEQ ID NO: 100 [B11]; and SEQ ID NO: 101 [C11],
   or a variant thereof having one, two, or three amino acid substitutions, additions, and/or deletions,
   wherein the variant maintains both a cysteine residue corresponding to the conserved cysteine residue at position 75 of SEQ ID NO: 1 (ComP$_{ADP1}$:

AAC45886.1) and a cysteine residue corresponding to the conserved cysteine residue at position 95 of SEQ ID NO: 1; and wherein the variant maintains a serine residue corresponding to the conserved serine residue at position 84 of SEQ ID NO: 1.

34. The fusion protein of claim 12, wherein the ComP glycosylation tag comprises an amino acid sequence selected from the group consisting of: SEQ ID NO: 32 [C1]; SEQ ID NO: 33 [D1]; SEQ ID NO: 34 [E1]; SEQ ID NO: 41 [E2]; SEQ ID NO: 42 [F2]; SEQ ID NO: 43 [G2]; SEQ ID NO: 44 [H2]; SEQ ID NO: 45 [A3]; SEQ ID NO: 46 [B3]; SEQ ID NO: 47 [C3]; SEQ ID NO: 55 [D4]; SEQ ID NO: 56 [E4]; SEQ ID NO: 57 [F4]; SEQ ID NO: 58 [G4]; SEQ ID NO: 59 [A5]; SEQ ID NO: 60 [B5]; SEQ ID NO: 61 [D5]; SEQ ID NO: 62 [E5]; SEQ ID NO: 63 [F5]; SEQ ID NO: 72 [H6]; SEQ ID NO: 73 [B7]; SEQ ID NO: 74 [C7]; SEQ ID NO: 75 [D7]; SEQ ID NO: 76 [E7]; SEQ ID NO: 77 [F7]; SEQ ID NO: 78 [A8]; SEQ ID NO: 79 [B8]; SEQ ID NO: 92 [A10]; SEQ ID NO: 93 [B10]; SEQ ID NO: 94 [C10]; SEQ ID NO: 95 [D10]; SEQ ID NO: 96 [F10]; SEQ ID NO: 97 [G10]; SEQ ID NO: 98 [H10]; SEQ ID NO: 99 [A11]; SEQ ID NO: 100 [B11]; and SEQ ID NO: 101 [C11].

35. The fusion protein of claim 12, wherein the ComP glycosylation tag consists of an amino acid sequence selected from the group consisting of: SEQ ID NO: 32 [C1]; SEQ ID NO: 33 [D1]; SEQ ID NO: 34 [E1]; SEQ ID NO: 41 [E2]; SEQ ID NO: 42 [F2]; SEQ ID NO: 43 [G2]; SEQ ID NO: 44 [H2]; SEQ ID NO: 45 [A3]; SEQ ID NO: 46 [B3]; SEQ ID NO: 47 [C3]; SEQ ID NO: 55 [D4]; SEQ ID NO: 56 [E4]; SEQ ID NO: 57 [F4]; SEQ ID NO: 58 [G4]; SEQ ID NO: 59 [A5]; SEQ ID NO: 60 [B5]; SEQ ID NO: 61 [D5]; SEQ ID NO: 62 [E5]; SEQ ID NO: 63 [F5]; SEQ ID NO: 72 [H6]; SEQ ID NO: 73 [B7]; SEQ ID NO: 74 [C7]; SEQ ID NO: 75 [D7]; SEQ ID NO: 76 [E7]; SEQ ID NO: 77 [F7]; SEQ ID NO: 78 [A8]; SEQ ID NO: 79 [B8]; SEQ ID NO: 92 [A10]; SEQ ID NO: 93 [B10]; SEQ ID NO: 94 [C10]; SEQ ID NO: 95 [D10]; SEQ ID NO: 96 [F10]; SEQ ID NO: 97 [G10]; SEQ ID NO: 98 [H10]; SEQ ID NO: 99 [A11]; SEQ ID NO: 100 [B11]; and SEQ ID NO: 101 [C11].

\* \* \* \* \*